US010407690B2

(12) United States Patent
Ronen et al.

(10) Patent No.: US 10,407,690 B2
(45) Date of Patent: Sep. 10, 2019

(54) ISOLATED POLYPEPTIDES, POLYNUCLEOTIDES USEFUL FOR MODIFYING WATER USER EFFICIENCY, FERTILIZER USE EFFICIENCY, BIOTIC/ABIOTIC STRESS TOLERANCE, YIELD AND BIOMASS IN PLANTS

(71) Applicant: Evogene Ltd., Rehovot (IL)

(72) Inventors: Gil Ronen, Moshav Ometz (IL); Basia Judith Vinocur, Rechovot (IL); Alex Diber, Rishon-LeZion (IL); Sharon Ayal, Kiryat-Ekron (IL); Hagai Karchi, Moshav Sitriya (IL); Yoav Herschkovitz, Givataim (IL)

(73) Assignee: Evogene Ltd., Rehovot (IL)

(*) Notice: Subject to any disclaimer, the term of this patent is extended or adjusted under 35 U.S.C. 154(b) by 0 days.

(21) Appl. No.: 15/478,253

(22) Filed: Apr. 4, 2017

(65) Prior Publication Data
US 2017/0204428 A1  Jul. 20, 2017

Related U.S. Application Data

(60) Division of application No. 13/867,185, filed on Apr. 22, 2013, now Pat. No. 9,670,501, which is a continuation of application No. 13/450,547, filed on Apr. 19, 2012, now Pat. No. 8,426,682, which is a continuation of application No. 12/810,855, filed as application No. PCT/IL2008/001657 on Dec. 23, 2008, now abandoned.

(60) Provisional application No. 61/136,238, filed on Aug. 20, 2008, provisional application No. 61/009,166, filed on Dec. 27, 2007.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8242* (2013.01); *C12N 15/8245* (2013.01); *C12N 15/8247* (2013.01); *C12N 15/8261* (2013.01); *C12N 15/8271* (2013.01); *Y02A 40/146* (2018.01)

(58) Field of Classification Search
CPC ............ C12N 15/8271; C12N 15/8261; C12N 15/8273
See application file for complete search history.

(56) References Cited

U.S. PATENT DOCUMENTS

| 6,084,153 | A | 7/2000 | Good et al. |
| 8,426,682 | B2 | 4/2013 | Ronen et al. |
| 2002/0046419 | A1 | 4/2002 | Choo et al. |
| 2003/0233670 | A1 | 12/2003 | Edgerton et al. |
| 2004/0172684 | A1 | 9/2004 | Kovalic et al. |
| 2005/0108791 | A1 | 5/2005 | Edgerton |
| 2006/0179511 | A1 | 8/2006 | Chomet et al. |
| 2008/0148432 | A1* | 6/2008 | Abad .................. C07K 14/415 800/279 |
| 2012/0222169 | A1 | 8/2012 | Ronen et al. |
| 2013/0219562 | A1 | 8/2013 | Ronen et al. |

FOREIGN PATENT DOCUMENTS

| AU | 2008344935 | 7/2009 |
| CN | 1212014 | 3/1999 |
| CN | 1840664 | 10/2006 |
| CN | 1884542 | 12/2006 |
| CN | 10197792 | 12/2014 |
| JP | 10-229883 | 9/1998 |
| WO | WO 2004/077010 | 9/2004 |
| WO | WO 2004/081173 | 9/2004 |
| WO | WO 2004/104162 | 12/2004 |
| WO | WO 2004/111183 | 12/2004 |
| WO | WO 2005/121364 | 12/2005 |
| WO | WO 2006/076423 | 7/2006 |
| WO | WO 2007/020638 | 2/2007 |
| WO | WO 2007/049275 | 5/2007 |
| WO | WO 2008/075364 | 6/2008 |
| WO | WO 2008/122980 | 10/2008 |
| WO | WO 2009/013750 | 1/2009 |
| WO | WO 2009/083958 | 7/2009 |
| WO | WO 2009/141824 | 11/2009 |
| WO | WO 2010/020941 | 2/2010 |

(Continued)

OTHER PUBLICATIONS

Davletona et al (Plant Physiology, Oct. 2005, vol. 139, pp. 847-856) (Year: 2005).*
Jang et al (Plant Mol Biol (2007) 64:621-632) (Year: 2007).*
Katsuhara et al Plant Cell Physiol. 44(12): 1378-1383 (2003) (Year: 2003).*
Aharon et al The Plant Cell, vol. 15, 439-447, Feb. 2003, (Year: 2003).*
Communication Pursuant to Article 94(3) EPC Dated May 4, 2016 From the European Patent Office Re. Application No. 08869158.9.
Communication Pursuant to Article 94(3) EPC Dated Oct. 9, 2013 From the European Patent Office Re. Application No. 08869158.9.
Communication Pursuant to Article 94(3) EPC Dated Mar. 17, 2015 From the European Patent Office Re. Application No. 08869158.9.
Communication Relating to the Results of the Partial International Search dated Jul. 8, 2009 From the International Searching Authority Re.: Application No. PCT/IL2008/001657.

(Continued)

*Primary Examiner* — Lee A Visone

(57) ABSTRACT

Polynucleotides, polypeptides, plant cells expressing same and methods of using same for increasing abiotic stress tolerance water use efficiency (WUE), fertilizer use efficiency (FUE), biomass, vigor and/or yield of a plant. The method is effected by expressing within the plant an exogenous polynucleotide encoding a polypeptide comprising an amino acid sequence at least 80% homologous to the amino acid sequence selected from the group consisting of SEQ ID NOs:33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065 and 3067-3259, thereby increasing the water use efficiency (WUE), the fertilizer use efficiency (FUE), the biomass, the vigor and/or the yield of the plant.

14 Claims, 4 Drawing Sheets

Specification includes a Sequence Listing.

(56) References Cited

FOREIGN PATENT DOCUMENTS

| | | |
|---|---|---|
| WO | WO 2010/049897 | 5/2010 |
| WO | WO 2010/076756 | 7/2010 |
| WO | WO 2010/100595 | 9/2010 |
| WO | WO 2010/143138 | 12/2010 |
| WO | WO 2011/015985 | 2/2011 |
| WO | WO 2011/080674 | 7/2011 |
| WO | WO 2011/135527 | 11/2011 |
| WO | WO 2012/028993 | 3/2012 |
| WO | WO 2012/085862 | 6/2012 |
| WO | WO 2012/150598 | 11/2012 |
| WO | WO 2013/027223 | 2/2013 |
| WO | WO 2013/078153 | 5/2013 |
| WO | WO 2013/080203 | 6/2013 |
| WO | WO 2013/098819 | 7/2013 |
| WO | WO 2013/128448 | 9/2013 |
| WO | WO 2013/179211 | 12/2013 |
| WO | WO 2014/033714 | 3/2014 |
| WO | WO 2014/102773 | 7/2014 |
| WO | WO 2014/102774 | 7/2014 |
| WO | WO 2014/188428 | 11/2014 |
| WO | WO 2015/029031 | 3/2015 |
| WO | WO 2015/181823 | 12/2015 |
| WO | WO 2016/030885 | 3/2016 |

OTHER PUBLICATIONS

Examination Report dated Mar. 2, 2017 From the Instituto Mexicano de la Propiedad Industrial, IMPI Re. Application No. MX/a/2016/004764 and Its Translation Into English. (5 Pages).
Examination Report dated Sep. 5, 2017 From the Ministry of Law and Human Rights of the Republic of Indonesia, Directorate General of Intellectual Property Rights Re. Application No. W00201002202. (2 Pages).
Examination Report dated Jul. 9, 2013 From the Instituto Mexicano de la Propiedad Industrial Re. Application No. MX/a/2010/007169 and Its Translation Into English.
Examination Report dated Dec. 13, 2016 From the Australian Government, IP Australia Re. Application No. 2015261690. (4 Pages).
Examination Report dated Aug. 14, 2015 From the Government of India, Patent Office, Intellectual Property Building Re. Application No. 1425/MUMNP/2010.
Examination Report dated Aug. 17, 2017 From the Australian Government, IP Australia Re. Application No. 2015261690. (6 Pages).
Examination Report dated Feb. 17, 2016 From the Instituto Mexicano de la Propiedad Industrial Re. Application No. MX/a/2013/011073 and Its Translation Into English.
Examination Report dated Apr. 26, 2014 From the National Office of Intellectual Property (NOIP) of the Social Republic of Vietnam Re. Application No. 1-2010-01939 and Its Translation Into English.
Examination Report dated May 29, 2017 From the Australian Government, IP Australia Re. Application No. 2015261690. (12 Pages).
Examination Report dated Aug. 31, 2016 From the Ministry of Law and Human Rights of the Republic of Indonesia, Directorate General of Intellectual Property Rights Re. Application No. W00201002202 and its Translation Into English.
Examination Report on Voluntary Amendments dated Jan. 28, 2016 From the Australian Government, IP Australia Re. Application No. 2008344935.
Hearing Notice dated Dec. 14, 2016 From the Government of India, Patent Office, Intellectual Property Building Re. Application No. 1425/MUMNP/2010. (8 Pages).
International Preliminary Report on Patentability dated Jul. 8, 2010 From the International Bureau of WIPO Re. Application No. PCT/IL2008/001657.
International Search Report and the Written Opinion dated Oct. 30, 2009 From the International Searching Authority Re. Application No. PCT/IL2008/001657.
Notice of Allowance dated Feb. 3, 2017 From the U.S. Appl. No. 13/867,185. (8 pages).
Office Action dated Apr. 1, 2013 From the State Intellectual Property Office of the People's Republic of China Re. Application No. 200880127757.X and Its Translation Into English.
Office Action dated Dec. 23, 2013 From the State Intellectual Property Office of the People's Republic of China Re. Application No. 200880127757.X and Its Translation Into English.
Official Action dated Mar. 3, 2016 From the U.S. Appl. No. 13/867,185.
Official Action dated Jul. 11, 2016 From the U.S. Appl. No. 13/867,185.
Official Action dated Jun. 19, 2012 From the U.S. Appl. No. 13/450,547.
Official Action dated Sep. 19, 2011 From the U.S. Appl. No. 12/810,855.
Official Action dated Dec. 21, 2011 From the U.S. Appl. No. 12/810,855.
Official Action dated Nov. 22, 2016 From the U.S. Appl. No. 13/867,185. (13 pages).
Official Action dated Aug. 31, 2015 From the U.S. Appl. No. 13/867,185.
Patent Examination Report dated Jan. 4, 2013 From the Australian Government, IP Australia Re. Application No. 2008344935.
Patent Examination Report dated May 21, 2015 From the Australian Government, IP Australia Re. Application No. 2013263801.
Requisition by the Examiner and Examination Search Report dated Feb. 5, 2015 From the Canadian Intellectual Property Office Re. Application No. 2,709,517.
Requisition by the Examiner dated Aug. 4, 2016 From the Canadian Intellectual Property Office Re. Application No. 2,709,517.
Requisition by the Examiner dated Jun. 5, 2017 From the Canadian Intellectual Property Office Re. Application No. 2,709,517. (13 Pages).
Requisition by the Examiner dated Jan. 7, 2016 From the Canadian Intellectual Property Office Re. Application No. 2,709,517.
Restriction Official Action dated Jun. 5, 2015 From the U.S. Appl. No. 13/867,185.
Search Report dated Dec. 23, 2013 From the State Intellectual Property Office of the People's Republic of China Re. Application No. 200880127757.X and Its Translation Into English.
Substantive Examination dated Aug. 14, 2014 From the Intellectual Property Office of the Philippines, Bureau of Patents Re. Application No. 1/2010/501474.
Translation of Notice of Paying Restoration Fee for Unity of Invention Dated Oct. 29, 2012 From the State Intellectual Property Office of the People's Republic of China Re. Application No. 200880127757.X.
Aharon et al. "Overexpression of a Plasma Membrane Aquaporin in Transgenic Tobacco Improves Plant Vigor Under Favorable Growth Conditions But Not Under Drought or Salt Stress", The Plant Cell, 15: 439-447, Feb. 2003.
Danielson et al. "Unexpected Complexity of the Aquaporin Gene Family in the Moss Physcomitrella Patens", BMC Plant Biology, 8: 45, pp. 1-15, Piblished Online Apr. 22, 2008.
Davletova et al. "The Zinc-Finger Protein Zat12 Plays a Central Role in Reactive Oxygen and Abiotic Stress Signaling in Arabidopsis", Plant Physiology, 139: 847-856, Oct. 2005.
Fray et al. "Nucleotide Sequence and Expression of a Ripening and Water Stress-Related cDNA From Tomato With Homology to the MIP Class of Membrane Channel Proteins", Plant Molecular Biology, XP009117320, 24(3): 539-543, 1994. Figs.1, 2. & Database UniProt, REcName: Full=Probable Aquaporin PIP-Type pTOM75; AltName: Full=Ripening-Associated Membrane Protein; Short= Ramp, Oct. 1, 1994.
Friedberg "Automated Protein Function Prediction—The Genomic Challenge", Briefings in Bioinformatics, 7(3): 225-242, 2006.
Gerbeau et al. "Nicotiana Tabacum mRNA for Tonoplast Intrinsic Protein (TIPa)", Database NCBI [Online], GenBank Accession No. AJ237751.1, Database Accession No. AJ237751, Apr. 15, 2005.
Hachez et al. "Modulating the Expression of Aquaporin Genes in Planta: A Key to Understand Their Physiological Functions?",

(56) References Cited

OTHER PUBLICATIONS

Biochimica et Biophysica Acta, XP005655605, 1758(8): 1142-1156, Aug. 1, 2006. p. 1151, col. 1, § 2-p. 1153, col. 1, § 1, Table 1.
Kirkness et al. "Lycopersicon Esculentum Clone 133453R, mRNA Sequence", Database EMBL [Online], XP002529190, Retrieved From EBI Accession No. EMBL:BT014251.1, Database Accession No. BT014251, May 11, 2004.
Lacombe et al. "The Identity of Plant Glutamate Receptors", Science, 292(5521): 1486-1487, May 25, 2001.
Maurel "Plant Aquaporins: Novel Functions and Regulation Properties", FEBS Letters, XP022078418, 581(12): 2227-2236, May 25, 2007. p. 2230, col. 2, Last §-p. 2231, col. 1, § 2, Fig.1.
Peng et al. "Overexpression of a Panax Ginseng Tonoplast Aquaporin Alters Salt Tolerance, Drought Tolerance and Cold Acclimation Ability in Transgenic Arabidopsis Plants", Planta, 226(3): 729-740, Published Online Apr. 19, 2007.
To "To01000 Tomato CL5915 Roots Under Different Development Stages Solanum Lycopersicum cDNA Clone LE2TR03K03, mRNA Sequence", Database NCBI [Online], GenBank Accession No. EG553376.1, Database Accession No. EG553376, Oct. 25, 2006.
Wu et al. "SubName: Full=Major Intrinsic Protein", Database UniProt [Online], XP002529191, Retrieved From EBI Accession No. UNIPROT:AOFI89, Database Accession No. AOFI89, Nov. 28, 2006.
Examination Report dated Sep. 28, 2017 From the Instituto Nacional de la Propiedad Industrial, Administracion Nacional de Patentes, INPI Argentina Re. Application No. P080105728 and Its Summary in English. (6 Pages).
Requisition by the Examiner dated Mar. 23, 2018 From the Innovation, Science and Economic Development Canada, Canadian Intellectual Property Office Re. Application No. 2,709,517. (3 Pages).
Yanagisawa et al. "Metabolic Engineering With Dof1 Transcription Factor in Plants: Improved Nitrogen Assimilation and Growth Under Low-Nitrogen Conditions", Proc. Natl. Acad. Sci USA, PNAS, 101(20): 7833-7838, May 18, 2004.
Examination Report dated Oct. 5, 2017 From the Instituto Mexicano de la Propiedad Industrial, IMPI Re. Application No. MX/a/2016/004764 and Its Translation Into English. (5 Pages).
Examination Report dated Mar. 13, 2019 From the Servico Publico Federal, Ministerio da Industria, Comercio Exterior e Servicos, Instituto Nacional da Propriedade Industrial do Brasil Re. application No. PI 0819476-9 and Its Summary in English. (14 pages).
Examination Report dated Mar. 14, 2019 From the Instituto Nacional de la Propiedad Industrial, Administracion Nacional de Patentes, INPI Argentina Re. Application No. P080105728 and Its Summary in English. (10 Pages).
Maurel et al "Molecular Physiology of Aquaporins in Plants", International Review of Cytology 215: 105-148, 2002.
Yamamoto et al. "Expressed Sequence Rags from the Laboratory-Grown Miniature Tomato (*Lycopersicon esculentum*) Cultivar Micro-Tom and Mining for Single Nucleotide Polymorphisms and Insertions/Deletions in Tomato Cultivars", Gene 356: 127-134, 2005.

* cited by examiner

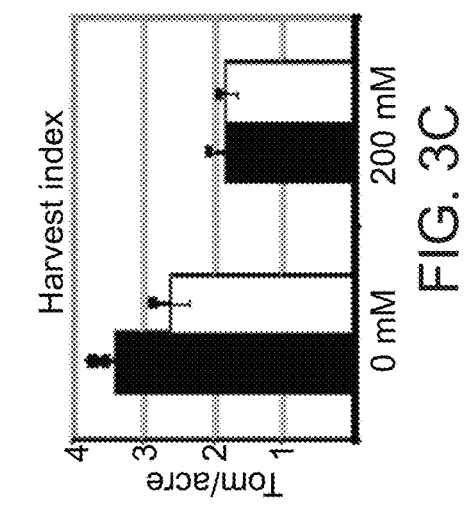
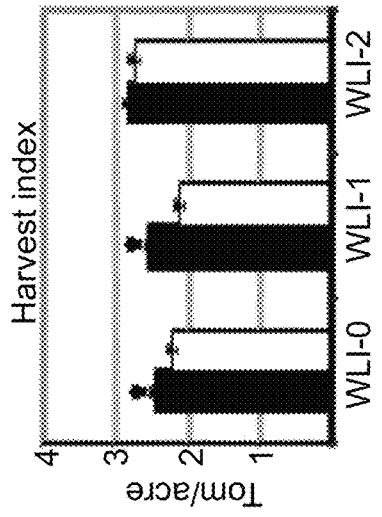
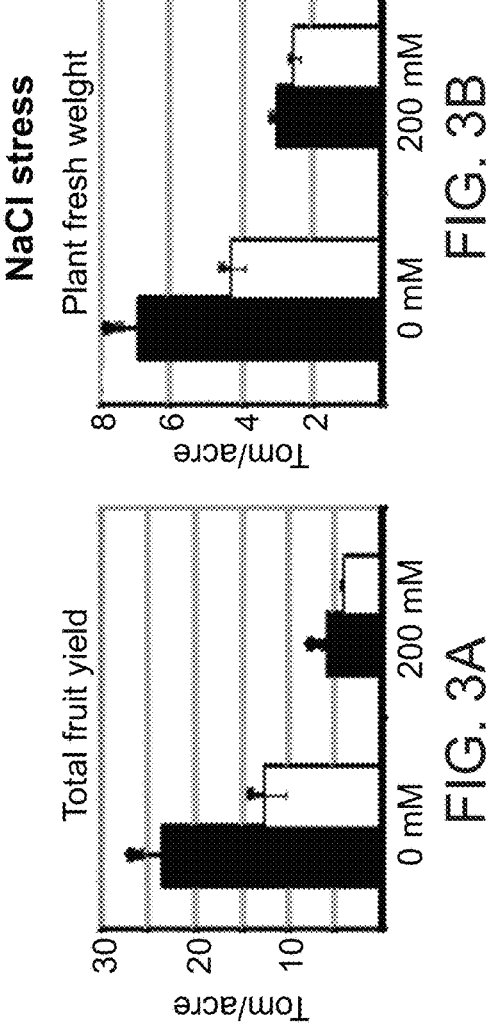
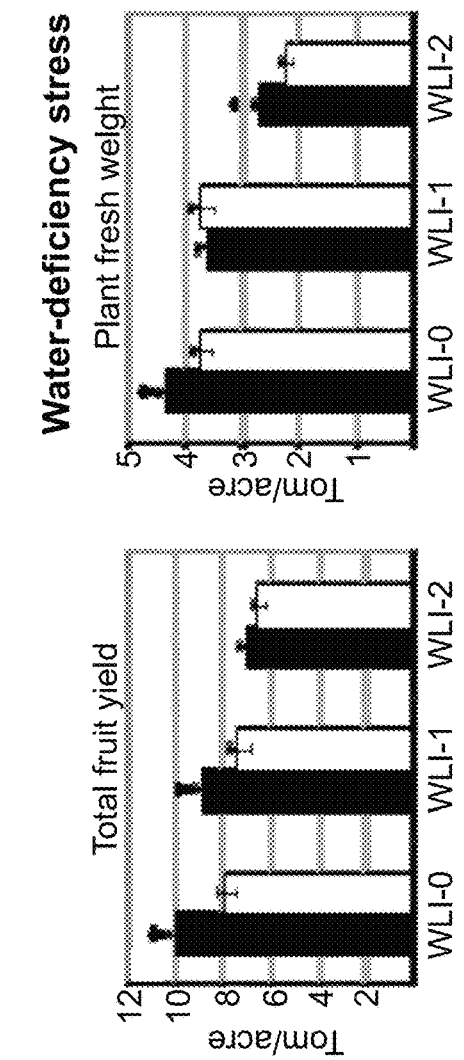

Standard irrigation    200 mM NaCl irrigation

ISOLATED POLYPEPTIDES, POLYNUCLEOTIDES USEFUL FOR MODIFYING WATER USER EFFICIENCY, FERTILIZER USE EFFICIENCY, BIOTIC/ABIOTIC STRESS TOLERANCE, YIELD AND BIOMASS IN PLANTS

RELATED APPLICATIONS

This application is division of U.S. patent application Ser. No. 13/867,185 filed on Apr. 22, 2013 which is a continuation of U.S. patent application Ser. No. 13/450,547 filed on Apr. 19, 2012, now U.S. Pat. No. 8,426,682, which is a continuation of U.S. patent application Ser. No. 12/810,855 filed on Jun. 28, 2010, which is a National Phase of PCT Patent Application No. PCT/IL2008/001657 having International filing date of Dec. 23, 2008, which claims the benefit of priority of U.S. Provisional Patent Applications Nos. 61/136,238 filed on Aug. 20, 2008 and 61/009,166 filed on Dec. 27, 2007. The contents of the above Applications are all incorporated herein by reference.

SEQUENCE LISTING STATEMENT

The ASCII file, entitled 69617SequenceListing.txt, created on Apr. 3, 2017, comprising 5,820,776 bytes, submitted concurrently with the filing of this application is incorporated herein by reference.

FIELD AND BACKGROUND OF THE INVENTION

The present invention, in some embodiments thereof, relates to novel aquaporin polynucleotides and polypeptides, and more particularly, but not exclusively, to methods of using same for increasing abiotic stress tolerance, water use efficiency (WUE), fertilizer use efficiency (FUE), biomass, vigor and/or yield of a plant.

Abiotic stress conditions such as salinity, drought, flood, suboptimal temperature and toxic chemical pollution, cause substantial damage to agricultural plants. Most plants have evolved strategies to protect themselves against these conditions. However, if the severity and duration of the stress conditions are too great, the effects on plant development, growth and yield of most crop plants are profound. Furthermore, most of the crop plants are highly susceptible to abiotic stress (ABS) and thus necessitate optimal growth conditions for commercial crop yields. Continuous exposure to stress causes major alterations in the plant metabolism which ultimately leads to cell death and consequently yield losses.

The global shortage of water supply is one of the most severe agricultural problems affecting plant growth and crop yield and efforts are made to mitigate the harmful effects of desertification and salinization of the world's arable land. Thus, Agbiotech companies attempt to create new crop varieties which are tolerant to different abiotic stresses focusing mainly in developing new varieties that can tolerate water shortage for longer periods.

Studies have shown that plant adaptations to adverse environmental conditions are complex genetic traits with polygenic nature. When water supply is limited, the plant WUE is critical for the survival and yield of crop. Since water scarcity is increasing and water quality is reducing worldwide it is important to increase water productivity and plant WUE. Many of the environmental abiotic stresses, such as drought, low temperature or high salt, decrease root hydraulic conductance, affect plant growth and decrease crop productivity.

Genetic improvement of FUE in plants can be generated either via traditional breeding or via genetic engineering. Attempts to improve FUE in transgenic plants are described in U.S. Patent Applications 20020046419 to Choo, et al.; U.S. Pat. Appl. 20030233670 to Edgerton et al.; U.S. Pat. Appl. 20060179511 to Chomet et al.; Yanagisawa et al. [Proc. Natl. Acad. Sci. U.S.A. 2004, 101(20):7833-8]; Good A G et al. [Trends Plant Sci. 2004, 9(12):597-605]; and U.S. Pat. No. 6,084,153 to Good et al.

Aquaporins (AQPs), the water channel proteins, are involved in transport of water through the membranes, maintenance of cell water balance and homeostasis under changing environmental and developmental conditions [Maurel C. Plant aquaporins: Novel functions and regulation properties. FEBS Lett. 2007, 581(12):2227-36]. These proteins are considered to be the main passage enabling transport of water and small neutral solutes such as urea and $CO_2$ through the membrane [Maurel C. Plant aquaporins: Novel functions and regulation properties. FEBS Lett. 2007 Jun. 12; 581(12):2227-36]. In plants, AQPs are present as four subfamilies of intrinsic proteins: plasma membrane (PIP), tonoplast (TIP), small and basic (SIP) and NOD26-like (NIP). The total number of AQP members in plants, as compared to animals, appears to be surprisingly high [Maurel C., 2007 (Supra)]. For instance, 35 AQP genes have been identified in the *Arabidopsis* genome [Quigley F, et al., "From genome to function: the *Arabidopsis* aquaporins". Genome Biol. 2002, 3(1):RESEARCH0001.1-1.17], 36 in maize [Chaumont F, et al., 2001, "Aquaporins constitute a large and highly divergent protein family in maize. Plant Physiol", 125(3):1206-15], and 33 in rice [Sakurai, J., et a., 2005, Identification of 33 rice aquaporin genes and analysis of their expression and function. Plant Cell Physiol. 46, 1568-1577]. The high number of AQPs in plants suggests a diverse role and differential regulation under variable environmental conditions [Maurel C., 2007 (Supra)].

WO2004/104162 to the present inventors teaches polynucleotide sequences and methods of utilizing same for increasing the tolerance of a plant to abiotic stresses and/or increasing the biomass of a plant.

WO2007/020638 to the present inventors teaches polynucleotide sequences and methods of utilizing same for increasing the tolerance of a plant to abiotic stresses and/or increasing the biomass, vigor and/or yield of a plant.

Lian H L, et al., 2006 (Cell Res. 16: 651-60) overexpressed members of the PIP1 subgroup of AQPs in rice. Aharon R., et al. 2003 (Plant Cell, 15: 439-47) overexpressed the *Arabidopsis* plasma membrane aquaporin, PIP1b, in transgenic tobacco plants.

SUMMARY OF THE INVENTION

According to an aspect of some embodiments of the present invention there is provided a method of increasing abiotic stress tolerance of a plant, comprising expressing within the plant an exogenous polynucleotide encoding a polypeptide comprising an amino acid sequence at least 80% homologous to the amino acid sequence selected from the group consisting of SEQ ID NOs: 33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065 and 3067-3259, thereby increasing the abiotic stress tolerance of the plant.

According to an aspect of some embodiments of the present invention there is provided a method of increasing water use efficiency (WUE), fertilizer use efficiency (FUE), biomass, vigor and/or yield of a plant, comprising expressing within the plant an exogenous polynucleotide encoding a polypeptide comprising an amino acid sequence at least 80% homologous to the amino acid sequence selected from the group consisting of SEQ ID NOs:33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065 and 3067-3259, thereby increasing the water use efficiency (WUE), the fertilizer use efficiency (FUE), the biomass, the vigor and/or the yield of the plant.

According to an aspect of some embodiments of the present invention there is provided an isolated polynucleotide comprising a nucleic acid sequence at least 80% identical to the nucleic acid sequence selected from the group consisting of SEQ ID NOs:7, 8, 4, 1-3, 5, 6, 9-26, 53-55, 57-87, 89-147, 149-195, 197-206, 208-212, 214-480, 482-519, 521-1103, 1106-1111, 1113-1116, 1118-1134, 1136, 1138-1400, 2748-2764, 2843-2857 and 2859-3051.

According to an aspect of some embodiments of the present invention there is provided a nucleic acid construct, comprising the isolated polynucleotide of the invention and a promoter for directing transcription of the nucleic acid sequence.

According to an aspect of some embodiments of the present invention there is provided an isolated polypeptide, comprising an amino acid sequence at least 80% homologous to the amino acid sequence selected from the group consisting of SEQ ID NOs:33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065 and 3067-3259.

According to an aspect of some embodiments of the present invention there is provided a plant cell comprising an exogenous polypeptide having an amino acid sequence at least 80% homologous to the amino acid sequence selected from the group consisting of SEQ ID NOs:33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065 and 3067-3259.

According to an aspect of some embodiments of the present invention there is provided a plant cell comprising an exogenous polynucleotide comprising a nucleic acid sequence at least 80% homologous to the nucleic acid sequence selected from the group consisting of SEQ ID NOs:7, 8, 4, 1-3, 5, 6, 9-26, 53-55, 57-87, 89-147, 149-195, 197-206, 208-212, 214-480, 482-519, 521-1103, 1106-1111, 1113-1116, 1118-1134, 1136, 1138-1400, 2748-2764, 2843-2857 and 2859-3051.

According to an aspect of some embodiments of the present invention there is provided a method of increasing abiotic stress tolerance of a plant, comprising expressing within the plant an exogenous polynucleotide encoding a polypeptide comprising the amino acid sequence set forth by SEQ ID NO:33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065, 3067-3258 or 3259, thereby increasing the abiotic stress tolerance of the plant.

According to an aspect of some embodiments of the present invention there is provided a method of increasing water use efficiency (WUE), fertilizer use efficiency (FUE), biomass, vigor and/or yield of a plant, comprising expressing within the plant an exogenous polynucleotide encoding a polypeptide comprising the amino acid sequence set forth by SEQ ID NO:33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065, 3067-3258 or 3259, thereby increasing the water use efficiency (WUE), the fertilizer use efficiency (FUE), the biomass, the vigor and/or the yield of the plant.

According to an aspect of some embodiments of the present invention there is provided an isolated polynucleotide comprising the nucleic acid sequence set forth by SEQ ID NO:7, 8, 4, 1-3, 5, 6, 9-26, 53-55, 57-87, 89-147, 149-195, 197-206, 208-212, 214-480, 482-519, 521-1103, 1106-1111, 1113-1116, 1118-1134, 1136, 1138-1400, 2748-2764, 2843-2857, 2859-3050 or 3051.

According to an aspect of some embodiments of the present invention there is provided a nucleic acid construct, comprising the isolated polynucleotide of the invention and a promoter for directing transcription of the nucleic acid sequence.

According to an aspect of some embodiments of the present invention there is provided an isolated polypeptide, comprising the amino acid sequence set forth by SEQ ID NO:33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065, 3067-3258 or 3259.

According to an aspect of some embodiments of the present invention there is provided a plant cell comprising an exogenous polypeptide having the amino acid sequence set forth by SEQ ID NO:33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065, 3067-3258 or 3259.

According to an aspect of some embodiments of the present invention there is provided a plant cell comprising an exogenous polynucleotide comprising the nucleic acid sequence set forth by SEQ ID NO:7, 8, 4, 1-3, 5, 6, 9-26, 53-55, 57-87, 89-147, 149-195, 197-206, 208-212, 214-480, 482-519, 521-1103, 1106-1111, 1113-1116, 1118-1134, 1136, 1138-1400, 2748-2764, 2843-2857, 2859-3050 or 3051.

According to some embodiments of the invention, the polynucleotide is selected from the group consisting of SEQ ID NOs:7, 8, 4, 1-3, 5, 6, 9-26, 53-55, 57-87, 89-147, 149-195, 197-206, 208-212, 214-480, 482-519, 521-1103, 1106-1111, 1113-1116, 1118-1134, 1136, 1138-1400, 2748-2764, 2843-2857 and 2859-3051.

According to some embodiments of the invention, the amino acid sequence is selected from the group consisting of SEQ ID NOs:33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065 and 3067-3259.

According to some embodiments of the invention, the polypeptide is selected from the group consisting of SEQ ID NOs:33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065 and 3067-3259.

According to some embodiments of the invention, the abiotic stress is selected from the group consisting of salinity, water deprivation, low temperature, high temperature, heavy metal toxicity, anaerobiosis, nutrient deficiency, nutrient excess, atmospheric pollution and UV irradiation.

According to some embodiments of the invention, the method further comprising growing the plant expressing the exogenous polynucleotide under the abiotic stress.

According to some embodiments of the invention, the promoter is a constitutive promoter.

According to some embodiments of the invention, the plant cell forms a part of a plant.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2A—An exemplary image of plants taken following 12 days on agar plates. FIG. 2B—An exemplary image of root analysis in which the length of the root measured is represented by a red arrow.

FIGS. 3A-F are histograms depicting the total economic fruit yield, plant biomass and harvest index for TOM-ABST36 (black bar) vs. control (white bar) plants growing in the commercial greenhouse under a 200 mM sodium chloride (NaCl) irrigation regime (FIG. 3A-C, respectively), or under two different water-stress regimes (WLI-1 and WLI-2; FIG. 3D-F, respectively). Yield performance was compared to plants growing under standard irrigation conditions (0 mM NaCl and WLI-0). Results are the average of the four independent events. *Significantly different at P≤0.05.

FIG. 3G—TOM-ABST36 plants growing under regular irrigation conditions; FIG. 3H—control plants growing under regular irrigation conditions; FIG. 3I—TOM-ABST36 plants after growing under a 200-mM NaCl-irrigation regime during the entire growing season; FIG. 3J—control plants after growing under a 200-mM NaCl-irrigation regime during the entire growing season.

DESCRIPTION OF SPECIFIC EMBODIMENTS OF THE INVENTION

Figure 1:
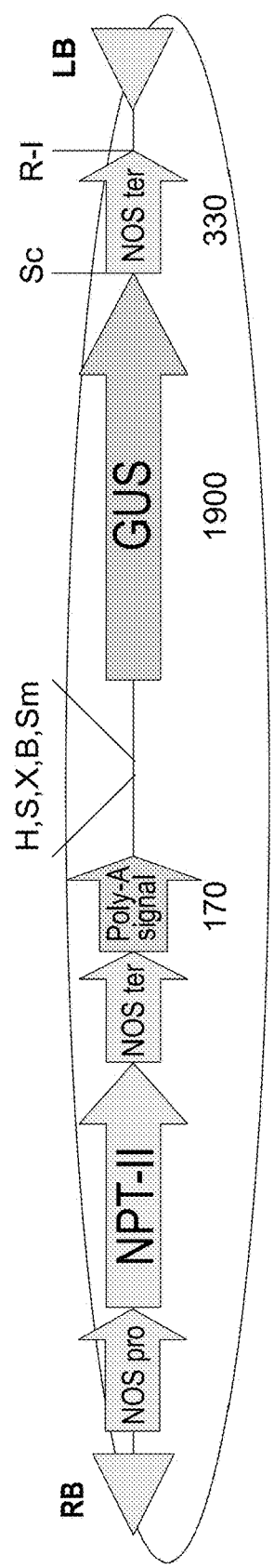
FIG. 1 is a schematic illustration of the pGI binary plasmid used for expressing the isolated polynucleotide sequences of the invention. RB—T-DNA right border; LB—T-DNA left border; H— HindIII restriction enzyme; X—XbaI restriction enzyme; B—BamHI restriction enzyme; S—SalI restriction enzyme; Sm—SmaI restriction enzyme; R-I—EcoRI restriction enzyme; Sc—SacI/SstI/Ecl136II; (numbers)—Length in base-pairs; NOS pro=nopaline synthase promoter; NPT-II=neomycin phosphotransferase gene; NOS ter=nopaline synthase terminator; Poly-A signal (polyadenylation signal); GUSintron—the GUS reporter gene (coding sequence and intron). The isolated polynucleotide sequences of some embodiments of the invention were cloned into the vector while replacing the GUSintron reporter gene.

The present invention, in some embodiments thereof, relates to novel aquaporin polynucleotides and polypeptides, and more particularly, but not exclusively, to methods of using same for increasing abiotic stress tolerance, water use efficiency, fertilizer use efficiency, biomass, vigor and/or yield of a plant.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the invention to practice, the present inventors have identified novel aquaporin (AQP) polynucleotides and polypeptides encoded thereby.

Thus, as shown in the Examples section which follows, the present inventors have employed a bioinformatics approach which combines digital expression analysis and cross-species comparative genomics and screened 7.2 million expressed sequence tags (ESTs) from 1,195 relevant EST's libraries of both monocot and dicot plant species. Using this approach 1,114 different AQP genes have been identified and were further classified to 11 subgroups (Table 1). Further analysis revealed that ESTs of the TIP2 subgroup are significantly over-represented in both plants' roots and in plants exposed to abiotic stress (ABS), and that polypeptides (e.g., SEQ ID NOs: 27-28, 45-48, Table 2) encoded by polynucleotides of the TIP2 subgroup (e.g., SEQ ID NOs:1, 2, 19-22, Table 2) share a common consensus sequence TLXFXFAGVGS (SEQ ID NO:2826). Based on over-representation in roots, ABS conditions and tissues with low water levels (such as seed and pollen) additional polynucleotides of the aquaporin gene family were identified (SEQ ID NOs: 3-18, 23-26, Table 2), as well as homologues or orthologues thereof (SEQ ID NOs:53-1400, 2844-3051 for polynucleotides and SEQ ID NOs:1401-2746, 3052-3259 for polypeptides; Table 3). Moreover, quantitative RT-PCR analysis demonstrated increased expression of representative AQP genes (e.g., SEQ ID NOs:5, 6 and 7) under salt stress, which was higher in plants exhibiting salt tolerance as compared to plants which are sensitive to salt stress (Table 5, Example 2 of the Examples section which follows). As is further described in Examples 3-4 of the Examples section which follows, representative AQP polynucleotides were cloned (Tables 7, 8 and 9) and transgenic plants overexpressing same were generated (Example 4). These plants were shown to exhibit increased tolerance to various abiotic stresses such as osmotic stress (Tables 10-14; Example 5) and salinity stress (Tables 30-44; Example 6), increased fertilizer use efficiency (under nitrogen limiting conditions, Tables 60-69, Example 7) and increased growth, biomass and yield under normal [Tables 15-29 (Example 5), 45-59 (Example 6)] or abiotic stress conditions conditions (Examples 5-8). Altogether, these results suggest the use of the AQP polynucleotides and polypeptides of the invention for increasing abiotic stress tolerance, water use efficiency, fertilizer use efficiency, biomass, vigor and/or yield of a plant.

It should be noted that polypeptides or polynucleotides which affect (e.g., increase) plant metabolism, growth, reproduction and/or viability under stress, can also affect the plant growth, biomass, yield and/or vigor under optimal conditions.

Thus, according to one aspect of the invention, there is provided a method of increasing abiotic stress tolerance, water use efficiency, fertilizer use efficiency, growth, biomass, yield and/or vigor of a plant. The method is effected by expressing within the plant an exogenous polynucleotide encoding a polypeptide comprising the amino acid consensus sequence TLXFXFAGVGS as set forth by SEQ ID NO:2826, wherein expression of the polypeptide promotes plants' biomass/vigor and/or yield under normal or stress conditions.

It is suggested that the polypeptide's activity is structurally associated with the integrity of the above consensus sequence (SEQ ID NO:2826). In some embodiments of this aspect of the present invention, the activity is a water channel activity which typically resides in the vacuaolar membrane (tonoplast) and/or the plasma membrane of the plant cell and enables the transport of water and/or small neutral solutes such as urea, nitrates and carbon dioxide ($CO_2$) through the membrane.

The phrase "abiotic stress" as used herein refers to any adverse effect on metabolism, growth, reproduction and/or viability of a plant. Accordingly, abiotic stress can be induced by suboptimal environmental growth conditions such as, for example, salinity, water deprivation, flooding, freezing, low or high temperature, heavy metal toxicity, anaerobiosis, nutrient deficiency, atmospheric pollution or UV irradiation. The implications of abiotic stress are discussed in the Background section.

The phrase "abiotic stress tolerance" as used herein refers to the ability of a plant to endure an abiotic stress without suffering a substantial alteration in metabolism, growth, productivity and/or viability.

As used herein the phrase "water use efficiency (WUE)" refers to the level of organic matter produced per unit of water consumed by the plant, i.e., the dry weight of a plant in relation to the plant's water use, e.g., the biomass produced per unit transpiration.

As used herein the phrase "fertilizer use efficiency" refers to the uptake, spread, absorbent, accumulation, relocation (within the plant) and use of one or more of the minerals and organic moieties absorbed from the soil, such as nitrogen, phosphates and/or potassium.

As used herein the phrase "plant biomass" refers to the amount (measured in grams of air-dry tissue) of a tissue produced from the plant in a growing season, which could also determine or affect the plant yield or the yield per growing area.

As used herein the phrase "plant yield" refers to the amount (as determined by weight/size) or quantity (numbers) of tissue produced per plant or per growing season. Hence increased yield could affect the economic benefit one can obtain from the plant in a certain growing area and/or growing time.

As used herein the phrase "plant vigor" refers to the amount (measured by weight) of tissue produced by the plant in a given time. Hence increase vigor could determine or affect the plant yield or the yield per growing time or growing area.

As used herein the term "increasing" refers to at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, increase in plant abiotic stress tolerance, water use efficiency, fertilizer use efficiency, growth, biomass, yield and/or vigor as compared to a native plant [i.e., a plant not modified with the biomolecules (polynucleotide or polypeptides) of the invention, e.g., a non-transformed plant of the same species which is grown under the same growth conditions).

As used herein, the phrase "exogenous polynucleotide" refers to a heterologous nucleic acid sequence which may not be naturally expressed within the plant or which overexpression in the plant is desired. The exogenous polynucleotide may be introduced into the plant in a stable or transient manner, so as to produce a ribonucleic acid (RNA) molecule and/or a polypeptide molecule. It should be noted that the exogenous polynucleotide may comprise a nucleic acid sequence which is identical or partially homologous to an endogenous nucleic acid sequence of the plant.

According to some embodiments of the invention, the exogenous polynucleotide of the invention encodes a polypeptide having an amino acid sequence at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to the amino acid sequence selected from the group consisting of SEQ ID NOs: 27-28, 45-48, 1401-1403, 1405-1435, 1437-1494, 1496-1542, 1544-1553, 1555-1559, 1561, 2449-2450, 2453-2458, 2460-2463, 2465-2481, 2483, 2484 and 2765.

Homology (e.g., percent homology) can be determined using any homology comparison software, including for example, the BlastP or TBLASTN software of the National Center of Biotechnology Information (NCBI) such as by using default parameters, when starting from a polypeptide sequence; or the tBLASTX algorithm (available via the NCBI) such as by using default parameters, which compares the six-frame conceptual translation products of a nucleotide query sequence (both strands) against a protein sequence database.

Homologous sequences include both orthologous and paralogous sequences. The term "paralogous" relates to gene-duplications within the genome of a species leading to paralogous genes. The term "orthologous" relates to homologous genes in different organisms due to ancestral relationship.

One option to identify orthologues in monocot plant species is by performing a reciprocal blast search. This may be done by a first blast involving blasting the sequence-of-interest against any sequence database, such as the publicly available NCBI database which may be found at: Hypertext Transfer Protocol://World Wide Web (dot) ncbi (dot) nlm (dot) nih (dot) gov. If orthologues in rice were sought, the sequence-of-interest would be blasted against, for example, the 28,469 full-length cDNA clones from *Oryza sativa* Nipponbare available at NCBI. The blast results may be filtered. The full-length sequences of either the filtered results or the non-filtered results are then blasted back (second blast) against the sequences of the organism from which the sequence-of-interest is derived. The results of the first and second blasts are then compared. An orthologue is identified when the sequence resulting in the highest score (best hit) in the first blast identifies in the second blast the query sequence (the original sequence-of-interest) as the best hit. Using the same rational a paralogue (homolog to a gene in the same organism) is found. In case of large sequence families, the ClustalW program may be used [Hypertext Transfer Protocol://World Wide Web (dot) ebi (dot) ac (dot) uk/Tools/clustalw2/index (dot) html], followed by a neighbor-joining tree (Hypertext Transfer Protocol://en (dot) wikipedia (dot) org/wiki/Neighbor-joining) which helps visualizing the clustering.

According to some embodiments of the invention, the exogenous polynucleotide encodes a polypeptide consisting of the amino acid sequence set forth by SEQ ID NO:27-28, 45-48, 1401-1403, 1405-1435, 1437-1494, 1496-1542, 1544-1553, 1555-1559, 1561, 2449-2450, 2453-2458, 2460-2463, 2465-2481, 2483, 2484 or 2765.

According to some embodiments of the invention the exogenous polynucleotide comprises a nucleic acid sequence which is at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the nucleic acid sequence selected from the group consisting of SEQ ID NOs:1, 2, 19, 20-22, 53-55, 57-87, 89-141, 143-147, 149-195, 197-206, 208-212, 214, 1102-1103, 1106-1111, 1113-1116, 1118-1134, 1136, 2751-2752 and 2748-2750.

Identity (e.g., percent homology) can be determined using any homology comparison software, including for example, the BlastN software of the National Center of Biotechnology Information (NCBI) such as by using default parameters.

According to some embodiments of the invention the exogenous polynucleotide is set forth by SEQ ID NO:1, 2, 19, 20-22, 53-55, 57-87, 89-141, 143-147, 149-195, 197-206, 208-212, 214, 1102-1103, 1106-1111, 1113-1116, 1118-1134, 1136, 2751-2752, 2748-2749, or 2750.

Notwithstanding the above, additional AQP polynucleotides and polypeptides encoded thereby are contemplated by the present teachings.

According to some embodiments of the invention, the exogenous polynucleotide encodes a polypeptide having an amino acid sequence at least about 60%, at least about 65%, at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, e.g., 100% homologous to SEQ ID NO:33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065, 3067-3258 or 3259.

According to some embodiments of the invention, the exogenous polynucleotide encodes a polypeptide consisting of the amino acid sequence set forth by SEQ ID NO:33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065, 3067-3258 or 3259.

In an exemplary embodiment the exogenous polynucleotide does not encode a polypeptide having the amino acid sequence selected from the group consisting of SEQ ID NOs: 1828, 1867, 1404, 1436, 1495, 1543, 1554, 1560, 2451, 2452, 2459, 2464, 2482, 2484 and 3066.

According to some embodiments of the invention, the exogenous polynucleotide is at least at least about 60%, least at least about 65%, least at least about 70%, least at least about 75% least at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, e.g., 100% identical to SEQ ID NO:7, 8, 4, 1-3, 5, 6, 9-26, 53-55, 57-87, 89-147, 149-195, 197-206, 208-212, 214-480, 482-519, 521-1103, 1106-1111, 1113-1116, 1118-1134, 1136, 1138-1400, 2748-2764, 2843-2857, 2859-3050 or 3051.

According to some embodiments of the invention, the polynucleotide is set forth by SEQ ID NO:7, 8, 4, 1-3, 5, 6, 9-26, 53-55, 57-87, 89-147, 149-195, 197-206, 208-212, 214-480, 482-519, 521-1103, 1106-1111, 1113-1116, 1118-1134, 1136, 1138-1400, 2748-2764, 2843-2857, 2859-3050 or 3051.

In an exemplary embodiments the exogenous polynucleotide is not the polynucleotide set forth by SEQ ID NO: 481, 520, 56, 88, 148, 196, 207, 213, 1104, 1105, 1112, 1117, 1135, 1137 or 2858.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to some embodiments of the invention, the polynucleotide of the invention comprises no more than 5000 nucleic acids in length. According to some embodiments of the invention, the polynucleotide of the invention comprises no more than 4000 nucleic acids in length, e.g., no more than 3000 nucleic acids, e.g., no more than 2500 nucleic acids.

Nucleic acid sequences encoding the polypeptides of the present invention may be optimized for expression. A non-limiting example of an optimized nucleic acid sequence is provided in SEQ ID NO:2751, which encodes an optimized polypeptide comprising the amino acid sequence set forth by SEQ ID NO:27. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A Table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization Tables such as those provided on-line at the Codon Usage Database through the NIAS (National Institute of Agrobiological Sciences) DNA bank in Japan (Hypertext Transfer Protocol://World Wide Web (dot) kazusa (dot) or (dot) jp/codon/). The Codon Usage Database contains codon usage tables for a number of different species, with each codon usage Table having been statistically determined based on the data present in Genbank.

By using the above Tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Thus, the invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

As mentioned, the present inventors have uncovered previously uncharacterized polypeptides which share the amino acid consensus sequence set forth by SEQ ID NO:2826.

Thus, the invention provides an isolated polypeptide having an amino acid sequence at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to an amino acid sequence selected from the group consisting of SEQ ID NO: 27-28, 45-48, 1401-1403, 1405-1435, 1437-1494, 1496-1542, 1544-1553, 1555-1559, 1561, 2449-2450, 2453-2458, 2460-2463, 2465-2481, 2483, 2484 and 2765.

According to some embodiments of the invention, the invention provides an isolated polypeptide having an amino acid sequence at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to an amino acid sequence selected from the group consisting of SEQ ID NOs:33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065 and 3067-3259.

According to some embodiments of the invention, the polypeptide is set forth by SEQ ID NO: 33, 34, 30, 27-29, 31, 32, 35-52, 1401-1403, 1405-1435, 1437-1494, 1496-1542, 1544-1553, 1555-1559, 1561-1827, 1829-1866, 1868-2450, 2453-2458, 2460-2463, 2465-2481, 2483, 2485-2746, 2765-2769, 3052-3065, 3067-3258 or 3259.

In an exemplary embodiment the polypeptide is not the polypeptide set forth by SEQ ID NO: 1828, 1867, 1404, 1436, 1495, 1543, 1554, 1560, 2451, 2452, 2459, 2464, 2482, 2484 or 3066.

The invention also encompasses fragments of the above described polypeptides and polypeptides having mutations, such as deletions, insertions or substitutions of one or more amino acids, either naturally occurring or man induced, either randomly or in a targeted fashion.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalypfus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barely, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present invention.

According to some embodiments of the invention, the plant used by the method of the invention is a crop plant such as rice, maize, wheat, barley, peanut, potato, sesame, olive tree, palm oil, banana, soybean, sunflower, canola, sugarcane, alfalfa, millet, leguminosae (bean, pea), flax, *lupinus*, rapeseed, tobacco, poplar and cotton.

Expressing the exogenous polynucleotide of the invention within the plant can be effected by transforming one or more cells of the plant with the exogenous polynucleotide, followed by generating a mature plant from the transformed cells and cultivating the mature plant under conditions suitable for expressing the exogenous polynucleotide within the mature plant.

According to some embodiments of the invention, the transformation is effected by introducing to the plant cell a nucleic acid construct which includes the exogenous polynucleotide of some embodiments of the invention and at least one promoter capable of directing transcription of the exogenous polynucleotide in the plant cell. Further details of suitable transformation approaches are provided hereinbelow.

As used herein, the term "promoter" refers to a region of DNA which lies upstream of the transcriptional initiation site of a gene to which RNA polymerase binds to initiate transcription of RNA. The promoter controls where (e.g., which portion of a plant) and/or when (e.g., at which stage or condition in the lifetime of an organism) the gene is expressed.

Any suitable promoter sequence can be used by the nucleic acid construct of the present invention. Preferably the promoter is a constitutive promoter, a tissue-specific, or an abiotic stress-inducible promoter.

Suitable constitutive promoters include, for example, CaMV 35S promoter (SEQ ID NO:2825; Odell et al., Nature 313:810-812, 1985); *Arabidopsis* At6669 promoter (SEQ ID NO:2823; see PCT Publication No. WO04081173A2); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al, Plant J November; 2(6):837-44, 1992); ubiquitin (Christensen et al, Plant Mol. Biol. 18: 675-689, 1992); Rice cyclophilin (Bucholz et al, Plant Mol Biol. 25(5):837-43, 1994); Maize H3 histone (Lepetit et al, Mol. Gen. Genet. 231: 276-285, 1992); Actin 2 (An et al, Plant J. 10(1); 107-121, 1996) and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.

Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], seed-preferred promoters [e.g., from seed specific genes (Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson' et al., Plant Mol. Biol. 18: 235-245, 1992), legumin (Ellis, et al. Plant Mol. Biol. 10: 203-214, 1988), Glutelin (rice) (Takaiwa, et al., Mol. Gen. Genet. 208:

15-22, 1986; Takaiwa, et al., FEBS Letts. 221: 43-47, 1987), Zein (Matzke et al Plant Mol Biol, 143).323-32 1990), napA (Stalberg, et al, Planta 199: 515-519, 1996), Wheat SPA (Albani et al, Plant Cell, 9: 171-184, 1997), sunflower oleosin (Cummins, et al., Plant Mol. Biol. 19: 873-876, 1992)], endosperm specific promoters [e.g., wheat LMW and HMW, glutenin-1 (Mol Gen Genet 216:81-90, 1989; NAR 17:461-2), wheat a, b and g gliadins (EMBO3:1409-15, 1984), Barley ltrl promoter, barley B1, C, D hordein (Theor Appl Gen 98:1253-62, 1999; Plant J 4:343-55, 1993; Mol Gen Genet 250:750-60, 1996), Barley DOF (Mena et al, The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al, Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (PMB 32:1029-35, 1996)], embryo specific promoters [e.g., rice OSH1 (Sato et al, Proc. Nati. Acad. Sci. USA, 93: 8117-8122), KNOX (Postma-Haarsma of al, Plant Mol. Biol. 39:257-71, 1999), rice oleosin (Wu et at, J. Biochem., 123:386, 1998)], and flower-specific promoters [e.g., AtPRP4, chalene synthase (chsA) (Van der Meer, et al., Plant Mol. Biol. 15, 95-109, 1990), LAT52 (Twell et al Mol. Gen Genet. 217:240-245; 1989), *apetala*-3].

Suitable abiotic stress-inducible promoters include, but not limited to, salt-inducible promoters such as RD29A (Yamaguchi-Shinozalei et al., Mol. Gen. Genet. 236:331-340, 1993); drought-inducible promoters such as maize rab17 gene promoter (Pla et. al., Plant Mol. Biol. 21:259-266, 1993), maize rab28 gene promoter (Busk et. al., Plant J. 11:1285-1295, 1997) and maize Ivr2 gene promoter (Pelleschi et. al., Plant Mol. Biol. 39:373-380, 1999); heat-inducible promoters such as heat tomato hsp80-promoter from tomato (U.S. Pat. No. 5,187,267).

The nucleic acid construct of some embodiments of the invention can further include an appropriate selectable marker and/or an origin of replication. According to some embodiments of the invention, the nucleic acid construct utilized is a shuttle vector, which can propagate both in *E. coli* (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of some embodiments of the invention can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Since abiotic stress tolerance, water use efficiency, fertilizer use efficiency, growth, biomass, yield and/or vigor in plants can involve multiple genes acting additively or in synergy (see, for example, in Quesda et al., Plant Physiol. 130:951-063, 2002), the present invention also envisages expressing a plurality of exogenous polynucleotides in a single host plant to thereby achieve superior effect on abiotic stress tolerance, water use efficiency, fertilizer use efficiency, growth, biomass, yield and/or vigor.

Expressing a plurality of exogenous polynucleotides in a single host plant can be effected by co-introducing multiple nucleic acid constructs, each including a different exogenous polynucleotide, into a single plant cell. The transformed cell can than be regenerated into a mature plant using the methods described hereinabove.

Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic messenger RNA including all the different exogenous polynucleotide sequences. To enable co-translation of the different polypeptides encoded by the polycistronic messenger RNA, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all different polypeptides. Alternatively, the construct can include several promoter sequences each linked to a different exogenous polynucleotide sequence.

The plant cell transformed with the construct including a plurality of different exogenous polynucleotides, can be regenerated into a mature plant, using the methods described hereinabove.

Alternatively, expressing a plurality of exogenous polynucleotides in a single host plant can be effected by introducing different nucleic acid constructs, including different exogenous polynucleotides, into a plurality of plants. The regenerated transformed plants can then be cross-bred and resultant progeny selected for superior abiotic stress tolerance, water use efficiency, fertilizer use efficiency, growth, biomass, yield and/or vigor traits, using conventional plant breeding techniques.

Thus, the invention encompasses plants exogenously expressing (as described above) the polynucleotide(s) and/or polypeptide(s) of the invention. Once expressed within the plant cell or the entire plant, the level of the polypeptide encoded by the exogenous polynucleotide can be determined by methods well known in the art such as, activity assays, Western blots using antibodies capable of specifically binding the polypeptide, Enzyme-Linked ImmunoSorbent Assay (ELISA), radio-immuno-assays (RIA), immunohistochemistry, immunocytochemistry, immunofluorescence and the like.

Methods of determining the level in the plant of the RNA transcribed from the exogenous polynucleotide are well known in the art and include, for example, Northern blot analysis, reverse transcription polymerase chain reaction (RT-PCR) analysis (including quantitative, semi-quantitative or real-time RT-PCR) and RNA-in situ hybridization.

As mentioned, the polypeptide according to some embodiments of the invention, functions as a water channel. Thus, the invention according to some embodiments encompasses functional equivalents of the polypeptide (e.g., polypeptides capable of the biological activity of a water channel) which can be identified by functional assays (e.g., being capable of transporting water in a plant) using e.g., a cell-swelling assay (Meng, Q. X. et al. 2008. Cell Physiol Biochem, 21. pp. 123-128).

The polynucleotides and polypeptides described hereinabove can be used in a wide range of economical plants, in a safe and cost effective manner.

The effect of the transgene (the exogenous polynucleotide encoding the polypeptide) on abiotic stress tolerance, water use efficiency, fertilizer use efficiency, growth, biomass, yield and/or vigor can be determined using known methods.

Abiotic Stress Tolerance—

Transformed (i.e., expressing the transgene) and non-transformed (wild type) plants are exposed to an abiotic stress condition, such as water deprivation, suboptimal temperature (low temperature, high temperature), nutrient deficiency, nutrient excess, a salt stress condition, osmotic stress, heavy metal toxicity, anaerobiosis, atmospheric pollution and UV irradiation.

Salinity Tolerance Assay—

Transgenic plants with tolerance to high salt concentrations are expected to exhibit better germination, seedling vigor or growth in high salt. Salt stress can be effected in many ways such as, for example, by irrigating the plants with a hyperosmotic solution, by cultivating the plants hydroponically in a hyperosmotic growth solution (e.g., Hoagland solution), or by culturing the plants in a hyperosmotic growth medium [e.g., 50% Murashige-Skoog medium (MS medium)]. Since different plants vary considerably in their tolerance to salinity, the salt concentration in the irrigation water, growth solution, or growth medium can be adjusted according to the specific characteristics of the specific plant cultivar or variety, so as to inflict a mild or moderate effect on the physiology and/or morphology of the plants (for guidelines as to appropriate concentration see, Bernstein and Kafkafi, Root Growth Under Salinity Stress In: Plant Roots, The Hidden Half 3rd ed. Waisel Y, Eshel A and Kafkafi U. (editors) Marcel Dekker Inc., New York, 2002, and reference therein).

For example, a salinity tolerance test can be performed by irrigating plants at different developmental stages with increasing concentrations of sodium chloride (for example 50 mM, 100 mM, 200 mM, 400 mM NaCl) applied from the bottom and from above to ensure even dispersal of salt. Following exposure to the stress condition the plants are frequently monitored until substantial physiological and/or morphological effects appear in wild type plants. Thus, the external phenotypic appearance, degree of wilting and overall success to reach maturity and yield progeny are compared between control and transgenic plants. Quantitative parameters of tolerance measured include, but are not limited to, the average wet and dry weight, the weight of the seeds yielded, the average seed size and the number of seeds produced per plant. Transformed plants not exhibiting substantial physiological and/or morphological effects, or exhibiting higher biomass than wild-type plants, are identified as abiotic stress tolerant plants.

Osmotic Tolerance Test—

Osmotic stress assays (including sodium chloride and mannitol assays) are conducted to determine if an osmotic stress phenotype was sodium chloride-specific or if it was a general osmotic stress related phenotype. Plants which are tolerant to osmotic stress may have more tolerance to drought and/or freezing. For salt and osmotic stress germination experiments, the medium is supplemented for example with 50 mM, 100 mM, 200 mM NaCl or 100 mM, 200 mM NaCl, 400 mM mannitol. See also Example 5 of the Examples section which follows.

Drought Tolerance Assay/Osmoticum Assay—

Tolerance to drought is performed to identify the genes conferring better plant survival after acute water deprivation. To analyze whether the transgenic plants are more tolerant to drought, an osmotic stress produced by the non-ionic osmolyte sorbitol in the medium can be performed. Control and transgenic plants are germinated and grown in plant-agar plates for 4 days, after which they are transferred to plates containing 500 mM sorbitol. The treatment causes growth retardation, then both control and transgenic plants are compared, by measuring plant weight (wet and dry), yield, and by growth rates measured as time to flowering.

Conversely, soil-based drought screens are performed with plants overexpressing the polynucleotides detailed above. Seeds from control *Arabidopsis* plants, or other transgenic plants overexpressing the polypeptide of the invention are germinated and transferred to pots. Drought stress is obtained after irrigation is ceased accompanied by placing the pots on absorbent paper to enhance the soil-drying rate. Transgenic and control plants are compared to each other when the majority of the control plants develop severe wilting. Plants are re-watered after obtaining a significant fraction of the control plants displaying a severe wilting. Plants are ranked comparing to controls for each of two criteria: tolerance to the drought conditions and recovery (survival) following re-watering.

Cold Stress Tolerance—

To analyze cold stress, mature (25 day old) plants are transferred to 4° C. chambers for 1 or 2 weeks, with constitutive light. Later on plants are moved back to greenhouse. Two weeks later damages from chilling period, resulting in growth retardation and other phenotypes, are compared between both control and transgenic plants, by measuring plant weight (wet and dry), and by comparing growth rates measured as time to flowering, plant size, yield, and the like.

Heat Stress Tolerance—

Heat stress tolerance is achieved by exposing the plants to temperatures above 34° C. for a certain period. Plant tolerance is examined after transferring the plants back to 22° C. for recovery and evaluation after 5 days relative to internal controls (non-transgenic plants) or plants not exposed to neither cold or heat stress.

Germination Tests—

Germination tests compare the percentage of seeds from transgenic plants that could complete the germination process to the percentage of seeds from control plants that are treated in the same manner. Normal conditions are considered for example, incubations at 22° C. under 22-hour light 2-hour dark daily cycles. Evaluation of germination and seedling vigor is conducted between 4 and 14 days after planting. The basal media is 50% MS medium (Murashige and Skoog, 1962 Plant Physiology 15, 473-497).

Germination is checked also at unfavorable conditions such as cold (incubating at temperatures lower than 10° C. instead of 22° C.) or using seed inhibition solutions that contain high concentrations of an osmolyte such as sorbitol (at concentrations of 50 mM, 100 mM, 200 mM, 300 mM, 500 mM, and up to 1000 mM) or applying increasing concentrations of salt (of 50 mM, 100 mM, 200 mM, 300 mM, 500 mM NaCl).

Water Use Efficiency— can be determined as the biomass produced per unit transpiration. To analyze WUE, leaf relative water content can be measured in control and transgenic plants. Fresh weight (FW) is immediately recorded; then leaves are soaked for 8 hours in distilled water at room temperature in the dark, and the turgid weight (TW) is recorded. Total dry weight (DW) is recorded after drying the leaves at 60° C. to a constant weight. Relative water content (RWC) is calculated according to the following Formula I:

$$(FW-DW/TW-DW) \times 100 \qquad \text{Formula I}$$

Fertilizer Use Efficiency—

To analyze whether the transgenic plants are more responsive to fertilizers, plants are grown in agar plates or pots with a limited amount of fertilizer, as described, for example, in Example 6, hereinbelow and in Yanagisawa et al (Proc Natl Acad Sci USA. 2004; 101:7833-8). The plants are analyzed for their overall size, time to flowering, yield, protein content of shoot and/or grain. The parameters checked are the overall size of the mature plant, its wet and dry weight, the weight of the seeds yielded, the average seed size and the number of seeds produced per plant. Other parameters that may be tested are: the chlorophyll content of leaves (as nitrogen plant status and the degree of leaf verdure is highly correlated), amino acid and the total protein content of the seeds or other plant parts such as leaves or shoots, oil content, etc. Similarly, instead of providing nitrogen at limiting amounts, phosphate or potassium can be added at increasing concentrations. Again, the same parameters measured are the same as listed above. In this way, nitrogen use efficiency (NUE), phosphate use efficiency (PUE) and potassium use efficiency (KUE) are assessed, checking the ability of the transgenic plants to thrive under nutrient restraining conditions.

Nitrogen Determination—

The procedure for N (nitrogen) concentration determination in the structural parts of the plants involves the potassium persulfate digestion method to convert organic N to $NO_3^-$ (Purcell and King 1996 Argon. J. 88:111-113, the modified $Cd^-$ mediated reduction of $NO_3^-$ to $NO_2^-$ (Vodovotz 1996 Biotechniques 20:390-394) and the measurement of nitrite by the Griess assay (Vodovotz 1996, supra). The absorbance values are measured at 550 nm against a standard curve of $NaNO_2$. The procedure is described in details in Samonte et al. 2006 Agron. J. 98:168-176.

Grain Protein Concentration—

Grain protein content (g grain protein $m^{-2}$) is estimated as the product of the mass of grain N (g grain N $m^{-2}$) multiplied by the N/protein conversion ratio of k-5.13 (Mosse 1990, supra). The grain protein concentration is estimated as the ratio of grain protein content per unit mass of the grain (g grain protein $kg^{-1}$ grain).

Oil Content—

The oil content of a plant can be determined by extraction of the oil from the seed or the vegetative portion of the plant. Briefly, lipids (oil) can be removed from the plant (e.g., seed) by grinding the plant tissue in the presence of specific solvents (e.g., hexane or petroleum ether) and extracting the oil in a continuous extractor. Indirect oil content analysis can be carried out using various known methods such as Nuclear Magnetic Resonance (NMR) Spectroscopy, which measures the resonance energy absorbed by hydrogen atoms in the liquid state of the sample [See for example, Conway T F. and Earle F R., 1963, Journal of the American Oil Chemists' Society; Springer Berlin/Heidelberg, ISSN: 0003-021X (Print) 1558-9331 (Online)]; the Near Infrared (NI) Spectroscopy, which utilizes the absorption of near infrared energy (1100-2500 nm) by the sample; and a method described in WO/2001/023884, which is based on extracting oil a solvent, evaporating the solvent in a gas stream which forms oil particles, and directing a light into the gas stream and oil particles which forms a detectable reflected light.

The plant vigor can be calculated by the increase in growth parameters such as leaf area, fiber length, rosette diameter, plant fresh weight and the like per time.

The growth rate can be measured using digital analysis of growing plants. For example, images of plants growing in greenhouse on plot basis can be captured every 3 days and the rosette area can be calculated by digital analysis. Rosette area growth is calculated using the difference of rosette area between days of sampling divided by the difference in days between samples.

Measurements of seed yield can be done by collecting the total seeds from 8-16 plants together, weighting them using analytical balance and dividing the total weight by the number of plants. Seed per growing area can be calculated in the same manner while taking into account the growing area given to a single plant. Increase seed yield per growing area could be achieved by increasing seed yield per plant, and/or by increasing number of plants capable of growing in a given area.

Evaluation of the seed yield per plant can be done by measuring the amount (weight or size) or quantity (i.e., number) of dry seeds produced and harvested from 8-16 plants and divided by the number of plants.

Evaluation of growth rate can be done by measuring plant biomass produced, rosette area, leaf size or root length per time (can be measured in $cm^2$ per day of leaf area).

Fiber length can be measured using fibrograph. The fibrograph system was used to compute length in terms of "Upper Half Mean" length. The upper half mean (UHM) is the average length of longer half of the fiber distribution. The fibrograph measures length in span lengths at a given percentage point (Hypertext Transfer Protocol://World Wide Web (dot) cottoninc (dot) com/ClassificationofCotton/?Pg=4#Length).

Thus, the present invention is of high agricultural value for promoting the yield of commercially desired crops (e.g., biomass of vegetative organ such as poplar wood, or reproductive organ such as number of seeds or seed biomass).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Identification of AQP Genes Using Digital Expression Analysis and Cross-Species Comparative Genomic The large number of AQPs in plants and the contradictory results obtained when AQPs were overexpressed in plants demonstrate the need to selectively identify the AQP genes which can improve water use efficiency (WUE) in plants, lead to increased yield and biomass under abiotic stress as well as under favorable conditions.

Under unfavorable stress conditions, some biological activities of the plant are stopped or reduced, while others, not earlier active, initiate. Still, some of the activities, which are vital for plant survival, are maintained. One hypothesis is that key genes needed for plants to maintain vital activities under unfavorable conditions would be active under broad spectrum of biotic and abiotic stresses.

To test this hypothesis and to identify the key AQP genes having the potential to improve plant performance under different biotic and/or abiotic stress conditions (e.g., salt or drought stress) a combination of digital expression analysis (also known as Electronic Northern blot) and cross-species comparative genomics was performed. The database used was available from NCBI (Hypertext Transfer Protocol:// World Wide Web (dot) ncbi (dot) nlm (dot) nih (dot) gov/dbEST/) and included 7.2 million expressed sequence tags (ESTs) from 1,195 relevant EST's libraries originated from 15 different species, including both monocot and dicot species, namely: *Arabidopsis*, barley, *Brassica rapa*, cotton, grape, maize, *medicago*, poplar, potato, rice, *sorghum*, soybean, sugarcane, tomato and wheat.

Tomato plants were selected as a model plant based on the high quality tomato database from several tomato species which can be used for data-mining and the present inventors' experience in using the tomato genome as a model plant. In addition, the relatively high salt tolerance exhibited by various tomato species makes the tomato genome an excellent candidate for identifying new stress tolerance mechanisms. Moreover, tomato is not only used as a model plant for genetic studies, it is also used as an important crop with well-defined yield parameters, which can be used to distinguish between genes affecting abiotic-stress tolerance and genes preventing yield loss under abiotic-stress conditions.

Gene Analysis and Data Mining—

For gene analysis and data mining the bioinformatic filtering approach used had three phases:

1. Clustering and Assembly:

EST and mRNA sequences of each of the 15 species were extracted from GenBank versions 157, 160, 161, 162, 164, 165, 166, clustered and assembled using Compugen's LEADS clustering and assembly platform (Compugen Ltd., Tel Aviv, Israel; Yelin et. al. 2003, Nature Biotechnology 21, 379-85). Automatically extracted EST library annotations were manually accurated and classified by anatomy, developmental stage, abiotic/biotic stress treatment and cultivars. The results were loaded into Oracle database. The predicted proteins were then annotated using InterPro(2) (Hypertext Transfer Protocol://World Wide Web (dot) ebi (dot) ac (dot) uk/interpro/).

2. Selection of Clusters—

All clusters that contained the Major intrinsic protein domain (IPR000425) were selected for further analysis (n=1,114).

3. Obtaining Expression Profile of the Clusters—

By digital expression approach the expression profile of all clusters was obtained in terms of plant anatomy (i.e., in what tissues/organs the gene was expressed), developmental stage (i.e., the developmental stages at which a gene can be found) and profile of treatment (provides the physiological conditions under which a gene is expressed such as drought, cold, pathogen infection, etc).

addition, AQP genes which are overrepresented in various abiotic stresses such as nutrient deficiency, heat, salinity and heavy metal stresses and biotic stresses such as application of elicitors and pathogens were selected considering that they can provide high tolerance to a wide spectrum of stresses.

The same set of 1,114 AQPs was classified according to the accepted groups known in the literature: first into the four major sub-groups: PIPs, TIPs, NIPs and SIPs, and a second classification divided these four sub-groups into eleven sub-groups according to their homology in amino acid sequences. A Fisher's exact test was then used to identify subgroups having significant EST over-presentation both in roots and upon exposure to different abiotic stresses. As shown in Table 1, hereinbelow, from the eleven sub-groups, only the TIP2 subgroup showed a significant EST overrepresentation both in roots and upon exposure to abiotic stresses (P-value $1.7 \times 10^{-5}$ and $1.6 \times 10^{-3}$, respectively).

TABLE 1

AQP type distribution and over-expression in roots and abiotic stresses

| AQP type | Total No. of genes in database | Roots | | | Exposure to abiotic stresses | | |
|---|---|---|---|---|---|---|---|
| | | No. of over-expressed genes | % over-expressed/all | P-value | No. of over-expressed genes | % over-expressed/all | P-value |
| PIP1 | 243 | 26 | 10.7 | 0.13 | 10 | 4.1 | 0.34 |
| PIP2 | 336 | 25 | 7.4 | 0.87 | 12 | 3.6 | 0.53 |
| PIP3 | 11 | 0 | 0.0 | 1 | 0 | 0 | 1 |
| SIP1 | 39 | 0 | 0.0 | 1 | 0 | 0 | 1 |
| SIP2 | 16 | 0 | 0.0 | 1 | 0 | 0 | 1 |
| TIP1 | 152 | 11 | 7.2 | 0.8 | 3 | 2 | 0.92 |
| TIP2 | 101 | 22 | 21.8 | 1.70E−05 | 10 | 9.9 | 1.6E−0.3 |
| TIP3 | 29 | 0 | 0.0 | 1 | 0 | 0 | 1 |
| TIP4 | 48 | 5 | 10.4 | 0.41 | 1 | 2.1 | 0.83 |
| TIP5 | 3 | 0 | 0.0 | 1 | 0 | 0 | 1 |
| NIP | 136 | 8 | 5.9 | 0.93 | 3 | 2.2 | 0.88 |
| Total | 1114 | 97 | | | 39 | | |

Table 1

Digital expression computations was calculated as follows: over-expression fold was computed as m/(n*M/N), where "N" is total number of ESTs of specific organism; "M is number of ESTs in a given library/tissue/category; "n" is total number of ESTs in a given contig; "m" is the number of ESTs from the library/tissue/category in the contig; P-value was computed using Exact Fisher Test statistic. The combined P-value for over-expression in both Root and Abiotic stresses conditions was computed as 1−(1−p1)×(1−p2). 1,114 different AQP genes were identified in the inter species transcriptional databases. For the data mining process, the present inventors used a combination of two approaches: selection of AQP clusters showing significant over expression (EST distribution versus normal is more than two folds; statistical significance of over-expression—p Value<0.05) either in roots compared to shoots or under various abiotic stresses (including drought, cold, salinity, heat, chemical treatments, etc.), compared to non stress control. It was found that ESTs of about 9% of the AQP genes were significantly overrepresented in roots and 3.5% of them were induced under different abiotic stresses. AQP genes which are highly overrepresented in roots were selected since plants with an efficient root system are expected to capture more water from a drying soil. In These results suggest that over-expression and/or protein over-accumulation of the Tip2 subgroup can improve plant water use efficiency, ABST and yield.

Genes of the Tip2 Subgroup are Highly Expressed in Roots and in Abiotic Stresses—

As shown in Table 1, hereinabove, the TIP2 subgroup (or subfamily) is highly expressed in roots and in abiotic stresses. The TIP2 subgroup is found in 38 plant species and other organisms (nucleic acid SEQ ID NOs: 1, 2, 19, 20-22; Table 2), available in public databases [Hypertext Transfer Protocol://World Wide Web (dot) ncbi (dot) nlm (dot) nih (dot) gov/dbEST/]. In tomato, the TIP2 gene was highly expressed in roots (6 fold, p≤1.01 E-24) and in both biotic (2 fold, p≤4.6 E-02) and abiotic stresses (4.5 fold, p≤E-02) (data not shown).

Identification of a Short Consensus Sequence of the Tip2 Sub-Family—

While comparing the consensus amino-acid sequences of Aquaporins, a short consensus sequence was identified which is unique to proteins of the Tip2 sub-family. The present inventors have suggested that this motif has an important role in managing water use efficiency (WUE), and when over-expressed in a plant can confer ABST and improved yield. The amino-acid consensus sequence identified is TLXFXFAGVGS (SEQ ID NO:2826), wherein X stands for any amino acid.

In addition, other genes of the aquaporin gene family were identified by bioinformatics tools as improving ABST and yield, based on combined digital gene expression profile in roots, tissues with low water levels (such as seed and pollen) and under abiotic stress conditions. These include SEQ ID NOs: 3-18, 23-26 (Table 2).

TABLE 2

Identified Aquaporin Genes

| SEQ ID NO: (Polynucleotide) | Gene name | Cluster name | Organism | SEQ ID NO: (Polypeptide) |
|---|---|---|---|---|
| 1 | MAB54 | tomato\|gb164\|BG125449 | tomato | 27 |
| 2 | MAB55 | tomato\|gb164\|BG134896 | tomato | 28 |
| 3 | MAB56 | tomato\|gb164\|AW218990 | tomato | 29 |
| 4 | MAB57 | tomato\|gb164\|AA824812 | tomato | 30 |
| 6 | MAB58 | tomato\|gb164\|AW934056 | tomato | 32 |
| 7 | MAB69 | tomato\|gb164\|AI637360 | tomato | 33 |
| 8 | MAB70 | tomato\|gb164\|BG133531 | tomato | 34 |
| 9 | MAB71 | tomato\|gb164\|BG629975 | tomato | 35 |
| 10 | MAB72 | tomato\|gb164\|BG136017 | tomato | 36 |
| 11 | MAB73 | tomato\|gb164\|BG131871 | tomato | 37 |
| 12 | MAB74 | tomato\|gb164\|AI775489 | tomato | 38 |
| 13 | MAB75 | tomato\|gb164\|BG136239 | tomato | 39 |
| 14 | MAB76 | tomato\|gb164\|BG134058 | tomato | 40 |
| 15 | MAB77 | tomato\|gb164\|BG629900 | tomato | 41 |
| 16 | MAB78 | tomato\|gb164\|BG130774 | tomato | 42 |
| 17 | MAB79 | tomato\|gb164\|BG124486 | tomato | 43 |
| 18 | MAB80 | tomato\|gb164\|AI483521 | tomato | 44 |
| 19 | MAB81 | tomato\|gb164\|CO751453 | tomato | 45 |
| 20 | MAB115 | barley\|gb157.2\|BF626376 | barley | 46 |
| 22 | MAB117 | barley\|gb157.2\|BE412516 | barley | 48 |
| 23 | MAB119 | tomato\|gb164\|BG134199 | tomato | 49 |
| 24 | MAB176 | tomato\|gb164\|CO635830 | tomato | 50 |
| 25 | MAB177 | tomato\|gb164\|CO751496 | tomato | 51 |
| 26 | MAB178 | tomato\|gb164\|CO751374 | tomato | 52 |

Table 2.

Sequences which are homologous [showing at least 80% protein sequence identity on 80% of the global hit or query length, as calculated using BlastP and tBlastN algorithms of the National Center of Biotechnology Information (NCBI)] or orthologues of the AQP genes described in Table 2, and are expected to possess the same role in ABST and yield improvement in plants, are disclosed in Table 3 hereinbelow (SEQ ID NOs:6, 215-1101 and 1138-1400; Table 3). In addition, Table 3 also includes homologous and orthologues of the AQP TIP2 subfamily (SEQ ID NOs:21, 53-214, 1102-1137) and additional homologous and orthologues (SEQ ID NOs:2844-3051).

TABLE 3

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 53 | apple\|gb157.3\|CN883304_T1 | apple | 1401 | 27 | 84 | 92.3387097 | 100 | blastp |
| 54 | apple\|gb157.3\|CN489003_T1 | apple | 1402 | 27 | 83 | 100 | 100 | blastp |
| 55 | aquilegia\|gb157.3\|DR915168_T1 | aquilegia | 1403 | 27 | 85 | 100 | 100 | blastp |
| 56 | arabidopsis\|gb165\|AT3G16240_T1 | arabidopsis | 1404 | 27 | 81 | 99.1935484 | 98.8 | blastp |
| 57 | artemisia\|gb164\|EY035829_T1 | artemisia | 1405 | 27 | 80 | 98.7903226 | 99.1902834 | blastp |
| 58 | artemisia\|gb164\|EY113320_T1 | artemisia | 1406 | 27 | 85 | 62.9032258 | 100 | blastp |
| 59 | artemisia\|gb164\|EY070770_T1 | artemisia | 1407 | 27 | 81 | 98.7903226 | 99.1902834 | blastp |
| 60 | avocado\|gb164\|CV002132_T1 | avocado | 1408 | 27 | 84 | 50 | 100 | blastp |
| 61 | b_juncea\|gb164\|EVGN00333108491419_T1 | b_juncea | 1409 | 27 | 83 | 100 | 100 | blastp |
| 62 | b_juncea\|gb164\|EVGN00503709641655_T1 | b_juncea | 1410 | 27 | 82 | 53.6290323 | 97.0588235 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 63 | b_juncea\|gb164\|EVGN01003711220829_T1 | b_juncea | 1411 | 27 | 84 | 63.7096774 | 100 | blastp |
| 64 | b_oleracea\|gb161\|AM059585_T1 | b_oleracea | 1412 | 27 | 84 | 100 | 100 | blastp |
| 65 | b_oleracea\|gb161\|AM385334_T1 | b_oleracea | 1413 | 27 | 82 | 100 | 100 | blastp |
| 66 | b_oleracea\|gb161\|AM385915_T1 | b_oleracea | 1414 | 27 | 81 | 100 | 100 | blastp |
| 67 | b_rapa\|gb162\|BG543171_T1 | b_rapa | 1415 | 27 | 82 | 100 | 100 | blastp |
| 68 | b_rapa\|gb162\|BG543223_T1 | b_rapa | 1416 | 27 | 83 | 100 | 100 | blastp |
| 69 | b_rapa\|gb162\|L37478_T1 | b_rapa | 1417 | 27 | 81 | 100 | 100 | blastp |
| 70 | banana\|gb160\|DN238689_T1 | banana | 1418 | 27 | 83 | 76.6129032 | 100 | blastp |
| 71 | bean\|gb164\|CB540614_T1 | bean | 1419 | 27 | 83 | 98.7903226 | 98.7903226 | blastp |
| 72 | canola\|gb161\|EV092237_T1 | canola | 1420 | 27 | 84 | 100 | 100 | blastp |
| 73 | canola\|gb161\|CN828178_T1 | canola | 1421 | 27 | 81 | 100 | 100 | blastp |
| 74 | canola\|gb161\|CX188169_T1 | canola | 1422 | 27 | 82 | 100 | 100 | blastp |
| 75 | canola\|gb161\|CD840590_T1 | canola | 1423 | 27 | 81 | 100 | 100 | blastp |
| 76 | cassava\|gb164\|CK650415_T1 | cassava | 1424 | 27 | 85 | 100 | 100 | blastp |
| 77 | castorbean\|gb160\|EE254645_T1 | castorbean | 1425 | 27 | 87 | 100 | 100 | blastp |
| 78 | centaurea\|gb161\|EH725826_T1 | centaurea | 1426 | 27 | 84 | 95.9677419 | 84.3971631 | blastp |
| 79 | centaurea\|gb161\|EL932474_T1 | centaurea | 1427 | 27 | 88 | 89.1129032 | 97.7876106 | blastp |
| 80 | cherry\|gb157.2\|EE488049_T1 | cherry | 1428 | 27 | 80 | 69.3548387 | 100 | blastp |
| 81 | cichorium\|gb161\|DT211633_T1 | cichorium | 1429 | 27 | 80 | 100 | 92.8571429 | blastp |
| 82 | cichorium\|gb161\|EH672622_T1 | cichorium | 1430 | 27 | 87 | 100 | 100 | blastp |
| 83 | citrus\|gb157.2\|CX663669_T1 | citrus | 1431 | 27 | 88 | 98.7903226 | 99.1902834 | blastp |
| 84 | citrus\|gb157.2\|CF417983_T1 | citrus | 1432 | 27 | 88 | 98.7903226 | 99.1902834 | blastp |
| 85 | citrus\|gb157.2\|CK665344_T1 | citrus | 1433 | 27 | 88 | 98.7903226 | 99.1902834 | blastp |
| 86 | citrus\|gb157.2\|CK665344_T2 | citrus | 1434 | 27 | 87 | 82.2580645 | 100 | blastp |
| 87 | clover\|gb162\|BB908328_T1 | clover | 1435 | 27 | 81 | 69.7580645 | 100 | blastp |
| 88 | cotton\|gb164\|AF009567_T1 | cotton | 1436 | 27 | 87 | 100 | 100 | blastp |
| 89 | cowpea\|gb166\|FF397761_T1 | cowpea | 1437 | 27 | 84 | 100 | 100 | blastp |
| 90 | cowpea\|gb166\|FC457059_T1 | cowpea | 1438 | 27 | 83 | 98.7903226 | 98.7903226 | blastp |
| 91 | dandelion\|gb161\|DY818755_T1 | dandelion | 1439 | 27 | 85 | 100 | 100 | blastp |
| 92 | ginger\|gb164\|DY358186_T1 | ginger | 1440 | 27 | 80 | 98.3870968 | 99.1836735 | blastp |
| 93 | ginger\|gb164\|DY351866_T1 | ginger | 1441 | 27 | 80 | 98.3870968 | 99.1836735 | blastp |
| 94 | iceplant\|gb164\|AF133532_T1 | iceplant | 1442 | 27 | 81 | 100 | 100 | blastp |
| 95 | ipomoea\|gb157.2\|BJ576630_T1 | ipomoea | 1443 | 27 | 87 | 100 | 100 | blastp |
| 96 | lettuce\|gb157.2\|DW074363_T1 | lettuce | 1444 | 27 | 87 | 100 | 100 | blastp |
| 97 | lettuce\|gb157.2\|DW074363_T2 | lettuce | 1445 | 27 | 85 | 50.8064516 | 90.647482 | blastp |
| 98 | lettuce\|gb157.2\|DW145132_T1 | lettuce | 1446 | 27 | 87 | 100 | 100 | blastp |
| 99 | lettuce\|gb157.2\|DW043760_T1 | lettuce | 1447 | 27 | 87 | 100 | 100 | blastp |
| 100 | lettuce\|gb157.2\|DW104999_T1 | lettuce | 1448 | 27 | 87 | 100 | 100 | blastp |
| 101 | lotus\|gb157.2\|BI420407_T1 | lotus | 1449 | 27 | 84 | 100 | 100 | blastp |
| 102 | lotus\|gb157.2\|BF177457_T1 | lotus | 1450 | 27 | 86 | 98.7903226 | 98.7951807 | blastp |
| 103 | medicago\|gb157.2\|AI974300_T1 | medicago | 1451 | 27 | 83 | 89.1129032 | 94.8497854 | blastp |
| 104 | medicago\|gb157.2\|AA660400_T1 | medicago | 1452 | 27 | 84 | 100 | 100 | blastp |
| 105 | nicotiana_benthamiana\|gb162\|CN741988_T1 | nicotiana_benthamiana | 1453 | 27 | 86 | 98.7903226 | 98.7903226 | blastp |
| 106 | nicotiana_benthamiana\|gb162\|CN655366_T1 | nicotiana_benthamiana | 1454 | 27 | 92 | 100 | 100 | blastp |
| 107 | nicotiana_benthamiana\|gb162\|CN741998_T1 | nicotiana_benthamiana | 1455 | 27 | 89 | 98.7903226 | 98.7903226 | blastp |
| 108 | nicotiana_benthamiana\|gb162\|CN742343_T1 | nicotiana_benthamiana | 1456 | 27 | 93 | 100 | 100 | blastp |
| 109 | peach\|gb157.2\|BU045214_T1 | peach | 1457 | 27 | 82 | 100 | 100 | blastp |
| 110 | pepper\|gb157.2\|CO776446_T1 | pepper | 1458 | 27 | 84 | 61.6935484 | 100 | blastp |
| 111 | pepper\|gb157.2\|CA518313_T1 | pepper | 1459 | 27 | 86 | 63.3064516 | 100 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 112 | periwinkle\|gb164\|EG555051_T1 | periwinkle | 1460 | 27 | 88 | 99.1935484 | 99.1935484 | blastp |
| 113 | petunia\|gb157.2\|CV296219_T1 | petunia | 1461 | 27 | 84 | 63.7096774 | 85.2517986 | tblastn |
| 114 | poplar\|gb157.2\|BI129443_T1 | poplar | 1462 | 27 | 86 | 100 | 100 | blastp |
| 115 | poplar\|gb157.2\|AI166943_T2 | poplar | 1463 | 27 | 83 | 61.6935484 | 100 | blastp |
| 116 | poplar\|gb157.2\|AI166943_T1 | poplar | 1464 | 27 | 85 | 100 | 100 | blastp |
| 117 | poplar\|gb157.2\|BI127662_T1 | poplar | 1465 | 27 | 89 | 79.0322581 | 100 | blastp |
| 118 | potato\|gb157.2\|BQ513382_T1 | potato | 1466 | 27 | 97 | 100 | 100 | blastp |
| 119 | potato\|gb157.2\|BQ513382_T2 | potato | 1467 | 27 | 97 | 50.8064516 | 96.1832061 | blastp |
| 120 | radish\|gb164\|EV538411_T1 | radish | 1468 | 27 | 82 | 92.3387097 | 100 | blastp |
| 121 | radish\|gb164\|AB010416_T1 | radish | 1469 | 27 | 81 | 100 | 100 | blastp |
| 122 | radish\|gb164\|EW725945_T1 | radish | 1470 | 27 | 82 | 100 | 100 | blastp |
| 123 | radish\|gb164\|EV527946_T1 | radish | 1471 | 27 | 81 | 100 | 100 | blastp |
| 124 | rose\|gb157.2\|BQ104096_T1 | rose | 1472 | 27 | 85 | 85.0806452 | 95.045045 | blastp |
| 125 | safflower\|gb162\|EL374001_T1 | safflower | 1473 | 27 | 87 | 100 | 100 | blastp |
| 126 | safflower\|gb162\|EL406178_T1 | safflower | 1474 | 27 | 83 | 100 | 100 | blastp |
| 127 | sesame\|gb157.2\|BU668161_T1 | sesame | 1475 | 27 | 81 | 61.2903226 | 86.3636364 | tblastn |
| 128 | soybean\|gb166\|AW349399_T1 | soybean | 1476 | 27 | 84 | 98.7903226 | 98.7903226 | blastp |
| 129 | soybean\|gb166\|CD416937_T1 | soybean | 1477 | 27 | 85 | 75.4032258 | 100 | blastp |
| 130 | soybean\|gb166\|CA786095_T1 | soybean | 1478 | 27 | 84 | 98.7903226 | 98.7903226 | blastp |
| 131 | soybean\|gb166\|AW350817_T1 | soybean | 1479 | 27 | 81 | 100 | 100 | blastp |
| 132 | spruce\|gb162\|CO216479_T1 | spruce | 1480 | 27 | 80 | 98.7903226 | 98.4 | blastp |
| 133 | strawberry\|gb164\|DV438565_T1 | strawberry | 1481 | 27 | 82 | 100 | 100 | blastp |
| 134 | sunflower\|gb162\|X95952_T1 | sunflower | 1482 | 27 | 82 | 100 | 100 | blastp |
| 135 | sunflower\|gb162\|CD847513_T1 | sunflower | 1483 | 27 | 83 | 100 | 100 | blastp |
| 136 | sunflower\|gb162\|CD845750_T1 | sunflower | 1484 | 27 | 84 | 100 | 100 | blastp |
| 137 | sunflower\|gb162\|CD848081_T1 | sunflower | 1485 | 27 | 86 | 100 | 100 | blastp |
| 138 | sunflower\|gb162\|CD849577_T1 | sunflower | 1486 | 27 | 83 | 100 | 100 | blastp |
| 139 | tobacco\|gb162\|CV016921_T1 | tobacco | 1487 | 27 | 88 | 100 | 100 | blastp |
| 140 | tobacco\|gb162\|CV018684_T1 | tobacco | 1488 | 27 | 93 | 100 | 100 | blastp |
| 141 | tobacco\|gb162\|CV019641_T1 | tobacco | 1489 | 27 | 91 | 100 | 100 | blastp |
| 142 | tomato\|gb164\|AW626247_T1 | tomato | No predicted protein | 27 | 83 | 50 | 88.3610451 | tblastn |
| 143 | triphysaria\|gb164\|EX999390_T1 | triphysaria | 1490 | 27 | 81 | 100 | 100 | blastp |
| 144 | triphysaria\|gb164\|BM356478_T1 | triphysaria | 1491 | 27 | 80 | 100 | 100 | blastp |
| 145 | triphysaria\|gb164\|BM356478_T2 | triphysaria | 1492 | 27 | 81 | 81.0483871 | 98.0487805 | blastp |
| 146 | aquilegia\|gb157.3\|DR922172_T1 | aquilegia | 1493 | 28 | 86 | 100 | 100 | blastp |
| 147 | arabidopsis\|gb165\|AT5G47450_T1 | arabidopsis | 1494 | 28 | 82 | 98.8 | 98.8 | blastp |
| 148 | arabidopsis\|gb165\|AT4G17340_T1 | arabidopsis | 1495 | 28 | 85 | 99.6 | 99.6 | blastp |
| 149 | artemisia\|gb164\|EY080612_T1 | artemisia | 1496 | 28 | 83 | 69.2 | 100 | blastp |
| 150 | b_rapa\|gb162\|EX104899_T1 | b_rapa | 1497 | 28 | 84 | 95.2 | 99.1666667 | blastp |
| 151 | canola\|gb161\|EE430505_T1 | canola | 1498 | 28 | 85 | 95.2 | 94.8207171 | blastp |
| 152 | canola\|gb161\|DY017904_T1 | canola | 1499 | 28 | 82 | 98.8 | 98.8 | blastp |
| 153 | canola\|gb161\|EL590702_T1 | canola | 1500 | 28 | 84 | 99.6 | 99.6 | blastp |
| 154 | canola\|gb161\|CD818320_T1 | canola | 1501 | 28 | 85 | 99.6 | 99.6 | blastp |
| 155 | cassava\|gb164\|DB923860_T1 | cassava | 1502 | 28 | 81 | 100 | 100 | blastp |
| 156 | centaurea\|gb161\|EL932179_T1 | centaurea | 1503 | 28 | 84 | 98.8 | 99.1935484 | blastp |
| 157 | centaurea\|gb161\|EH718862_T1 | centaurea | 1504 | 28 | 82 | 87.6 | 88.9795918 | blastp |
| 158 | cichorium\|gb161\|EH689841_T1 | cichorium | 1505 | 28 | 86 | 88.8 | 64.7230321 | tblastn |
| 159 | citrus\|gb157.2\|CO913277_T1 | citrus | 1506 | 28 | 84 | 100 | 100 | blastp |
| 160 | citrus\|gb157.2\|CO912449_T1 | citrus | 1507 | 28 | 82 | 95.6 | 75.2360965 | tblastn |
| 161 | cotton\|gb164\|DV437956_T1 | cotton | 1508 | 28 | 88 | 50.8 | 100 | blastp |
| 162 | cotton\|gb164\|CD486503_T1 | cotton | 1509 | 28 | 86 | 100 | 100 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 163 | dandelion\|gb161\|DY827614_T1 | dandelion | 1510 | 28 | 84 | 100 | 100 | blastp |
| 164 | dandelion\|gb161\|DY822865_T1 | dandelion | 1511 | 28 | 86 | 100 | 100 | blastp |
| 165 | dandelion\|gb161\|DY819043_T1 | dandelion | 1512 | 28 | 86 | 100 | 100 | blastp |
| 166 | iceplant\|gb164\|AF133533_T1 | iceplant | 1513 | 28 | 82 | 82 | 99.5145631 | blastp |
| 167 | lettuce\|gb157.2\|DW057721_T1 | lettuce | 1514 | 28 | 85 | 100 | 100 | blastp |
| 168 | lettuce\|gb157.2\|DW045203_T1 | lettuce | 1515 | 28 | 85 | 100 | 100 | blastp |
| 169 | lettuce\|gb157.2\|DW046133_T1 | lettuce | 1516 | 28 | 84 | 100 | 100 | blastp |
| 170 | lettuce\|gb157.2\|DW080742_T1 | lettuce | 1517 | 28 | 85 | 85.6 | 100 | blastp |
| 171 | lettuce\|gb157.2\|DW075611_T1 | lettuce | 1518 | 28 | 86 | 100 | 100 | blastp |
| 172 | lettuce\|gb157.2\|DW123899_T1 | lettuce | 1519 | 28 | 86 | 100 | 100 | blastp |
| 173 | lettuce\|gb157.2\|DW103468_T1 | lettuce | 1520 | 28 | 84 | 100 | 100 | blastp |
| 174 | lettuce\|gb157.2\|DW161237_T1 | lettuce | 1521 | 28 | 85 | 100 | 100 | blastp |
| 175 | lettuce\|gb157.2\|DW079798_T1 | lettuce | 1522 | 28 | 85 | 100 | 100 | blastp |
| 176 | lettuce\|gb157.2\|DW079554_T1 | lettuce | 1523 | 28 | 85 | 100 | 100 | blastp |
| 177 | lettuce\|gb157.2\|DW147378_T1 | lettuce | 1524 | 28 | 85 | 100 | 100 | blastp |
| 178 | lettuce\|gb157.2\|DW052373_T1 | lettuce | 1525 | 28 | 83 | 100 | 100 | blastp |
| 179 | lettuce\|gb157.2\|DW105592_T1 | lettuce | 1526 | 28 | 86 | 100 | 100 | blastp |
| 180 | lettuce\|gb157.2\|DW075384_T1 | lettuce | 1527 | 28 | 85 | 100 | 100 | blastp |
| 181 | lettuce\|gb157.2\|DW155153_T1 | lettuce | 1528 | 28 | 86 | 100 | 100 | blastp |
| 182 | lettuce\|gb157.2\|CV699993_T1 | lettuce | 1529 | 28 | 85 | 100 | 100 | blastp |
| 183 | lettuce\|gb157.2\|DW078166_T1 | lettuce | 1530 | 28 | 84 | 100 | 100 | blastp |
| 184 | lotus\|gb157.2\|AV409092_T1 | lotus | 1531 | 28 | 80 | 53.2 | 100 | blastp |
| 185 | medicago\|gb157.2\|AI974377_T1 | medicago | 1532 | 28 | 81 | 98.8 | 99.5951417 | blastp |
| 186 | melon\|gb165\|AM725511_T1 | melon | 1533 | 28 | 84 | 100 | 100 | blastp |
| 187 | nicotiana_benthamiana\|gb162\|EH370474_T1 | nicotiana_benthamiana | 1534 | 28 | 90 | 70.4 | 100 | blastp |
| 188 | onion\|gb162\|BE205571_T1 | onion | 1535 | 28 | 83 | 99.6 | 99.5967742 | blastp |
| 189 | onion\|gb162\|AA601764_T1 | onion | 1536 | 28 | 86 | 95.2 | 96.3414634 | blastp |
| 190 | papaya\|gb165\|EX255759_T1 | papaya | 1537 | 28 | 82 | 99.6 | 99.5983936 | blastp |
| 191 | peanut\|gb161\|EH043676_T1 | peanut | 1538 | 28 | 82 | 99.6 | 99.5967742 | blastp |
| 192 | pepper\|gb157.2\|CK901741_T1 | pepper | 1539 | 28 | 94 | 86.4 | 100 | blastp |
| 193 | periwinkle\|gb164\|FD423620_T1 | periwinkle | 1540 | 28 | 86 | 64.4 | 96.4071856 | blastp |
| 194 | poplar\|gb157.2\|BU886993_T1 | poplar | 1541 | 28 | 84 | 100 | 100 | blastp |
| 195 | poplar\|gb157.2\|CA826065_T1 | poplar | 1542 | 28 | 85 | 86.8 | 100 | blastp |
| 196 | potato\|gb157.2\|BG591546_T2 | potato | 1543 | 28 | 81 | 100 | 100 | blastp |
| 197 | radish\|gb164\|EV531940_T1 | radish | 1544 | 28 | 83 | 94.8 | 94.8 | blastp |
| 198 | radish\|gb164\|EV527785_T1 | radish | 1545 | 28 | 84 | 92.8 | 95.473251 | blastp |
| 199 | radish\|gb164\|EV550763_T1 | radish | 1546 | 28 | 84 | 95.2 | 94.8207171 | blastp |
| 200 | radish\|gb164\|EX902593_T1 | radish | 1547 | 28 | 85 | 95.2 | 99.58159 | blastp |
| 201 | radish\|gb164\|EV535199_T1 | radish | 1548 | 28 | 84 | 96 | 98.7654321 | blastp |
| 202 | radish\|gb164\|EV525705_T1 | radish | 1549 | 28 | 85 | 96 | 98.7654321 | blastp |
| 203 | safflower\|gb162\|EL399548_T1 | safflower | 1550 | 28 | 86 | 86.8 | 100 | blastp |
| 204 | safflower\|gb162\|EL376421_T1 | safflower | 1551 | 28 | 87 | 100 | 100 | blastp |
| 205 | spurge\|gb161\|DV127241_T1 | spurge | 1552 | 28 | 85 | 88.4 | 99.103139 | blastp |
| 206 | strawberry\|gb164\|GFXDQ178022X1_T1 | strawberry | 1553 | 28 | 82 | 100 | 100 | blastp |
| 207 | sunflower\|gb162\|X95953_T1 | sunflower | 1554 | 28 | 86 | 100 | 100 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 208 | sunflower\|gb162\|DY911049_T1 | sunflower | 1555 | 28 | 85 | 100 | 100 | blastp |
| 209 | sunflower\|gb162\|DY921796_T1 | sunflower | 1556 | 28 | 81 | 88.8 | 98.2300885 | blastp |
| 210 | sunflower\|gb162\|DY918762_T1 | sunflower | 1557 | 28 | 85 | 100 | 100 | blastp |
| 211 | sunflower\|gb162\|DY906198_T1 | sunflower | 1558 | 28 | 81 | 100 | 100 | blastp |
| 212 | sunflower\|gb162\|DY932268_T1 | sunflower | 1559 | 28 | 81 | 100 | 100 | blastp |
| 213 | tobacco\|gb162\|GFXS45406X1_T1 | tobacco | 1560 | 28 | 93 | 100 | 100 | blastp |
| 214 | tobacco\|gb162\|EB445911_T1 | tobacco | 1561 | 28 | 89 | 100 | 100 | blastp |
| 215 | apricot\|gb157.2\|CB818493_T1 | apricot | 1562 | 29 | 81 | 54.5454545 | 95.8333333 | blastp |
| 216 | arabidopsis\|gb165\|AT4G01470_T1 | arabidopsis | 1563 | 29 | 80 | 99.2094862 | 99.6031746 | blastp |
| 217 | avocado\|gb164\|CK760396_T1 | avocado | 1564 | 29 | 81 | 54.5454545 | 93.877551 | blastp |
| 218 | b_rapa\|gb162\|EX017183_T1 | b_rapa | 1565 | 29 | 83 | 69.5652174 | 94.1176471 | blastp |
| 219 | barley\|gb157.3\|BE413237_T1 | barley | 1566 | 29 | 81 | 99.2094862 | 99.6031746 | blastp |
| 220 | cassava\|gb164\|CK644827_T1 | cassava | 1567 | 29 | 90 | 57.312253 | 99.3150685 | blastp |
| 221 | cassava\|gb164\|BM259770_T1 | cassava | 1568 | 29 | 82 | 99.2094862 | 99.6031746 | blastp |
| 222 | cassava\|gb164\|CK645124_T1 | cassava | 1569 | 29 | 80 | 99.2094862 | 99.6031746 | blastp |
| 223 | castorbean\|gb160\|EG666198_T1 | castorbean | 1570 | 29 | 84 | 99.2094862 | 99.6031746 | blastp |
| 224 | castorbean\|gb160\|AJ605571_T1 | castorbean | 1571 | 29 | 82 | 99.2094862 | 99.6015936 | blastp |
| 225 | castorbean\|gb160\|AJ605570_T1 | castorbean | 1572 | 29 | 83 | 99.2094862 | 99.6031746 | blastp |
| 226 | centaurea\|gb161\|EL931525_T1 | centaurea | 1573 | 29 | 88 | 74.7035573 | 97.9274611 | blastp |
| 227 | cichorium\|gb161\|EH707617_T1 | cichorium | 1574 | 29 | 87 | 65.6126482 | 99.4011976 | blastp |
| 228 | citrus\|gb157.2\|CF834233_T1 | citrus | 1575 | 29 | 80 | 94.4664032 | 94.4444444 | blastp |
| 229 | citrus\|gb157.2\|BQ624227_T1 | citrus | 1576 | 29 | 87 | 99.2094862 | 99.6031746 | blastp |
| 230 | citrus\|gb157.2\|BQ623056_T1 | citrus | 1577 | 29 | 87 | 97.2332016 | 98.4 | blastp |
| 231 | citrus\|gb157.2\|BQ624617_T1 | citrus | 1578 | 29 | 87 | 99.2094862 | 99.6031746 | blastp |
| 232 | cotton\|gb164\|CD486523_T1 | cotton | 1579 | 29 | 81 | 99.2094862 | 99.6031746 | blastp |
| 233 | cotton\|gb164\|AI729919_T1 | cotton | 1580 | 29 | 82 | 99.2094862 | 99.6031746 | blastp |
| 234 | cotton\|gb164\|BG442315_T1 | cotton | 1581 | 29 | 86 | 99.2094862 | 99.6031746 | blastp |
| 235 | cotton\|gb164\|EX167179_T1 | cotton | 1582 | 29 | 84 | 56.916996 | 100 | blastp |
| 236 | cotton\|gb164\|AI726375_T1 | cotton | 1583 | 29 | 82 | 99.2094862 | 99.6031746 | blastp |
| 237 | cowpea\|gb166\|FF384697_T1 | cowpea | 1584 | 29 | 84 | 99.2094862 | 99.6031746 | blastp |
| 238 | dandelion\|gb161\|DY825779_T1 | dandelion | 1585 | 29 | 88 | 99.2094862 | 99.6031746 | blastp |
| 239 | fescue\|gb161\|CK802772_T1 | fescue | 1586 | 29 | 80 | 99.2094862 | 99.6031746 | blastp |
| 240 | grape\|gb160\|BQ796848_T1 | grape | 1587 | 29 | 84 | 99.2094862 | 99.6015936 | blastp |
| 241 | grape\|gb160\|CF605030_T1 | grape | 1588 | 29 | 82 | 99.2094862 | 99.6031746 | blastp |
| 242 | ipomoea\|gb157.2\|EE883704_T1 | ipomoea | 1589 | 29 | 85 | 53.7549407 | 100 | blastp |
| 243 | ipomoea\|gb157.2\|BJ554617_T1 | ipomoea | 1590 | 29 | 85 | 99.2094862 | 99.6031746 | blastp |
| 244 | lettuce\|gb157.2\|DW074608_T1 | lettuce | 1591 | 29 | 87 | 99.2094862 | 99.6031746 | blastp |
| 245 | lettuce\|gb157.2\|DY977540_T1 | lettuce | 1592 | 29 | 87 | 99.2094862 | 99.6031746 | blastp |
| 246 | lotus\|gb157.2\|BW615882_T1 | lotus | 1593 | 29 | 80 | 50.1976285 | 100 | blastp |
| 247 | maize\|gb164\|DQ245749_T1 | maize | 1594 | 29 | 81 | 99.2094862 | 99.6031746 | blastp |
| 248 | medicago\|gb157.2\|BI266516_T1 | medicago | 1595 | 29 | 82 | 99.2094862 | 99.6031746 | blastp |
| 249 | nicotiana_benthamiana\|gb162\|CN743053_T1 | nicotiana_benthamiana | 1596 | 29 | 94 | 83.0039526 | 99.5260664 | blastp |
| 250 | papaya\|gb165\|EX256526_T1 | papaya | 1597 | 29 | 80 | 99.2094862 | 99.6031746 | blastp |
| 251 | papaya\|gb165\|EX255270_T1 | papaya | 1598 | 29 | 86 | 99.2094862 | 99.6031746 | blastp |
| 252 | peach\|gb157.2\|AF367456_T1 | peach | 1599 | 29 | 84 | 53.7549407 | 100 | blastp |
| 253 | pepper\|gb157.2\|CK902019_T1 | pepper | 1600 | 29 | 81 | 73.1225296 | 98.9304813 | blastp |
| 254 | poplar\|gb157.2\|AI163470_T1 | poplar | 1601 | 29 | 81 | 99.2094862 | 99.6031746 | blastp |
| 255 | poplar\|gb157.2\|AI166549_T1 | poplar | 1602 | 29 | 82 | 99.2094862 | 99.6031746 | blastp |
| 256 | poplar\|gb157.2\|BU887722_T1 | poplar | 1603 | 29 | 81 | 99.2094862 | 99.6031746 | blastp |
| 257 | poplar\|gb157.2\|BU875073_T1 | poplar | 1604 | 29 | 83 | 99.2094862 | 99.6031746 | blastp |
| 258 | poplar\|gb157.2\|CA823737_T1 | poplar | 1605 | 29 | 88 | 53.3596838 | 99.2647059 | blastp |
| 259 | poplar\|gb157.2\|AI166136_T1 | poplar | 1606 | 29 | 80 | 99.2094862 | 99.6031746 | blastp |
| 260 | radish\|gb164\|EV544876_T1 | radish | 1607 | 29 | 80 | 99.2094862 | 99.6031746 | blastp |
| 261 | rice\|gb157.2\|AA752956_T1 | rice | 1608 | 29 | 80 | 99.2094862 | 99.6031746 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 262 | soybean\|gb166\|CX703984_T1 | soybean | 1609 | 29 | 80 | 99.2094862 | 99.6031746 | blastp |
| 263 | soybean\|gb166\|SOYNODB_T1 | soybean | 1610 | 29 | 86 | 99.2094862 | 99.6031746 | blastp |
| 264 | spurge\|gb161\|DV146067_T1 | spurge | 1611 | 29 | 84 | 87.3517787 | 100 | blastp |
| 265 | spurge\|gb161\|AW990927_T1 | spurge | 1612 | 29 | 80 | 99.2094862 | 99.6031746 | blastp |
| 266 | sunflower\|gb162\|DY919534_T1 | sunflower | 1613 | 29 | 86 | 99.2094862 | 99.6031746 | blastp |
| 267 | tobacco\|gb162\|EB443312_T1 | tobacco | 1614 | 29 | 92 | 99.2094862 | 99.6031746 | blastp |
| 268 | tobacco\|gb162\|CV019217_T1 | tobacco | 1615 | 29 | 81 | 98.0237154 | 99.5967742 | blastp |
| 269 | tobacco\|gb162\|EB443618_T1 | tobacco | 1616 | 29 | 92 | 99.2094862 | 99.6031746 | blastp |
| 270 | tobacco\|gb162\|CV018899_T1 | tobacco | 1617 | 29 | 81 | 98.0237154 | 99.5967742 | blastp |
| 271 | wheat\|gb164\|BE418306_T1 | wheat | 1618 | 29 | 80 | 99.2094862 | 99.6031746 | blastp |
| 272 | wheat\|gb164\|BE404792_T1 | wheat | 1619 | 29 | 82 | 52.9644269 | 99.2592593 | blastp |
| 273 | wheat\|gb164\|BE216922_T1 | wheat | 1620 | 29 | 81 | 99.2094862 | 99.6031746 | blastp |
| 274 | artemisia\|gb164\|EY083433_T1 | artemisia | 1621 | 30 | 80 | 79.6 | 100 | blastp |
| 275 | banana\|gb160\|ES432704_T1 | banana | 1622 | 30 | 81 | 88.8 | 93.6708861 | blastp |
| 276 | banana\|gb160\|DN238541_T1 | banana | 1623 | 30 | 80 | 100 | 100 | blastp |
| 277 | barley\|gb157.3\|BE412510_T1 | barley | 1624 | 30 | 80 | 100 | 100 | blastp |
| 278 | cotton\|gb164\|AI726168_T1 | cotton | 1625 | 30 | 80 | 98.8 | 99.5983936 | blastp |
| 279 | cotton\|gb164\|AI731742_T1 | cotton | 1626 | 30 | 80 | 100 | 100 | blastp |
| 280 | cotton\|gb164\|AI055329_T1 | cotton | 1627 | 30 | 80 | 100 | 100 | blastp |
| 281 | grape\|gb160\|BQ794219_T1 | grape | 1628 | 30 | 81 | 100 | 100 | blastp |
| 282 | ipomoea\|gb157.2\|BJ554855_T1 | ipomoea | 1629 | 30 | 81 | 98 | 100 | blastp |
| 283 | ipomoea\|gb157.2\|BM878761_T1 | ipomoea | 1630 | 30 | 84 | 100 | 100 | blastp |
| 284 | lettuce\|gb157.2\|DW045084_T1 | lettuce | 1631 | 30 | 80 | 86.8 | 98.1981982 | blastp |
| 285 | lettuce\|gb157.2\|DW114621_T1 | lettuce | 1632 | 30 | 80 | 88 | 99.103139 | blastp |
| 286 | lettuce\|gb157.2\|DW078778_T1 | lettuce | 1633 | 30 | 81 | 50.8 | 100 | blastp |
| 287 | maize\|gb164\|CO528320_T1 | maize | 1634 | 30 | 82 | 69.6 | 100 | blastp |
| 288 | maize\|gb164\|AW257922_T1 | maize | 1635 | 30 | 80 | 52.4 | 100 | blastp |
| 289 | maize\|gb164\|BI675058_T1 | maize | 1636 | 30 | 80 | 54 | 99.2592593 | blastp |
| 290 | maize\|gb164\|AW352518_T1 | maize | 1637 | 30 | 80 | 51.2 | 100 | blastp |
| 291 | maize\|gb164\|AF037061_T1 | maize | 1638 | 30 | 81 | 100 | 100 | blastp |
| 292 | nicotiana_benthamiana\|gb162\|CN655062_T1 | nicotiana_benthamiana | 1639 | 30 | 90 | 100 | 100 | blastp |
| 293 | nicotiana_benthamiana\|gb162\|CN741621_T1 | nicotiana_benthamiana | 1640 | 30 | 90 | 100 | 100 | blastp |
| 294 | oil_palm\|gb166\|CN599861_T1 | oil_palm | 1641 | 30 | 80 | 100 | 100 | blastp |
| 295 | papaya\|gb165\|EX246150_T1 | papaya | 1642 | 30 | 82 | 100 | 100 | blastp |
| 296 | pepper\|gb157.2\|BM060520_T1 | pepper | 1643 | 30 | 91 | 99.2 | 98.8 | blastp |
| 297 | periwinkle\|gb164\|EG554262_T1 | periwinkle | 1644 | 30 | 82 | 100 | 100 | blastp |
| 298 | petunia\|gb157.2\|AF452015_T1 | petunia | 1645 | 30 | 89 | 100 | 100 | blastp |
| 299 | potato\|gb157.2\|CK853059_T1 | potato | 1646 | 30 | 96 | 92 | 91.3043478 | blastp |
| 300 | potato\|gb157.2\|CK852742_T1 | potato | 1647 | 30 | 82 | 60.4 | 100 | blastp |
| 301 | potato\|gb157.2\|BM407759_T1 | potato | 1648 | 30 | 99 | 81.2 | 97.5961538 | blastp |
| 302 | potato\|gb157.2\|CK718033_T1 | potato | 1649 | 30 | 98 | 65.2 | 92.0903955 | blastp |
| 303 | potato\|gb157.2\|CK717899_T1 | potato | 1650 | 30 | 100 | 62 | 95.0920245 | blastp |
| 304 | potato\|gb157.2\|CV472240_T1 | potato | 1651 | 30 | 97 | 79.6 | 95.215311 | blastp |
| 305 | potato\|gb157.2\|BG098199_T1 | potato | 1652 | 30 | 95 | 93.2 | 99.5726496 | blastp |
| 306 | rice\|gb157.2\|U37925_T1 | rice | 1653 | 30 | 81 | 100 | 100 | blastp |
| 307 | rye\|gb164\|BE494266_T1 | rye | 1654 | 30 | 80 | 100 | 100 | blastp |
| 308 | sorghum\|gb161.xeno\|AF037061_T1 | sorghum | 1655 | 30 | 80 | 100 | 100 | blastp |
| 309 | sugarcane\|gb157.2\|BQ535365_T1 | sugarcane | 1656 | 30 | 80 | 80.4 | 100 | blastp |
| 310 | switchgrass\|gb165\|DN141449_T1 | switchgrass | 1657 | 30 | 81 | 100 | 100 | blastp |
| 311 | switchgrass\|gb165\|DN142089_T1 | switchgrass | 1658 | 30 | 81 | 100 | 100 | blastp |
| 312 | tobacco\|gb162\|CN824866_T1 | tobacco | 1659 | 30 | 90 | 100 | 100 | blastp |
| 313 | tobacco\|gb162\|CV017118_T1 | tobacco | 1660 | 30 | 90 | 100 | 100 | blastp |
| 314 | wheat\|gb164\|TAU86762_T1 | wheat | 1661 | 30 | 80 | 100 | 100 | blastp |
| 315 | wheat\|gb164\|BE499589_T1 | wheat | 1662 | 30 | 80 | 72 | 100 | blastp |
| 316 | lettuce\|gb157.2\|DW087170_T1 | lettuce | 1663 | 31 | 80 | 100 | 100 | blastp |
| 317 | tobacco\|gb162\|EH616288_T1 | tobacco | 1664 | 32 | 87 | 50.7692308 | 85.1612903 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 318 | apple\|gb157.3\|CO068608__T1 | apple | 1665 | 33 | 86 | 98.2638889 | 98.951049 | blastp |
| 319 | apple\|gb157.3\|AB100869__T1 | apple | 1666 | 33 | 83 | 98.2638889 | 99.3079585 | blastp |
| 320 | apple\|gb157.3\|AB100870__T1 | apple | 1667 | 33 | 83 | 98.2638889 | 99.3079585 | blastp |
| 321 | apple\|gb157.3\|CN860225__T1 | apple | 1668 | 33 | 86 | 54.8611111 | 90.2857143 | blastp |
| 322 | apple\|gb157.3\|CK900645__T1 | apple | 1669 | 33 | 85 | 98.2638889 | 98.951049 | blastp |
| 323 | apricot\|gb157.2\|CB822297__T1 | apricot | 1670 | 33 | 89 | 51.0416667 | 98.6577181 | blastp |
| 324 | apricot\|gb157.2\|CB819647__T1 | apricot | 1671 | 33 | 83 | 98.2638889 | 98.9655172 | blastp |
| 325 | aquilegia\|gb157.3\|DR917005__T1 | aquilegia | 1672 | 33 | 86 | 98.2638889 | 98.9547038 | blastp |
| 326 | arabidopsis\|gb165\|AT4G00430__T2 | arabidopsis | 1673 | 33 | 84 | 73.6111111 | 97.260274 | blastp |
| 327 | arabidopsis\|gb165\|AT2G45960__T3 | arabidopsis | 1674 | 33 | 86 | 88.1944444 | 84.3853821 | blastp |
| 328 | arabidopsis\|gb165\|AT4G23400__T1 | arabidopsis | 1675 | 33 | 87 | 98.2638889 | 98.9547038 | blastp |
| 329 | arabidopsis\|gb165\|AT2G45960__T1 | arabidopsis | 1676 | 33 | 86 | 98.2638889 | 98.951049 | blastp |
| 330 | arabidopsis\|gb165\|AT4G00430__T1 | arabidopsis | 1677 | 33 | 87 | 98.2638889 | 98.9547038 | blastp |
| 331 | arabidopsis\|gb165\|AT1G01620__T1 | arabidopsis | 1678 | 33 | 88 | 98.2638889 | 98.951049 | blastp |
| 332 | arabidopsis\|gb165\|AT3G61430__T1 | arabidopsis | 1679 | 33 | 85 | 98.2638889 | 98.951049 | blastp |
| 333 | arabidopsis\|gb165\|AT2G45960__T4 | arabidopsis | 1680 | 33 | 86 | 88.1944444 | 92.7007299 | blastp |
| 334 | artemisia\|gb164\|EY046087__T1 | artemisia | 1681 | 33 | 86 | 98.2638889 | 98.9547038 | blastp |
| 335 | artemisia\|gb164\|EY046310__T1 | artemisia | 1682 | 33 | 87 | 73.6111111 | 99.0697674 | blastp |
| 336 | artemisia\|gb164\|EY032836__T1 | artemisia | 1683 | 33 | 84 | 97.5694444 | 98.2758621 | blastp |
| 337 | artemisia\|gb164\|EY031810__T1 | artemisia | 1684 | 33 | 84 | 89.2361111 | 99.2307692 | blastp |
| 338 | avocado\|gb164\|CK751385__T1 | avocado | 1685 | 33 | 86 | 98.2638889 | 98.9547038 | blastp |
| 339 | avocado\|gb164\|CK745633__T1 | avocado | 1686 | 33 | 91 | 73.6111111 | 99.0654206 | blastp |
| 340 | b_juncea\|gb164\|EVGN00081008450640__T1 | b_juncea | 1687 | 33 | 87 | 98.2638889 | 98.951049 | blastp |
| 341 | b_juncea\|gb164\|EVGN00515811862066__T1 | b_juncea | 1688 | 33 | 90 | 60.4166667 | 96.1325967 | blastp |
| 342 | b_juncea\|gb164\|EVGN00230716760965__T1 | b_juncea | 1689 | 33 | 89 | 73.6111111 | 99.0654206 | blastp |
| 343 | b_juncea\|gb164\|EVGN01776308261252__T1 | b_juncea | 1690 | 33 | 84 | 66.3194444 | 96.4646465 | blastp |
| 344 | b_juncea\|gb164\|EVGN00910030360678__T1 | b_juncea | 1691 | 33 | 91 | 65.2777778 | 98.9473684 | blastp |
| 345 | b_juncea\|gb164\|EVGN03812526911787__T1 | b_juncea | 1692 | 33 | 88 | 51.0416667 | 98.6577181 | blastp |
| 346 | b_juncea\|gb164\|EVGN00227203510305__T1 | b_juncea | 1693 | 33 | 91 | 65.2777778 | 98.9473684 | blastp |
| 347 | b_juncea\|gb164\|EVGN00462518410866__T1 | b_juncea | 1694 | 33 | 87 | 98.2638889 | 98.951049 | blastp |
| 348 | b_juncea\|gb164\|EVGN00248411120906__T1 | b_juncea | 1695 | 33 | 89 | 73.2638889 | 99.0610329 | blastp |
| 349 | b_juncea\|gb164\|EF471211__T1 | b_juncea | 1696 | 33 | 86 | 98.2638889 | 98.2638889 | blastp |
| 350 | b_juncea\|gb164\|EVGN00440012650683__T1 | b_juncea | 1697 | 33 | 86 | 98.2638889 | 98.951049 | blastp |
| 351 | b_juncea\|gb164\|EVGN00452211183349__T1 | b_juncea | 1698 | 33 | 86 | 98.2638889 | 98.951049 | blastp |
| 352 | b_juncea\|gb164\|EVGN03595331210044__T1 | b_juncea | 1699 | 33 | 89 | 57.6388889 | 93.258427 | blastp |
| 353 | b_juncea\|gb164\|EVGN00088009631302__T1 | b_juncea | 1700 | 33 | 87 | 98.2638889 | 98.951049 | blastp |
| 354 | b_juncea\|gb164\|EVGN00512912541009__T1 | b_juncea | 1701 | 33 | 85 | 51.7361111 | 93.907563 | tblastn |
| 355 | b_juncea\|gb164\|EVGN00756014550623__T1 | b_juncea | 1702 | 33 | 84 | 69.0972222 | 90.3177005 | tblastn |
| 356 | b_oleracea\|gb161\|AF299051__T1 | b_oleracea | 1703 | 33 | 86 | 98.2638889 | 98.951049 | blastp |
| 357 | b_oleracea\|gb161\|AM391520__T1 | b_oleracea | 1704 | 33 | 87 | 75.3472222 | 99.5412844 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 358 | b_oleracea\|gb161\|AM058918_T1 | b_oleracea | 1705 | 33 | 87 | 98.2638889 | 98.951049 | blastp |
| 359 | b_oleracea\|gb161\|AF299050_T1 | b_oleracea | 1706 | 33 | 86 | 98.2638889 | 98.951049 | blastp |
| 360 | b_oleracea\|gb161\|DY029936_T1 | b_oleracea | 1707 | 33 | 86 | 98.2638889 | 98.951049 | blastp |
| 361 | b_oleracea\|gb161\|EH422530_T1 | b_oleracea | 1708 | 33 | 87 | 78.4722222 | 100 | blastp |
| 362 | b_rapa\|gb162\|CV546930_T1 | b_rapa | 1709 | 33 | 84 | 71.5277778 | 99.5169082 | blastp |
| 363 | b_rapa\|gb162\|BG544387_T1 | b_rapa | 1710 | 33 | 86 | 95.4861111 | 99.2779783 | blastp |
| 364 | b_rapa\|gb162\|CA992432_T1 | b_rapa | 1711 | 33 | 86 | 98.2638889 | 98.951049 | blastp |
| 365 | b_rapa\|gb162\|CV546129_T2 | b_rapa | 1712 | 33 | 83 | 54.8611111 | 99.3710692 | blastp |
| 366 | b_rapa\|gb162\|EE526280_T1 | b_rapa | 1713 | 33 | 87 | 98.2638889 | 98.951049 | blastp |
| 367 | b_rapa\|gb162\|L33552_T1 | b_rapa | 1714 | 33 | 86 | 98.2638889 | 98.951049 | blastp |
| 368 | b_rapa\|gb162\|BG543719_T1 | b_rapa | 1715 | 33 | 84 | 77.0833333 | 99.5515695 | blastp |
| 369 | b_rapa\|gb162\|AF004293_T1 | b_rapa | 1716 | 33 | 87 | 98.2638889 | 98.951049 | blastp |
| 370 | b_rapa\|gb162\|BG544086_T1 | b_rapa | 1717 | 33 | 87 | 98.2638889 | 98.951049 | blastp |
| 371 | b_rapa\|gb162\|CX267412_T1 | b_rapa | 1718 | 33 | 86 | 98.2638889 | 99.2982456 | blastp |
| 372 | b_rapa\|gb162\|CV546129_T1 | b_rapa | 1719 | 33 | 86 | 98.2638889 | 98.2638889 | blastp |
| 373 | b_rapa\|gb162\|CV545634_T1 | b_rapa | 1720 | 33 | 83 | 56.5972222 | 90.5555556 | blastp |
| 374 | banana\|gb160\|DN238827_T1 | banana | 1721 | 33 | 84 | 60.7638889 | 99.4285714 | blastp |
| 375 | banana\|gb160\|ES431094_T1 | banana | 1722 | 33 | 89 | 63.8888889 | 98.9247312 | blastp |
| 376 | barley\|gb157.3\|BE412959_T2 | barley | 1723 | 33 | 83 | 98.2638889 | 98.9726027 | blastp |
| 377 | barley\|gb157.3\|AL507831_T1 | barley | 1724 | 33 | 85 | 99.3055556 | 99.6551724 | blastp |
| 378 | barley\|gb157.3\|BE412959_T1 | barley | 1725 | 33 | 83 | 98.2638889 | 98.9726027 | blastp |
| 379 | barley\|gb157.3\|BE412959_T5 | barley | 1726 | 33 | 82 | 98.2638889 | 98.9830508 | blastp |
| 380 | barley\|gb157.3\|BE412959_T4 | barley | 1727 | 33 | 82 | 98.2638889 | 98.9830508 | blastp |
| 381 | barley\|gb157.3\|AL502020_T1 | barley | 1728 | 33 | 82 | 98.2638889 | 98.9726027 | blastp |
| 382 | barley\|gb157.3\|BE412972_T1 | barley | 1729 | 33 | 85 | 98.2638889 | 98.9583333 | blastp |
| 383 | basilicum\|gb157.3\|DY340092_T1 | basilicum | 1730 | 33 | 88 | 61.8055556 | 99.4413408 | blastp |
| 384 | basilicum\|gb157.3\|DY332264_T1 | basilicum | 1731 | 33 | 87 | 73.9583333 | 99.5327103 | blastp |
| 385 | bean\|gb164\|CB543592_T1 | bean | 1732 | 33 | 88 | 98.2638889 | 98.9547038 | blastp |
| 386 | bean\|gb164\|PVU97023_T1 | bean | 1733 | 33 | 84 | 98.2638889 | 99.3079585 | blastp |
| 387 | bean\|gb164\|CB542193_T1 | bean | 1734 | 33 | 84 | 98.6111111 | 99.6539792 | blastp |
| 388 | beet\|gb162\|BVU60149_T1 | beet | 1735 | 33 | 84 | 98.2638889 | 98.951049 | blastp |
| 389 | brachypodium\|gb161.xeno\|BE443278_T1 | brachypodium | 1736 | 33 | 83 | 82.9861111 | 95.6521739 | blastp |
| 390 | brachypodium\|gb161.xeno\|BE216990_T1 | brachypodium | 1737 | 33 | 85 | 98.2638889 | 98.9583333 | blastp |
| 391 | brachypodium\|gb161.xeno\|BE403307_T1 | brachypodium | 1738 | 33 | 82 | 86.8055556 | 72.7011494 | blastp |
| 392 | canola\|gb161\|CN731957_T1 | canola | 1739 | 33 | 86 | 98.2638889 | 98.951049 | blastp |
| 393 | canola\|gb161\|CX194503_T1 | canola | 1740 | 33 | 86 | 98.2638889 | 98.951049 | blastp |
| 394 | canola\|gb161\|CD814405_T1 | canola | 1741 | 33 | 87 | 98.2638889 | 98.951049 | blastp |
| 395 | canola\|gb161\|EG020906_T1 | canola | 1742 | 33 | 86 | 98.2638889 | 98.951049 | blastp |
| 396 | canola\|gb161\|H74720_T1 | canola | 1743 | 33 | 86 | 98.2638889 | 98.951049 | blastp |
| 397 | canola\|gb161\|CN831315_T1 | canola | 1744 | 33 | 86 | 84.0277778 | 93.4362934 | blastp |
| 398 | canola\|gb161\|CD817408_T1 | canola | 1745 | 33 | 87 | 98.2638889 | 98.951049 | blastp |
| 399 | canola\|gb161\|EE502121_T1 | canola | 1746 | 33 | 89 | 52.7777778 | 98.7096774 | blastp |
| 400 | canola\|gb161\|CX187544_T1 | canola | 1747 | 33 | 87 | 98.2638889 | 98.951049 | blastp |
| 401 | canola\|gb161\|CD822064_T1 | canola | 1748 | 33 | 86 | 98.2638889 | 98.951049 | blastp |
| 402 | canola\|gb161\|CD824965_T1 | canola | 1749 | 33 | 81 | 92.0138889 | 93.0313589 | blastp |
| 403 | canola\|gb161\|EE485551_T1 | canola | 1750 | 33 | 87 | 98.2638889 | 98.951049 | blastp |
| 404 | canola\|gb161\|CB686274_T1 | canola | 1751 | 33 | 86 | 98.2638889 | 98.951049 | blastp |
| 405 | canola\|gb161\|CD814573_T1 | canola | 1752 | 33 | 83 | 76.3888889 | 94.0425532 | blastp |
| 406 | canola\|gb161\|CX193398_T1 | canola | 1753 | 33 | 86 | 98.2638889 | 98.2638889 | blastp |
| 407 | canola\|gb161\|CD818853_T1 | canola | 1754 | 33 | 86 | 98.2638889 | 98.951049 | blastp |
| 408 | canola\|gb161\|DY005979_T1 | canola | 1755 | 33 | 85 | 78.4722222 | 99.5594714 | blastp |
| 409 | canola\|gb161\|EE464964_T1 | canola | 1756 | 33 | 85 | 81.5972222 | 99.5762712 | blastp |
| 410 | cassava\|gb164\|BM260264_T1 | cassava | 1757 | 33 | 85 | 97.9166667 | 99.3031359 | blastp |
| 411 | cassava\|gb164\|CK901165_T1 | cassava | 1758 | 33 | 87 | 73.6111111 | 99.0697674 | blastp |
| 412 | cassava\|gb164\|CK642415_T1 | cassava | 1759 | 33 | 87 | 98.2638889 | 98.9547038 | blastp |
| 413 | cassava\|gb164\|DV455398_T1 | cassava | 1760 | 33 | 85 | 97.9166667 | 99.3031359 | blastp |
| 414 | castorbean\|gb160\|T14819_T1 | castorbean | 1761 | 33 | 89 | 98.2638889 | 98.9547038 | blastp |
| 415 | castorbean\|gb160\|EG691229_T1 | castorbean | 1762 | 33 | 86 | 98.2638889 | 98.951049 | blastp |
| 416 | castorbean\|gb160\|AJ605566_T1 | castorbean | 1763 | 33 | 87 | 97.9166667 | 99.3031359 | blastp |
| 417 | castorbean\|gb160\|MDL29969M000266_T1 | castorbean | 1764 | 33 | 84 | 98.2638889 | 99.3055556 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 418 | castorbean\|gb160\|AJ605574_T1 | castorbean | 1765 | 33 | 87 | 97.9166667 | 98.9583333 | blastp |
| 419 | *centaurea*\|gb161\|EH732068_T1 | *centaurea* | 1766 | 33 | 82 | 97.5694444 | 98.6062718 | blastp |
| 420 | *cichorium*\|gb161\|EH673032_T1 | *cichorium* | 1767 | 33 | 87 | 98.2638889 | 98.9547038 | blastp |
| 421 | *cichorium*\|gb161\|EH706808_T1 | *cichorium* | 1768 | 33 | 90 | 51.7361111 | 98.6842105 | blastp |
| 422 | *cichorium*\|gb161\|EH701938_T1 | *cichorium* | 1769 | 33 | 86 | 64.9305556 | 95.4314721 | blastp |
| 423 | citrus\|gb157.2\|CO912471_T1 | citrus | 1770 | 33 | 82 | 69.4444444 | 99.5098039 | blastp |
| 424 | citrus\|gb157.2\|BQ624312_T1 | citrus | 1771 | 33 | 88 | 98.2638889 | 98.9547038 | blastp |
| 425 | citrus\|gb157.2\|CN182376_T1 | citrus | 1772 | 33 | 84 | 92.7083333 | 94.0559441 | blastp |
| 426 | citrus\|gb157.2\|CB291370_T1 | citrus | 1773 | 33 | 89 | 98.2638889 | 98.9547038 | blastp |
| 427 | citrus\|gb157.2\|CF833327_T1 | citrus | 1774 | 33 | 85 | 98.2638889 | 99.3031359 | blastp |
| 428 | citrus\|gb157.2\|BQ624860_T1 | citrus | 1775 | 33 | 85 | 97.9166667 | 99.6503497 | blastp |
| 429 | citrus\|gb157.2\|CF508404_T1 | citrus | 1776 | 33 | 81 | 97.9166667 | 99.6503497 | blastp |
| 430 | citrus\|gb157.2\|CB293694_T1 | citrus | 1777 | 33 | 84 | 98.2638889 | 99.3031359 | blastp |
| 431 | citrus\|gb157.2\|BQ622975_T1 | citrus | 1778 | 33 | 85 | 97.9166667 | 99.6503497 | blastp |
| 432 | citrus\|gb157.2\|BE213453_T1 | citrus | 1779 | 33 | 86 | 73.6111111 | 99.5305164 | blastp |
| 433 | citrus\|gb157.2\|CF828110_T1 | citrus | 1780 | 33 | 85 | 98.6111111 | 99.6527778 | blastp |
| 434 | citrus\|gb157.2\|BQ623397_T1 | citrus | 1781 | 33 | 86 | 93.4027778 | 99.6336996 | blastp |
| 435 | clover\|gb162\|BB903117_T1 | clover | 1782 | 33 | 85 | 98.6111111 | 99.6539792 | blastp |
| 436 | *coffea*\|gb157.2\|BQ449035_T1 | *coffea* | 1783 | 33 | 88 | 98.9583333 | 99.3055556 | blastp |
| 437 | *coffea*\|gb157.2\|DV663743_T1 | *coffea* | 1784 | 33 | 85 | 98.2638889 | 98.9473684 | blastp |
| 438 | cotton\|gb164\|CD486529_T1 | cotton | 1785 | 33 | 83 | 98.2638889 | 99.3055556 | blastp |
| 439 | cotton\|gb164\|BE052445_T1 | cotton | 1786 | 33 | 87 | 98.2638889 | 98.9547038 | blastp |
| 440 | cotton\|gb164\|AI726690_T1 | cotton | 1787 | 33 | 86 | 98.2638889 | 98.9547038 | blastp |
| 441 | cotton\|gb164\|DN803576_T1 | cotton | 1788 | 33 | 83 | 87.8472222 | 98.828125 | blastp |
| 442 | cotton\|gb164\|BM358242_T1 | cotton | 1789 | 33 | 81 | 98.2638889 | 99.2882562 | blastp |
| 443 | cotton\|gb164\|CO085369_T1 | cotton | 1790 | 33 | 81 | 52.7777778 | 99.3506494 | blastp |
| 444 | cotton\|gb164\|CO098674_T1 | cotton | 1791 | 33 | 84 | 98.2638889 | 99.3055556 | blastp |
| 445 | cotton\|gb164\|CO070796_T1 | cotton | 1792 | 33 | 84 | 98.2638889 | 99.3031359 | blastp |
| 446 | cotton\|gb164\|AI729945_T1 | cotton | 1793 | 33 | 85 | 98.2638889 | 99.3079585 | blastp |
| 447 | cotton\|gb164\|DW496760_T1 | cotton | 1794 | 33 | 86 | 80.5555556 | 98.3122363 | blastp |
| 448 | cowpea\|gb166\|FF384916_T1 | cowpea | 1795 | 33 | 82 | 98.2638889 | 99.3031359 | blastp |
| 449 | cowpea\|gb166\|FF555791_T1 | cowpea | 1796 | 33 | 82 | 98.6111111 | 99.6539792 | blastp |
| 450 | cowpea\|gb166\|FC457489_T1 | cowpea | 1797 | 33 | 87 | 98.2638889 | 98.9547038 | blastp |
| 451 | cowpea\|gb166\|AB037241_T1 | cowpea | 1798 | 33 | 84 | 98.2638889 | 99.3079585 | blastp |
| 452 | *cryptomeria*\|gb166\|DC429824_T1 | *cryptomeria* | 1799 | 33 | 84 | 71.5277778 | 99.5215311 | blastp |
| 453 | *cryptomeria*\|gb166\|AU036730_T1 | *cryptomeria* | 1800 | 33 | 85 | 98.6111111 | 99.6515679 | blastp |
| 454 | dandelion\|gb161\|DY814032_T1 | dandelion | 1801 | 33 | 84 | 82.2916667 | 93.7007874 | blastp |
| 455 | dandelion\|gb161\|DY802714_T1 | dandelion | 1802 | 33 | 82 | 98.2638889 | 99.3031359 | blastp |
| 456 | dandelion\|gb161\|DY822683_T1 | dandelion | 1803 | 33 | 84 | 95.8333333 | 99.6415771 | blastp |
| 457 | dandelion\|gb161\|DY806788_T1 | dandelion | 1804 | 33 | 87 | 98.2638889 | 98.9583333 | blastp |
| 458 | dandelion\|gb161\|DY808781_T1 | dandelion | 1805 | 33 | 84 | 84.0277778 | 99.5918367 | blastp |
| 459 | dandelion\|gb161\|DY810613_T1 | dandelion | 1806 | 33 | 81 | 76.3888889 | 94.8497854 | blastp |
| 460 | fescue\|gb161\|CK803261_T1 | fescue | 1807 | 33 | 85 | 97.9166667 | 98.6111111 | blastp |
| 461 | fescue\|gb161\|DT682664_T1 | fescue | 1808 | 33 | 84 | 67.3611111 | 99.4923858 | blastp |
| 462 | fescue\|gb161\|DT677062_T1 | fescue | 1809 | 33 | 83 | 98.2638889 | 98.9655172 | blastp |
| 463 | fescue\|gb161\|DT679061_T1 | fescue | 1810 | 33 | 86 | 98.2638889 | 98.9619377 | blastp |
| 464 | flax\|gb157.3\|CV478314_T1 | flax | 1811 | 33 | 84 | 71.875 | 99.5260664 | blastp |
| 465 | ginger\|gb164\|DY345344_T1 | ginger | 1812 | 33 | 88 | 98.2638889 | 98.951049 | blastp |
| 466 | ginger\|gb164\|DY358322_T1 | ginger | 1813 | 33 | 85 | 98.2638889 | 98.9473684 | blastp |
| 467 | ginger\|gb164\|DY360757_T1 | ginger | 1814 | 33 | 84 | 98.6111111 | 99.6478873 | blastp |
| 468 | ginger\|gb164\|DY345596_T1 | ginger | 1815 | 33 | 86 | 98.2638889 | 98.9473684 | blastp |
| 469 | grape\|gb160\|AF188844_T1 | grape | 1816 | 33 | 87 | 98.2638889 | 98.9547038 | blastp |
| 470 | grape\|gb160\|AF188843_T1 | grape | 1817 | 33 | 85 | 98.2638889 | 98.951049 | blastp |
| 471 | grape\|gb160\|AF188843_T3 | grape | 1818 | 33 | 85 | 98.2638889 | 98.951049 | blastp |
| 472 | grape\|gb160\|CB971128_T1 | grape | 1819 | 33 | 87 | 98.2638889 | 99.3006993 | blastp |
| 473 | grape\|gb160\|AF188843_T4 | grape | 1820 | 33 | 84 | 72.2222222 | 86.3070539 | blastp |
| 474 | iceplant\|gb164\|MCU26537_T1 | iceplant | 1821 | 33 | 85 | 98.2638889 | 98.9473684 | blastp |
| 475 | iceplant\|gb164\|CIPMIPA_T1 | iceplant | 1822 | 33 | 85 | 98.2638889 | 99.2957746 | blastp |
| 476 | iceplant\|gb164\|CIPMIPB_T1 | iceplant | 1823 | 33 | 87 | 98.2638889 | 98.9473684 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 477 | ipomoea|gb157.2|BM878883_T1 | ipomoea | 1824 | 33 | 87 | 98.9583333 | 99.3031359 | blastp |
| 478 | ipomoea|gb157.2|BJ553988_T1 | ipomoea | 1825 | 33 | 85 | 98.6111111 | 99.6491228 | blastp |
| 479 | ipomoea|gb157.2|BJ553369_T1 | ipomoea | 1826 | 33 | 84 | 98.6111111 | 99.6478873 | blastp |
| 480 | ipomoea|gb157.2|BJ553198_T1 | ipomoea | 1827 | 33 | 89 | 98.9583333 | 99.3031359 | blastp |
| 481 | lettuce|gb157.2|DW079915_T1 | lettuce | 1828 | 33 | 86 | 98.2638889 | 97.9310345 | blastp |
| 482 | lettuce|gb157.2|DW043941_T1 | lettuce | 1829 | 33 | 87 | 98.2638889 | 98.9547038 | blastp |
| 483 | lettuce|gb157.2|DW047538_T1 | lettuce | 1830 | 33 | 87 | 96.875 | 98.245614 | blastp |
| 484 | lettuce|gb157.2|DW104582_T1 | lettuce | 1831 | 33 | 84 | 98.2638889 | 99.3031359 | blastp |
| 485 | lettuce|gb157.2|DW044606_T1 | lettuce | 1832 | 33 | 84 | 98.2638889 | 99.3031359 | blastp |
| 486 | lettuce|gb157.2|DW148209_T1 | lettuce | 1833 | 33 | 85 | 89.2361111 | 94.1605839 | blastp |
| 487 | lettuce|gb157.2|DW148478_T1 | lettuce | 1834 | 33 | 83 | 98.6111111 | 95.3333333 | blastp |
| 488 | lettuce|gb157.2|DW108503_T1 | lettuce | 1835 | 33 | 86 | 98.2638889 | 98.9547038 | blastp |
| 489 | lettuce|gb157.2|DW046100_T1 | lettuce | 1836 | 33 | 86 | 96.875 | 99.6441281 | blastp |
| 490 | lettuce|gb157.2|DW075079_T1 | lettuce | 1837 | 33 | 85 | 98.2638889 | 99.3031359 | blastp |
| 491 | lettuce|gb157.2|DW076402_T1 | lettuce | 1838 | 33 | 87 | 98.2638889 | 98.9547038 | blastp |
| 492 | lettuce|gb157.2|DW084041_T1 | lettuce | 1839 | 33 | 86 | 89.5833333 | 92.8315412 | blastp |
| 493 | lettuce|gb157.2|DW145601_T1 | lettuce | 1840 | 33 | 87 | 98.2638889 | 98.9547038 | blastp |
| 494 | lettuce|gb157.2|CV699980_T1 | lettuce | 1841 | 33 | 86 | 98.2638889 | 98.9547038 | blastp |
| 495 | lettuce|gb157.2|DW064849_T1 | lettuce | 1842 | 33 | 87 | 98.2638889 | 98.9547038 | blastp |
| 496 | lettuce|gb157.2|DW147179_T1 | lettuce | 1843 | 33 | 83 | 98.6111111 | 89.0965732 | blastp |
| 497 | lettuce|gb157.2|DW045991_T1 | lettuce | 1844 | 33 | 83 | 98.6111111 | 97.2789116 | blastp |
| 498 | lotus|gb157.2|AF145707_T1 | lotus | 1845 | 33 | 84 | 98.2638889 | 99.3079585 | blastp |
| 499 | lotus|gb157.2|AI967594_T1 | lotus | 1846 | 33 | 86 | 96.875 | 98.245614 | blastp |
| 500 | lotus|gb157.2|AF145708_T1 | lotus | 1847 | 33 | 87 | 66.6666667 | 100 | blastp |
| 501 | maize|gb164|EC881658_T1 | maize | 1848 | 33 | 86 | 54.5138889 | 98.7421384 | blastp |
| 502 | maize|gb164|AI372377_T1 | maize | 1849 | 33 | 85 | 98.2638889 | 98.9583333 | blastp |
| 503 | maize|gb164|AF145706_T1 | maize | 1850 | 33 | 83 | 60.7638889 | 100 | blastp |
| 504 | maize|gb164|AI855222_T1 | maize | 1851 | 33 | 84 | 98.2638889 | 98.9726027 | blastp |
| 505 | maize|gb164|AI619392_T1 | maize | 1852 | 33 | 86 | 98.2638889 | 98.9619377 | blastp |
| 506 | maize|gb164|AI861086_T1 | maize | 1853 | 33 | 84 | 98.2638889 | 98.9583333 | blastp |
| 507 | medicago|gb157.2|AW684000_T1 | medicago | 1854 | 33 | 84 | 98.2638889 | 99.3079585 | blastp |
| 508 | medicago|gb157.2|AI974398_T1 | medicago | 1855 | 33 | 83 | 98.2638889 | 99.3079585 | blastp |
| 509 | medicago|gb157.2|AL366983_T1 | medicago | 1856 | 33 | 88 | 97.5694444 | 98.6062718 | blastp |
| 510 | medicago|gb157.2|AI737528_T1 | medicago | 1857 | 33 | 84 | 98.6111111 | 99.3103448 | blastp |
| 511 | medicago|gb157.2|BQ151876_T1 | medicago | 1858 | 33 | 84 | 82.2916667 | 87.2262774 | blastp |
| 512 | melon|gb165|DV632745_T1 | melon | 1859 | 33 | 84 | 98.2638889 | 99.3150685 | blastp |
| 513 | melon|gb165|CF674915_T1 | melon | 1860 | 33 | 83 | 98.2638889 | 99.3150685 | blastp |
| 514 | melon|gb165|DV632772_T1 | melon | 1861 | 33 | 85 | 98.2638889 | 98.951049 | blastp |
| 515 | millet|gb161|CD724341_T1 | millet | 1862 | 33 | 83 | 57.2916667 | 92.1787709 | blastp |
| 516 | nicotiana_benthamiana|gb162|ES885295_T1 | nicotiana_benthamiana | 1863 | 33 | 84 | 66.6666667 | 97.9487179 | blastp |
| 517 | oil_palm|gb166|CN600863_T1 | oil_palm | 1864 | 33 | 85 | 98.2638889 | 98.9547038 | blastp |
| 518 | oil_palm|gb166|CN600797_T1 | oil_palm | 1865 | 33 | 86 | 98.2638889 | 98.9547038 | blastp |
| 519 | onion|gb162|AF255796_T1 | onion | 1866 | 33 | 86 | 98.2638889 | 98.9583333 | blastp |
| 520 | papaya|gb165|EX228092_T1 | papaya | 1867 | 33 | 84 | 72.2222222 | 93.2735426 | blastp |
| 521 | papaya|gb165|AJ000031_T1 | papaya | 1868 | 33 | 85 | 98.2638889 | 99.3079585 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 522 | papaya\|gb165\|EX257869_T1 | papaya | 1869 | 33 | 83 | 98.2638889 | 99.3031359 | blastp |
| 523 | papaya\|gb165\|AM903842_T1 | papaya | 1870 | 33 | 90 | 98.2638889 | 98.951049 | blastp |
| 524 | peach\|gb157.2\|BU039203_T1 | peach | 1871 | 33 | 84 | 98.2638889 | 98.9655172 | blastp |
| 525 | peach\|gb157.2\|BU040913_T1 | peach | 1872 | 33 | 90 | 51.3888889 | 98.6666667 | blastp |
| 526 | peanut\|gb161\|CD038184_T1 | peanut | 1873 | 33 | 83 | 98.6111111 | 99.6539792 | blastp |
| 527 | peanut\|gb161\|ES490696_T1 | peanut | 1874 | 33 | 82 | 73.9583333 | 99.5348837 | blastp |
| 528 | peanut\|gb161\|CD038104_T1 | peanut | 1875 | 33 | 83 | 98.2638889 | 99.3079585 | blastp |
| 529 | pepper\|gb157.2\|CA523071_T1 | pepper | 1876 | 33 | 97 | 96.875 | 100 | blastp |
| 530 | pepper\|gb157.2\|BM063708_T1 | pepper | 1877 | 33 | 95 | 99.3055556 | 100 | blastp |
| 531 | periwinkle\|gb164\|EG554502_T1 | periwinkle | 1878 | 33 | 88 | 98.9583333 | 99.3031359 | blastp |
| 532 | periwinkle\|gb164\|EG554518_T1 | periwinkle | 1879 | 33 | 87 | 98.9583333 | 99.3031359 | blastp |
| 533 | periwinkle\|gb164\|EG556773_T1 | periwinkle | 1880 | 33 | 83 | 84.0277778 | 96.8 | blastp |
| 534 | petunia\|gb157.2\|AF452010_T1 | petunia | 1881 | 33 | 93 | 99.3055556 | 100 | blastp |
| 535 | petunia\|gb157.2\|CV292775_T1 | petunia | 1882 | 33 | 92 | 61.8055556 | 100 | blastp |
| 536 | petunia\|gb157.2\|AF452011_T1 | petunia | 1883 | 33 | 86 | 98.2638889 | 99.3006993 | blastp |
| 537 | pine\|gb157.2\|AL751335_T1 | pine | 1884 | 33 | 83 | 98.2638889 | 98.9583333 | blastp |
| 538 | pine\|gb157.2\|AA556193_T1 | pine | 1885 | 33 | 85 | 98.2638889 | 98.9583333 | blastp |
| 539 | pine\|gb157.2\|AL750485_T1 | pine | 1886 | 33 | 85 | 98.2638889 | 98.9583333 | blastp |
| 540 | pineapple\|gb157.2\|DT335964_T1 | pineapple | 1887 | 33 | 83 | 98.2638889 | 97.9452055 | blastp |
| 541 | pineapple\|gb157.2\|DT338557_T1 | pineapple | 1888 | 33 | 86 | 98.2638889 | 98.9583333 | blastp |
| 542 | poplar\|gb157.2\|BU817536_T1 | poplar | 1889 | 33 | 83 | 98.2638889 | 99.3031359 | blastp |
| 543 | poplar\|gb157.2\|AI162483_T1 | poplar | 1890 | 33 | 88 | 98.2638889 | 98.9583333 | blastp |
| 544 | poplar\|gb157.2\|BI122420_T1 | poplar | 1891 | 33 | 87 | 97.9166667 | 99.3031359 | blastp |
| 545 | poplar\|gb157.2\|AI165418_T1 | poplar | 1892 | 33 | 85 | 97.9166667 | 99.3031359 | blastp |
| 546 | poplar\|gb157.2\|BU817536_T3 | poplar | 1893 | 33 | 82 | 88.1944444 | 92.0863309 | blastp |
| 547 | poplar\|gb157.2\|BU881784_T1 | poplar | 1894 | 33 | 83 | 98.2638889 | 99.3031359 | blastp |
| 548 | potato\|gb157.2\|BE923816_T1 | potato | 1895 | 33 | 85 | 98.2638889 | 99.3006993 | blastp |
| 549 | potato\|gb157.2\|CK260061_T1 | potato | 1896 | 33 | 91 | 62.5 | 98.9010989 | blastp |
| 550 | potato\|gb157.2\|BE924585_T1 | potato | 1897 | 33 | 86 | 98.2638889 | 98.9473684 | blastp |
| 551 | potato\|gb157.2\|BF153976_T1 | potato | 1898 | 33 | 86 | 61.1111111 | 100 | blastp |
| 552 | potato\|gb157.2\|AJ487323_T1 | potato | 1899 | 33 | 97 | 100 | 100 | blastp |
| 553 | potato\|gb157.2\|BF154021_T1 | potato | 1900 | 33 | 92 | 99.3055556 | 100 | blastp |
| 554 | potato\|gb157.2\|BG599633_T1 | potato | 1901 | 33 | 95 | 98.9583333 | 99.3031359 | blastp |
| 555 | potato\|gb157.2\|BE922307_T1 | potato | 1902 | 33 | 85 | 98.2638889 | 99.3006993 | blastp |
| 556 | radish\|gb164\|EV536875_T1 | radish | 1903 | 33 | 86 | 98.2638889 | 98.951049 | blastp |
| 557 | radish\|gb164\|EW726189_T1 | radish | 1904 | 33 | 83 | 60.0694444 | 96.1111111 | blastp |
| 558 | radish\|gb164\|EX756217_T1 | radish | 1905 | 33 | 86 | 98.2638889 | 98.951049 | blastp |
| 559 | radish\|gb164\|AB030696_T1 | radish | 1906 | 33 | 86 | 98.2638889 | 98.951049 | blastp |
| 560 | radish\|gb164\|AB030695_T1 | radish | 1907 | 33 | 87 | 98.2638889 | 98.951049 | blastp |
| 561 | radish\|gb164\|AB012044_T1 | radish | 1908 | 33 | 85 | 98.2638889 | 98.951049 | blastp |
| 562 | radish\|gb164\|EV567230_T1 | radish | 1909 | 33 | 87 | 98.2638889 | 98.9547038 | blastp |
| 563 | radish\|gb164\|EY936735_T1 | radish | 1910 | 33 | 86 | 98.2638889 | 98.951049 | blastp |
| 564 | rice\|gb157.2\|U37951_T1 | rice | 1911 | 33 | 86 | 98.2638889 | 98.9619377 | blastp |
| 565 | rice\|gb157.2\|U40140_T1 | rice | 1912 | 33 | 86 | 98.2638889 | 98.9583333 | blastp |
| 566 | rice\|gb157.2\|BE039992_T1 | rice | 1913 | 33 | 82 | 98.2638889 | 98.9583333 | blastp |
| 567 | rice\|gb157.2\|U37951_T2 | rice | 1914 | 33 | 86 | 73.6111111 | 99.0654206 | blastp |
| 568 | rose\|gb157.2\|BQ104887_T1 | rose | 1915 | 33 | 83 | 97.5694444 | 98.6206897 | blastp |
| 569 | rose\|gb157.2\|BQ103877_T1 | rose | 1916 | 33 | 85 | 98.2638889 | 98.9547038 | blastp |
| 570 | rose\|gb157.2\|EC586734_T1 | rose | 1917 | 33 | 80 | 62.1527778 | 99.4444444 | blastp |
| 571 | rye\|gb164\|BE586240_T1 | rye | 1918 | 33 | 83 | 98.2638889 | 98.9726027 | blastp |
| 572 | safflower\|gb162\|EL407054_T1 | safflower | 1919 | 33 | 86 | 89.5833333 | 94.5454545 | blastp |
| 573 | safflower\|gb162\|EL400504_T1 | safflower | 1920 | 33 | 85 | 98.2638889 | 92.5081433 | blastp |
| 574 | safflower\|gb162\|EL400004_T1 | safflower | 1921 | 33 | 83 | 84.375 | 99.5934959 | blastp |
| 575 | sesame\|gb157.2\|BU668587_T1 | sesame | 1922 | 33 | 91 | 57.2916667 | 100 | blastp |
| 576 | sesame\|gb157.2\|BU669929_T1 | sesame | 1923 | 33 | 87 | 55.2083333 | 99.375 | blastp |
| 577 | sorghum\|gb161.xeno\|AI372377_T1 | sorghum | 1924 | 33 | 85 | 98.2638889 | 98.9583333 | blastp |
| 578 | sorghum\|gb161.xeno\|AI861086_T1 | sorghum | 1925 | 33 | 82 | 98.2638889 | 98.9655172 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 579 | sorghum|gb161.xeno|SBU87981__T1 | sorghum | 1926 | 33 | 86 | 98.2638889 | 98.9619377 | blastp |
| 580 | soybean|gb166|CD401115__T1 | soybean | 1927 | 33 | 82 | 98.2638889 | 99.3031359 | blastp |
| 581 | soybean|gb166|AW348556__T1 | soybean | 1928 | 33 | 84 | 98.6111111 | 99.6539792 | blastp |
| 582 | soybean|gb166|BE352670__T1 | soybean | 1929 | 33 | 86 | 98.2638889 | 98.9547038 | blastp |
| 583 | soybean|gb166|BI967765__T1 | soybean | 1930 | 33 | 86 | 98.2638889 | 98.9619377 | blastp |
| 584 | soybean|gb166|BE661219__T1 | soybean | 1931 | 33 | 82 | 98.2638889 | 99.3079585 | blastp |
| 585 | soybean|gb166|BE352747__T5 | soybean | 1932 | 33 | 81 | 88.1944444 | 98.4732824 | blastp |
| 586 | soybean|gb166|CD416359__T1 | soybean | 1933 | 33 | 85 | 97.5694444 | 98.6013986 | blastp |
| 587 | soybean|gb166|AW350352__T1 | soybean | 1934 | 33 | 84 | 97.5694444 | 98.6013986 | blastp |
| 588 | soybean|gb166|BE352747__T1 | soybean | 1935 | 33 | 82 | 98.2638889 | 99.3079585 | blastp |
| 589 | soybean|gb166|BE820629__T1 | soybean | 1936 | 33 | 85 | 98.2638889 | 99.2957746 | blastp |
| 590 | spikemoss|gb165|DN838148__T4 | spikemoss | 1937 | 33 | 82 | 51.0416667 | 99.3243243 | blastp |
| 591 | spruce|gb162|CO224550__T1 | spruce | 1938 | 33 | 80 | 96.875 | 98.9473684 | blastp |
| 592 | spruce|gb162|CO216100__T1 | spruce | 1939 | 33 | 86 | 98.2638889 | 98.9726027 | blastp |
| 593 | spruce|gb162|CO216028__T1 | spruce | 1940 | 33 | 85 | 98.2638889 | 98.9583333 | blastp |
| 594 | spurge|gb161|BG354070__T1 | spurge | 1941 | 33 | 87 | 97.9166667 | 98.2638889 | blastp |
| 595 | strawberry|gb164|CO378647__T1 | strawberry | 1942 | 33 | 82 | 98.2638889 | 99.3103448 | blastp |
| 596 | strawberry|gb164|CX661400__T1 | strawberry | 1943 | 33 | 84 | 98.2638889 | 98.9547038 | blastp |
| 597 | strawberry|gb164|DV438296__T1 | strawberry | 1944 | 33 | 83 | 98.2638889 | 98.951049 | blastp |
| 598 | sugarcane|gb157.2|CA264801__T1 | sugarcane | 1945 | 33 | 80 | 60.0694444 | 88.8888889 | blastp |
| 599 | sugarcane|gb157.2|CA086058__T1 | sugarcane | 1946 | 33 | 85 | 98.2638889 | 98.9583333 | blastp |
| 600 | sugarcane|gb157.2|CA071197__T1 | sugarcane | 1947 | 33 | 84 | 97.2222222 | 98.2638889 | blastp |
| 601 | sugarcane|gb157.2|BQ530399__T1 | sugarcane | 1948 | 33 | 84 | 91.6666667 | 99.2537313 | blastp |
| 602 | sugarcane|gb157.2|CA085969__T1 | sugarcane | 1949 | 33 | 82 | 74.3055556 | 99.5391705 | blastp |
| 603 | sugarcane|gb157.2|CA074778__T1 | sugarcane | 1950 | 33 | 84 | 71.1805556 | 93.6936937 | blastp |
| 604 | sugarcane|gb157.2|CA130651__T1 | sugarcane | 1951 | 33 | 81 | 62.1527778 | 99.4505495 | blastp |
| 605 | sugarcane|gb157.2|AA525652__T1 | sugarcane | 1952 | 33 | 88 | 53.4722222 | 98.7179487 | blastp |
| 606 | sugarcane|gb157.2|BQ536359__T1 | sugarcane | 1953 | 33 | 86 | 98.2638889 | 98.9619377 | blastp |
| 607 | sunflower|gb162|DY909123__T1 | sunflower | 1954 | 33 | 86 | 98.2638889 | 98.9547038 | blastp |
| 608 | sunflower|gb162|CD846367__T1 | sunflower | 1955 | 33 | 85 | 98.2638889 | 98.9547038 | blastp |
| 609 | sunflower|gb162|CD846084__T1 | sunflower | 1956 | 33 | 86 | 98.2638889 | 98.9547038 | blastp |
| 610 | sunflower|gb162|DY915760__T1 | sunflower | 1957 | 33 | 84 | 72.2222222 | 100 | blastp |
| 611 | sunflower|gb162|CF080940__T1 | sunflower | 1958 | 33 | 83 | 73.6111111 | 99.5327103 | blastp |
| 612 | sunflower|gb162|CF087907__T1 | sunflower | 1959 | 33 | 83 | 96.875 | 97.5694444 | blastp |
| 613 | sunflower|gb162|CX946986__T1 | sunflower | 1960 | 33 | 84 | 98.2638889 | 98.6111111 | blastp |
| 614 | sunflower|gb162|DY918780__T1 | sunflower | 1961 | 33 | 87 | 73.6111111 | 99.0697674 | blastp |
| 615 | switchgrass|gb165|FE619753__T1 | switchgrass | 1962 | 33 | 86 | 98.2638889 | 98.9583333 | blastp |
| 616 | switchgrass|gb165|DN142591__T1 | switchgrass | 1963 | 33 | 85 | 98.2638889 | 98.9583333 | blastp |
| 617 | switchgrass|gb165|DN141716__T1 | switchgrass | 1964 | 33 | 85 | 98.2638889 | 98.9619377 | blastp |
| 618 | switchgrass|gb165|DN141343__T1 | switchgrass | 1965 | 33 | 86 | 98.2638889 | 98.9583333 | blastp |
| 619 | switchgrass|gb165|DN142037__T1 | switchgrass | 1966 | 33 | 85 | 98.2638889 | 98.9619377 | blastp |
| 620 | thellungiella|gb157.2|DN774595__T1 | thellungiella | 1967 | 33 | 85 | 98.2638889 | 98.951049 | blastp |
| 621 | thellungiella|gb157.2|BM986095__T1 | thellungiella | 1968 | 33 | 86 | 98.2638889 | 98.951049 | blastp |
| 622 | thellungiella|gb157.2|BI698563__T1 | thellungiella | 1969 | 33 | 85 | 72.5694444 | 99.5238095 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 623 | tobacco|gb162|EB426225_T1 | tobacco | 1970 | 33 | 87 | 98.2638889 | 98.2578397 | blastp |
| 624 | tobacco|gb162|CK720591_T1 | tobacco | 1971 | 33 | 95 | 99.3055556 | 99.6515679 | blastp |
| 625 | tobacco|gb162|CK720595_T1 | tobacco | 1972 | 33 | 96 | 73.6111111 | 99.0654206 | blastp |
| 626 | tobacco|gb162|EB427872_T1 | tobacco | 1973 | 33 | 88 | 98.2638889 | 99.2982456 | blastp |
| 627 | tobacco|gb162|CK720593_T1 | tobacco | 1974 | 33 | 87 | 97.9166667 | 98.9473684 | blastp |
| 628 | tobacco|gb162|AF024511_T1 | tobacco | 1975 | 33 | 95 | 99.3055556 | 99.6515679 | blastp |
| 629 | tobacco|gb162|CK720596_T1 | tobacco | 1976 | 33 | 96 | 98.9583333 | 99.3031359 | blastp |
| 630 | tobacco|gb162|NTU62280_T1 | tobacco | 1977 | 33 | 96 | 98.9583333 | 99.3031359 | blastp |
| 631 | tomato|gb164|AW622243_T1 | tomato | 1978 | 33 | 94 | 98.9583333 | 99.3031359 | blastp |
| 632 | tomato|gb164|BG123213_T1 | tomato | 1979 | 33 | 94 | 99.3055556 | 100 | blastp |
| 633 | tomato|gb164|AI637363_T1 | tomato | 1980 | 33 | 87 | 98.2638889 | 98.9473684 | blastp |
| 634 | tomato|gb164|BG123955_T1 | tomato | 1981 | 33 | 85 | 98.2638889 | 99.3006993 | blastp |
| 635 | tomato|gb164|BP876517_T1 | tomato | 1982 | 33 | 80 | 55.9027778 | 86.8705036 | tblastn |
| 636 | triphysaria|gb164|BM357654_T1 | triphysaria | 1983 | 33 | 86 | 73.6111111 | 99.5305164 | blastp |
| 637 | triphysaria|gb164|EY141207_T1 | triphysaria | 1984 | 33 | 90 | 65.625 | 99.4736842 | blastp |
| 638 | triphysaria|gb164|DR174621_T1 | triphysaria | 1985 | 33 | 87 | 69.0972222 | 100 | blastp |
| 639 | triphysaria|gb164|BM356761_T1 | triphysaria | 1986 | 33 | 86 | 88.5416667 | 99.6108949 | blastp |
| 640 | triphysaria|gb164|DR169763_T1 | triphysaria | 1987 | 33 | 87 | 98.2638889 | 99.6466431 | blastp |
| 641 | triphysaria|gb164|BM356902_T1 | triphysaria | 1988 | 33 | 86 | 96.5277778 | 99.6428571 | blastp |
| 642 | triphysaria|gb164|DR174271_T1 | triphysaria | 1989 | 33 | 86 | 92.7083333 | 97.4545455 | blastp |
| 643 | triphysaria|gb164|DR171777_T1 | triphysaria | 1990 | 33 | 88 | 100 | 99.6539792 | blastp |
| 644 | wheat|gb164|BE406715_T1 | wheat | 1991 | 33 | 83 | 98.2638889 | 98.9726027 | blastp |
| 645 | wheat|gb164|BQ838456_T1 | wheat | 1992 | 33 | 83 | 98.2638889 | 98.9726027 | blastp |
| 646 | wheat|gb164|BE426386_T1 | wheat | 1993 | 33 | 82 | 98.2638889 | 98.9726027 | blastp |
| 647 | wheat|gb164|BE403388_T1 | wheat | 1994 | 33 | 88 | 51.0416667 | 98.6577181 | blastp |
| 648 | wheat|gb164|BE403307_T1 | wheat | 1995 | 33 | 83 | 98.2638889 | 98.9726027 | blastp |
| 649 | wheat|gb164|BE498268_T1 | wheat | 1996 | 33 | 81 | 60.4166667 | 96.7213115 | blastp |
| 650 | wheat|gb164|AL828763_T1 | wheat | 1997 | 33 | 84 | 84.7222222 | 96.4705882 | blastp |
| 651 | wheat|gb164|AF139816_T1 | wheat | 1998 | 33 | 83 | 98.2638889 | 98.9726027 | blastp |
| 652 | wheat|gb164|BE216990_T1 | wheat | 1999 | 33 | 86 | 98.2638889 | 98.9583333 | blastp |
| 653 | wheat|gb164|BE403886_T1 | wheat | 2000 | 33 | 85 | 99.3055556 | 99.6551724 | blastp |
| 654 | wheat|gb164|BE430165_T1 | wheat | 2001 | 33 | 85 | 99.3055556 | 99.6551724 | blastp |
| 655 | wheat|gb164|CA484202_T1 | wheat | 2002 | 33 | 87 | 56.9444444 | 97.6190476 | blastp |
| 656 | wheat|gb164|BE404199_T1 | wheat | 2003 | 33 | 86 | 98.2638889 | 98.9583333 | blastp |
| 657 | wheat|gb164|BE406086_T1 | wheat | 2004 | 33 | 83 | 98.2638889 | 98.9726027 | blastp |
| 658 | wheat|gb164|BF293776_T1 | wheat | 2005 | 33 | 83 | 98.2638889 | 98.9655172 | blastp |
| 659 | wheat|gb164|CK193386_T1 | wheat | 2006 | 33 | 81 | 97.2222222 | 96.6216216 | blastp |
| 660 | castorbean|gb160|AJ605572_T1 | castorbean | 2007 | 34 | 80 | 99.1902834 | 98.7854251 | blastp |
| 661 | citrus|gb157.2|CK740163_T1 | citrus | 2008 | 34 | 80 | 99.1902834 | 98.7854251 | blastp |
| 662 | coffea|gb157.2|DV664793_T1 | coffea | 2009 | 34 | 80 | 100 | 100 | blastp |
| 663 | lettuce|gb157.2|DW074942_T1 | lettuce | 2010 | 34 | 80 | 99.1902834 | 99.5934959 | blastp |
| 664 | pepper|gb157.2|BM063938_T1 | pepper | 2011 | 34 | 95 | 76.1133603 | 100 | blastp |
| 665 | periwinkle|gb164|EG558295_T1 | periwinkle | 2012 | 34 | 81 | 99.1902834 | 98.7903226 | blastp |
| 666 | potato|gb157.2|BM112462_T1 | potato | 2013 | 34 | 98 | 94.7368421 | 99.5744681 | blastp |
| 667 | tobacco|gb162|AJ237751_T1 | tobacco | 2014 | 34 | 95 | 100 | 100 | blastp |
| 668 | tobacco|gb162|EB425012_T1 | tobacco | 2015 | 34 | 93 | 100 | 100 | blastp |
| 669 | nicotiana_benthamiana|gb162|CK284579_T1 | nicotiana_benthamiana | 2016 | 35 | 86 | 74.617737 | 97.5903614 | blastp |
| 670 | potato|gb157.2|BG594926_T1 | potato | 2017 | 35 | 96 | 100 | 96.4497041 | blastp |
| 671 | tomato|gb164|DB679435_T1 | tomato | 2018 | 35 | 90 | 76.146789 | 100 | blastp |
| 672 | tobacco|gb162|CK720588_T1 | tobacco | 2019 | 36 | 81 | 53.5580524 | 100 | blastp |
| 673 | apple|gb157.3|CN494715_T1 | apple | 2020 | 37 | 84 | 85.7142857 | 94.7368421 | blastp |
| 674 | apple|gb157.3|CO066689_T1 | apple | 2021 | 37 | 81 | 94.2857143 | 76.1538462 | blastp |
| 675 | castorbean|gb160|MDL30026M001488_T1 | castorbean | 2022 | 37 | 90 | 95.2380952 | 36.900369 | blastp |
| 676 | citrus|gb157.2|CX300349_T1 | citrus | 2023 | 37 | 83 | 99.047619 | 72.7272727 | blastp |
| 677 | coffea|gb157.2|DV663640_T1 | coffea | 2024 | 37 | 80 | 93.3333333 | 34.5070423 | blastp |
| 678 | cowpea|gb166|FF395821_T1 | cowpea | 2025 | 37 | 82 | 93.3333333 | 95.1456311 | blastp |
| 679 | cowpea|gb166|FF395821_T2 | cowpea | 2026 | 37 | 82 | 94.2857143 | 13.2450331 | tblastn |
| 680 | ipomoea|gb157.2|CJ769054_T1 | ipomoea | 2027 | 37 | 87 | 100 | 59.3220339 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 681 | lettuce\|gb157.2\|CV699989_T1 | lettuce | 2028 | 37 | 83 | 98.0952381 | 36.5248227 | blastp |
| 682 | medicago\|gb157.2\|AW208262_T1 | medicago | 2029 | 37 | 80 | 95.2380952 | 37.1747212 | blastp |
| 683 | melon\|gb165\|AM727408_T1 | melon | 2030 | 37 | 82 | 97.1428571 | 36.9565217 | blastp |
| 684 | poplar\|gb157.2\|CN517706_T1 | poplar | 2031 | 37 | 84 | 96.1904762 | 36.5942029 | blastp |
| 685 | poplar\|gb157.2\|BU813630_T1 | poplar | 2032 | 37 | 84 | 99.047619 | 37.6811594 | blastp |
| 686 | potato\|gb157.2\|DN587628_T1 | potato | 2033 | 37 | 90 | 96.1904762 | 93.5185185 | blastp |
| 687 | rice\|gb157.2\|BI805522_T1 | rice | 2034 | 37 | 80 | 97.1428571 | 35.915493 | blastp |
| 688 | soybean\|gb166\|FK397604_T1 | soybean | 2035 | 37 | 82 | 54.2857143 | 98.2758621 | blastp |
| 689 | sunflower\|gb162\|DY951259_T1 | sunflower | 2036 | 37 | 82 | 98.0952381 | 39.0151515 | blastp |
| 690 | sunflower\|gb162\|DY942645_T1 | sunflower | 2037 | 37 | 83 | 98.0952381 | 37.3188406 | blastp |
| 691 | triphysaria\|gb164\|EY130232_T1 | triphysaria | 2038 | 37 | 85 | 99.047619 | 37.6811594 | blastp |
| 692 | arabidopsis\|gb165\|AT4G10380_T1 | arabidopsis | 2039 | 38 | 80 | 97.6271186 | 96.0526316 | blastp |
| 693 | artemisia\|gb164\|EY089420_T1 | artemisia | 2040 | 38 | 87 | 55.5932203 | 100 | blastp |
| 694 | artemisia\|gb164\|EY113317_T1 | artemisia | 2041 | 38 | 89 | 51.8644068 | 100 | blastp |
| 695 | b_oleracea\|gb161\|AM391026_T1 | b_oleracea | 2042 | 38 | 81 | 93.8983051 | 95.862069 | blastp |
| 696 | b_rapa\|gb162\|CV545128_T1 | b_rapa | 2043 | 38 | 81 | 97.6271186 | 96.013289 | blastp |
| 697 | canola\|gb161\|ES903871_T1 | canola | 2044 | 38 | 85 | 52.2033898 | 100 | blastp |
| 698 | cassava\|gb164\|CK641734_T1 | cassava | 2045 | 38 | 89 | 93.8983051 | 98.9247312 | blastp |
| 699 | castorbean\|gb160\|EG668085_T1 | castorbean | 2046 | 38 | 85 | 100 | 100 | blastp |
| 700 | castorbean\|gb160\|EG668085_T2 | castorbean | 2047 | 38 | 90 | 62.0338983 | 100 | blastp |
| 701 | centaurea\|gb161\|EH739099_T1 | centaurea | 2048 | 38 | 83 | 69.1525424 | 98.0487805 | blastp |
| 702 | centaurea\|gb161\|EH710762_T1 | centaurea | 2049 | 38 | 89 | 80.6779661 | 95.9677419 | blastp |
| 703 | citrus\|gb157.2\|CX299695_T1 | citrus | 2050 | 38 | 98 | 62.0338983 | 100 | blastp |
| 704 | citrus\|gb157.2\|CO912981_T1 | citrus | 2051 | 38 | 80 | 100 | 100 | blastp |
| 705 | citrus\|gb157.2\|CO912981_T2 | citrus | 2052 | 38 | 81 | 78.3050847 | 95.5465587 | blastp |
| 706 | cotton\|gb164\|CO071578_T1 | cotton | 2053 | 38 | 90 | 77.9661017 | 95.4356846 | blastp |
| 707 | cotton\|gb164\|BE052767_T1 | cotton | 2054 | 38 | 88 | 86.440678 | 100 | blastp |
| 708 | grape\|gb160\|CB350030_T1 | grape | 2055 | 38 | 86 | 100 | 100 | blastp |
| 709 | lettuce\|gb157.2\|DW123895_T1 | lettuce | 2056 | 38 | 86 | 97.6271186 | 96.6555184 | blastp |
| 710 | melon\|gb165\|AM726471_T1 | melon | 2057 | 38 | 80 | 78.6440678 | 92.8 | blastp |
| 711 | nicotiana_benthamiana\|gb162\|CK281387_T1 | nicotiana_benthamiana | 2058 | 38 | 94 | 100 | 100 | blastp |
| 712 | onion\|gb162\|CF436356_T1 | onion | 2059 | 38 | 83 | 86.1016949 | 98.0988593 | blastp |
| 713 | poplar\|gb157.2\|BU895174_T1 | poplar | 2060 | 38 | 84 | 97.6271186 | 96.3333333 | blastp |
| 714 | poplar\|gb157.2\|BI126692_T1 | poplar | 2061 | 38 | 85 | 100 | 100 | blastp |
| 715 | radish\|gb164\|EX772276_T1 | radish | 2062 | 38 | 87 | 62.0338983 | 100 | blastp |
| 716 | safflower\|gb162\|EL376221_T1 | safflower | 2063 | 38 | 87 | 55.5932203 | 94.2528736 | blastp |
| 717 | soybean\|gb166\|AW351195_T1 | soybean | 2064 | 38 | 83 | 57.2881356 | 100 | blastp |
| 718 | spurge\|gb161\|DV120704_T1 | spurge | 2065 | 38 | 81 | 66.1016949 | 100 | blastp |
| 719 | strawberry\|gb164\|EX663538_T1 | strawberry | 2066 | 38 | 87 | 73.559322 | 100 | blastp |
| 720 | sunflower\|gb162\|BQ915292_T1 | sunflower | 2067 | 38 | 83 | 69.8305085 | 95.0636943 | tblastn |
| 721 | tobacco\|gb162\|EB426773_T1 | tobacco | 2068 | 38 | 94 | 100 | 100 | blastp |
| 722 | triphysaria\|gb164\|EY008469_T1 | triphysaria | 2069 | 38 | 90 | 67.7966102 | 100 | blastp |
| 723 | pepper\|gb157.2\|BM066463_T1 | pepper | 2070 | 39 | 91 | 60 | 100 | blastp |
| 724 | tobacco\|gb162\|EB445778_T1 | tobacco | 2071 | 39 | 88 | 85.8333333 | 100 | blastp |
| 725 | pepper\|gb157.2\|CA515996_T1 | pepper | 2072 | 40 | 82 | 64.4628099 | 100 | blastp |
| 726 | potato\|gb157.2\|BE341068_T1 | potato | 2073 | 40 | 92 | 100 | 100 | blastp |
| 727 | potato\|gb157.2\|BG887984_T1 | potato | 2074 | 41 | 100 | 79.4238683 | 91.4691943 | blastp |
| 728 | apple\|gb157.3\|CN898142_T1 | apple | 2075 | 42 | 86 | 70.9677419 | 98.0582524 | blastp |
| 729 | apple\|gb157.3\|CN492544_T1 | apple | 2076 | 42 | 82 | 99.6415771 | 98.9399293 | blastp |
| 730 | apple\|gb157.3\|CN495819_T1 | apple | 2077 | 42 | 84 | 99.6415771 | 98.9547038 | blastp |
| 731 | apple\|gb157.3\|CN869175_T1 | apple | 2078 | 42 | 86 | 100 | 100 | blastp |
| 732 | apple\|gb157.3\|CN488973_T1 | apple | 2079 | 42 | 87 | 100 | 100 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 733 | apricot\|gb157.2\|CB820380_T1 | apricot | 2080 | 42 | 88 | 69.8924731 | 98.4848485 | blastp |
| 734 | aquilegia\|gb157.3\|DR921860_T1 | aquilegia | 2081 | 42 | 85 | 94.9820789 | 100 | blastp |
| 735 | arabidopsis\|gb165\|AT2G37170_T1 | arabidopsis | 2082 | 42 | 80 | 100 | 99.2982456 | blastp |
| 736 | arabidopsis\|gb165\|AT3G54820_T1 | arabidopsis | 2083 | 42 | 81 | 95.6989247 | 94.7552448 | blastp |
| 737 | arabidopsis\|gb165\|AT3G53420_T1 | arabidopsis | 2084 | 42 | 81 | 100 | 99.3031359 | blastp |
| 738 | arabidopsis\|gb165\|AT5G60660_T1 | arabidopsis | 2085 | 42 | 80 | 99.2831541 | 97.2508591 | blastp |
| 739 | artemisia\|gb164\|EY056827_T1 | artemisia | 2086 | 42 | 89 | 79.5698925 | 100 | blastp |
| 740 | artemisia\|gb164\|EY033689_T1 | artemisia | 2087 | 42 | 83 | 100 | 100 | blastp |
| 741 | artemisia\|gb164\|EY032199_T1 | artemisia | 2088 | 42 | 81 | 100 | 100 | blastp |
| 742 | artemisia\|gb164\|EY042731_T1 | artemisia | 2089 | 42 | 88 | 100 | 100 | blastp |
| 743 | artemisia\|gb164\|EX980079_T1 | artemisia | 2090 | 42 | 82 | 99.6415771 | 98.9473684 | blastp |
| 744 | avocado\|gb164\|CK754546_T1 | avocado | 2091 | 42 | 86 | 51.6129032 | 97.2972973 | blastp |
| 745 | b_juncea\|gb164\|EVGN00454408761136_T1 | b_juncea | 2092 | 42 | 81 | 100 | 99.2982456 | blastp |
| 746 | b_juncea\|gb164\|EVGN00454408761136_T2 | b_juncea | 2093 | 42 | 81 | 98.9247312 | 97.9020979 | blastp |
| 747 | b_juncea\|gb164\|EVGN00748222952488_T2 | b_juncea | 2094 | 42 | 80 | 100 | 88.7850467 | blastp |
| 748 | b_juncea\|gb164\|EVGN00204411253360_T1 | b_juncea | 2095 | 42 | 84 | 82.078853 | 97.8991597 | blastp |
| 749 | b_juncea\|gb164\|EVGN00054208600715_T1 | b_juncea | 2096 | 42 | 80 | 100 | 99.2982456 | blastp |
| 750 | b_juncea\|gb164\|EVGN00049614332152_T1 | b_juncea | 2097 | 42 | 83 | 64.516129 | 96.2566845 | blastp |
| 751 | b_juncea\|gb164\|EVGN01023711071914_T1 | b_juncea | 2098 | 42 | 85 | 58.4229391 | 100 | blastp |
| 752 | b_juncea\|gb164\|EVGN00247216171316_T1 | b_juncea | 2099 | 42 | 81 | 100 | 99.3031359 | blastp |
| 753 | b_juncea\|gb164\|EVGN00778009020884_T1 | b_juncea | 2100 | 42 | 88 | 64.1577061 | 100 | blastp |
| 754 | b_juncea\|gb164\|EVGN02648808940517_T1 | b_juncea | 2101 | 42 | 85 | 53.4050179 | 98.6754967 | blastp |
| 755 | b_juncea\|gb164\|EVGN00316414413452_T1 | b_juncea | 2102 | 42 | 82 | 82.7956989 | 100 | blastp |
| 756 | b_juncea\|gb164\|DT317706_T1 | b_juncea | 2103 | 42 | 81 | 100 | 99.3031359 | blastp |
| 757 | b_juncea\|gb164\|EVGN00748222952488_T1 | b_juncea | 2104 | 42 | 81 | 100 | 99.3031359 | blastp |
| 758 | b_oleracea\|gb161\|AM386520_T1 | b_oleracea | 2105 | 42 | 80 | 100 | 100 | blastp |
| 759 | b_oleracea\|gb161\|AM058395_T1 | b_oleracea | 2106 | 42 | 83 | 57.3476703 | 91.954023 | blastp |
| 760 | b_oleracea\|gb161\|AM385504_T1 | b_oleracea | 2107 | 42 | 81 | 100 | 99.2982456 | blastp |
| 761 | b_rapa\|gb162\|BG544498_T1 | b_rapa | 2108 | 42 | 81 | 100 | 100 | blastp |
| 762 | b_rapa\|gb162\|BQ791962_T2 | b_rapa | 2109 | 42 | 81 | 100 | 99.2982456 | blastp |
| 763 | b_rapa\|gb162\|BQ791962_T1 | b_rapa | 2110 | 42 | 81 | 100 | 99.2982456 | blastp |
| 764 | b_rapa\|gb162\|EX065729_T1 | b_rapa | 2111 | 42 | 81 | 92.1146953 | 100 | blastp |
| 765 | b_rapa\|gb162\|CA992278_T1 | b_rapa | 2112 | 42 | 83 | 89.9641577 | 98.8372093 | blastp |
| 766 | b_rapa\|gb162\|CO749284_T1 | b_rapa | 2113 | 42 | 81 | 100 | 99.2982456 | blastp |
| 767 | barley\|gb157.3\|BE412486_T1 | barley | 2114 | 42 | 81 | 100 | 100 | blastp |
| 768 | bean\|gb164\|CB542746_T1 | bean | 2115 | 42 | 80 | 100 | 100 | blastp |
| 769 | bean\|gb164\|CB280567_T1 | bean | 2116 | 42 | 86 | 99.6415771 | 98.9473684 | blastp |
| 770 | bean\|gb164\|BQ481649_T1 | bean | 2117 | 42 | 82 | 100 | 100 | blastp |
| 771 | bean\|gb164\|CV532291_T1 | bean | 2118 | 42 | 86 | 99.6415771 | 98.9547038 | blastp |
| 772 | brachypodium\|gb161.xeno\|BE416137_T1 | brachypodium | 2119 | 42 | 80 | 94.9820789 | 100 | blastp |
| 773 | brachypodium\|gb161.xeno\|AF139814_T1 | brachypodium | 2120 | 42 | 80 | 100 | 100 | blastp |
| 774 | canola\|gb161\|CN729066_T1 | canola | 2121 | 42 | 81 | 100 | 99.3031359 | blastp |
| 775 | canola\|gb161\|DQ068169_T1 | canola | 2122 | 42 | 81 | 100 | 99.2982456 | blastp |
| 776 | canola\|gb161\|AF118382_T1 | canola | 2123 | 42 | 81 | 100 | 99.3031359 | blastp |
| 777 | canola\|gb161\|AF118383_T1 | canola | 2124 | 42 | 81 | 100 | 100 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 778 | canola\|gb161\|CD819509_T1 | canola | 2125 | 42 | 80 | 100 | 99.2982456 | blastp |
| 779 | canola\|gb161\|EE419467_T1 | canola | 2126 | 42 | 81 | 100 | 100 | blastp |
| 780 | canola\|gb161\|EE459735_T1 | canola | 2127 | 42 | 81 | 100 | 99.2982456 | blastp |
| 781 | canola\|gb161\|CX192356_T1 | canola | 2128 | 42 | 80 | 100 | 100 | blastp |
| 782 | canola\|gb161\|CN827413_T1 | canola | 2129 | 42 | 81 | 100 | 99.2982456 | blastp |
| 783 | canola\|gb161\|EE432011_T1 | canola | 2130 | 42 | 81 | 100 | 99.2982456 | blastp |
| 784 | cassava\|gb164\|DB922106_T1 | cassava | 2131 | 42 | 81 | 93.90681 | 92.5266904 | blastp |
| 785 | cassava\|gb164\|CK640888_T1 | cassava | 2132 | 42 | 83 | 100 | 100 | blastp |
| 786 | cassava\|gb164\|CK642866_T1 | cassava | 2133 | 42 | 84 | 99.6415771 | 98.951049 | blastp |
| 787 | cassava\|gb164\|CK642551_T1 | cassava | 2134 | 42 | 86 | 100 | 99.3055556 | blastp |
| 788 | castorbean\|gb160\|AJ605565_T1 | castorbean | 2135 | 42 | 86 | 100 | 99.3055556 | blastp |
| 789 | castorbean\|gb160\|AJ605568_T1 | castorbean | 2136 | 42 | 87 | 99.6415771 | 98.9399293 | blastp |
| 790 | castorbean\|gb160\|EE259660_T1 | castorbean | 2137 | 42 | 85 | 100 | 100 | blastp |
| 791 | centaurea\|gb161\|EL933765_T1 | centaurea | 2138 | 42 | 84 | 87.0967742 | 92.8571429 | blastp |
| 792 | centaurea\|gb161\|EL931761_T1 | centaurea | 2139 | 42 | 82 | 75.9856631 | 89.2561983 | blastp |
| 793 | cichorium\|gb161\|DT212328_T1 | cichorium | 2140 | 42 | 86 | 100 | 100 | blastp |
| 794 | citrus\|gb157.2\|BQ625054_T1 | citrus | 2141 | 42 | 83 | 100 | 100 | blastp |
| 795 | citrus\|gb157.2\|CF509045_T1 | citrus | 2142 | 42 | 86 | 100 | 99.3031359 | blastp |
| 796 | citrus\|gb157.2\|CB291797_T1 | citrus | 2143 | 42 | 80 | 100 | 84.0707965 | blastp |
| 797 | citrus\|gb157.2\|BQ623325_T1 | citrus | 2144 | 42 | 86 | 100 | 99.3031359 | blastp |
| 798 | citrus\|gb157.2\|BQ623742_T1 | citrus | 2145 | 42 | 88 | 94.9820789 | 99.2619926 | blastp |
| 799 | citrus\|gb157.2\|CF417769_T1 | citrus | 2146 | 42 | 83 | 100 | 99.3031359 | blastp |
| 800 | citrus\|gb157.2\|BQ623128_T1 | citrus | 2147 | 42 | 88 | 68.4587814 | 98.9637306 | blastp |
| 801 | citrus\|gb157.2\|CB293000_T1 | citrus | 2148 | 42 | 82 | 93.1899642 | 98.8847584 | blastp |
| 802 | citrus\|gb157.2\|BQ622991_T1 | citrus | 2149 | 42 | 84 | 96.4157706 | 98.5559567 | blastp |
| 803 | citrus\|gb157.2\|CF503882_T1 | citrus | 2150 | 42 | 83 | 100 | 100 | blastp |
| 804 | cotton\|gb164\|BE052942_T1 | cotton | 2151 | 42 | 84 | 99.2831541 | 98.5815603 | blastp |
| 805 | cotton\|gb164\|AF064467_T1 | cotton | 2152 | 42 | 80 | 100 | 100 | blastp |
| 806 | cotton\|gb164\|BG443494_T1 | cotton | 2153 | 42 | 85 | 100 | 99.2982456 | blastp |
| 807 | cotton\|gb164\|CO086106_T1 | cotton | 2154 | 42 | 88 | 70.2508961 | 100 | blastp |
| 808 | cotton\|gb164\|BQ406033_T1 | cotton | 2155 | 42 | 82 | 100 | 99.2982456 | blastp |
| 809 | cotton\|gb164\|CO109551_T1 | cotton | 2156 | 42 | 82 | 100 | 100 | blastp |
| 810 | cotton\|gb164\|DV437970_T1 | cotton | 2157 | 42 | 80 | 64.1577061 | 95.3608247 | blastp |
| 811 | cotton\|gb164\|AI725803_T1 | cotton | 2158 | 42 | 84 | 100 | 99.2982456 | blastp |
| 812 | cotton\|gb164\|CD486305_T1 | cotton | 2159 | 42 | 81 | 98.9247312 | 94.0199336 | blastp |
| 813 | cowpea\|gb166\|ES884222_T2 | cowpea | 2160 | 42 | 85 | 86.3799283 | 93.5606061 | blastp |
| 814 | cowpea\|gb166\|ES884222_T1 | cowpea | 2161 | 42 | 86 | 99.6415771 | 98.9547038 | blastp |
| 815 | cowpea\|gb166\|FF538675_T1 | cowpea | 2162 | 42 | 89 | 52.688172 | 98 | blastp |
| 816 | cowpea\|gb166\|FC458151_T1 | cowpea | 2163 | 42 | 80 | 100 | 100 | blastp |
| 817 | cowpea\|gb166\|FC458381_T1 | cowpea | 2164 | 42 | 85 | 99.6415771 | 98.9473684 | blastp |
| 818 | cryptomeria\|gb166\|AU036821_T1 | cryptomeria | 2165 | 42 | 83 | 95.6989247 | 93.639576 | blastp |
| 819 | cryptomeria\|gb166\|BW995927_T1 | cryptomeria | 2166 | 42 | 81 | 53.046595 | 98.013245 | blastp |
| 820 | dandelion\|gb161\|DY827637_T1 | dandelion | 2167 | 42 | 87 | 93.90681 | 88.9632107 | blastp |
| 821 | dandelion\|gb161\|DY814583_T1 | dandelion | 2168 | 42 | 85 | 93.5483871 | 93.2862191 | blastp |
| 822 | dandelion\|gb161\|DY828216_T1 | dandelion | 2169 | 42 | 85 | 100 | 100 | blastp |
| 823 | dandelion\|gb161\|DY818322_T1 | dandelion | 2170 | 42 | 80 | 85.3046595 | 98.7654321 | blastp |
| 824 | dandelion\|gb161\|DY805523_T1 | dandelion | 2171 | 42 | 82 | 98.9247312 | 98.245614 | blastp |
| 825 | fescue\|gb161\|DT675934_T1 | fescue | 2172 | 42 | 82 | 61.2903226 | 93.9226519 | blastp |
| 826 | ginger\|gb164\|DY345807_T1 | ginger | 2173 | 42 | 81 | 100 | 100 | blastp |
| 827 | ginger\|gb164\|DY373920_T1 | ginger | 2174 | 42 | 88 | 69.5340502 | 100 | blastp |
| 828 | grape\|gb160\|BQ792080_T1 | grape | 2175 | 42 | 81 | 100 | 99.3031359 | blastp |
| 829 | grape\|gb160\|CB973593_T1 | grape | 2176 | 42 | 84 | 100 | 100 | blastp |
| 830 | grape\|gb160\|BM437196_T1 | grape | 2177 | 42 | 84 | 100 | 99.2957746 | blastp |
| 831 | iceplant\|gb164\|CIPMIPC_T1 | iceplant | 2178 | 42 | 83 | 100 | 100 | blastp |
| 832 | iceplant\|gb164\|BE035661_T1 | iceplant | 2179 | 42 | 82 | 99.6415771 | 98.6254296 | blastp |
| 833 | ipomoea\|gb157.2\|BM878800_T1 | ipomoea | 2180 | 42 | 80 | 99.6415771 | 100 | blastp |
| 834 | ipomoea\|gb157.2\|AU224434_T2 | ipomoea | 2181 | 42 | 90 | 86.7383513 | 93.2330827 | blastp |
| 835 | ipomoea\|gb157.2\|BJ553793_T1 | ipomoea | 2182 | 42 | 82 | 100 | 99.2957746 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 836 | ipomoea\|gb157.2\|AU224434_T1 | ipomoea | 2183 | 42 | 89 | 100 | 100 | blastp |
| 837 | lettuce\|gb157.2\|DW115660_T1 | lettuce | 2184 | 42 | 85 | 99.2831541 | 98.5964912 | blastp |
| 838 | lettuce\|gb157.2\|DW113963_T1 | lettuce | 2185 | 42 | 80 | 97.8494624 | 95.7894737 | blastp |
| 839 | lettuce\|gb157.2\|DW110249_T1 | lettuce | 2186 | 42 | 84 | 99.6415771 | 98.9399293 | blastp |
| 840 | lettuce\|gb157.2\|DW051453_T1 | lettuce | 2187 | 42 | 86 | 100 | 100 | blastp |
| 841 | lettuce\|gb157.2\|DW076507_T1 | lettuce | 2188 | 42 | 84 | 100 | 100 | blastp |
| 842 | lettuce\|gb157.2\|DW127617_T1 | lettuce | 2189 | 42 | 84 | 100 | 100 | blastp |
| 843 | lettuce\|gb157.2\|AJ937963_T1 | lettuce | 2190 | 42 | 80 | 100 | 100 | blastp |
| 844 | lettuce\|gb157.2\|DW049421_T1 | lettuce | 2191 | 42 | 83 | 92.8315412 | 98.5018727 | blastp |
| 845 | lettuce\|gb157.2\|DW114305_T1 | lettuce | 2192 | 42 | 87 | 99.2831541 | 98.9473684 | blastp |
| 846 | lettuce\|gb157.2\|DW053722_T1 | lettuce | 2193 | 42 | 80 | 100 | 100 | blastp |
| 847 | lettuce\|gb157.2\|DW146178_T1 | lettuce | 2194 | 42 | 81 | 100 | 100 | blastp |
| 848 | lettuce\|gb157.2\|DW077710_T1 | lettuce | 2195 | 42 | 85 | 99.2831541 | 98.5964912 | blastp |
| 849 | lettuce\|gb157.2\|DW070566_T1 | lettuce | 2196 | 42 | 84 | 100 | 100 | blastp |
| 850 | lettuce\|gb157.2\|DW093078_T1 | lettuce | 2197 | 42 | 85 | 94.9820789 | 100 | blastp |
| 851 | lettuce\|gb157.2\|DW074446_T1 | lettuce | 2198 | 42 | 84 | 97.4910394 | 96.1672474 | blastp |
| 852 | lettuce\|gb157.2\|DW153482_T1 | lettuce | 2199 | 42 | 83 | 99.6415771 | 98.9399293 | blastp |
| 853 | lettuce\|gb157.2\|DW080306_T1 | lettuce | 2200 | 42 | 86 | 100 | 100 | blastp |
| 854 | lettuce\|gb157.2\|DW043674_T1 | lettuce | 2201 | 42 | 84 | 99.6415771 | 98.9399293 | blastp |
| 855 | lettuce\|gb157.2\|DW095979_T1 | lettuce | 2202 | 42 | 83 | 97.1326165 | 98.5559567 | blastp |
| 856 | lettuce\|gb157.2\|DW077206_T1 | lettuce | 2203 | 42 | 84 | 100 | 100 | blastp |
| 857 | lettuce\|gb157.2\|DW047573_T1 | lettuce | 2204 | 42 | 86 | 98.9247312 | 99.6453901 | blastp |
| 858 | lettuce\|gb157.2\|DW096304_T1 | lettuce | 2205 | 42 | 87 | 100 | 100 | blastp |
| 859 | lettuce\|gb157.2\|DW075191_T1 | lettuce | 2206 | 42 | 81 | 100 | 100 | blastp |
| 860 | lotus\|gb157.2\|AI967757_T1 | lotus | 2207 | 42 | 85 | 99.6415771 | 98.9547038 | blastp |
| 861 | lotus\|gb157.2\|AI967387_T2 | lotus | 2208 | 42 | 80 | 99.6415771 | 99.6515679 | blastp |
| 862 | lotus\|gb157.2\|BG662315_T1 | lotus | 2209 | 42 | 82 | 99.6415771 | 98.9619377 | blastp |
| 863 | maize\|gb164\|BE552783_T1 | maize | 2210 | 42 | 80 | 97.4910394 | 95.890411 | blastp |
| 864 | maize\|gb164\|AI622334_T1 | maize | 2211 | 42 | 83 | 97.4910394 | 95.862069 | blastp |
| 865 | maize\|gb164\|AI855280_T1 | maize | 2212 | 42 | 81 | 96.7741935 | 95.1557093 | blastp |
| 866 | medicago\|gb157.2\|AW981259_T1 | medicago | 2213 | 42 | 80 | 100 | 99.3031359 | blastp |
| 867 | medicago\|gb157.2\|AA660788_T1 | medicago | 2214 | 42 | 83 | 99.6415771 | 98.9547038 | blastp |
| 868 | melon\|gb165\|DV631824_T1 | melon | 2215 | 42 | 84 | 100 | 100 | blastp |
| 869 | melon\|gb165\|DV633977_T1 | melon | 2216 | 42 | 83 | 64.516129 | 100 | blastp |
| 870 | melon\|gb165\|AM720039_T1 | melon | 2217 | 42 | 81 | 86.0215054 | 100 | blastp |
| 871 | nicotiana_benthamiana\|gb162\|CN743200_T1 | nicotiana_benthamiana | 2218 | 42 | 80 | 100 | 100 | blastp |
| 872 | nicotiana_benthamiana\|gb162\|CK294539_T1 | nicotiana_benthamiana | 2219 | 42 | 80 | 98.2078853 | 96.8641115 | blastp |
| 873 | onion\|gb162\|AF255795_T1 | onion | 2220 | 42 | 82 | 97.1326165 | 95.532646 | blastp |
| 874 | onion\|gb162\|CF434704_T1 | onion | 2221 | 42 | 80 | 99.2831541 | 99.2957746 | blastp |
| 875 | papaya\|gb165\|EL784273_T1 | papaya | 2222 | 42 | 82 | 82.078853 | 97.5206612 | blastp |
| 876 | papaya\|gb165\|AM904340_T1 | papaya | 2223 | 42 | 84 | 100 | 99.2882562 | blastp |
| 877 | peach\|gb157.2\|AF367458_T1 | peach | 2224 | 42 | 84 | 87.0967742 | 100 | blastp |
| 878 | peach\|gb157.2\|BU040116_T1 | peach | 2225 | 42 | 83 | 99.6415771 | 98.9547038 | blastp |
| 879 | peach\|gb157.2\|AF367460_T1 | peach | 2226 | 42 | 86 | 87.0967742 | 100 | blastp |
| 880 | peanut\|gb161\|CD037924_T1 | peanut | 2227 | 42 | 86 | 99.6415771 | 98.9547038 | blastp |
| 881 | peanut\|gb161\|CD038296_T1 | peanut | 2228 | 42 | 85 | 99.6415771 | 98.9547038 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 882 | peanut\|gb161\|CD037924__T2 | peanut | 2229 | 42 | 86 | 99.6415771 | 98.9547038 | blastp |
| 883 | peanut\|gb161\|CD037884__T1 | peanut | 2230 | 42 | 88 | 51.2544803 | 97.9452055 | blastp |
| 884 | pepper\|gb157.2\|BM061612__T1 | pepper | 2231 | 42 | 96 | 100 | 100 | blastp |
| 885 | pepper\|gb157.2\|BM061611__T1 | pepper | 2232 | 42 | 97 | 100 | 100 | blastp |
| 886 | pepper\|gb157.2\|BM061005__T1 | pepper | 2233 | 42 | 81 | 92.4731183 | 97.3977695 | blastp |
| 887 | petunia\|gb157.2\|AF452014__T1 | petunia | 2234 | 42 | 83 | 97.4910394 | 98.2332155 | blastp |
| 888 | petunia\|gb157.2\|CV295523__T1 | petunia | 2235 | 42 | 95 | 53.046595 | 93.6708861 | blastp |
| 889 | petunia\|gb157.2\|CV293001__T1 | petunia | 2236 | 42 | 83 | 55.5555556 | 100 | blastp |
| 890 | pine\|gb157.2\|AI813221__T1 | pine | 2237 | 42 | 81 | 96.0573477 | 94.3262411 | blastp |
| 891 | pine\|gb157.2\|CA844411__T1 | pine | 2238 | 42 | 81 | 56.6308244 | 98.75 | blastp |
| 892 | poplar\|gb157.2\|BI130501__T3 | poplar | 2239 | 42 | 85 | 100 | 99.2982456 | blastp |
| 893 | poplar\|gb157.2\|AI165755__T1 | poplar | 2240 | 42 | 86 | 99.6415771 | 98.9473684 | blastp |
| 894 | poplar\|gb157.2\|BU835712__T1 | poplar | 2241 | 42 | 85 | 99.6415771 | 98.9473684 | blastp |
| 895 | poplar\|gb157.2\|BI130501__T1 | poplar | 2242 | 42 | 85 | 100 | 99.2982456 | blastp |
| 896 | poplar\|gb157.2\|BI130501__T4 | poplar | 2243 | 42 | 85 | 100 | 99.2982456 | blastp |
| 897 | poplar\|gb157.2\|AI162288__T1 | poplar | 2244 | 42 | 86 | 99.2831541 | 98.5964912 | blastp |
| 898 | poplar\|gb157.2\|AJ534524__T1 | poplar | 2245 | 42 | 84 | 100 | 100 | blastp |
| 899 | potato\|gb157.2\|BG096672__T1 | potato | 2246 | 42 | 96 | 100 | 100 | blastp |
| 900 | potato\|gb157.2\|BM109370__T1 | potato | 2247 | 42 | 80 | 98.2078853 | 96.8641115 | blastp |
| 901 | potato\|gb157.2\|BG589618__T1 | potato | 2248 | 42 | 80 | 98.2078853 | 96.8641115 | blastp |
| 902 | potato\|gb157.2\|CK261080__T1 | potato | 2249 | 42 | 83 | 70.2508961 | 100 | blastp |
| 903 | potato\|gb157.2\|BG098124__T1 | potato | 2250 | 42 | 97 | 99.2831541 | 100 | blastp |
| 904 | potato\|gb157.2\|BI406400__T1 | potato | 2251 | 42 | 80 | 98.2078853 | 96.8641115 | blastp |
| 905 | potato\|gb157.2\|BE920139__T1 | potato | 2252 | 42 | 90 | 100 | 100 | blastp |
| 906 | potato\|gb157.2\|BM112017__T1 | potato | 2253 | 42 | 80 | 98.2078853 | 96.8641115 | blastp |
| 907 | potato\|gb157.2\|BE921679__T1 | potato | 2254 | 42 | 96 | 100 | 100 | blastp |
| 908 | potato\|gb157.2\|BG600158__T1 | potato | 2255 | 42 | 80 | 98.2078853 | 96.8641115 | blastp |
| 909 | potato\|gb157.2\|BI406047__T1 | potato | 2256 | 42 | 80 | 100 | 100 | blastp |
| 910 | potato\|gb157.2\|CK719282__T1 | potato | 2257 | 42 | 80 | 98.2078853 | 96.8641115 | blastp |
| 911 | radish\|gb164\|EV545956__T1 | radish | 2258 | 42 | 81 | 100 | 99.2982456 | blastp |
| 912 | radish\|gb164\|EX904869__T1 | radish | 2259 | 42 | 80 | 100 | 100 | blastp |
| 913 | radish\|gb164\|EV545247__T1 | radish | 2260 | 42 | 80 | 100 | 100 | blastp |
| 914 | radish\|gb164\|EX756889__T1 | radish | 2261 | 42 | 80 | 100 | 100 | blastp |
| 915 | radish\|gb164\|EV539533__T1 | radish | 2262 | 42 | 81 | 100 | 99.3031359 | blastp |
| 916 | radish\|gb164\|EV546186__T1 | radish | 2263 | 42 | 82 | 55.5555556 | 95.6790123 | blastp |
| 917 | radish\|gb164\|AB012045__T1 | radish | 2264 | 42 | 81 | 100 | 99.3031359 | blastp |
| 918 | radish\|gb164\|EV573001__T1 | radish | 2265 | 42 | 83 | 62.0071685 | 98.8571429 | blastp |
| 919 | radish\|gb164\|AB030698__T1 | radish | 2266 | 42 | 81 | 100 | 100 | blastp |
| 920 | radish\|gb164\|EX749049__T1 | radish | 2267 | 42 | 83 | 78.4946237 | 100 | blastp |
| 921 | radish\|gb164\|AB030697__T1 | radish | 2268 | 42 | 80 | 100 | 100 | blastp |
| 922 | radish\|gb164\|EW735060__T1 | radish | 2269 | 42 | 80 | 96.4157706 | 95.4545455 | blastp |
| 923 | radish\|gb164\|FD936119__T1 | radish | 2270 | 42 | 83 | 50.5376344 | 100 | blastp |
| 924 | radish\|gb164\|EV543747__T1 | radish | 2271 | 42 | 81 | 100 | 99.3031359 | blastp |
| 925 | rice\|gb157.2\|BE040651__T2 | rice | 2272 | 42 | 80 | 86.7383513 | 94.3820225 | blastp |
| 926 | rice\|gb157.2\|BE040651__T1 | rice | 2273 | 42 | 80 | 100 | 100 | blastp |
| 927 | rice\|gb157.2\|AA754435__T5 | rice | 2274 | 42 | 80 | 85.6630824 | 87.7192982 | blastp |
| 928 | rice\|gb157.2\|AA754435__T1 | rice | 2275 | 42 | 81 | 100 | 100 | blastp |
| 929 | rose\|gb157.2\|BI977420__T1 | rose | 2276 | 42 | 84 | 69.8924731 | 91.627907 | blastp |
| 930 | rose\|gb157.2\|BI977750__T1 | rose | 2277 | 42 | 84 | 77.7777778 | 100 | blastp |
| 931 | rose\|gb157.2\|BI978110__T1 | rose | 2278 | 42 | 83 | 64.516129 | 98.3783784 | blastp |
| 932 | safflower\|gb162\|EL406648__T1 | safflower | 2279 | 42 | 81 | 98.5663082 | 100 | blastp |
| 933 | safflower\|gb162\|EL411110__T1 | safflower | 2280 | 42 | 86 | 92.4731183 | 97.761194 | blastp |
| 934 | safflower\|gb162\|EL401452__T1 | safflower | 2281 | 42 | 85 | 100 | 100 | blastp |
| 935 | safflower\|gb162\|EL402424__T1 | safflower | 2282 | 42 | 83 | 97.1326165 | 100 | blastp |
| 936 | safflower\|gb162\|EL400227__T1 | safflower | 2283 | 42 | 85 | 86.7383513 | 67.9193401 | tblastn |
| 937 | sorghum\|gb161.xeno\|AI622334__T1 | sorghum | 2284 | 42 | 83 | 97.4910394 | 95.862069 | blastp |
| 938 | soybean\|gb166\|CD393286__T1 | soybean | 2285 | 42 | 80 | 99.6415771 | 99.6515679 | blastp |
| 939 | soybean\|gb166\|GMU27347__T1 | soybean | 2286 | 42 | 86 | 99.6415771 | 98.9473684 | blastp |
| 940 | soybean\|gb166\|AW349289__T1 | soybean | 2287 | 42 | 85 | 99.6415771 | 98.9473684 | blastp |
| 941 | soybean\|gb166\|BE823946__T1 | soybean | 2288 | 42 | 87 | 99.6415771 | 98.943662 | blastp |
| 942 | soybean\|gb166\|BE352729__T2 | soybean | 2289 | 42 | 80 | 56.2724014 | 100 | blastp |
| 943 | soybean\|gb166\|AW350475__T1 | soybean | 2290 | 42 | 85 | 99.6415771 | 98.9547038 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 944 | soybean\|gb166\|BI119558__T1 | soybean | 2291 | 42 | 80 | 100 | 100 | blastp |
| 945 | soybean\|gb166\|AW349392__T1 | soybean | 2292 | 42 | 80 | 100 | 100 | blastp |
| 946 | spruce\|gb162\|AF051202__T1 | spruce | 2293 | 42 | 81 | 96.0573477 | 94.3262411 | blastp |
| 947 | spruce\|gb162\|CO227554__T1 | spruce | 2294 | 42 | 80 | 96.0573477 | 93.6619718 | blastp |
| 948 | spruce\|gb162\|CO220480__T1 | spruce | 2295 | 42 | 80 | 96.4157706 | 94.6808511 | blastp |
| 949 | spruce\|gb162\|CO217151__T1 | spruce | 2296 | 42 | 80 | 96.0573477 | 94.3262411 | blastp |
| 950 | spurge\|gb161\|AW990929__T1 | spurge | 2297 | 42 | 80 | 59.8566308 | 91.5343915 | blastp |
| 951 | spurge\|gb161\|BG354126__T1 | spurge | 2298 | 42 | 83 | 100 | 100 | blastp |
| 952 | spurge\|gb161\|DV125170__T1 | spurge | 2299 | 42 | 87 | 83.5125448 | 99.5780591 | blastp |
| 953 | strawberry\|gb164\|DV438166__T1 | strawberry | 2300 | 42 | 85 | 99.6415771 | 98.9473684 | blastp |
| 954 | strawberry\|gb164\|EX665494__T1 | strawberry | 2301 | 42 | 86 | 100 | 99.2957746 | blastp |
| 955 | strawberry\|gb164\|CO817390__T1 | strawberry | 2302 | 42 | 85 | 100 | 100 | blastp |
| 956 | sugarcane\|gb157.2\|BQ536871__T2 | sugarcane | 2303 | 42 | 85 | 70.2508961 | 100 | blastp |
| 957 | sugarcane\|gb157.2\|BU103568__T1 | sugarcane | 2304 | 42 | 83 | 97.4910394 | 92.6666667 | blastp |
| 958 | sugarcane\|gb157.2\|BQ536871__T1 | sugarcane | 2305 | 42 | 81 | 97.4910394 | 95.862069 | blastp |
| 959 | sugarcane\|gb157.2\|BQ535332__T1 | sugarcane | 2306 | 42 | 84 | 97.4910394 | 95.862069 | blastp |
| 960 | sunflower\|gb162\|CD849689__T1 | sunflower | 2307 | 42 | 83 | 100 | 100 | blastp |
| 961 | sunflower\|gb162\|CD849494__T1 | sunflower | 2308 | 42 | 83 | 94.9820789 | 95.0704225 | blastp |
| 962 | sunflower\|gb162\|CF091932__T1 | sunflower | 2309 | 42 | 81 | 83.5125448 | 98.75 | blastp |
| 963 | sunflower\|gb162\|DY915644__T1 | sunflower | 2310 | 42 | 81 | 100 | 100 | blastp |
| 964 | sunflower\|gb162\|EL462160__T1 | sunflower | 2311 | 42 | 81 | 78.4946237 | 88.8446215 | blastp |
| 965 | sunflower\|gb162\|DY918039__T1 | sunflower | 2312 | 42 | 87 | 95.6989247 | 100 | blastp |
| 966 | sunflower\|gb162\|DY951506__T1 | sunflower | 2313 | 42 | 87 | 89.9641577 | 95.5223881 | blastp |
| 967 | sunflower\|gb162\|DY933519__T1 | sunflower | 2314 | 42 | 84 | 99.6415771 | 98.9473684 | blastp |
| 968 | sunflower\|gb162\|DY917102__T1 | sunflower | 2315 | 42 | 82 | 100 | 100 | blastp |
| 969 | sunflower\|gb162\|DY932916__T1 | sunflower | 2316 | 42 | 86 | 58.0645161 | 100 | blastp |
| 970 | sunflower\|gb162\|CD857425__T1 | sunflower | 2317 | 42 | 84 | 100 | 100 | blastp |
| 971 | sunflower\|gb162\|CD846314__T1 | sunflower | 2318 | 42 | 85 | 53.4050179 | 97.4683544 | blastp |
| 972 | sunflower\|gb162\|CX944368__T1 | sunflower | 2319 | 42 | 88 | 68.1003584 | 89.6226415 | blastp |
| 973 | sunflower\|gb162\|DY908592__T1 | sunflower | 2320 | 42 | 80 | 100 | 100 | blastp |
| 974 | switchgrass\|gb165\|DN141399__T1 | switchgrass | 2321 | 42 | 81 | 96.7741935 | 98.9208633 | blastp |
| 975 | switchgrass\|gb165\|FE621421__T1 | switchgrass | 2322 | 42 | 86 | 51.9713262 | 99.3150685 | blastp |
| 976 | switchgrass\|gb165\|DN145656__T1 | switchgrass | 2323 | 42 | 83 | 97.4910394 | 95.862069 | blastp |
| 977 | switchgrass\|gb165\|FE637674__T1 | switchgrass | 2324 | 42 | 81 | 82.437276 | 100 | blastp |
| 978 | switchgrass\|gb165\|DN141334__T1 | switchgrass | 2325 | 42 | 83 | 77.0609319 | 94.8497854 | blastp |
| 979 | switchgrass\|gb165\|FE621578__T1 | switchgrass | 2326 | 42 | 83 | 85.6630824 | 100 | blastp |
| 980 | *thellungiella*\|gb157.2\|DN775526__T1 | *thellungiella* | 2327 | 42 | 81 | 72.4014337 | 100 | blastp |
| 981 | tobacco\|gb162\|CK720599__T1 | tobacco | 2328 | 42 | 95 | 100 | 100 | blastp |
| 982 | tobacco\|gb162\|CK720599__T2 | tobacco | 2329 | 42 | 94 | 100 | 100 | blastp |
| 983 | tobacco\|gb162\|EB445427__T1 | tobacco | 2330 | 42 | 81 | 100 | 100 | blastp |
| 984 | tobacco\|gb162\|EB443112__T1 | tobacco | 2331 | 42 | 89 | 100 | 100 | blastp |
| 985 | tobacco\|gb162\|AF154641__T1 | tobacco | 2332 | 42 | 80 | 100 | 100 | blastp |
| 986 | tobacco\|gb162\|EB425288__T1 | tobacco | 2333 | 42 | 94 | 98.2078853 | 100 | blastp |
| 987 | tomato\|gb164\|BG123951__T2 | tomato | 2334 | 42 | 81 | 92.8315412 | 97.4074074 | blastp |
| 988 | tomato\|gb164\|BG123951__T1 | tomato | 2335 | 42 | 80 | 98.2078853 | 96.8641115 | blastp |
| 989 | tomato\|gb164\|BG713781__T1 | tomato | 2336 | 42 | 92 | 53.4050179 | 98.0519481 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 990 | tomato\|gb164\|AW219533__T1 | tomato | 2337 | 42 | 81 | 97.1326165 | 98.2142857 | blastp |
| 991 | triphysaria\|gb164\|DR170852__T1 | triphysaria | 2338 | 42 | 88 | 99.2831541 | 99.2857143 | blastp |
| 992 | triphysaria\|gb164\|BM356582__T1 | triphysaria | 2339 | 42 | 88 | 64.874552 | 100 | blastp |
| 993 | triphysaria\|gb164\|BE574767__T1 | triphysaria | 2340 | 42 | 80 | 100 | 100 | blastp |
| 994 | wheat\|gb164\|BE444481__T1 | wheat | 2341 | 42 | 82 | 55.5555556 | 100 | blastp |
| 995 | wheat\|gb164\|BE398316__T1 | wheat | 2342 | 42 | 81 | 100 | 100 | blastp |
| 996 | wheat\|gb164\|BE404002__T1 | wheat | 2343 | 42 | 82 | 51.6129032 | 99.3055556 | blastp |
| 997 | apple\|gb157.3\|CN892655__T1 | apple | 2344 | 43 | 84 | 100 | 100 | blastp |
| 998 | apple\|gb157.3\|AU223658__T1 | apple | 2345 | 43 | 85 | 100 | 100 | blastp |
| 999 | aquilegia\|gb157.3\|DR914359__T1 | aquilegia | 2346 | 43 | 84 | 100 | 100 | blastp |
| 1000 | arabidopsis\|gb165\|AT2G16850__T1 | arabidopsis | 2347 | 43 | 84 | 100 | 100 | blastp |
| 1001 | arabidopsis\|gb165\|AT4G35100__T1 | arabidopsis | 2348 | 43 | 86 | 100 | 100 | blastp |
| 1002 | avocado\|gb164\|CK753629__T1 | avocado | 2349 | 43 | 85 | 66.4310954 | 92.6108374 | blastp |
| 1003 | avocado\|gb164\|CK752541__T1 | avocado | 2350 | 43 | 84 | 62.1908127 | 100 | blastp |
| 1004 | b_juncea\|gb164\|EVGN01060535361904__T1 | b_juncea | 2351 | 43 | 86 | 67.1378092 | 100 | blastp |
| 1005 | b_juncea\|gb164\|EVGN00138211060167__T1 | b_juncea | 2352 | 43 | 86 | 85.1590106 | 100 | blastp |
| 1006 | b_juncea\|gb164\|EVGN01177009332048__T1 | b_juncea | 2353 | 43 | 86 | 66.0777385 | 100 | blastp |
| 1007 | b_juncea\|gb164\|EVGN00071418640425__T1 | b_juncea | 2354 | 43 | 86 | 90.459364 | 100 | blastp |
| 1008 | b_juncea\|gb164\|EVGN01391814101746__T1 | b_juncea | 2355 | 43 | 92 | 53.0035336 | 100 | blastp |
| 1009 | b_juncea\|gb164\|EVGN00206114600060__T1 | b_juncea | 2356 | 43 | 85 | 100 | 100 | blastp |
| 1010 | b_oleracea\|gb161\|AF314656__T1 | b_oleracea | 2357 | 43 | 85 | 100 | 100 | blastp |
| 1011 | b_oleracea\|gb161\|DY029187__T1 | b_oleracea | 2358 | 43 | 86 | 100 | 100 | blastp |
| 1012 | b_oleracea\|gb161\|DY014978__T1 | b_oleracea | 2359 | 43 | 87 | 54.770318 | 100 | blastp |
| 1013 | b_rapa\|gb162\|BQ791230__T1 | b_rapa | 2360 | 43 | 86 | 77.0318021 | 97.7375566 | blastp |
| 1014 | b_rapa\|gb162\|EX033370__T1 | b_rapa | 2361 | 43 | 87 | 100 | 100 | blastp |
| 1015 | b_rapa\|gb162\|CV432651__T1 | b_rapa | 2362 | 43 | 86 | 100 | 100 | blastp |
| 1016 | b_rapa\|gb162\|BG543906__T1 | b_rapa | 2363 | 43 | 85 | 100 | 100 | blastp |
| 1017 | bean\|gb164\|CB539790__T1 | bean | 2364 | 43 | 83 | 100 | 100 | blastp |
| 1018 | beet\|gb162\|BVU60148__T1 | beet | 2365 | 43 | 80 | 100 | 100 | blastp |
| 1019 | canola\|gb161\|DY007064__T1 | canola | 2366 | 43 | 86 | 100 | 100 | blastp |
| 1020 | canola\|gb161\|CD815284__T1 | canola | 2367 | 43 | 85 | 100 | 100 | blastp |
| 1021 | canola\|gb161\|CD817684__T1 | canola | 2368 | 43 | 85 | 100 | 100 | blastp |
| 1022 | canola\|gb161\|CD821191__T1 | canola | 2369 | 43 | 86 | 100 | 100 | blastp |
| 1023 | canola\|gb161\|CD820375__T1 | canola | 2370 | 43 | 87 | 100 | 100 | blastp |
| 1024 | cassava\|gb164\|BM259748__T1 | cassava | 2371 | 43 | 84 | 100 | 100 | blastp |
| 1025 | castorbean\|gb160\|AJ605569__T1 | castorbean | 2372 | 43 | 84 | 100 | 100 | blastp |
| 1026 | castorbean\|gb160\|AJ605569__T2 | castorbean | 2373 | 43 | 84 | 69.9646643 | 95.1219512 | blastp |
| 1027 | cichorium\|gb161\|EH704748__T1 | cichorium | 2374 | 43 | 89 | 67.1378092 | 100 | blastp |
| 1028 | citrus\|gb157.2\|BQ623127__T1 | citrus | 2375 | 43 | 85 | 100 | 100 | blastp |
| 1029 | citrus\|gb157.2\|CX664964__T1 | citrus | 2376 | 43 | 84 | 100 | 100 | blastp |
| 1030 | clover\|gb162\|BB911260__T1 | clover | 2377 | 43 | 82 | 54.0636042 | 100 | blastp |
| 1031 | coffea\|gb157.2\|BQ448890__T1 | coffea | 2378 | 43 | 86 | 100 | 100 | blastp |
| 1032 | cotton\|gb164\|AI726086__T1 | cotton | 2379 | 43 | 84 | 97.8798587 | 88.02589 | blastp |
| 1033 | cotton\|gb164\|CO098535__T1 | cotton | 2380 | 43 | 82 | 92.2261484 | 95.5719557 | blastp |
| 1034 | cotton\|gb164\|BE051956__T1 | cotton | 2381 | 43 | 83 | 100 | 100 | blastp |
| 1035 | cotton\|gb164\|BQ414250__T1 | cotton | 2382 | 43 | 85 | 59.0106007 | 100 | blastp |
| 1036 | cotton\|gb164\|BF268907__T1 | cotton | 2383 | 43 | 87 | 90.1060071 | 100 | blastp |
| 1037 | cotton\|gb164\|CO075847__T1 | cotton | 2384 | 43 | 84 | 62.5441696 | 100 | blastp |
| 1038 | cotton\|gb164\|BQ405584__T1 | cotton | 2385 | 43 | 82 | 95.4063604 | 95.7142857 | blastp |
| 1039 | cotton\|gb164\|AI055551__T1 | cotton | 2386 | 43 | 85 | 100 | 100 | blastp |
| 1040 | cowpea\|gb166\|FC456786__T1 | cowpea | 2387 | 43 | 84 | 100 | 100 | blastp |
| 1041 | dandelion\|gb161\|DY803814__T1 | dandelion | 2388 | 43 | 85 | 100 | 100 | blastp |
| 1042 | ginger\|gb164\|DY347270__T1 | ginger | 2389 | 43 | 80 | 100 | 100 | blastp |
| 1043 | ginger\|gb164\|DY347296__T1 | ginger | 2390 | 43 | 84 | 94.6996466 | 92.733564 | blastp |
| 1044 | ginger\|gb164\|DY358056__T1 | ginger | 2391 | 43 | 81 | 100 | 100 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 1045 | ginger\|gb164\|DY347277_T1 | ginger | 2392 | 43 | 81 | 100 | 100 | blastp |
| 1046 | ginger\|gb164\|DY360032_T1 | ginger | 2393 | 43 | 81 | 81.9787986 | 93.902439 | blastp |
| 1047 | grape\|gb160\|BM437910_T1 | grape | 2394 | 43 | 84 | 100 | 100 | blastp |
| 1048 | iceplant\|gb164\|MCU26538_T1 | iceplant | 2395 | 43 | 82 | 100 | 100 | blastp |
| 1049 | ipomoea\|gb157.2\|BJ553491_T1 | ipomoea | 2396 | 43 | 83 | 100 | 100 | blastp |
| 1050 | lettuce\|gb157.2\|DW046509_T1 | lettuce | 2397 | 43 | 84 | 100 | 100 | blastp |
| 1051 | lettuce\|gb157.2\|DW106553_T1 | lettuce | 2398 | 43 | 84 | 97.8798587 | 100 | blastp |
| 1052 | lettuce\|gb157.2\|DW146059_T1 | lettuce | 2399 | 43 | 84 | 100 | 100 | blastp |
| 1053 | lettuce\|gb157.2\|DW110223_T1 | lettuce | 2400 | 43 | 83 | 97.1731449 | 100 | blastp |
| 1054 | lettuce\|gb157.2\|DW079482_T1 | lettuce | 2401 | 43 | 84 | 100 | 100 | blastp |
| 1055 | lettuce\|gb157.2\|DW094572_T1 | lettuce | 2402 | 43 | 83 | 97.5265018 | 92.8327645 | blastp |
| 1056 | lotus\|gb157.2\|AW163949_T1 | lotus | 2403 | 43 | 85 | 54.4169611 | 93.902439 | blastp |
| 1057 | lotus\|gb157.2\|AI967574_T1 | lotus | 2404 | 43 | 82 | 98.5865724 | 97.5352113 | blastp |
| 1058 | melon\|gb165\|DV632217_T1 | melon | 2405 | 43 | 83 | 100 | 100 | blastp |
| 1059 | oil_palm\|gb166\|CN600073_T1 | oil_palm | 2406 | 43 | 80 | 100 | 100 | blastp |
| 1060 | papaya\|gb165\|EX227970_T1 | papaya | 2407 | 43 | 85 | 100 | 100 | blastp |
| 1061 | peach\|gb157.2\|AF367457_T1 | peach | 2408 | 43 | 85 | 85.1590106 | 99.5833333 | blastp |
| 1062 | pepper\|gb157.2\|BM066074_T1 | pepper | 2409 | 43 | 96 | 67.4911661 | 98.9637306 | blastp |
| 1063 | pepper\|gb157.2\|CA518686_T1 | pepper | 2410 | 43 | 88 | 53.7102473 | 100 | blastp |
| 1064 | periwinkle\|gb164\|AM232518_T1 | periwinkle | 2411 | 43 | 90 | 100 | 100 | blastp |
| 1065 | petunia\|gb157.2\|AF452013_T1 | petunia | 2412 | 43 | 89 | 100 | 100 | blastp |
| 1066 | poplar\|gb157.2\|AI163573_T1 | poplar | 2413 | 43 | 84 | 100 | 100 | blastp |
| 1067 | poplar\|gb157.2\|AI162424_T1 | poplar | 2414 | 43 | 83 | 100 | 100 | blastp |
| 1068 | potato\|gb157.2\|BF053675_T1 | potato | 2415 | 43 | 89 | 83.745583 | 100 | blastp |
| 1069 | potato\|gb157.2\|BF459952_T1 | potato | 2416 | 43 | 97 | 100 | 100 | blastp |
| 1070 | radish\|gb164\|EV526465_T1 | radish | 2417 | 43 | 86 | 100 | 100 | blastp |
| 1071 | radish\|gb164\|EV539317_T1 | radish | 2418 | 43 | 85 | 100 | 100 | blastp |
| 1072 | radish\|gb164\|EV525026_T1 | radish | 2419 | 43 | 85 | 100 | 100 | blastp |
| 1073 | rose\|gb157.2\|BQ103996_T1 | rose | 2420 | 43 | 82 | 100 | 100 | blastp |
| 1074 | safflower\|gb162\|EL372747_T1 | safflower | 2421 | 43 | 83 | 100 | 100 | blastp |
| 1075 | sesame\|gb157.2\|BU669158_T1 | sesame | 2422 | 43 | 88 | 50.8833922 | 100 | blastp |
| 1076 | sesame\|gb157.2\|BU668646_T1 | sesame | 2423 | 43 | 87 | 51.9434629 | 100 | blastp |
| 1077 | soybean\|gb166\|BE823128_T1 | soybean | 2424 | 43 | 82 | 100 | 100 | blastp |
| 1078 | soybean\|gb166\|BE352716_T1 | soybean | 2425 | 43 | 82 | 100 | 100 | blastp |
| 1079 | spruce\|gb162\|CO217407_T1 | spruce | 2426 | 43 | 80 | 93.2862191 | 93.5714286 | blastp |
| 1080 | spurge\|gb161\|AW821924_T1 | spurge | 2427 | 43 | 84 | 100 | 97.2125436 | blastp |
| 1081 | strawberry\|gb164\|CX661107_T1 | strawberry | 2428 | 43 | 82 | 100 | 100 | blastp |
| 1082 | sunflower\|gb162\|CD853582_T1 | sunflower | 2429 | 43 | 85 | 100 | 100 | blastp |
| 1083 | sunflower\|gb162\|DY939653_T1 | sunflower | 2430 | 43 | 80 | 97.1731449 | 97.833935 | blastp |
| 1084 | sunflower\|gb162\|CD849663_T1 | sunflower | 2431 | 43 | 81 | 100 | 100 | blastp |
| 1085 | thellungiella\|gb157.2\|DN777165_T1 | thellungiella | 2432 | 43 | 86 | 72.0848057 | 90.5829596 | blastp |
| 1086 | tobacco\|gb162\|CK720587_T1 | tobacco | 2433 | 43 | 90 | 99.6466431 | 100 | blastp |
| 1087 | tobacco\|gb162\|CK720585_T1 | tobacco | 2434 | 43 | 90 | 100 | 100 | blastp |
| 1088 | tobacco\|gb162\|CV016422_T1 | tobacco | 2435 | 43 | 96 | 59.7173145 | 100 | blastp |
| 1089 | tobacco\|gb162\|CK720589_T1 | tobacco | 2436 | 43 | 94 | 100 | 100 | blastp |
| 1090 | tomato\|gb164\|BG124140_T1 | tomato | 2437 | 43 | 88 | 100 | 100 | blastp |
| 1091 | triphysaria\|gb164\|EY018490_T1 | triphysaria | 2438 | 43 | 83 | 100 | 100 | blastp |
| 1092 | triphysaria\|gb164\|EY007858_T1 | triphysaria | 2439 | 43 | 84 | 100 | 100 | blastp |
| 1093 | apple\|gb157.3\|CN494428_T1 | apple | 2440 | 44 | 80 | 79.1390728 | 93.0232558 | blastp |
| 1094 | castorbean\|gb160\|EG696741_T1 | castorbean | 2441 | 44 | 82 | 99.0066225 | 97.7272727 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 1095 | citrus\|gb157.2\|CX074332_T1 | citrus | 2442 | 44 | 82 | 99.0066225 | 97.6973684 | blastp |
| 1096 | citrus\|gb157.2\|CX674035_T1 | citrus | 2443 | 44 | 80 | 86.7549669 | 85.8085809 | blastp |
| 1097 | cotton\|gb164\|DW234737_T1 | cotton | 2444 | 44 | 80 | 99.6688742 | 98.3333333 | blastp |
| 1098 | lettuce\|gb157.2\|DW066284_T1 | lettuce | 2445 | 44 | 80 | 95.0331126 | 100 | blastp |
| 1099 | petunia\|gb157.2\|CV298254_T1 | petunia | 2446 | 44 | 84 | 65.8940397 | 100 | blastp |
| 1100 | potato\|gb157.2\|CV500020_T1 | potato | 2447 | 44 | 94 | 72.1854305 | 99.543379 | blastp |
| 1101 | tobacco\|gb162\|EB426672_T1 | tobacco | 2448 | 44 | 89 | 99.0066225 | 97.689769 | blastp |
| 1102 | brachypodium\|gb161.xeno\|BE415047_T1 | brachypodium | 2449 | 46 | 92 | 100 | 100 | blastp |
| 1103 | maize\|gb164\|CF244342_T1 | maize | 2450 | 46 | 90 | 90.7630522 | 100 | blastp |
| 1104 | maize\|gb164\|AF057183_T1 | maize | 2451 | 46 | 89 | 100 | 100 | blastp |
| 1105 | sorghum\|gb161.xeno\|AF057183_T1 | sorghum | 2452 | 46 | 88 | 100 | 100 | blastp |
| 1106 | sugarcane\|gb157.2\|CA132045_T1 | sugarcane | 2453 | 46 | 89 | 100 | 100 | blastp |
| 1107 | switchgrass\|gb165\|FE617713_T1 | switchgrass | 2454 | 46 | 90 | 100 | 100 | blastp |
| 1108 | wheat\|gb164\|BE430088_T1 | wheat | 2455 | 46 | 95 | 100 | 100 | blastp |
| 1109 | apple\|gb157.3\|DT001281_T1 | apple | 2456 | 47 | 81 | 87.9518072 | 100 | blastp |
| 1110 | brachypodium\|gb161.xeno\|BE402447_T1 | brachypodium | 2457 | 47 | 95 | 100 | 100 | blastp |
| 1111 | ginger\|gb164\|DY364894_T1 | ginger | 2458 | 47 | 88 | 64.2570281 | 98.7654321 | blastp |
| 1112 | maize\|gb164\|AI855402_T1 | maize | 2459 | 47 | 89 | 100 | 100 | blastp |
| 1113 | maize\|gb164\|AW017703_T1 | maize | 2460 | 47 | 85 | 100 | 100 | blastp |
| 1114 | onion\|gb162\|ACU58207_T1 | onion | 2461 | 47 | 83 | 99.5983936 | 99.5967742 | blastp |
| 1115 | onion\|gb162\|CF437464_T1 | onion | 2462 | 47 | 85 | 95.9839357 | 98.75 | blastp |
| 1116 | onion\|gb162\|CF435351_T1 | onion | 2463 | 47 | 84 | 100 | 100 | blastp |
| 1117 | rice\|gb157.2\|AU031632_T1 | rice | 2464 | 47 | 91 | 100 | 100 | blastp |
| 1118 | rice\|gb157.2\|CA756239_T1 | rice | 2465 | 47 | 87 | 97.5903614 | 31.640625 | blastp |
| 1119 | sorghum\|gb161.xeno\|AI855402_T1 | sorghum | 2466 | 47 | 89 | 100 | 100 | blastp |
| 1120 | sugarcane\|gb157.2\|CA132045_T2 | sugarcane | 2467 | 47 | 90 | 99.5983936 | 99.5967742 | blastp |
| 1121 | switchgrass\|gb165\|FE624217_T1 | switchgrass | 2468 | 47 | 90 | 100 | 100 | blastp |
| 1122 | wheat\|gb164\|BE404100_T1 | wheat | 2469 | 47 | 97 | 100 | 100 | blastp |
| 1123 | fescue\|gb161\|DT700572_T1 | fescue | 2470 | 48 | 94 | 100 | 100 | blastp |
| 1124 | ginger\|gb164\|DY361836_T1 | ginger | 2471 | 48 | 80 | 95.1612903 | 96.7346939 | blastp |
| 1125 | rice\|gb157.2\|U37952_T1 | rice | 2472 | 48 | 90 | 100 | 100 | blastp |
| 1126 | rice\|gb157.2\|U37952_T3 | rice | 2473 | 48 | 89 | 51.6129032 | 89.5104895 | blastp |
| 1127 | rye\|gb164\|BE495605_T1 | rye | 2474 | 48 | 98 | 80.6451613 | 100 | blastp |
| 1128 | sorghum\|gb161.xeno\|AI724211_T1 | sorghum | 2475 | 48 | 90 | 100 | 100 | blastp |
| 1129 | sugarcane\|gb157.2\|CA110414_T1 | sugarcane | 2476 | 48 | 82 | 92.3387097 | 100 | blastp |
| 1130 | sugarcane\|gb157.2\|CA065356_T1 | sugarcane | 2477 | 48 | 83 | 90.3225806 | 96.5517241 | blastp |
| 1131 | sugarcane\|gb157.2\|CA143208_T1 | sugarcane | 2478 | 48 | 83 | 71.3709677 | 95.6756757 | blastp |
| 1132 | sugarcane\|gb157.2\|CA101765_T1 | sugarcane | 2479 | 48 | 91 | 100 | 100 | blastp |
| 1133 | sugarcane\|gb157.2\|CA133231_T1 | sugarcane | 2480 | 48 | 90 | 83.4677419 | 95.8333333 | blastp |
| 1134 | switchgrass\|gb165\|FE605472_T1 | switchgrass | 2481 | 48 | 91 | 100 | 100 | blastp |
| 1135 | wheat\|gb164\|BE489764_T1 | wheat | 2482 | 48 | 95 | 100 | 100 | blastp |
| 1136 | wheat\|gb164\|TAU86763_T1 | wheat | 2483 | 48 | 95 | 100 | 100 | blastp |
| 1137 | wheat\|gb164\|BE415001_T1 | wheat | 2484 | 48 | 95 | 100 | 100 | blastp |
| 1138 | b_juncea\|gb164\|EVGN00504508791211_T1 | b_juncea | 2485 | 50 | 80 | 85.0931677 | 100 | blastp |
| 1139 | b_juncea\|gb164\|EVGN01684214261870_T1 | b_juncea | 2486 | 50 | 84 | 50.931677 | 91.954023 | blastp |
| 1140 | banana\|gb160\|DN239388_T1 | banana | 2487 | 50 | 84 | 80.1242236 | 91.9708029 | blastp |
| 1141 | barley\|gb157.3\|BF253694_T1 | barley | 2488 | 50 | 91 | 58.3850932 | 98.9690722 | blastp |
| 1142 | barley\|gb157.3\|BE412959_T3 | barley | 2489 | 50 | 95 | 100 | 62.6923077 | blastp |
| 1143 | bean\|gb164\|FD793482_T1 | bean | 2490 | 50 | 82 | 100 | 91.9075145 | blastp |
| 1144 | canola\|gb161\|CX193398_T3 | canola | 2491 | 50 | 83 | 99.378882 | 66.9527897 | blastp |
| 1145 | canola\|gb161\|EV123336_T1 | canola | 2492 | 50 | 81 | 52.7950311 | 91.2087912 | blastp |
| 1146 | centaurea\|gb161\|EL931277_T1 | centaurea | 2493 | 50 | 81 | 98.136646 | 62.248996 | blastp |
| 1147 | cichorium\|gb161\|DT213939_T1 | cichorium | 2494 | 50 | 83 | 64.5962733 | 95.3271028 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 1148 | fescue\|gb161\|DT703843_T1 | fescue | 2495 | 50 | 99 | 100 | 94.1520468 | blastp |
| 1149 | lotus\|gb157.2\|BI418499_T1 | lotus | 2496 | 50 | 86 | 98.136646 | 88.700565 | blastp |
| 1150 | onion\|gb162\|BQ579939_T1 | onion | 2497 | 50 | 86 | 100 | 57.1942446 | blastp |
| 1151 | peach\|gb157.2\|BU040795_T1 | peach | 2498 | 50 | 82 | 98.136646 | 56.2043796 | blastp |
| 1152 | peach\|gb157.2\|DW351857_T1 | peach | 2499 | 50 | 83 | 98.136646 | 91.8128655 | blastp |
| 1153 | rye\|gb164\|BF429463_T1 | rye | 2500 | 50 | 88 | 93.1677019 | 100 | blastp |
| 1154 | soybean\|gb166\|BE352747_T4 | soybean | 2501 | 50 | 81 | 98.136646 | 70.7207207 | blastp |
| 1155 | sugarcane\|gb157.2\|CA194640_T1 | sugarcane | 2502 | 50 | 81 | 98.136646 | 56.6787004 | blastp |
| 1156 | sugarcane\|gb157.2\|CA103332_T1 | sugarcane | 2503 | 50 | 84 | 96.2732919 | 87.0056497 | blastp |
| 1157 | sugarcane\|gb157.2\|CA167616_T1 | sugarcane | 2504 | 50 | 82 | 93.7888199 | 74.2574257 | blastp |
| 1158 | sugarcane\|gb157.2\|CA103740_T1 | sugarcane | 2505 | 50 | 90 | 100 | 68.5344828 | blastp |
| 1159 | sugarcane\|gb157.2\|CA184547_T1 | sugarcane | 2506 | 50 | 82 | 97.515528 | 77.4834437 | tblastn |
| 1160 | sunflower\|gb162\|CF089373_T1 | sunflower | 2507 | 50 | 87 | 98.136646 | 87.5 | blastp |
| 1161 | wheat\|gb164\|CA484201_T1 | wheat | 2508 | 50 | 89 | 96.8944099 | 65.9574468 | blastp |
| 1162 | apricot\|gb157.2\|CV049856_T1 | apricot | 2509 | 51 | 86 | 100 | 65.9574468 | blastp |
| 1163 | arabidopsis\|gb165\|AT2G37180_T1 | arabidopsis | 2510 | 51 | 89 | 100 | 32.6315789 | blastp |
| 1164 | arabidopsis\|gb165\|AT2G39010_T1 | arabidopsis | 2511 | 51 | 92 | 100 | 32.1799308 | blastp |
| 1165 | b_juncea\|gb164\|EVGN00130608921231_T1 | b_juncea | 2512 | 51 | 87 | 100 | 86.9158879 | blastp |
| 1166 | b_juncea\|gb164\|EVGN00605203140273_T1 | b_juncea | 2513 | 51 | 86 | 90.3225806 | 86.5979381 | blastp |
| 1167 | b_juncea\|gb164\|EVGN21262514941904_T1 | b_juncea | 2514 | 51 | 86 | 56.9892473 | 91.3793103 | blastp |
| 1168 | b_juncea\|gb164\|EVGN00733314152324_T1 | b_juncea | 2515 | 51 | 86 | 100 | 85.3211009 | blastp |
| 1169 | b_juncea\|gb164\|EVGN00041211340240_T1 | b_juncea | 2516 | 51 | 86 | 89.2473118 | 49.4047619 | blastp |
| 1170 | b_juncea\|gb164\|DT317704_T1 | b_juncea | 2517 | 51 | 91 | 100 | 80.1724138 | blastp |
| 1171 | b_juncea\|gb164\|EVGN00208014701957_T1 | b_juncea | 2518 | 51 | 85 | 89.2473118 | 79.8076923 | blastp |
| 1172 | b_juncea\|gb164\|EVGN00550314491066_T1 | b_juncea | 2519 | 51 | 90 | 100 | 36.328125 | blastp |
| 1173 | b_juncea\|gb164\|EVGN01267508262672_T1 | b_juncea | 2520 | 51 | 90 | 90.3225806 | 95.4545455 | blastp |
| 1174 | b_juncea\|gb164\|EVGN01803715320789_T1 | b_juncea | 2521 | 51 | 89 | 100 | 51.3812155 | blastp |
| 1175 | b_juncea\|gb164\|EVGN00397011681539_T1 | b_juncea | 2522 | 51 | 91 | 100 | 34.4019729 | tblastn |
| 1176 | b_rapa\|gb162\|DN965016_T1 | b_rapa | 2523 | 51 | 88 | 100 | 69.4029851 | blastp |
| 1177 | b_rapa\|gb162\|EX025548_T1 | b_rapa | 2524 | 51 | 87 | 100 | 32.5174825 | blastp |
| 1178 | b_rapa\|gb162\|BG543764_T1 | b_rapa | 2525 | 51 | 92 | 100 | 32.2916667 | blastp |
| 1179 | banana\|gb160\|DN238638_T1 | banana | 2526 | 51 | 89 | 100 | 27.8721279 | blastp |
| 1180 | banana\|gb160\|DN238638_T2 | banana | 2527 | 51 | 89 | 100 | 30.5921053 | tblastn |
| 1181 | barley\|gb157.3\|BE421292_T1 | barley | 2528 | 51 | 87 | 100 | 32.7464789 | blastp |
| 1182 | barley\|gb157.3\|BJ446923_T1 | barley | 2529 | 51 | 83 | 100 | 64.5833333 | blastp |
| 1183 | beet\|gb162\|BQ488455_T1 | beet | 2530 | 51 | 81 | 100 | 26.686217 | blastp |
| 1184 | beet\|gb162\|BVU60147_T1 | beet | 2531 | 51 | 84 | 100 | 32.2916667 | blastp |
| 1185 | canola\|gb161\|CX189721_T1 | canola | 2532 | 51 | 87 | 100 | 32.5174825 | blastp |
| 1186 | canola\|gb161\|CB686155_T1 | canola | 2533 | 51 | 92 | 100 | 32.2916667 | blastp |
| 1187 | canola\|gb161\|DY007249_T1 | canola | 2534 | 51 | 87 | 100 | 32.5174825 | blastp |
| 1188 | canola\|gb161\|ES986486_T1 | canola | 2535 | 51 | 86 | 96.7741935 | 87.3786408 | blastp |
| 1189 | canola\|gb161\|EV203446_T1 | canola | 2536 | 51 | 82 | 100 | 38.0108992 | tblastn |
| 1190 | cassava\|gb164\|DN740353_T1 | cassava | 2537 | 51 | 93 | 100 | 62.8378378 | blastp |
| 1191 | cassava\|gb164\|DV449516_T1 | cassava | 2538 | 51 | 94 | 100 | 68.8888889 | blastp |
| 1192 | cassava\|gb164\|BM259717_T1 | cassava | 2539 | 51 | 81 | 100 | 32.8621908 | blastp |
| 1193 | castorbean\|gb160\|EE257493_T2 | castorbean | 2540 | 51 | 81 | 100 | 46.5 | blastp |
| 1194 | castorbean\|gb160\|EE257493_T1 | castorbean | 2541 | 51 | 81 | 100 | 34.4444444 | blastp |
| 1195 | cichorium\|gb161\|EH706421_T1 | cichorium | 2542 | 51 | 94 | 100 | 80.8695652 | blastp |
| 1196 | cichorium\|gb161\|EH708948_T1 | cichorium | 2543 | 51 | 90 | 100 | 32.5554259 | tblastn |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 1197 | cichorium\|gb161\|EH692078_T1 | cichorium | 2544 | 51 | 90 | 100 | 24.668435 | tblastn |
| 1198 | citrus\|gb157.2\|CB291468_T1 | citrus | 2545 | 51 | 82 | 100 | 86.1111111 | blastp |
| 1199 | citrus\|gb157.2\|BQ624699_T1 | citrus | 2546 | 51 | 90 | 100 | 27.56917 | tblastn |
| 1200 | clover\|gb162\|BB903718_T1 | clover | 2547 | 51 | 91 | 100 | 32.6315789 | blastp |
| 1201 | clover\|gb162\|BB930902_T1 | clover | 2548 | 51 | 88 | 100 | 32.4041812 | blastp |
| 1202 | clover\|gb162\|BB911526_T1 | clover | 2549 | 51 | 91 | 92.4731183 | 80.3738318 | blastp |
| 1203 | clover\|gb162\|BB913405_T1 | clover | 2550 | 51 | 90 | 96.7741935 | 81.0810811 | blastp |
| 1204 | cotton\|gb164\|ES804497_T1 | cotton | 2551 | 51 | 86 | 100 | 58.490566 | blastp |
| 1205 | cotton\|gb164\|EX172153_T1 | cotton | 2552 | 51 | 89 | 90.3225806 | 41.5156507 | tblastn |
| 1206 | cowpea\|gb166\|FF384339_T1 | cowpea | 2553 | 51 | 89 | 90.3225806 | 80 | blastp |
| 1207 | cowpea\|gb166\|FF396241_T1 | cowpea | 2554 | 51 | 82 | 97.8494624 | 88.3495146 | blastp |
| 1208 | cowpea\|gb166\|ES884224_T1 | cowpea | 2555 | 51 | 88 | 100 | 32.4041812 | blastp |
| 1209 | cowpea\|gb166\|FG857474_T1 | cowpea | 2556 | 51 | 89 | 100 | 68.8888889 | blastp |
| 1210 | cryptomeria\|gb166\|BY902595_T1 | cryptomeria | 2557 | 51 | 81 | 100 | 78.8135593 | blastp |
| 1211 | cryptomeria\|gb166\|BJ937695_T1 | cryptomeria | 2558 | 51 | 83 | 100 | 31.7406143 | blastp |
| 1212 | cryptomeria\|gb166\|BW993227_T1 | cryptomeria | 2559 | 51 | 82 | 88.172043 | 86.3157895 | blastp |
| 1213 | dandelion\|gb161\|DY802675_T1 | dandelion | 2560 | 51 | 87 | 91.3978495 | 75.2212389 | blastp |
| 1214 | fescue\|gb161\|DT674412_T1 | fescue | 2561 | 51 | 82 | 84.9462366 | 85.8695652 | blastp |
| 1215 | fescue\|gb161\|DT695652_T1 | fescue | 2562 | 51 | 84 | 100 | 76.8595041 | blastp |
| 1216 | fescue\|gb161\|DT702501_T1 | fescue | 2563 | 51 | 83 | 95.6989247 | 96.7391304 | blastp |
| 1217 | fescue\|gb161\|DT688112_T1 | fescue | 2564 | 51 | 83 | 100 | 85.3211009 | blastp |
| 1218 | fescue\|gb161\|DT688728_T1 | fescue | 2565 | 51 | 92 | 100 | 81.5789474 | blastp |
| 1219 | ginger\|gb164\|DY358169_T1 | ginger | 2566 | 51 | 87 | 100 | 32.9787234 | blastp |
| 1220 | ginger\|gb164\|DY366672_T1 | ginger | 2567 | 51 | 82 | 93.5483871 | 87 | blastp |
| 1221 | ginger\|gb164\|DY360033_T1 | ginger | 2568 | 51 | 91 | 100 | 27.7888446 | tblastn |
| 1222 | grape\|gb160\|AF188843_T5 | grape | 2569 | 51 | 82 | 100 | 32.5174825 | blastp |
| 1223 | ipomoea\|gb157.2\|BJ556470_T1 | ipomoea | 2570 | 51 | 88 | 100 | 32.4041812 | blastp |
| 1224 | lettuce\|gb157.2\|DW158018_T1 | lettuce | 2571 | 51 | 90 | 100 | 32.6315789 | blastp |
| 1225 | lettuce\|gb157.2\|DW091407_T1 | lettuce | 2572 | 51 | 90 | 100 | 34.7014925 | blastp |
| 1226 | lettuce\|gb157.2\|DW060777_T1 | lettuce | 2573 | 51 | 89 | 89.2473118 | 32.6771654 | blastp |
| 1227 | lotus\|gb157.2\|AV775277_T1 | lotus | 2574 | 51 | 83 | 100 | 88.5714286 | blastp |
| 1228 | lotus\|gb157.2\|AI967387_T1 | lotus | 2575 | 51 | 84 | 100 | 32.4041812 | blastp |
| 1229 | lotus\|gb157.2\|AV774377_T1 | lotus | 2576 | 51 | 81 | 100 | 88.5714286 | blastp |
| 1230 | lotus\|gb157.2\|BP059122_T1 | lotus | 2577 | 51 | 80 | 73.1182796 | 85 | blastp |
| 1231 | lotus\|gb157.2\|BI419853_T1 | lotus | 2578 | 51 | 81 | 94.6236559 | 88 | blastp |
| 1232 | lotus\|gb157.2\|BP049219_T1 | lotus | 2579 | 51 | 81 | 100 | 76.2295082 | blastp |
| 1233 | lotus\|gb157.2\|AV775053_T1 | lotus | 2580 | 51 | 82 | 84.9462366 | 86.8131868 | blastp |
| 1234 | lotus\|gb157.2\|AV775249_T1 | lotus | 2581 | 51 | 85 | 95.6989247 | 80.9090909 | blastp |
| 1235 | maize\|gb164\|AF326496_T1 | maize | 2582 | 51 | 88 | 100 | 32.4041812 | blastp |
| 1236 | maize\|gb164\|AY107589_T1 | maize | 2583 | 51 | 84 | 100 | 32.8621908 | blastp |
| 1237 | medicago\|gb157.2\|AI974409_T1 | medicago | 2584 | 51 | 87 | 100 | 32.4041812 | blastp |
| 1238 | medicago\|gb157.2\|AI974231_T1 | medicago | 2585 | 51 | 89 | 100 | 32.6315789 | blastp |
| 1239 | melon\|gb165\|EB715587_T1 | melon | 2586 | 51 | 86 | 100 | 23.4848485 | tblastn |
| 1240 | oat\|gb164\|CN816056_T1 | oat | 2587 | 51 | 82 | 100 | 84.5454545 | blastp |
| 1241 | oil_palm\|gb166\|CN601069_T1 | oil_palm | 2588 | 51 | 89 | 100 | 32.9787234 | blastp |
| 1242 | oil_palm\|gb166\|EL686181_T1 | oil_palm | 2589 | 51 | 84 | 100 | 32.9787234 | blastp |
| 1243 | peanut\|gb161\|CD037823_T1 | peanut | 2590 | 51 | 82 | 100 | 31.8493151 | blastp |
| 1244 | peanut\|gb161\|CD038014_T1 | peanut | 2591 | 51 | 88 | 100 | 32.1799308 | blastp |
| 1245 | periwinkle\|gb164\|AM232518_T2 | periwinkle | 2592 | 51 | 87 | 100 | 65.9574468 | blastp |
| 1246 | physcomitrella\|gb157\|BI436955_T1 | physcomitrella | 2593 | 51 | 89 | 100 | 33.3333333 | blastp |
| 1247 | physcomitrella\|gb157\|BJ198543_T1 | physcomitrella | 2594 | 51 | 82 | 100 | 32.5174825 | blastp |
| 1248 | physcomitrella\|gb157\|AW476973_T3 | physcomitrella | 2595 | 51 | 90 | 100 | 33.2142857 | blastp |
| 1249 | physcomitrella\|gb157\|BJ962015_T1 | physcomitrella | 2596 | 51 | 82 | 100 | 32.5259516 | blastp |
| 1250 | pine\|gb157.2\|AW870138_T1 | pine | 2597 | 51 | 82 | 100 | 34.7014925 | blastp |
| 1251 | pine\|gb157.2\|AI813147_T1 | pine | 2598 | 51 | 87 | 100 | 33.0960854 | blastp |
| 1252 | pine\|gb157.2\|AA739836_T1 | pine | 2599 | 51 | 87 | 100 | 33.0960854 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 1253 | pine\|gb157.2\|AL750425_T1 | pine | 2600 | 51 | 88 | 100 | 33.0960854 | blastp |
| 1254 | pine\|gb157.2\|BG038984_T1 | pine | 2601 | 51 | 80 | 100 | 32.8621908 | blastp |
| 1255 | pine\|gb157.2\|AW225939_T1 | pine | 2602 | 51 | 80 | 100 | 34.1911765 | blastp |
| 1256 | pine\|gb157.2\|BQ696500_T1 | pine | 2603 | 51 | 81 | 100 | 32.8621908 | blastp |
| 1257 | pine\|gb157.2\|AL751198_T1 | pine | 2604 | 51 | 87 | 100 | 33.3333333 | blastp |
| 1258 | pine\|gb157.2\|BQ695693_T1 | pine | 2605 | 51 | 82 | 100 | 32.8621908 | blastp |
| 1259 | pine\|gb157.2\|BF517326_T1 | pine | 2606 | 51 | 80 | 100 | 60.3896104 | blastp |
| 1260 | pine\|gb157.2\|AA739625_T1 | pine | 2607 | 51 | 81 | 100 | 34.7014925 | blastp |
| 1261 | pine\|gb157.2\|BG317873_T1 | pine | 2608 | 51 | 82 | 100 | 32.8621908 | blastp |
| 1262 | pine\|gb157.2\|AI813147_T2 | pine | 2609 | 51 | 87 | 100 | 32.9787234 | blastp |
| 1263 | pine\|gb157.2\|CF388120_T1 | pine | 2610 | 51 | 87 | 100 | 33.3333333 | blastp |
| 1264 | pine\|gb157.2\|BE662590_T1 | pine | 2611 | 51 | 81 | 100 | 35.7692308 | blastp |
| 1265 | pine\|gb157.2\|BG318657_T1 | pine | 2612 | 51 | 82 | 100 | 32.8621908 | blastp |
| 1266 | pine\|gb157.2\|AA557104_T1 | pine | 2613 | 51 | 88 | 100 | 33.3333333 | blastp |
| 1267 | pine\|gb157.2\|AW870138_T2 | pine | 2614 | 51 | 82 | 100 | 32.8621908 | blastp |
| 1268 | pine\|gb157.2\|AW289749_T1 | pine | 2615 | 51 | 82 | 100 | 32.8621908 | blastp |
| 1269 | pine\|gb157.2\|H75016_T1 | pine | 2616 | 51 | 88 | 100 | 32.7464789 | blastp |
| 1270 | pine\|gb157.2\|AA740005_T1 | pine | 2617 | 51 | 80 | 100 | 35.0943396 | blastp |
| 1271 | pine\|gb157.2\|CA305579_T1 | pine | 2618 | 51 | 91 | 100 | 75.6097561 | blastp |
| 1272 | pine\|gb157.2\|BE187350_T1 | pine | 2619 | 51 | 83 | 100 | 32.8621908 | blastp |
| 1273 | pine\|gb157.2\|CF473539_T1 | pine | 2620 | 51 | 84 | 100 | 32.9787234 | blastp |
| 1274 | pine\|gb157.2\|AW290370_T1 | pine | 2621 | 51 | 83 | 100 | 32.7464789 | blastp |
| 1275 | pine\|gb157.2\|AW290691_T1 | pine | 2622 | 51 | 82 | 75.2688172 | 88.6075949 | blastp |
| 1276 | pine\|gb157.2\|BG318695_T1 | pine | 2623 | 51 | 82 | 100 | 34.7014925 | blastp |
| 1277 | pineapple\|gb157.2\|DT339628_T1 | pineapple | 2624 | 51 | 91 | 98.9247312 | 78.6324786 | blastp |
| 1278 | poplar\|gb157.2\|AI162483_T2 | poplar | 2625 | 51 | 86 | 100 | 24.3455497 | tblastn |
| 1279 | poplar\|gb157.2\|BU817536_T4 | poplar | 2626 | 51 | 87 | 100 | 22.6094003 | tblastn |
| 1280 | potato\|gb157.2\|BQ515617_T1 | potato | 2627 | 51 | 80 | 98.9247312 | 36.6533865 | blastp |
| 1281 | potato\|gb157.2\|BE920139_T2 | potato | 2628 | 51 | 90 | 100 | 41.5178571 | blastp |
| 1282 | radish\|gb164\|EV526963_T1 | radish | 2629 | 51 | 87 | 100 | 32.5174825 | blastp |
| 1283 | radish\|gb164\|EV567230_T1 | radish | 2630 | 51 | 84 | 100 | 46.039604 | blastp |
| 1284 | radish\|gb164\|EV551004_T1 | radish | 2631 | 51 | 92 | 100 | 32.2916667 | blastp |
| 1285 | radish\|gb164\|EX756464_T1 | radish | 2632 | 51 | 86 | 100 | 48.1865285 | blastp |
| 1286 | radish\|gb164\|EY910551_T1 | radish | 2633 | 51 | 91 | 100 | 31.9587629 | blastp |
| 1287 | radish\|gb164\|EW730466_T1 | radish | 2634 | 51 | 84 | 98.9247312 | 87.6190476 | blastp |
| 1288 | radish\|gb164\|AF051128_T1 | radish | 2635 | 51 | 81 | 87.0967742 | 48.6 | tblastn |
| 1289 | radish\|gb164\|EX756028_T1 | radish | No predicted Protein | 51 | 86 | 100 | 40.0286944 | tblastn |
| 1290 | rice\|gb157.2\|BE229418_T1 | rice | 2636 | 51 | 90 | 100 | 32.9787234 | blastp |
| 1291 | rice\|gb157.2\|BE229418_T3 | rice | 2637 | 51 | 90 | 100 | 38.5892116 | blastp |
| 1292 | rice\|gb157.2\|AK107700_T1 | rice | 2638 | 51 | 91 | 100 | 68.8888889 | blastp |
| 1293 | rice\|gb157.2\|BE229418_T4 | rice | 2639 | 51 | 90 | 100 | 54.0697674 | blastp |
| 1294 | rice\|gb157.2\|NM001066078_T1 | rice | 2640 | 51 | 92 | 100 | 41.7040359 | blastp |
| 1295 | rice\|gb157.2\|AW155505_T1 | rice | 2641 | 51 | 83 | 100 | 32.0689655 | blastp |
| 1296 | rice\|gb157.2\|AW155505_T2 | rice | 2642 | 51 | 83 | 98.9247312 | 35.7976654 | blastp |
| 1297 | rice\|gb157.2\|AK106746_T1 | rice | 2643 | 51 | 83 | 100 | 22.6461039 | tblastn |
| 1298 | sorghum\|gb161.xeno\|AY107589_T1 | sorghum | 2644 | 51 | 86 | 100 | 33.3333333 | blastp |
| 1299 | sorghum\|gb161.xeno\|AI947598_T1 | sorghum | 2645 | 51 | 92 | 100 | 32.5174825 | blastp |
| 1300 | sorghum\|gb161.xeno\|AI855413_T1 | sorghum | 2646 | 51 | 80 | 100 | 31.4189189 | blastp |
| 1301 | sorghum\|gb161.xeno\|AW565915_T1 | sorghum | 2647 | 51 | 81 | 100 | 31.1418685 | blastp |
| 1302 | sorghum\|gb161.xeno\|CF481617_T1 | sorghum | 2648 | 51 | 90 | 100 | 79.6610169 | blastp |
| 1303 | soybean\|gb166\|BU549322_T1 | soybean | 2649 | 51 | 89 | 100 | 32.5174825 | blastp |
| 1304 | soybean\|gb166\|BE352729_T1 | soybean | 2650 | 51 | 88 | 100 | 32.4041812 | blastp |
| 1305 | soybean\|gb166\|BI974981_T1 | soybean | 2651 | 51 | 91 | 100 | 71.5384615 | blastp |
| 1306 | soybean\|gb166\|BE658685_T1 | soybean | 2652 | 51 | 89 | 100 | 32.6315789 | blastp |
| 1307 | soybean\|gb166\|BE352747_T3 | soybean | 2653 | 51 | 81 | 100 | 20.5904059 | tblastn |
| 1308 | spikemoss\|gb165\|DN838269_T1 | spikemoss | 2654 | 51 | 88 | 100 | 32.0689655 | blastp |
| 1309 | spikemoss\|gb165\|FE434019_T1 | spikemoss | 2655 | 51 | 88 | 100 | 32.0689655 | blastp |
| 1310 | spruce\|gb162\|CO225164_T1 | spruce | 2656 | 51 | 89 | 100 | 32.8621908 | blastp |
| 1311 | spruce\|gb162\|CO258147_T1 | spruce | 2657 | 51 | 81 | 100 | 33.8181818 | blastp |
| 1312 | spruce\|gb162\|CO230791_T1 | spruce | 2658 | 51 | 88 | 100 | 46.039604 | blastp |
| 1313 | spruce\|gb162\|DR546674_T1 | spruce | 2659 | 51 | 82 | 100 | 32.5 | blastp |
| 1314 | spruce\|gb162\|DR560237_T1 | spruce | 2660 | 51 | 81 | 100 | 34.1911765 | blastp |
| 1315 | spurge\|gb161\|DV116550_T1 | spurge | 2661 | 51 | 83 | 100 | 86.1111111 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 1316 | sugarcane\|gb157.2\|CA088464__T1 | sugarcane | 2662 | 51 | 87 | 88.172043 | 81.1881188 | blastp |
| 1317 | sugarcane\|gb157.2\|CA086583__T1 | sugarcane | 2663 | 51 | 92 | 100 | 62.4161074 | blastp |
| 1318 | sugarcane\|gb157.2\|CA234165__T1 | sugarcane | 2664 | 51 | 86 | 62.3655914 | 100 | blastp |
| 1319 | sugarcane\|gb157.2\|CA107998__T1 | sugarcane | 2665 | 51 | 89 | 100 | 32.5174825 | blastp |
| 1320 | sugarcane\|gb157.2\|CA204327__T1 | sugarcane | 2666 | 51 | 95 | 100 | 34.1911765 | tblastn |
| 1321 | sugarcane\|gb157.2\|CA067786__T1 | sugarcane | 2667 | 51 | 92 | 86.0215054 | 18.6480186 | tblastn |
| 1322 | sunflower\|gb162\|DY944685__T1 | sunflower | 2668 | 51 | 81 | 100 | 31.9587629 | blastp |
| 1323 | sunflower\|gb162\|BQ968590__T1 | sunflower | 2669 | 51 | 87 | 52.688172 | 100 | blastp |
| 1324 | sunflower\|gb162\|CD848850__T1 | sunflower | 2670 | 51 | 89 | 98.9247312 | 41.3173653 | tblastn |
| 1325 | tobacco\|gb162\|EB445876__T1 | tobacco | 2671 | 51 | 90 | 100 | 32.4041812 | blastp |
| 1326 | tobacco\|gb162\|EB445188__T1 | tobacco | 2672 | 51 | 88 | 100 | 32.4041812 | blastp |
| 1327 | tobacco\|gb162\|CK720586__T1 | tobacco | 2673 | 51 | 81 | 100 | 34.7014925 | blastp |
| 1328 | tomato\|gb164\|CO750818__T1 | tomato | 2674 | 51 | 92 | 88.172043 | 82.8282828 | blastp |
| 1329 | tomato\|gb164\|AI772191__T1 | tomato | 2675 | 51 | 81 | 98.9247312 | 33.6996337 | blastp |
| 1330 | tomato\|gb164\|AW219533__T2 | tomato | 2676 | 51 | 89 | 100 | 39.2405063 | tblastn |
| 1331 | triphysaria\|gb164\|DR173305__T1 | triphysaria | 2677 | 51 | 88 | 95.6989247 | 80.9090909 | blastp |
| 1332 | triphysaria\|gb164\|EX984185__T1 | triphysaria | 2678 | 51 | 90 | 100 | 75.6097561 | blastp |
| 1333 | triphysaria\|gb164\|DR174019__T1 | triphysaria | 2679 | 51 | 91 | 100 | 67.8832117 | blastp |
| 1334 | wheat\|gb164\|CA609068__T1 | wheat | 2680 | 51 | 94 | 100 | 67.3913043 | blastp |
| 1335 | wheat\|gb164\|BE430411__T1 | wheat | 2681 | 51 | 86 | 100 | 32.4041812 | blastp |
| 1336 | wheat\|gb164\|CK208980__T1 | wheat | 2682 | 51 | 80 | 100 | 30 | blastp |
| 1337 | wheat\|gb164\|CA620158__T1 | wheat | 2683 | 51 | 96 | 95.6989247 | 87.254902 | blastp |
| 1338 | wheat\|gb164\|BE405395__T1 | wheat | 2684 | 51 | 88 | 100 | 32.7464789 | blastp |
| 1339 | wheat\|gb164\|CA647310__T1 | wheat | 2685 | 51 | 80 | 77.4193548 | 93.5064935 | blastp |
| 1340 | wheat\|gb164\|BE492099__T1 | wheat | 2686 | 51 | 87 | 100 | 32.7464789 | blastp |
| 1341 | wheat\|gb164\|BE402029__T1 | wheat | 2687 | 51 | 87 | 100 | 32.7464789 | blastp |
| 1342 | wheat\|gb164\|CA618130__T1 | wheat | 2688 | 51 | 86 | 88.172043 | 73.2142857 | blastp |
| 1343 | wheat\|gb164\|CJ605707__T1 | wheat | 2689 | 51 | 82 | 100 | 69.4029851 | blastp |
| 1344 | wheat\|gb164\|CA614209__T1 | wheat | 2690 | 51 | 98 | 59.1397849 | 98.2142857 | blastp |
| 1345 | wheat\|gb164\|CA701714__T1 | wheat | 2691 | 51 | 82 | 100 | 77.5 | blastp |
| 1346 | wheat\|gb164\|BE403921__T1 | wheat | 2692 | 51 | 93 | 96.7741935 | 82.5688073 | blastp |
| 1347 | wheat\|gb164\|BE217049__T1 | wheat | 2693 | 51 | 83 | 100 | 31.9587629 | blastp |
| 1348 | wheat\|gb164\|CA602649__T1 | wheat | 2694 | 51 | 84 | 100 | 30.0322928 | tblastn |
| 1349 | wheat\|gb164\|CA486220__T1 | wheat | 2695 | 51 | 82 | 96.7741935 | 33.3759591 | tblastn |
| 1350 | b_juncea\|gb164\|EVGN00044413933329__T1 | b_juncea | 2696 | 52 | 85 | 64.3835616 | 99.2957746 | blastp |
| 1351 | b_juncea\|gb164\|EVGN00137910990746__T1 | b_juncea | 2697 | 52 | 90 | 53.4246575 | 99.1525424 | blastp |
| 1352 | barley\|gb157.3\|BE413268__T1 | barley | 2698 | 52 | 81 | 96.803653 | 73.4482759 | blastp |
| 1353 | barley\|gb157.3\|AJ433979__T1 | barley | 2699 | 52 | 81 | 96.803653 | 73.4482759 | blastp |
| 1354 | barley\|gb157.3\|BE412979__T1 | barley | 2700 | 52 | 82 | 96.803653 | 74.1258741 | blastp |
| 1355 | brachypodium\|gb161.xeno\|AF139815__T1 | brachypodium | 2701 | 52 | 83 | 96.803653 | 73.6111111 | blastp |
| 1356 | citrus\|gb157.2\|CX052950__T1 | citrus | 2702 | 52 | 84 | 50.2283105 | 100 | blastp |
| 1357 | clover\|gb162\|BB913131__T1 | clover | 2703 | 52 | 93 | 52.5114155 | 99.137931 | blastp |
| 1358 | clover\|gb162\|BB918704__T1 | clover | 2704 | 52 | 82 | 63.9269406 | 99.2957746 | blastp |
| 1359 | cotton\|gb164\|CO103246__T1 | cotton | 2705 | 52 | 91 | 56.6210046 | 93.9393939 | blastp |
| 1360 | cowpea\|gb166\|FG883860__T1 | cowpea | 2706 | 52 | 83 | 51.1415525 | 99.1150442 | blastp |
| 1361 | fescue\|gb161\|DT702489__T1 | fescue | 2707 | 52 | 96 | 57.0776256 | 93.2835821 | blastp |
| 1362 | fescue\|gb161\|DT702846__T1 | fescue | 2708 | 52 | 96 | 57.0776256 | 96.8992248 | blastp |
| 1363 | ipomoea\|gb157.2\|BU691146__T1 | ipomoea | 2709 | 52 | 81 | 87.2146119 | 74.7035573 | blastp |
| 1364 | maize\|gb164\|AI939909__T1 | maize | 2710 | 52 | 80 | 96.803653 | 73.6111111 | blastp |
| 1365 | maize\|gb164\|AF130975__T1 | maize | 2711 | 52 | 83 | 96.803653 | 74.3859649 | blastp |
| 1366 | maize\|gb164\|AI947831__T1 | maize | 2712 | 52 | 83 | 96.803653 | 73.6111111 | blastp |
| 1367 | oil_palm\|gb166\|EL692065__T1 | oil_palm | 2713 | 52 | 80 | 96.803653 | 75.177305 | blastp |
| 1368 | physcomitrella\|gb157\|AW476973__T1 | physcomitrella | 2714 | 52 | 80 | 93.6073059 | 73.4767025 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 1369 | physcomitrella\|gb157\|BI894596_T1 | physcomitrella | 2715 | 52 | 80 | 96.347032 | 73.0103806 | blastp |
| 1370 | physcomitrella\|gb157\|AW476973_T2 | physcomitrella | 2716 | 52 | 80 | 93.6073059 | 73.4767025 | blastp |
| 1371 | pine\|gb157.2\|CF387570_T1 | pine | 2717 | 52 | 88 | 51.1415525 | 99.1150442 | blastp |
| 1372 | radish\|gb164\|EY904434_T2 | radish | 2718 | 52 | 88 | 54.3378995 | 99.1666667 | blastp |
| 1373 | radish\|gb164\|FD960377_T1 | radish | 2719 | 52 | 84 | 63.0136986 | 99.2805755 | blastp |
| 1374 | rice\|gb157.2\|AU093957_T1 | rice | 2720 | 52 | 81 | 96.803653 | 74.1258741 | blastp |
| 1375 | rice\|gb157.2\|BE039992_T2 | rice | 2721 | 52 | 92 | 57.0776256 | 97.65625 | blastp |
| 1376 | rice\|gb157.2\|BE530955_T1 | rice | 2722 | 52 | 80 | 96.803653 | 73.1034483 | blastp |
| 1377 | rye\|gb164\|BE586469_T1 | rye | 2723 | 52 | 82 | 61.1872146 | 97.810219 | blastp |
| 1378 | sorghum\|gb161.xeno\|AW922622_T1 | sorghum | 2724 | 52 | 83 | 96.803653 | 72.6027397 | blastp |
| 1379 | sorghum\|gb161.xeno\|BE344582_T1 | sorghum | 2725 | 52 | 80 | 85.3881279 | 74.8 | blastp |
| 1380 | sorghum\|gb161.xeno\|AI855280_T1 | sorghum | 2726 | 52 | 82 | 96.803653 | 73.3564014 | blastp |
| 1381 | spikemoss\|gb165\|DN838148_T1 | spikemoss | 2727 | 52 | 83 | 91.7808219 | 71.5302491 | blastp |
| 1382 | spikemoss\|gb165\|DN838057_T1 | spikemoss | 2728 | 52 | 83 | 91.7808219 | 71.5302491 | blastp |
| 1383 | sugarcane\|gb157.2\|CA139573_T1 | sugarcane | 2729 | 52 | 82 | 90.4109589 | 71.8978102 | blastp |
| 1384 | sugarcane\|gb157.2\|CA145403_T1 | sugarcane | 2730 | 52 | 90 | 57.0776256 | 99.2063492 | blastp |
| 1385 | sunflower\|gb162\|CF083179_T1 | sunflower | 2731 | 52 | 80 | 57.0776256 | 93.2835821 | blastp |
| 1386 | sunflower\|gb162\|BU035823_T1 | sunflower | 2732 | 52 | 86 | 56.6210046 | 89.2086331 | blastp |
| 1387 | switchgrass\|gb165\|DN140790_T1 | switchgrass | 2733 | 52 | 83 | 61.6438356 | 99.2647059 | blastp |
| 1388 | switchgrass\|gb165\|FE631354_T1 | switchgrass | 2734 | 52 | 81 | 66.2100457 | 96.6666667 | blastp |
| 1389 | tobacco\|gb162\|DV159802_T1 | tobacco | 2735 | 52 | 81 | 87.6712329 | 48.7722269 | tblastn |
| 1390 | wheat\|gb164\|AF139815_T1 | wheat | 2736 | 52 | 82 | 96.803653 | 74.1258741 | blastp |
| 1391 | wheat\|gb164\|BE406301_T1 | wheat | 2737 | 52 | 81 | 96.803653 | 73.4482759 | blastp |
| 1392 | wheat\|gb164\|BE404904_T1 | wheat | 2738 | 52 | 81 | 96.803653 | 73.4482759 | blastp |
| 1393 | wheat\|gb164\|BE400219_T1 | wheat | 2739 | 52 | 81 | 96.803653 | 73.4482759 | blastp |
| 1394 | wheat\|gb164\|CA619093_T1 | wheat | 2740 | 52 | 81 | 54.7945205 | 90.1515152 | blastp |
| 1395 | wheat\|gb164\|BE605056_T1 | wheat | 2741 | 52 | 88 | 56.6210046 | 93.2330827 | blastp |
| 1396 | wheat\|gb164\|BQ245211_T1 | wheat | 2742 | 52 | 82 | 96.803653 | 74.1258741 | blastp |
| 1397 | wheat\|gb164\|BE497487_T1 | wheat | 2743 | 52 | 81 | 96.803653 | 73.4482759 | blastp |
| 1398 | wheat\|gb164\|BQ295206_T1 | wheat | 2744 | 52 | 89 | 64.8401826 | 100 | blastp |
| 1399 | wheat\|gb164\|BE499954_T1 | wheat | 2745 | 52 | 80 | 98.630137 | 74.8275862 | blastp |
| 1400 | wheat\|gb164\|BE405794_T1 | wheat | 2746 | 52 | 81 | 96.803653 | 73.4482759 | blastp |
| 5 | tomato\|gb164\|BP881534_T1 | tomato | 31 | 32 | 82 | 100 | 100 | blastp |
| 21 | barley\|gb157.3\|AL501410_T1 | barley | 47 | 46 | 87 | 98.3935743 | 98.79518072 | blastp |
| 2844 | antirrhinum\|gb166\|AJ559427_T1 | antirrhinum | 3052 | 25 | 88 | 100 | 100 | blastp |
| 2845 | antirrhinum\|gb166\|AJ791214_T1 | antirrhinum | 3053 | 25 | 85 | 100 | 100 | blastp |
| 2846 | bruguiera\|gb166\|BP939664_T1 | bruguiera | 3054 | 25 | 82 | 61.29032258 | 100 | blastp |
| 2847 | centaurea\|gb166\|EL931601_T1 | centaurea | 3055 | 25 | 84 | 98.79032258 | 100 | blastp |
| 2848 | eucalyptus\|gb166\|CD668425_T1 | eucalyptus | 3056 | 25 | 85 | 98.79032258 | 98.79032258 | blastp |
| 2849 | kiwi\|gb166\|FG409998_T1 | kiwi | 3057 | 25 | 85 | 100 | 100 | blastp |
| 2850 | kiwi\|gb166\|FG453166_T1 | kiwi | 3058 | 25 | 86 | 100 | 100 | blastp |
| 2851 | kiwi\|gb166\|FG401585_T1 | kiwi | 3059 | 25 | 87 | 99.59677419 | 100 | blastp |
| 2852 | kiwi\|gb166\|FG419790_T1 | kiwi | 3060 | 25 | 85 | 100 | 100 | blastp |
| 2853 | liriodendron\|gb166\|FD495170_T1 | liriodendron | 3061 | 25 | 82 | 99.19354839 | 98.79518072 | blastp |
| 2854 | poppy\|gb166\|FG607362_T1 | poppy | 3062 | 25 | 82 | 82.66129032 | 99.51456311 | blastp |
| 2855 | soybean\|gb167\|AA660186_T1 | soybean | 3063 | 25 | 83 | 100 | 100 | blastp |
| 2856 | soybean\|gb167\|CA990807_T1 | soybean | 3064 | 25 | 82 | 95.56451613 | 100 | blastp |
| 2857 | walnuts\|gb166\|CV196664_T1 | walnuts | 3065 | 25 | 83 | 100 | 100 | blastp |
| 2858 | antirrhinum\|gb166\|X70417_T1 | antirrhinum | 3066 | 26 | 90 | 100 | 100 | blastp |
| 2859 | banana\|gb167\|FF560721_T1 | banana | 3067 | 26 | 86 | 77.6 | 99.48717949 | blastp |
| 2860 | centaurea\|gb166\|EL932548_T1 | centaurea | 3068 | 26 | 86 | 100 | 100 | blastp |
| 2861 | antirrhinum\|gb166\|AJ789802_T1 | antirrhinum | 3069 | 27 | 86 | 90.90909091 | 100 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 2862 | bruguiera\|gb166\|BP938735_T1 | bruguiera | 3070 | 27 | 81 | 69.96047431 | 100 | blastp |
| 2863 | eucalyptus\|gb166\|ES589574_T1 | eucalyptus | 3071 | 27 | 82 | 90.90909091 | 100 | blastp |
| 2864 | kiwi\|gb166\|FG427735_T1 | kiwi | 3072 | 27 | 86 | 50.19762846 | 99.21875 | blastp |
| 2865 | kiwi\|gb166\|FG406415_T1 | kiwi | 3073 | 27 | 81 | 54.15019763 | 100 | blastp |
| 2866 | kiwi\|gb166\|FG406885_T1 | kiwi | 3074 | 27 | 84 | 99.20948617 | 99.6031746 | blastp |
| 2867 | liriodendron\|gb166\|CK744430_T1 | liriodendron | 3075 | 27 | 81 | 99.20948617 | 99.6031746 | blastp |
| 2868 | poppy\|gb166\|FG608493_T1 | poppy | 3076 | 27 | 84 | 83.00395257 | 99.52606635 | blastp |
| 2869 | soybean\|gb167\|EV269611_T1 | soybean | 3077 | 27 | 86 | 60.07905138 | 96.20253165 | blastp |
| 2870 | amborella\|gb166\|CD482678_T1 | amborella | 3078 | 28 | 82 | 100 | 100 | blastp |
| 2871 | cenchrus\|gb166\|BM084541_T1 | cenchrus | 3079 | 28 | 81 | 100 | 100 | blastp |
| 2872 | leymus\|gb166\|EG376267_T1 | leymus | 3080 | 28 | 80 | 100 | 100 | blastp |
| 2873 | leymus\|gb166\|EG386149_T1 | leymus | 3081 | 28 | 80 | 100 | 100 | blastp |
| 2874 | walnuts\|gb166\|EL895384_T1 | walnuts | 3082 | 28 | 83 | 82 | 94.49541284 | blastp |
| 2875 | amborella\|gb166\|CD481950_T1 | amborella | 3083 | 30 | 88 | 98.26388889 | 98.95470383 | blastp |
| 2876 | antirrhinum\|gb166\|AJ796874_T1 | antirrhinum | 3084 | 30 | 86 | 93.40277778 | 100 | blastp |
| 2877 | antirrhinum\|gb166\|AJ798039_T1 | antirrhinum | 3085 | 30 | 84 | 73.26388889 | 99.52606635 | blastp |
| 2878 | antirrhinum\|gb166\|AJ792331_T1 | antirrhinum | 3086 | 30 | 88 | 85.06944444 | 100 | blastp |
| 2879 | antirrhinum\|gb166\|AJ558770_T1 | antirrhinum | 3087 | 30 | 86 | 98.26388889 | 99.3006993 | blastp |
| 2880 | banana\|gb167\|FF558844_T1 | banana | 3088 | 30 | 88 | 98.26388889 | 98.95104895 | blastp |
| 2881 | bean\|gb167\|CA898412_T1 | bean | 3089 | 30 | 81 | 98.26388889 | 99.30313589 | blastp |
| 2882 | bruguiera\|gb166\|BP941115_T1 | bruguiera | 3090 | 30 | 86 | 52.77777778 | 95 | blastp |
| 2883 | bruguiera\|gb166\|BP939033_T1 | bruguiera | 3091 | 30 | 85 | 97.91666667 | 99.30313589 | blastp |
| 2884 | cenchrus\|gb166\|EB656428_T1 | cenchrus | 3092 | 30 | 85 | 98.26388889 | 98.95833333 | blastp |
| 2885 | centaurea\|gb166\|EH767475_T1 | centaurea | 3093 | 30 | 86 | 98.26388889 | 98.95470383 | blastp |
| 2886 | centaurea\|gb166\|EL935569_T1 | centaurea | 3094 | 30 | 86 | 98.26388889 | 98.95833333 | blastp |
| 2887 | cycas\|gb166\|CB089724_T1 | cycas | 3095 | 30 | 84 | 98.26388889 | 98.95470383 | blastp |
| 2888 | cycas\|gb166\|CB088798_T1 | cycas | 3096 | 30 | 83 | 98.26388889 | 98.26989619 | blastp |
| 2889 | eucalyptus\|gb166\|CD668044_T1 | eucalyptus | 3097 | 30 | 84 | 98.26388889 | 99.30555556 | blastp |
| 2890 | eucalyptus\|gb166\|AW191311_T1 | eucalyptus | 3098 | 30 | 87 | 98.26388889 | 98.95470383 | blastp |
| 2891 | kiwi\|gb166\|FG403284_T1 | kiwi | 3099 | 30 | 85 | 98.26388889 | 99.3006993 | blastp |
| 2892 | kiwi\|gb166\|FG404130_T1 | kiwi | 3100 | 30 | 86 | 98.26388889 | 99.3006993 | blastp |
| 2893 | kiwi\|gb166\|FG396354_T1 | kiwi | 3101 | 30 | 90 | 98.26388889 | 98.95104895 | blastp |
| 2894 | kiwi\|gb166\|FG404890_T1 | kiwi | 3102 | 30 | 85 | 72.22222222 | 99.5215311 | blastp |
| 2895 | kiwi\|gb166\|FG417962_T1 | kiwi | 3103 | 30 | 87 | 62.15277778 | 99.44444444 | blastp |
| 2896 | kiwi\|gb166\|FG403188_T1 | kiwi | 3104 | 30 | 89 | 98.26388889 | 96.91780822 | blastp |
| 2897 | kiwi\|gb166\|FG403647_T1 | kiwi | 3105 | 30 | 85 | 68.05555556 | 99.49238579 | blastp |
| 2898 | kiwi\|gb166\|FG397405_T1 | kiwi | 3106 | 30 | 85 | 98.26388889 | 99.3006993 | blastp |
| 2899 | leymus\|gb166\|EG384635_T1 | leymus | 3107 | 30 | 85 | 99.30555556 | 99.65517241 | blastp |
| 2900 | leymus\|gb166\|CN466016_T1 | leymus | 3108 | 30 | 83 | 98.26388889 | 98.97260274 | blastp |
| 2901 | leymus\|gb166\|CN466006_T1 | leymus | 3109 | 30 | 83 | 98.26388889 | 98.97260274 | blastp |
| 2902 | leymus\|gb166\|EG376500_T1 | leymus | 3110 | 30 | 83 | 98.26388889 | 98.97260274 | blastp |
| 2903 | liriodendron\|gb166\|CK749885_T1 | liriodendron | 3111 | 30 | 89 | 98.26388889 | 98.95470383 | blastp |
| 2904 | liriodendron\|gb166\|CV002697_T1 | liriodendron | 3112 | 30 | 88 | 98.26388889 | 98.95470383 | blastp |
| 2905 | lovegrass\|gb167\|DN480914_T1 | lovegrass | 3113 | 30 | 85 | 98.26388889 | 98.96193772 | blastp |
| 2906 | nuphar\|gb166\|CD472824_T1 | nuphar | 3114 | 30 | 86 | 98.26388889 | 98.94736842 | blastp |
| 2907 | nuphar\|gb166\|CD472574_T1 | nuphar | 3115 | 30 | 86 | 98.26388889 | 98.94736842 | blastp |
| 2908 | nuphar\|gb166\|CD473614_T1 | nuphar | 3116 | 30 | 84 | 51.73611111 | 98.02631579 | blastp |
| 2909 | peanut\|gb167\|ES759056_T1 | peanut | 3117 | 30 | 83 | 64.23611111 | 100 | blastp |
| 2910 | poppy\|gb166\|FE966578_T1 | poppy | 3118 | 30 | 83 | 98.61111111 | 98.62068966 | blastp |
| 2911 | pseudoroegneria\|gb167\|FF344096_T1 | pseudoroegneria | 3119 | 30 | 82 | 98.26388889 | 98.97260274 | blastp |
| 2912 | pseudoroegneria\|gb167\|FF346975_T1 | pseudoroegneria | 3120 | 30 | 85 | 98.61111111 | 98.62542955 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 2913 | pseudoroegneria\|gb167\|FF342094__T1 | pseudoroegneria | 3121 | 30 | 83 | 98.26388889 | 98.97260274 | blastp |
| 2914 | soybean\|gb167\|CA898412__T1 | soybean | 3122 | 30 | 84 | 94.44444444 | 95.0877193 | blastp |
| 2915 | switchgrass\|gb167\|FE621985__T1 | switchgrass | 3123 | 30 | 87 | 52.43055556 | 98.69281046 | blastp |
| 2916 | switchgrass\|gb167\|DN141371__T1 | switchgrass | 3124 | 30 | 86 | 98.26388889 | 98.95833333 | blastp |
| 2917 | tamarix\|gb166\|CF199714__T1 | tamarix | 3125 | 30 | 88 | 78.47222222 | 99.12280702 | blastp |
| 2918 | tamarix\|gb166\|CF226851__T1 | tamarix | 3126 | 30 | 85 | 98.26388889 | 99.30313589 | blastp |
| 2919 | walnuts\|gb166\|CB303847__T1 | walnuts | 3127 | 30 | 84 | 98.26388889 | 99.31034483 | blastp |
| 2920 | walnuts\|gb166\|CV194951__T1 | walnuts | 3128 | 30 | 86 | 98.26388889 | 99.30313589 | blastp |
| 2921 | walnuts\|gb166\|CV196162__T1 | walnuts | 3129 | 30 | 85 | 98.26388889 | 99.31506849 | blastp |
| 2922 | zamia\|gb166\|FD765004__T1 | zamia | 3130 | 30 | 84 | 98.26388889 | 98.95470383 | blastp |
| 2923 | antirrhinum\|gb166\|AJ799752__T1 | antirrhinum | 3131 | 31 | 80 | 98.7854251 | 100 | blastp |
| 2924 | kiwi\|gb166\|FG400670__T1 | kiwi | 3132 | 31 | 82 | 74.08906883 | 100 | blastp |
| 2925 | kiwi\|gb166\|FG418275__T1 | kiwi | 3133 | 31 | 83 | 98.7854251 | 98.38709677 | blastp |
| 2926 | centaurea\|gb166\|EL931588__T1 | centaurea | 3134 | 34 | 83 | 88.57142857 | 32.74021352 | blastp |
| 2927 | soybean\|gb167\|AW119586__T1 | soybean | 3135 | 34 | 83 | 94.28571429 | 36.26373626 | blastp |
| 2928 | soybean\|gb167\|AW573764__T1 | soybean | 3136 | 34 | 83 | 94.28571429 | 36.66666667 | blastp |
| 2929 | amborella\|gb166\|FD440187__T1 | amborella | 3137 | 35 | 81 | 65.76271186 | 100 | blastp |
| 2930 | centaurea\|gb166\|EL931433__T1 | centaurea | 3138 | 35 | 82 | 97.62711864 | 96.61016949 | blastp |
| 2931 | eucalyptus\|gb166\|CD668486__T1 | eucalyptus | 3139 | 35 | 85 | 73.89830508 | 100 | blastp |
| 2932 | petunia\|gb166\|DC243166__T1 | petunia | 3140 | 36 | 86 | 100 | 100 | blastp |
| 2933 | amborella\|gb166\|CD482946__T1 | amborella | 3141 | 39 | 82 | 99.64157706 | 98.93992933 | blastp |
| 2934 | antirrhinum\|gb166\|AJ559435__T1 | antirrhinum | 3142 | 39 | 88 | 99.28315412 | 98.57651246 | blastp |
| 2935 | antirrhinum\|gb166\|AJ793990__T1 | antirrhinum | 3143 | 39 | 89 | 71.32616487 | 100 | blastp |
| 2936 | antirrhinum\|gb166\|AJ559760__T1 | antirrhinum | 3144 | 39 | 83 | 61.29032258 | 87.24489796 | blastp |
| 2937 | antirrhinum\|gb166\|AJ558545__T1 | antirrhinum | 3145 | 39 | 88 | 88.53046595 | 100 | blastp |
| 2938 | bean\|gb167\|FE682762__T1 | bean | 3146 | 39 | 86 | 100 | 100 | blastp |
| 2939 | bean\|gb167\|CV531088__T1 | bean | 3147 | 39 | 86 | 99.64157706 | 98.94736842 | blastp |
| 2940 | bean\|gb167\|CA907460__T1 | bean | 3148 | 39 | 86 | 99.64157706 | 98.94736842 | blastp |
| 2941 | cenchrus\|gb166\|EB655519__T1 | cenchrus | 3149 | 39 | 83 | 97.49103943 | 95.86206897 | blastp |
| 2942 | centaurea\|gb166\|EL934360__T1 | centaurea | 3150 | 39 | 88 | 53.76344086 | 96.15384615 | blastp |
| 2943 | centaurea\|gb166\|EH751120__T1 | centaurea | 3151 | 39 | 80 | 88.53046595 | 100 | blastp |
| 2944 | centaurea\|gb166\|EH752971__T1 | centaurea | 3152 | 39 | 87 | 83.5125448 | 100 | blastp |
| 2945 | centaurea\|gb166\|EH768434__T1 | centaurea | 3153 | 39 | 80 | 91.7562724 | 99.61685824 | blastp |
| 2946 | centaurea\|gb166\|EH767287__T1 | centaurea | 3154 | 39 | 83 | 83.15412186 | 100 | blastp |
| 2947 | cichorium\|gb166\|DT212008__T1 | cichorium | 3155 | 39 | 82 | 89.96415771 | 100 | blastp |
| 2948 | cichorium\|gb166\|EL354583__T1 | cichorium | 3156 | 39 | 84 | 86.73835125 | 97.61904762 | blastp |
| 2949 | eucalyptus\|gb166\|CD668553__T1 | eucalyptus | 3157 | 39 | 87 | 83.87096774 | 100 | blastp |
| 2950 | eucalyptus\|gb166\|CD668534__T1 | eucalyptus | 3158 | 39 | 80 | 69.89247312 | 100 | blastp |
| 2951 | eucalyptus\|gb166\|CD668523__T1 | eucalyptus | 3159 | 39 | 88 | 100 | 99.3006993 | blastp |
| 2952 | eucalyptus\|gb166\|CD669942__T1 | eucalyptus | 3160 | 39 | 83 | 100 | 100 | blastp |
| 2953 | kiwi\|gb166\|FG405216__T1 | kiwi | 3161 | 39 | 84 | 100 | 99.29328622 | blastp |
| 2954 | kiwi\|gb166\|FG495821__T1 | kiwi | 3162 | 39 | 86 | 50.17921147 | 100 | blastp |
| 2955 | kiwi\|gb166\|FG417997__T1 | kiwi | 3163 | 39 | 86 | 64.51612903 | 100 | blastp |
| 2956 | kiwi\|gb166\|FG403725__T1 | kiwi | 3164 | 39 | 83 | 73.11827957 | 100 | blastp |
| 2957 | kiwi\|gb166\|FG397310__T1 | kiwi | 3165 | 39 | 88 | 100 | 100 | blastp |
| 2958 | kiwi\|gb166\|FG408531__T1 | kiwi | 3166 | 39 | 83 | 100 | 99.30313589 | blastp |
| 2959 | leymus\|gb166\|EG381236__T1 | leymus | 3167 | 39 | 81 | 55.55555556 | 97.46835443 | blastp |
| 2960 | leymus\|gb166\|EG376087__T1 | leymus | 3168 | 39 | 80 | 96.77419355 | 96.55172414 | blastp |
| 2961 | leymus\|gb166\|CD808804__T1 | leymus | 3169 | 39 | 81 | 100 | 100 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 2962 | leymus\|gb166\|EG378918_T1 | leymus | 3170 | 39 | 86 | 51.25448029 | 100 | blastp |
| 2963 | liriodendron\|gb166\|CK761396_T1 | liriodendron | 3171 | 39 | 81 | 99.64157706 | 98.96193772 | blastp |
| 2964 | nuphar\|gb166\|ES730700_T1 | nuphar | 3172 | 39 | 81 | 61.29032258 | 98.27586207 | blastp |
| 2965 | poppy\|gb166\|FE965621_T1 | poppy | 3173 | 39 | 84 | 88.53046595 | 100 | blastp |
| 2966 | pseudoroegneria\|gb167\|FF340233_T1 | pseudoroegneria | 3174 | 39 | 81 | 100 | 100 | blastp |
| 2967 | switchgrass\|gb167\|FE638368_T1 | switchgrass | 3175 | 39 | 80 | 100 | 100 | blastp |
| 2968 | switchgrass\|gb167\|FE657460_T1 | switchgrass | 3176 | 39 | 80 | 99.28315412 | 98.95833333 | blastp |
| 2969 | switchgrass\|gb167\|FE641178_T1 | switchgrass | 3177 | 39 | 82 | 78.85304659 | 86.59003831 | blastp |
| 2970 | switchgrass\|gb167\|FE619224_T1 | switchgrass | 3178 | 39 | 82 | 94.26523297 | 95.72953737 | blastp |
| 2971 | switchgrass\|gb167\|FE657460_T2 | switchgrass | 3179 | 39 | 81 | 100 | 100 | blastp |
| 2972 | tamarix\|gb166\|EH051524_T1 | tamarix | 3180 | 39 | 82 | 56.27240143 | 98.74213836 | blastp |
| 2973 | walnuts\|gb166\|CB304207_T1 | walnuts | 3181 | 39 | 84 | 100 | 99.30313589 | blastp |
| 2974 | walnuts\|gb166\|CB303561_T1 | walnuts | 3182 | 39 | 84 | 100 | 100 | blastp |
| 2975 | walnuts\|gb166\|EL892579_T1 | walnuts | 3183 | 39 | 84 | 89.60573477 | 98.82352941 | blastp |
| 2976 | zamia\|gb166\|DY032141_T1 | zamia | 3184 | 39 | 80 | 96.05734767 | 94.32624113 | blastp |
| 2977 | zamia\|gb166\|FD764669_T1 | zamia | 3185 | 39 | 80 | 99.64157706 | 98.92473118 | blastp |
| 2978 | zamia\|gb166\|DY034152_T1 | zamia | 3186 | 39 | 80 | 94.62365591 | 92.25352113 | blastp |
| 2979 | antirrhinum\|gb166\|AJ568195_T1 | antirrhinum | 3187 | 40 | 87 | 100 | 100 | blastp |
| 2980 | antirrhinum\|gb166\|AJ568110_T1 | antirrhinum | 3188 | 40 | 87 | 100 | 100 | blastp |
| 2981 | banana\|gb167\|FL657842_T1 | banana | 3189 | 40 | 81 | 83.03886926 | 92.49011858 | blastp |
| 2982 | bruguiera\|gb166\|EF126757_T1 | bruguiera | 3190 | 40 | 84 | 100 | 100 | blastp |
| 2983 | centaurea\|gb166\|EH765776_T1 | centaurea | 3191 | 40 | 84 | 92.5795053 | 100 | blastp |
| 2984 | eucalyptus\|gb166\|AJ627837_T1 | eucalyptus | 3192 | 40 | 85 | 100 | 100 | blastp |
| 2985 | kiwi\|gb166\|FG411924_T1 | kiwi | 3193 | 40 | 86 | 100 | 100 | blastp |
| 2986 | kiwi\|gb166\|FG400706_T1 | kiwi | 3194 | 40 | 85 | 100 | 100 | blastp |
| 2987 | kiwi\|gb166\|FG418898_T1 | kiwi | 3195 | 40 | 84 | 71.02473498 | 98.5 | blastp |
| 2988 | kiwi\|gb166\|FG420187_T1 | kiwi | 3196 | 40 | 85 | 72.79151943 | 100 | blastp |
| 2989 | kiwi\|gb166\|FG398010_T1 | kiwi | 3197 | 40 | 86 | 100 | 100 | blastp |
| 2990 | petunia\|gb166\|AF452012_T1 | petunia | 3198 | 40 | 88 | 100 | 100 | blastp |
| 2991 | tamarix\|gb166\|CV121772_T1 | tamarix | 3199 | 40 | 83 | 100 | 100 | blastp |
| 2992 | walnuts\|gb166\|EL893208_T1 | walnuts | 3200 | 40 | 84 | 100 | 100 | blastp |
| 2993 | bean\|gb167\|FD786218_T1 | bean | 3201 | 41 | 83 | 58.60927152 | 100 | blastp |
| 2994 | citrus\|gb166\|CX074333_T2 | citrus | 3202 | 41 | 81 | 72.51655629 | 99.5412844 | blastp |
| 2995 | citrus\|gb166\|CX074333_T1 | citrus | 3203 | 41 | 83 | 96.02649007 | 91.42857143 | blastp |
| 2996 | kiwi\|gb166\|FG420468_T2 | kiwi | 3204 | 41 | 84 | 87.08609272 | 97.04797048 | blastp |
| 2997 | kiwi\|gb166\|FG420468_T1 | kiwi | 3205 | 41 | 83 | 58.94039735 | 95.69892473 | blastp |
| 2998 | tamarix\|gb166\|EG972096_T1 | tamarix | 3206 | 42 | 82 | 60.97560976 | 95.23809524 | blastp |
| 2999 | pseudoroegneria\|gb167\|FF353501_T1 | pseudoroegneria | 3207 | 43 | 86 | 98.3935743 | 98.79518072 | blastp |
| 3000 | switchgrass\|gb167\|FE646459_T1 | switchgrass | 3208 | 43 | 86 | 98.79518072 | 99.19678715 | blastp |
| 3001 | switchgrass\|gb167\|FL887003_T1 | switchgrass | 3209 | 43 | 84 | 71.48594378 | 93.22916667 | blastp |
| 3002 | wheat\|gb164\|BE403397_T1 | wheat | 3210 | 43 | 86 | 98.3935743 | 98.79518072 | blastp |
| 3003 | leymus\|gb166\|EG381168_T1 | leymus | 3211 | 44 | 96 | 52.01612903 | 100 | blastp |
| 3004 | pseudoroegneria\|gb167\|FF341567_T1 | pseudoroegneria | 3212 | 44 | 97 | 100 | 100 | blastp |
| 3005 | switchgrass\|gb167\|FE618822_T1 | switchgrass | 3213 | 44 | 91 | 100 | 100 | blastp |
| 3006 | switchgrass\|gb167\|FE633786_T1 | switchgrass | 3214 | 44 | 92 | 78.22580645 | 100 | blastp |
| 3007 | eucalyptus\|gb166\|CB967586_T1 | eucalyptus | 3215 | 46 | 84 | 97.51552795 | 60.78431373 | blastp |
| 3008 | liriodendron\|gb166\|CK762443_T1 | liriodendron | 3216 | 46 | 80 | 74.53416149 | 100 | blastp |
| 3009 | switchgrass\|gb167\|FE615387_T1 | switchgrass | 3217 | 46 | 90 | 100 | 61.38996139 | blastp |
| 3010 | walnuts\|gb166\|EL893973_T1 | walnuts | 3218 | 46 | 82 | 97.51552795 | 55.47445255 | blastp |
| 3011 | bean\|gb167\|FD782805_T1 | bean | 3219 | 47 | 91 | 88.17204301 | 79.61165049 | blastp |
| 3012 | bean\|gb167\|EY457935_T1 | bean | 3220 | 47 | 82 | 100 | 38.58921162 | blastp |
| 3013 | cichorium\|gb166\|EH685648_T2 | cichorium | 3221 | 47 | 80 | 100 | 67.39130435 | blastp |

TABLE 3-continued

Polynucleotide and polypeptide sequences of AQP homologous and orthologous

| Polynuc. SEQ ID NO: | Cluster name | Organism | Polypep. SEQ ID NO: | Hom. of SEQ ID NO: | % Ident. | Query cover. | % Subject cover. | Algorithm |
|---|---|---|---|---|---|---|---|---|
| 3014 | cichorium\|gb166\|EH685648_T1 | cichorium | 3222 | 47 | 80 | 100 | 32.1799308 | blastp |
| 3015 | citrus\|gb166\|CK701147_T1 | citrus | 3223 | 47 | 90 | 100 | 76.85950413 | blastp |
| 3016 | citrus\|gb166\|CX544905_T1 | citrus | 3224 | 47 | 81 | 79.56989247 | 88.0952381 | blastp |
| 3017 | cycas\|gb166\|CB088978_T1 | cycas | 3225 | 47 | 82 | 87.09677419 | 30.68181818 | blastp |
| 3018 | cycas\|gb166\|EX920749_T1 | cycas | 3226 | 47 | 88 | 100 | 76.2295082 | blastp |
| 3019 | kiwi\|gb166\|FG429765_T1 | kiwi | 3227 | 47 | 84 | 98.92473118 | 77.96610169 | blastp |
| 3020 | leymus\|gb166\|CN466394_T1 | leymus | 3228 | 47 | 87 | 100 | 79.48717949 | blastp |
| 3021 | leymus\|gb166\|EG376019_T1 | leymus | 3229 | 47 | 88 | 100 | 32.74647887 | blastp |
| 3022 | leymus\|gb166\|EG390723_T1 | leymus | 3230 | 47 | 81 | 100 | 31.95876289 | blastp |
| 3023 | leymus\|gb166\|EG387193_T1 | leymus | 3231 | 47 | 81 | 100 | 32.1799308 | blastp |
| 3024 | nuphar\|gb166\|CD473277_T1 | nuphar | 3232 | 47 | 91 | 100 | 75.6097561 | blastp |
| 3025 | nuphar\|gb166\|FD384794_T1 | nuphar | 3233 | 47 | 86 | 96.77419355 | 81.08108108 | blastp |
| 3026 | nuphar\|gb166\|CD475538_T1 | nuphar | 3234 | 47 | 89 | 100 | 69.92481203 | blastp |
| 3027 | nuphar\|gb166\|CD472711_T1 | nuphar | 3235 | 47 | 91 | 100 | 48.94736842 | blastp |
| 3028 | petunia\|gb166\|DC240378_T1 | petunia | 3236 | 47 | 92 | 58.06451613 | 98.18181818 | blastp |
| 3029 | pseudoroegneria\|gb167\|FF344283_T1 | pseudoroegneria | 3237 | 47 | 87 | 100 | 32.74647887 | blastp |
| 3030 | sorghum\|gb161.crp\|AI724931_T1 | sorghum | 3238 | 47 | 92 | 100 | 32.51748252 | blastp |
| 3031 | switchgrass\|gb167\|FL923354_T1 | switchgrass | 3239 | 47 | 82 | 100 | 33.69565217 | blastp |
| 3032 | switchgrass\|gb167\|FE657461_T1 | switchgrass | 3240 | 47 | 92 | 98.92473118 | 74.79674797 | blastp |
| 3033 | switchgrass\|gb167\|FL765830_T1 | switchgrass | 3241 | 47 | 82 | 100 | 72.22222222 | blastp |
| 3034 | switchgrass\|gb167\|FL915169_T1 | switchgrass | 3242 | 47 | 83 | 97.84946237 | 87.5 | blastp |
| 3035 | tamarix\|gb166\|EH054604_T1 | tamarix | 3243 | 47 | 83 | 100 | 65.64705882 | tblastn |
| 3036 | walnuts\|gb166\|CB303798_T1 | walnuts | 3244 | 47 | 91 | 100 | 80.17241379 | blastp |
| 3037 | bruguiera\|gb166\|BP942548_T1 | bruguiera | 3245 | 48 | 82 | 52.05479452 | 100 | blastp |
| 3038 | bruguiera\|gb166\|BP938825_T1 | bruguiera | 3246 | 48 | 89 | 56.62100457 | 91.17647059 | blastp |
| 3039 | centaurea\|gb166\|EH739326_T1 | centaurea | 3247 | 48 | 83 | 87.21461187 | 50 | tblastn |
| 3040 | eucalyptus\|gb166\|CD669176_T1 | eucalyptus | 3248 | 48 | 87 | 56.16438356 | 91.79104478 | blastp |
| 3041 | leymus\|gb166\|EG382428_T1 | leymus | 3249 | 48 | 80 | 52.05479452 | 90.47619048 | blastp |
| 3042 | liriodendron\|gb166\|CK743477_T1 | liriodendron | 3250 | 48 | 81 | 94.06392694 | 54.54545455 | tblastn |
| 3043 | marchantia\|gb166\|BJ840587_T1 | marchantia | 3251 | 48 | 83 | 94.06392694 | 72.53521127 | blastp |
| 3044 | marchantia\|gb166\|C96070_T1 | marchantia | 3252 | 48 | 83 | 93.15068493 | 71.57894737 | blastp |
| 3045 | nuphar\|gb166\|CK748374_T1 | nuphar | 3253 | 48 | 82 | 65.75342466 | 99.31034483 | blastp |
| 3046 | pseudoroegneria\|gb167\|FF340047_T1 | pseudoroegneria | 3254 | 48 | 81 | 96.80365297 | 73.44827586 | blastp |
| 3047 | pseudoroegneria\|gb167\|FF340899_T1 | pseudoroegneria | 3255 | 48 | 81 | 96.80365297 | 73.44827586 | blastp |
| 3048 | pseudoroegneria\|gb167\|FF352644_T1 | pseudoroegneria | 3256 | 48 | 82 | 96.80365297 | 74.12587413 | blastp |
| 3049 | sorghum\|gb161.crp\|SBGWP030188_T1 | sorghum | 3257 | 48 | 80 | 96.80365297 | 74.12587413 | blastp |
| 3050 | switchgrass\|gb167\|FL718379_T1 | switchgrass | 3258 | 48 | 81 | 96.80365297 | 74.12587413 | blastp |
| 3051 | switchgrass\|gb167\|FE639195_T1 | switchgrass | 3259 | 48 | 82 | 96.80365297 | 73.10344828 | blastp |

Table 3: Homologues and orthologues of the AQP proteins are provided.
Homology was calculated as % of identity over the aligned sequences.
Polynuc. = Polynucleotide;
Polypep. = Polypeptide;
Hom. = Homologues/Orthologues;
% Ident. = percent identity;
Cover. = coverage.

Example 2 mRNA Expression of In-Silico Expressed Polynucleotides

Messenger RNA levels were determined using reverse transcription assay followed by quantitative Real-Time PCR (qRT-PCR) analysis. RNA levels were compared between leaves of 20 days old seedlings of tomato plants grown under salinity water. A correlation analysis between mRNA levels in different experimental conditions/genetic backgrounds was performed in order to determine the role of the gene in the plant.

Materials and Experimental Methods
Quantitative Real Time RT-PCR (qRT-PCR)—

To verify the level of expression, specificity and trait-association, Reverse Transcription followed by quantitative Real-Time PCR (qRTPCR) was performed on total RNA extracted from leaves of 2 tomato varieties namely YO361 (salt tolerant variety) and FA191 (salt sensitive variety). Messenger RNA (mRNA) levels were determined for AQP genes, expressed under normal and stressed conditions.

minutes, followed by 4° C. for 5 minutes. Mix of reverse transcriptase (RT) buffer, dithiothreitol (DTT) and RNAsin was added to the RT reactions followed by incubation at 25° C. for 10 minutes and at 42° C. for 2 minutes afterwards. Finally, Super Script II Reverse Transcriptase enzyme was added to the RT reactions that were further incubated for 50 minutes at 42° C., followed by 70° C. for 15 minutes.

cDNA was diluted 1:20 in Tris EDTA, pH=7.5 for MAB69 and housekeeping genes. For MAB58 and MAB59 cDNA was diluted 1:2 due to very weak expression and consequently for housekeeping genes cDNA was diluted 1:8 in order to insert the Ct values in calibration curve range. 5 µL of the diluted cDNA was used for qPCR.

For qPCR amplification, primers of the AQP genes were designed, as summarized in Table 4 below. The expression level of the housekeeping genes: Actin (SEQ ID NO: 2841), GAPDH (SEQ ID NO: 2842) and RPL19 (SEQ ID NO: 2747) was determined in order to normalize the expression level between the different tissues.

TABLE 4

Primers for qPCR amplification

| Gene | Forward primer SEQ ID NO: | Forward primer sequence (5'→3') | Reverse primer SEQ ID NO: | Reverse primer sequence (5'→3') |
| --- | --- | --- | --- | --- |
| MAB58 | 2829 | CTTTTGGTAGGGCCGATGAAG | 2830 | CGAAGATGAAGGTGGATAAGAGCT |
| MAB59 | 2831 | CAGTATGAACGTCTCCGGTGG | 2832 | CAACAGCACCTAGCAACTGACC |
| MAB69 | 2833 | TGTCTTGGATTCCATTGAGCACT | 2834 | GTTTGAGCTGCTGTCCCCA |
| Actin (SEQ ID NO: 2841) | 2835 | CCACATGCCATTCTCCGTCT | 2836 | GCTTTTCTTTCACGTCCCTGA |
| GAPDH (SEQ ID NO: 2842) | 2837 | TTGTTGTGGGTGTCAACGAGA | 2838 | ATGGCGTGGACAGTGGTCA |
| RPL19 (SEQ ID NO: 2747) | 2839 | CACTCTGGATATGGTAAGCGTAAGG | 2840 | TTCTTGGACTCCCTGTACTTACGA |

Twenty days-old tomato seedlings were grown in soil and soaked with 300 mM NaCl for 0, 1, 6, 24, 118 hours. Leaves were harvested and frozen in liquid nitrogen and then kept at −80° C. until RNA extraction. Total RNA was extracted from leaves using RNeasy plant mini kit (Qiagen, Hilden, Germany) and by using the protocol provided by the manufacturer. Reverse transcription was performed using 1 µg total RNA, using 200 U Super Script II Reverse Transcriptase enzyme (Invitrogen), 150 ng random deoxynucleotide hexamers (Invitrogen), 500 µM deoxynucleotide triphosphates (dNTPs) mix (Takara, Japan), 0.2 volume of ×5 reverse transcriptase (RT) buffer (Invitrogen), 0.01 M dithiothreitol (DTT), 40 U RNAsin (Promega), diethylpyrocarbonate (DEPC) treated double distilled water (DDW) was added up to 24 µl.

Mix of RNA, random deoxynucleotide hexamers, dNTPs mix and DEPC treated DDW was incubated at 65° C. for 5

Experimental Results

Changes in mRNA Levels of AQP Genes in Leaves of Plants Under Salt Tolerance—

Steady state levels of tomato AQP genes in leaves of tolerant versus sensitive lines, under salinity conditions are summarized in Table 5 below. In all 3 cases, aquaporin gene expression was increased after plant was exposed to salt stress. Gene peak expression was higher in the salt tolerance tomato line (YO361) versus the sensitive line (FA191). The elevated gene expression demonstrates the involvement of the tested AQP genes in tomato plants tolerating high salinity.

TABLE 5

Expression levels of tomato AQP genes

| Well name (cDNA) | MAB58 | MAB59 | MAB69* |
|---|---|---|---|
| leaf FA191 0 h | 2.86 | 5.97 | 875 |
| leaf FA191 1 h | 4.56 | 5.73 | 597 |
| leaf FA191 6 h | 5.34 | 8.2 | 945 |
| leaf FA191 24 h | 42.7 | 62.4 | 613 |
| leaf FA191 118 h | 55.4 | 22.2 | 1800 |
| leaf Y0361 0 h | 1.96 | 2.81 | 638 |
| leaf Y0361 1 h | 2.33 | 0.517 | 583 |
| leaf Y0361 6 h | 2.88 | 5.66 | 464 |
| leaf Y0361 24 h | 75.4 | 139 | 513 |
| leaf Y0361 118 h | 26.3 | Not determined | 2300 |

Table 5: Provided are the steady state levels of tomato AQP genes under salinity conditions [the incubation periods in the salt solution are provided in hours (h)]. Different dilutions of cDNA were used (1:20 for MAB69 and 1:2 for MAB58 and MAB59). Numbers are given after normalization for each sample.

Example 3

Gene Cloning and Generation of Binary Vectors for Plant Expression

To validate their role in improving ABST and yield, the AQP genes were over-expressed in plants, as follows.

Cloning Strategy

Selected genes from those presented in Example 1 were cloned into binary vectors for the generation of transgenic plants. For cloning, the full-length open reading frames (ORFs) were identified. EST clusters and in some cases mRNA sequences were analyzed to identify the entire open reading frame by comparing the results of several translation algorithms to known proteins from other plant species. In case where the entire coding sequence is not found, RACE kits from Ambion or Clontech (RACE=Rapid Access to cDNA Ends) were used to prepare RNA from the plant samples to thereby access the full cDNA transcript of the gene.

In order to clone the full-length cDNAs, Reverse Transcription followed by PCR (RT-PCR) was performed on total RNA extracted from leaves, roots or other plant tissues, growing under either normal or nutrient deficient conditions. Total RNA extraction, production of cDNA and PCR amplification was performed using standard protocols described elsewhere (Sambrook J., E. F. Fritsch, and T. Maniatis. 1989. Molecular Cloning. A Laboratory Manual., 2nd Ed. Cold Spring Harbor Laboratory Press, New York.), and are basic for those skilled in the art. PCR products were purified using PCR purification kit (Qiagen) and sequencing of the amplified PCR products was performed, using ABI 377 sequencer (Applied Biosystems).

Usually, 2 sets of primers were ordered for the amplification of each gene, via nested PCR (meaning first amplifying the gene using external primers and then using the produced PCR product as a template for a second PCR reaction, where the internal set of primers are used). Alternatively, one or two of the internal primers were used for gene amplification, both in the first and the second PCR reactions (meaning only 2-3 primers were designed for a gene). To facilitate further cloning of the cDNAs, a 8-12 bp extension is added to the 5' primer end of each internal primer. The primer extension includes an endonuclease restriction site. The restriction sites are selected using two parameters: (a) The restriction site does not exist in the cDNA sequence; and (b) The restriction sites in the forward and reverse primers are designed so the digested cDNA is inserted in the sense formation into the binary vector utilized for transformation. In Table 6 below, primers used for cloning tomato and barley AQPs are provided.

TABLE 6

Primers used for cloning tomato and barley AQP genes

| MAB gene No. | Forward external primer sequence from 5'→3' (SEQ ID NO:) | Forward internal primer sequence from 5'→3' (SEQ ID NO:) | Reverse external primer sequence from 5'→3' (SEQ ID NO:) | Reverse internal primer sequence from 5'→3' (SEQ ID NO:) |
|---|---|---|---|---|
| 55 | GGAGTCGACGACCAT CAAGTTTTAAGTGAC TTC (2770) | GGAGTCGACTT AAGTACATTCTT TAGTGAGAGCC (2771) | TGAGCTCACTTC AAAACCATCCG TTGTC (2772) | TGAGCTCCCATCC GTTGTCAAAATGA AC (2773) |
| 56 |  | GGAGTCGACGT AAGAAACAATA ATGCCAATTTC (2774) | CGAGCTCGTAA AGCCAAGTTTTG AAAGAC (2775) | CGAGCTCAAGAC AAACAAAGAGAA GAGGG (2776) |
| 57 |  | GTTAAAAATGC CGATCAACC (2777) | GCGATATCTAA ATAACAAAAGC CGTCCG (2778) | GCGATATCAGCCG TCCGAATAAACAA AG (2779) |
| 58 | AATGTCGACCGAATT GATCTCCTTCTTGATC (2780) | TATGTCGACTTC ATTTCTTGGGTC ACTCG (2781) | TTTCTAGAGGTC TGGGATTATCGT CTTG (2782) | TTTCTAGAGATGT GCAGGCAGCTAC ATAC (2783) |
| 59 | AATGTCGACTTTAAG CGGTGTGTTTTGTG (2784) | AATGTCGACTC ACAATTATGCA GCCACG (2785) |  | AATCTAGATTAGA CCCAAACATACAA ACTTCAC (2786)) |
| 69 | TAAGTCGACACAAAC CTTATCCTGGTCTCAT C (2787) | AATGTCGACCTT GGATTCCATTGA GCACTC (2788) |  | TGAGCTCTGGAGA AAGAAAACTTTAG ATACA (2789) |
| 70 | AACTGCAGAGCTGTA CATGGTCCTCCTCC (2790) | AACTGCAGTGT ACATGGTCCTCC TCCG (2791) | TCCCGGGCCAG ACAAACTTCA ATTTCATC (2792) | TCCCGGGCTTCAA TTTCATCTTCTGA TTTC (2793) |

TABLE 6-continued

Primers used for cloning tomato and barley AQP genes

| MAB gene No. | Forward external primer sequence from 5'→3' (SEQ ID NO:) | Forward internal primer sequence from 5'→3' (SEQ ID NO:) | Reverse external primer sequence from 5'→3' (SEQ ID NO:) | Reverse internal primer sequence from 5'→3' (SEQ ID NO:) |
|---|---|---|---|---|
| 71 | AAAGTCGACGGAAAA TGCATTAAAACCTTA AG (2794) | TTTGTCGACCTT AGTTTTCTCCCA CATATGG (2795) | AATCTAGACAA GTAGAGGTACT AGGTAGGGAC (2796) | AATCTAGAGTACT AGGTAGGGACAA TATGATATG (2797) |
| 72 | AATGTCGACGTGGAG GAGGAGTCTTTGATA C (2798) | AATGTCGACCTC CAACACTCTTAT CAATTACCA (2799) | | TATCTAGAGGATG CAACTACAAGA AATTG (2800) |
| 74 | | TTCTGCAGGTTT GGGAGTTATTG ATCTAAGATG (2801) | | TCCCGGGGCATAG TTCACACAGAGCA AATC (2802) |
| 76 | AATGTCGACCTGTAT CCTCTTAAGTATGAA TCG (2803) | AATGTCGACGT CGTCTTGTATGT ATTTGTACTACT G (2804) | TTTCTAGACTAG TGGTATAGATC ATTTTATGGTGA C (2805) | AATCTAGATTAGA GCTGGAGAATGA ACTGAAGC (2806) |
| 77 | AACTGCAGCTTCTTTC ACCGAGTGGGAG (2807) | AACTGCAGCTTT CACCGAGTGGG AGAG (2808) | ACCCGGGAATT CCAACTAGCTGT TATGATTC (2809) | TCCCGGGTCCAAC TAGCTGTTATGAT TCTG (2810) |
| 79 | AAGATATCAAAAAAA TGTCGAAGGACGTG (2811) | AAGATATCAAC AATGTCGAAGG ACGTGATTGA (2812) | | AAGATATCGACCA CCAACTCTAGTCT CATACC (2813) |
| 115 | AGATTCGAATCTTTA GCCTG (2814) | AATCTAGAGAA GTCACAGAGAA AACAGTCGAG (2815) | | AGAGCTCTTAAGG GAAATTCATCACA CAAGG (2816) |
| 116 | AAAGTCGACCTCATC AGTGTTAAAGCCATA AG (2817) | TTTGTCGACCAT AAGCCCTCTTTG AGTGTG (2818) | TATCTAGAATTG AATCGAAAGGG AAACAC (2819) | TTTCTAGAGACCG TGACACACCATTT GTAC (2820) |
| 117 | | TTTCTAGACTCA GCGACAACATT TCATCTC (2821) | | TGAGCTCCAGATA GAGAAGCATGCA TCATC (2822) |

PCR products were purified (PCR Purification Kit, Qiagen, Germany) and digested with the restriction endonucleases (Roche, Switzerland) according to the sites design in the primers (Tables 8 and 9 below). Each of the digested PCR products was cloned first into high copy plasmid pBlue-script KS [Hypertext Transfer Protocol://World Wide Web (dot) stratagene (dot) com/manuals/212205 (dot) pdf] which was digested with the same restriction enzymes. In some cases (Table 8, below) the Nopaline Synthase (NOS) terminator originated from the binary vector pBI101.3 [nucleotide coordinates 4417-4693 in GenBank Accession No. U12640 (SEQ ID NO:2824)] was already cloned into the pBlue-script KS, between the restriction endonuclease sites SacI and EcoRI, so the gene is introduced upstream of the terminator. In other cases (Table 9, below) the At6669 promoter (SEQ ID NO: 2823) is already cloned into the pBlue-script KS, so the gene is introduced downstream of the promoter. The digested PCR products and the linearized plasmid vector were ligated using T4 DNA ligase enzyme (Roche, Switzerland). Sequencing of the inserted genes was conducted, using ABI 377 sequencer (Applied Biosystems). Sequences of few of the cloned AQP genes, as well as their encoded proteins are listed in Table 7, below.

TABLE 7

Cloned sequences

| Serial No | Gene Name | Polynucleotide SEQ ID NO: | Polypeptide SEQ ID NO: |
|---|---|---|---|
| 1 | MAB115 | 2748 | 2765 |
| 2 | MAB116 | 2749 | 47 |
| 3 | MAB117 | 2750 | 48 |
| 4 | MAB54 | 2751 | 27 |
| 5 | MAB55 | 2752 | 28 |
| 6 | MAB56 | 2753 | 29 |
| 7 | MAB57 | 2754 | 30 |
| 8 | MAB58 | 2755 | 2766 |
| 9 | MAB59 | 2756 | 2767 |
| 10 | MAB69 | 2757 | 33 |
| 11 | MAB70 | 2758 | 34 |
| 12 | MAB71 | 2759 | 2768 |
| 13 | MAB72 | 2760 | 2769 |
| 14 | MAB72 (Optimized for expression in Arabidopsis, Tomato and Maize) | 2843 | 2769 |
| 15 | MAB74 | 2761 | 38 |
| 16 | MAB76 | 2762 | 40 |

TABLE 7-continued

Cloned sequences

| Serial No | Gene Name | Polynucleotide SEQ ID NO: | Polypeptide SEQ ID NO: |
|---|---|---|---|
| 17 | MAB77 | 2763 | 41 |
| 18 | MAB79 | 2764 | 43 |

Table 7.

The genes were digested again and ligated into pPI or pGI binary plasmids, harboring the At6669 promoter (between the HindIII and SalI restriction endonucleases site) (Table 8). In other cases the At6669 promoter together with the gene are digested out of the pBlue-script KS plasmid and ligated into pPI or pGI binary plasmids, using restriction endonucleases as given in Table 8.

TABLE 8

Restriction enzyme sites used to clone the MAB AQP genes into pKS + NOS terminator high copy plasmid, followed by cloning into the binary vector pGI + At6669 promoter

| MAB gene No. (SEQ ID NO:) | Restriction enzymes used for cloning into high copy plasmid-FORWARD | Restriction enzymes used for cloning into high copy plasmid-REVERSE | Restriction enzymes used for cloning into binary vector-FORWARD | Restriction enzymes used for cloning into binary vector-REVERSE | Restriction enzymes used for digesting the binary vector |
|---|---|---|---|---|---|
| 54 (SEQ ID NO: 2751) | XbaI | SacI | SalI | EcoRI | SalI/EcoRI |
| 55 (SEQ ID NO: 2752) | SalI | SacI | SalI | EcoRI | SalI/EcoRI |
| 56 (SEQ ID NO: 2753) | SalI | SacI | SalI | EcoRI | SalI/EcoRI |
| 58 (SEQ ID NO: 2755) | SalI | XbaI | SalI | EcoRI | SalI/EcoRI |
| 59 (SEQ ID NO: 2756) | SalI | XbaI | SalI | EcoRI | SalI/EcoRI |
| 69 (SEQ ID NO: 2757) | SalI | SacI | SalI | EcoRI | SalI/EcoRI |
| 71 (SEQ ID NO: 2759) | SalI | XbaI | SalI | EcoRI | SalI/EcoRI |
| 72 (SEQ ID NO: 2760) | SalI | XbaI | SalI | EcoRI | SalI/EcoRI |
| 76 (SEQ ID NO: 2762) | SalI | XbaI | SalI | EcoRI | SalI/EcoRI |
| 115 (SEQ ID NO: 2748) | XbaI | SacI | SalI | EcoRI | SalI/EcoRI |
| 116 (SEQ ID NO: 2749) | SalI | XbaI | SalI | EcoRI | SalI/EcoRI |
| 117 (SEQ ID NO: 2750) | XbaI | SacI | SalI | EcoRI | SalI/EcoRI |

Table 8: MAB AQP genes cloned into pKS + NOS terminator high copy plasmid, followed by cloning into the binary vector pGI + At6669 promoter.

TABLE 9

Restriction enzyme sites used to clone the MAB AQP genes into pKS + At6669 promoter high copy plasmid, followed by cloning promoter + gene into pGI binary vector

| MAB gene No. (SEQ ID NO:) | Restriction enzymes used for cloning into high copy plasmid-FORWARD | Restriction enzymes used for cloning into high copy plasmid-REVERSE | Restriction enzymes used for cloning into binary vector-FORWARD | Restriction enzymes used for cloning into binary vector-REVERSE | Restriction enzymes used for digesting the binary vector |
|---|---|---|---|---|---|
| 57 (SEQ ID NO: 2754) | Blunt | EcoRV | SalI | EcoRV | SalI/Ecl136 II |
| 70 (SEQ ID NO: 2758) | PstI | SmaI | BamHI | SmaI | BamHI/Ecl136II |
| 74 (SEQ ID NO: 2761) | PstI | SmaI | BamHI | SmaI | BamHI/Ecl136II |
| 77 (SEQ ID NO: 2763) | PstI | SmaI | BamHI | SmaI | BamHI/Ecl136II |
| 79 (SEQ ID NO: 2764) | EcoRI | EcoRV | SalI | SmaI | SalI/Ecl136 II |

Table 9: MAB AQP genes cloned into pKS + At6669 promoter high copy plasmid, followed by cloning promoter + gene into pGI binary vector.

The pPI plasmid vector was constructed by inserting a synthetic poly-(A) signal sequence, originating from pGL3 basic plasmid vector (Promega, Acc. No. U47295; bp 4658-4811) into the HindIII restriction site of the binary vector pBI101.3 (Clontech, Acc. No. U12640). pGI (FIG. 1) is similar to pPI, but the original gene in the back bone is GUS-Intron, rather than GUS. The cloned genes were sequenced.

Synthetic sequences (such as of MAB54, nucleotide SEQ ID NO: 2751, which encodes protein SEQ ID NO: 27; or MAB72 SEQ ID NO:2843, which encodes SEQ ID NO:2769) of some of the cloned polynucleotides were ordered from a commercial supplier (GeneArt, GmbH). To optimize the coding sequence, codon-usage Tables calculated from plant transcriptomes were used [example of such Tables can be found in the Codon Usage Database available online at Hypertext Transfer Protocol://World Wide Web (dot) kazusa (dot) or (dot) jp/codon/]. The optimized coding sequences were designed in a way that no changes were introduced in the encoded amino acid sequence while using codons preferred for expression in dicotyledonous plants mainly tomato and Arabidopsis; and monocotyledonous plants such as maize. Such optimized sequences promote better translation rate and therefore higher protein expression levels. To the optimized sequences flanking additional unique restriction enzymes sites were added to facilitate cloning genes in binary vectors.

Promoters used: CaMV 35S promoter (SEQ ID NO: 2825) and Arabidopsis At6669 promoter (SEQ ID NO: 2823; which is SEQ ID NO:61 of WO04081173 to Evogene Ltd.).

Example 4

Generation of Transgenic Plants Expressing the AQP Genes

Experimental Results

Arabidopsis Transformation—

Arabidopsis transformation of the following MAB genes and orthologues: MAB115, MAB54, MAB55, MAB56, MAB57, MAB58, MAB59 (ortholog of MAB58), MAB69, MAB70, MAB71, MAB72, MAB74, MAB76, MAB77, MAB79, MAB116 (ortholog of MAB115 and MAB55), and MAB117 (the sequence identifiers of the cloned polynucleotides and their expressed polypeptides are provided in Table 7 above) was performed according to Clough S J, Bent A F. (1998) "Floral dip: a simplified method for Agrobacterium-mediated transformation of Arabidopsis thaliana." Plant J. 16(6): 735-43; and Desfeux C, Clough S J, Bent A F. (2000) "Female reproductive tissues are the primary targets of Agrobacterium-mediated transformation by the Arabidopsis floral-dip method." Plant Physiol. 123(3): 895-904; with minor modifications. Briefly, Arabidopsis thaliana Columbia (Col0) $T_0$ Plants were sown in 250 ml pots filled with wet peat-based growth mix. The pots were covered with aluminum foil and a plastic dome, kept at 4° C. for 3-4 days, then uncovered and incubated in a growth chamber at 18-24° C. under 16/8 hours light/dark cycles. The $T_0$ plants were ready for transformation six days prior to anthesis. Single colonies of Agrobacterium carrying the binary vectors harboring the AQP genes are cultured in LB medium supplemented with kanamycin (50 mg/L) and gentamycin (50 mg/L). The cultures were incubated at 28° C. for 48 hours under vigorous shaking and centrifuged at 4000 rpm for 5 minutes. The pellets comprising Agrobacterium cells were resuspended in a transformation medium which contained half-strength (2.15 g/L) Murashige-Skoog (Duchefa); 0.044 μM benzylamino purine (Sigma); 112 μg/L B5 Gambourg vitamins (Sigma); 5% sucrose; and 0.2 ml/L Silwet L-77 (OSI Specialists, CT) in double-distilled water, at pH of 5.7.

Transformation of $T_0$ plants was performed by inverting each plant into an Agrobacterium suspension such that the flowering stem was submerged for 3-5 seconds. Each inoculated $T_0$ plant was immediately placed in a plastic tray, then covered with clear plastic dome to maintain humidity and kept in the dark at room temperature for 18 hours to facilitate infection and transformation. Transformed (transgenic) plants were then uncovered and transferred to a greenhouse for recovery and maturation. The transgenic $T_0$ plants were grown in the greenhouse for 3-5 weeks until siliques maturation, and then seeds were harvested and kept at room temperature until sowing.

For generating T1 and $T_2$ transgenic plants harboring the genes, seeds collected from transgenic $T_0$ plants are surface-sterilized by soaking in 70% ethanol for 1 minute, followed by soaking in 5% sodium hypochlorite and 0.05% Triton X-100 for 5 minutes. The surface-sterilized seeds are thoroughly washed in sterile distilled water then placed on culture plates containing half-strength Murashige-Skoog (Duchefa); 2% sucrose; 0.8% plant agar; 50 mM kanamycin; and 200 mM carbenicylin (Duchefa). The culture plates are incubated at 4° C. for 48 hours then transferred to a growth room at 25° C. for an additional week of incubation. Vital $T_1$ Arabidopsis plants are transferred to fresh culture plates for another week of incubation. Following incubation the $T_1$ plants are removed from culture plates and planted in growth mix contained in 250 ml pots. The transgenic plants were allowed to grow in a greenhouse to maturity. Seeds harvested from $T_1$ plants are cultured and grown to maturity as $T_2$ plants under the same conditions as used for culturing and growing the $T_1$ plants. At least 10 independent transformation events are created from each construct for which T2 seeds are collected. The introduction of the gene is determined for each event by PCR performed on genomic DNA extracted from each event produced.

Transformation of Tomato (Var M82) Plants with Putative Cotton Genes—

Tomato (Solanum esculentum, var M82) transformation and cultivation of transgenic plants is effected according to: "Curtis I. S, Davey M. R, and Power J. B. 1995. "Leaf disk transformation". Methods Mol. Biol. 44, 59-70 and Meissner R, Chague V, Zhu Q, Emmanuel E, Elkind Y, Levy A. A. 2000. "Technical advance: a high throughput system for transposon tagging and promoter trapping in tomato". Plant J. 22, 265-74; with slight modifications.

Example 5

Evaluating Transgenic Arabidopsis Plant Growth Under Abiotic Stress as Well as Under Favorable Conditions in Tissue Culture Assay Assay 1: Plant Growth Under Osmotic Stress [poly (ethylene glycol) (PEG)] in Tissue Culture Conditions—

One of the consequences of drought is the induction of osmotic stress in the area surrounding the roots; therefore, in many scientific studies, PEG (e.g., 25% PEG8000) is used to simulate the osmotic stress conditions resembling the high osmolarity found during drought stress.

Surface sterilized seeds were sown in basal media [50% Murashige-Skoog medium (MS) supplemented with 0.8% plant agar as solidifying agent] in the presence of Kanamycin (for selecting only transgenic plants). After sowing, plates were transferred for 2-3 days for stratification at 4° C. and then grown at 25° C. under 12-hour light 12-hour dark daily cycles for 7 to 10 days. At this time point, seedlings randomly chosen were carefully transferred to plates containing 25% PEG: 0.5 MS media or Normal growth conditions (0.5 MS media). Each plate contained 5 seedlings of the same transgenic event, and 3-4 different plates (replicates) for each event. For each polynucleotide of the invention at least four independent transformation events were analyzed from each construct. Plants expressing the polynucleotides of the invention were compared to the average measurement of the control plants (empty vector or GUS reporter gene under the same promoter) used in the same experiment.

Digital Imaging—

A laboratory image acquisition system, which consists of a digital reflex camera (Canon EOS 300D) attached with a 55 mm focal length lens (Canon EF-S series), mounted on a reproduction device (Kaiser RS), which included 4 light units (4×150 Watts light bulb) and located in a darkroom, was used for capturing images of plantlets sawn in agar plates.

Figure 2B:
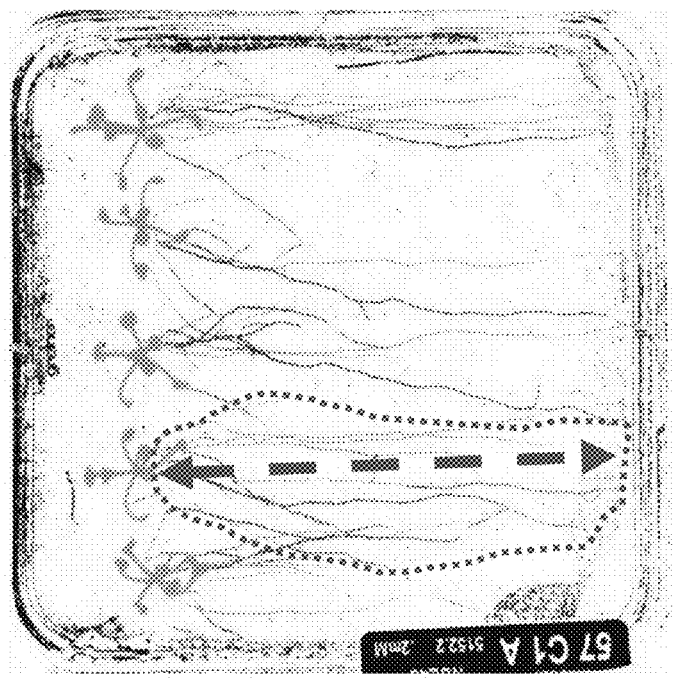
FIGS. 2A-B are images depicting root development of plants grown in transparent agar plates. The different transgenes were grown in transparent agar plates for 10-15 days and the plates were photographed every 2-5 days starting at day 1.
Figure 2A:
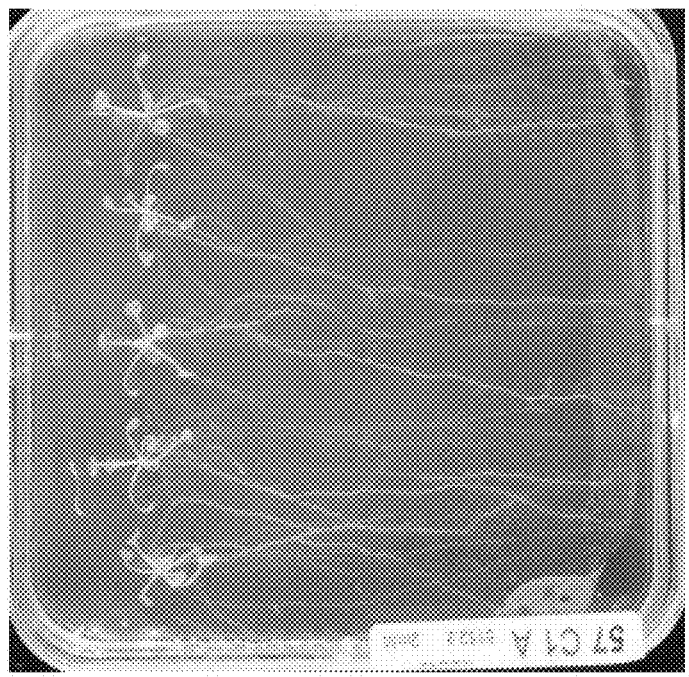

The image capturing process was repeated every 2-5 days starting at day 1 till day 10-15 (see for example the images in FIGS. 2A-B)

An image analysis system was used, which consists of a personal desktop computer (Intel P4 3.0 GHz processor) and a public domain program—ImageJ 1.39 (Java based image processing program which was developed at the U.S. National Institutes of Health and freely available on the internet at Hypertext Transfer Protocol://rsbweb (dot) nih (dot) gov/). Images were captured in resolution of 10 Mega Pixels (3888×2592 pixels) and stored in a low compression JPEG (Joint Photographic Experts Group standard) format. Next, analyzed data was saved to text files and processed using the JMP statistical analysis software (SAS institute).

Seedling Analysis—

Using the digital analysis seedling data was calculated, including leaf area, root coverage and root length.

The relative growth rate for the various seedling parameters was calculated according to the following formulas II, III and IV.

$$\text{Relative growth rate of leaf area} = (\Delta \text{rosette area}/\Delta t) * (1/\text{rosette area } t_1) \quad \text{Formula II:}$$

$\Delta$rosette area is the interval between the current rosette area (measured at $t_2$) and the rosette area measured at the previous day (Area $t_1$)

$\Delta t$ is the time interval ($t_2 - t_1$, in days) between the current analyzed image day ($t_2$) and the previous day ($t_1$).

Thus, the relative growth rate of leaf area is in units of 1/day.

$$\text{Relative growth rate of root coverage} = (\Delta \text{root coverage area}/\Delta t) * (1/\text{root coverage area } t_1) \quad \text{Formula III:}$$

$\Delta$root coverage area is the interval between the current root coverage area (measured at $t_2$) and the root coverage area measured at the previous day (Area $t_1$)

$\Delta t$ is the time interval ($t_2 - t_1$, in days) between the current analyzed image day ($t_2$) and the previous day ($t_1$).

Thus, the relative growth rate of root coverage area is in units of 1/day.

$$\text{Relative growth rate of root length} = (\Delta \text{root length}/\Delta t) * (1/\text{root length } t_1) \quad \text{Formula IV:}$$

$\Delta$root length is the interval between the current root length (measured at $t_2$) and the root length measured at the previous day (Area $t_1$)

$\Delta t$ is the time interval ($t_2 - t_1$, in days) between the current analyzed image day ($t_2$) and the previous day ($t_1$).

Thus, the relative growth rate of root length is in units of 1/day.

At the end of the experiment, plantlets were removed from the media and weighed for the determination of plant fresh weight. Plantlets were then dried for 24 hours at 60° C., and weighed again to measure plant dry weight for later statistical analysis. Growth rate was determined by comparing the leaf area coverage, root coverage and root length, between each couple of sequential photographs, and results were used to resolve the effect of the gene introduced on plant vigor, under osmotic stress, as well as under optimal conditions. Similarly, the effect of the gene introduced on biomass accumulation, under osmotic stress as well as under optimal conditions, was determined by comparing the plants' fresh and dry weight to that of control plants (containing an empty vector or the GUS reporter gene under the same promoter). From every construct created, 3-5 independent transformation events were examined in replicates.

Statistical Analyses—

To identify genes conferring significantly improved tolerance to abiotic stresses or enlarged root architecture, the results obtained from the transgenic plants were compared to those obtained from control plants. To identify outperforming genes and constructs, results from the independent transformation events tested were analyzed separately. To evaluate the effect of a gene event over a control the data was analyzed by Student's t-test and the p value was calculated. Results were considered significant if p≤0.1. The JMP statistics software package was used (Version 5.2.1, SAS Institute Inc., Cary, N.C., USA).

Experimental Results—

The polynucleotide sequences of the invention were assayed for a number of desired traits.

Tables 10-14 depict analyses of the above mentioned growth parameters of seedlings overexpressing the polynucleotides of the invention under the regulation of the At6669 promoter (SEQ ID NO:2823) when grown under osmotic stress (25% PEG) conditions.

TABLE 10

MAB70 - 25% PEG

| | Control | Event No. 7971.3 | | Event No. 7972.1 | | Event No. 7974.1 | |
|---|---|---|---|---|---|---|---|
| | | A | P | A | P | A | P |
| RGR of Roots Coverage between day 5 and 10 | 0.16 | 0.29 | 0.00 | 0.31 | 0.00 | 0.30 | 0.02 |
| RGR of Roots Length between day 1 and 5 | 0.07 | 0.12 | 0.05 | 0.13 | 0.03 | | |

Table 10: Provided are the growth and biomass parameters of transgenic or control plants as measured in Tissue Calture growth under 25% PEG.
A = average;
P = p value;
RGR = Relative Growth Rate.
The indicated days refer to days from planting.

TABLE 11

MAB76 - 25% PEG

| | Control | Event No. 7635.4 | | Event No. 7635.1 | |
|---|---|---|---|---|---|
| | | A | P | A | P |
| RGR of Roots Coverage between day 5 and 10 | 0.16 | 0.22 | 0.02 | 0.21 | 0.09 |

Table 11: Provided are the growth and biomass parameters of transgenic or control plants as measured in Tissue Calture growth under 25% PEG.
A = average;
P = p value;
RGR = Relative Growth Rate.
The indicated days refer to days from planting.

TABLE 12

MAB79 - 25% PEG

| | Control | Event No. 7324.1 | | Event No. 7961.1 | |
|---|---|---|---|---|---|
| | | A | P | A | P |
| Dry Weight [gr] | 0.01 | 0.01 | 0.06 | | |
| Fresh Wight [gr] | 0.08 | | | 0.13 | 0.07 |
| Leaf Area on day 5 | 0.15 | | | 0.19 | 0.05 |
| RGR of Roots Coverage between day 5 and 10 | 0.16 | | | 0.32 | 0.05 |
| RGR of Roots Length between day 1 and 5 | 0.07 | | | 0.11 | 0.02 |

Table 12: Provided are the growth and biomass parameters of transgenic or control plants as measured in Tissue Calture growth under 25% PEG.
A = average;
P = p value;
RGR = Relative Growth Rate.
The indicated days refer to days from planting.

TABLE 13

MAB56 - 25% PEG

| | Control | Event No. 6802.10 | |
|---|---|---|---|
| | | A | P |
| Roots Coverage on day 7 | 2.46 | 3.38 | 0.09 |
| Roots Length on day 7 | 2.81 | 3.43 | 0.07 |

Table 13: Provided are the growth and biomass parameters of transgenic or control plants as measured in Tissue Calture growth under 25% PEG.
A = average;
P = p value;
RGR = Relative Growth Rate.
The indicated days refer to days from planting.

TABLE 14

MAB58 - 25% PEG

| | Control | Event No. 6783.30 | |
|---|---|---|---|
| | | A | P |
| Leaf Area on day 7 | 0.31 | 0.41 | 0.03 |
| Leaf Area on day 14 | 0.80 | 1.09 | 0.02 |
| Fresh Weight | 0.18 | 0.31 | 0.00 |
| Dry Weight [gr] | 0.01 | 0.013 | 0.01 |

Table 14: Provided are the growth and biomass parameters of transgenic or control plants as measured in Tissue Calture growth under 25% PEG.
A = average;
P = p value;
RGR = Relative Growth Rate.
The indicated days refer to days from planting.

Tables 15-29 depict analyses of the above mentioned growth parameters of seedlings overexpressing the polynucleotides of the invention under the regulation of the At6669 promoter in Normal Growth conditions (0.5 MS medium).

TABLE 15

MAB70 - Normal Growth Conditions

| | Control | 7971.3 A | 7971.3 P | 7972.1 A | 7972.1 P | 7974.1 A | 7974.1 P | 7974.3 A | 7974.3 P |
|---|---|---|---|---|---|---|---|---|---|
| Dry Weight [gr] | 0.01 | 0.01 | 0.03 | 0.01 | 0.05 | 0.02 | 0.04 | 0.01 | 0.07 |
| Fresh Wight [gr] | 0.14 | | | | | 0.24 | 0.04 | 0.22 | 0.10 |
| Leaf Area on day 10 | 0.46 | 0.59 | 0.00 | | | | | | |
| Leaf Area on day 5 | 0.21 | | | | | 0.30 | 0.10 | | |
| RGR of Roots Coverage between day 5 and 10 | 0.18 | 0.42 | 0.00 | 0.37 | 0.00 | 0.32 | 0.01 | | |
| RGR of Roots Length between day 1 and 5 | 0.06 | 0.15 | 0.01 | 0.16 | 0.00 | 0.15 | 0.00 | | |
| RGR of Roots Length between day 5 and 10 | 0.22 | | | 0.32 | 0.09 | | | | |

Table 15: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 16

MAB71 - Normal Growth Conditions

| | Control | 7331.5 A | 7331.5 P | 7332.2 A | 7332.2 P | 7333.5 A | 7333.5 P |
|---|---|---|---|---|---|---|---|
| Dry Weight [gr] | 0.01 | 0.01 | 0.05 | | | | |
| Fresh Wight [gr] | 0.14 | 0.20 | 0.08 | | | | |
| RGR of Roots Coverage between day 5 and 10 | 0.18 | | | 0.28 | 0.04 | 0.26 | 0.07 |
| RGR of Roots Length between day 1 and 5 | 0.06 | | | 0.11 | 0.02 | 0.11 | 0.01 |

Table 16: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 17

MAB74 - Normal Growth Conditions

| | Control | 7981.1 A | 7981.1 P | 7982.4 A | 7982.4 P | 7983.9 A | 7983.9 P |
|---|---|---|---|---|---|---|---|
| Dry Weight [gr] | 0.01 | 0.01 | 0.09 | 0.02 | 0.05 | 0.01 | 0.06 |
| Fresh Wight [gr] | 0.14 | | | | | 0.21 | 0.01 |
| Leaf Area on day 10 | 0.46 | 0.67 | 0.01 | | | | |
| Leaf Area on day 5 | 0.21 | 0.29 | 0.04 | 0.29 | 0.01 | 0.27 | 0.00 |
| RGR of Roots Coverage between day 5 and 10 | 0.18 | | | 0.31 | 0.07 | | |
| RGR of Roots Coverage between day 1 and 5 | 0.73 | | | 1.70 | 0.07 | | |
| RGR of Roots Length between day 1 and 5 | 0.06 | | | 0.12 | 0.09 | 0.14 | 0.03 |
| RGR of Roots Length between day 5 and 10 | 0.22 | 0.45 | 0.05 | 0.58 | 0.00 | | |

Table 17: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 18

MAB76 - Normal Growth Conditions

| | Control | 7633.3 A | 7633.3 P | 7635.4 A | 7635.4 P | 7635.1 A | 7635.1 P |
|---|---|---|---|---|---|---|---|
| RGR Leaf Area between day 5 and 10 | 0.24 | 0.34 | 0.04 | 0.33 | 0.07 | | |
| RGR of Roots Coverage between day 5 and 10 | 0.18 | | | | | 0.38 | 0.08 |
| RGR of Roots Length between day 1 and 5 | 0.06 | | | | | 0.13 | 0.02 |

Table 18: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 19

MAB77 - Normal Growth Conditions

| | | Event No. | | | | | |
|---|---|---|---|---|---|---|---|
| | | 7931.11 | | 8211.2 | | 8212.2 | |
| | Control | A | P | A | P | A | P |
| Dry Weight [gr] | 0.01 | 0.01 | 0.08 | | | 0.01 | 0.10 |
| Roots Coverage on day 10 | 2.77 | | | | | 4.33 | 0.07 |
| RGR Leaf Area between day 5 and 10 | 0.24 | 0.38 | 0.10 | 0.35 | 0.04 | | |
| RGR of Roots Coverage between day 5 and 10 | 0.18 | 0.27 | 0.09 | 0.29 | 0.09 | | |
| RGR of Roots Length between day 1 and 5 | 0.06 | | | 0.10 | 0.03 | | |

Table 19: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 20

MAB79 - Normal Growth Conditions

| | | Event No. | | | | | | | |
|---|---|---|---|---|---|---|---|---|---|
| | | 7323.3 | | 7324.1 | | 7961.1 | | 7962.2 | |
| | Control | A | P | A | P | A | P | A | P |
| Dry Weight [gr] | 0.01 | 0.02 | 0.03 | 0.02 | 0.08 | 0.01 | 0.00 | | |
| Fresh Wight [gr] | 0.14 | 0.34 | 0.04 | 0.31 | 0.09 | | | | |
| Leaf Area on day 10 | 0.46 | 0.92 | 0.01 | 0.90 | 0.01 | 0.81 | 0.00 | | |
| Leaf Area on day 5 | 0.21 | | | | | 0.29 | 0.02 | 0.28 | 0.00 |
| Roots Coverage on day 10 | 2.77 | 5.31 | 0.02 | 4.59 | 0.07 | 3.81 | 0.00 | 3.71 | 0.01 |
| RGR Leaf Area between day 5 and 10 | 0.24 | | | | | 0.36 | 0.02 | | |
| RGR Leaf Area between day 1 and 5 | 0.82 | | | | | 1.34 | 0.00 | | |
| RGR of Roots Coverage between day 5 and 10 | 0.18 | | | | | 0.45 | 0.06 | 0.39 | 0.02 |
| RGR of Roots Length between day 1 and 5 | 0.06 | 0.12 | 0.02 | 0.17 | 0.06 | | | 0.14 | 0.00 |

Table 20: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 21

MAB115 - Normal Growth Conditions

| | | Event No. | | | | | | | |
|---|---|---|---|---|---|---|---|---|---|
| | | 8561.2 | | 8564.1 | | 8564.2 | | 8565.1 | |
| | Control | A | P | A | P | A | P | A | P |
| Dry Weight [gr] | 0.005 | 0.006 | 0.00 | | | | | 0.009 | 0.00 |
| Leaf Area on day 10 | 0.24 | | | | | | | 0.27 | 0.00 |
| Leaf Area on day 5 | 0.35 | | | | | | | 0.38 | 0.01 |
| Roots Coverage on day 10 | 1.67 | | | | | | | 2.13 | 0.02 |
| Roots Coverage on day 5 | 3.38 | | | | | | | 4.80 | 0.03 |
| Roots Length on day 10 | 2.39 | | | | | | | 2.74 | 0.00 |
| Roots Length on day 5 | 3.46 | | | | | | | 4.22 | 0.02 |
| RGR Leaf Area between day 5 and 10 | 0.37 | 0.43 | 0.00 | | | | | 0.48 | 0.00 |
| RGR Leaf Area between day 1 and 5 | 0.16 | 0.19 | 0.00 | | | | | | |
| RGR of Roots Coverage between day 5 and 10 | 1.89 | 3.21 | 0.00 | 2.24 | 0.02 | 2.23 | 0.02 | 3.47 | 0.01 |
| RGR of Roots Coverage between day 1 and 5 | 0.33 | 0.35 | 0.00 | 0.41 | 0.00 | 0.43 | 0.00 | 0.44 | 0.00 |
| RGR of Roots Length between day 1 and 5 | 0.37 | 0.56 | 0.02 | | | 0.53 | 0.06 | 0.68 | 0.00 |

TABLE 21-continued

| | | MAB115 - Normal Growth Conditions | | | | | | |
|---|---|---|---|---|---|---|---|---|
| | | \multicolumn{8}{c}{Event No.} | | | | | | | |
| | | 8561.2 ... | | 8564.1 ... | | 8564.2 ... | | 8565.1 ... |
| | Control | A | P | A | P | A | P | A | P |
| RGR of Roots Length between day 5 and 10 | 0.15 | | | 0.18 | 0.00 | 0.17 | 0.00 | 0.18 | 0.00 |

Table 21: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 22

| | MAB54 - Normal Growth Conditions | | | | | | | | |
|---|---|---|---|---|---|---|---|---|---|
| | | \multicolumn{8}{c}{Event No.} | | | | | | | |
| | | 8181.2 ... | | 8182.2 ... | | 8184.3 ... | | 8185.3 ... |
| | Control | A | P | A | P | A | P | A | P |
| Dry Weight [gr] | 0.005 | 0.009 | 0.00 | 0.008 | 0.00 | 0.008 | 0.00 | 0.007 | 0.00 |
| Roots Coverage on day 10 | 1.67 | 1.80 | 0.04 | | | | | | |
| Roots Coverage on day 5 | 3.38 | 4.27 | 0.02 | 3.40 | 0.00 | | | | |
| Roots Length on day 10 | 2.39 | 2.52 | 0.01 | | | | | | |
| Roots Length on day 5 | 3.46 | 4.11 | 0.02 | 3.50 | 0.00 | | | | |
| RGR Leaf Area between day 5 and 10 | 0.37 | 0.45 | 0.00 | | | | | | |
| RGR Leaf Area between day 1 and 5 | 0.16 | 0.17 | 0.04 | | | | | 0.19 | 0.00 |
| RGR of Roots Coverage between day 5 and 10 | 1.89 | 3.59 | 0.00 | 3.60 | 0.01 | 2.28 | 0.01 | 2.20 | 0.01 |
| RGR of Roots Coverage between day 1 and 5 | 0.33 | 0.52 | 0.00 | 0.55 | 0.00 | 0.39 | 0.00 | 0.36 | 0.00 |
| RGR of Roots Length between day 1 and 5 | 0.37 | 0.70 | 0.00 | 0.73 | 0.00 | 0.48 | 0.08 | 0.51 | 0.02 |
| RGR of Roots Length between day 5 and 10 | 0.15 | 0.21 | 0.01 | 0.22 | 0.01 | 0.17 | 0.00 | 0.17 | 0.00 |

Table 22: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 23

| | MAB55 - Normal Growth Conditions | | | | | | | | |
|---|---|---|---|---|---|---|---|---|---|
| | | \multicolumn{8}{c}{Event No.} | | | | | | | |
| | | 6802.1 | | 6802.11 | | 6802.8 | | 6805.3 | |
| | | A | P | A | P | A | P | A | P |
| Roots Coverage on day 7 | 3.67 | 5.93 | 0.04 | | | | | | |
| Roots Coverage on day 14 | 7.40 | 13.26 | 0.04 | | | | | | |
| Roots Length on day 7 | 3.99 | 5.32 | 0.01 | | | | | | |
| Roots Length on day 14 | 6.14 | 7.80 | 0.04 | | | | | 7.65 | 0.04 |
| RGR of Roots Coverage between day 1 and 7 | 0.53 | 1.30 | 0.00 | 1.11 | 0.02 | 0.93 | 0.02 | | |
| RGR of Roots Length between day 1 and 7 | 0.29 | 0.48 | 0.00 | 0.45 | 0.03 | 0.43 | 0.02 | | |
| Fresh Weight | 0.19 | | | | | 0.10 | 0.00 | 0.12 | 0.01 |
| Dry Weight [gr] | 0.01 | | | | | 0.01 | 0.00 | 0.01 | 0.00 |

Table 23: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 24

MAB56 - Normal Growth Conditions

| | | Event No. | | | | | | |
|---|---|---|---|---|---|---|---|---|
| | | 6691.2 | | 6691.3 | | 6693.2 | | 6693.5 | |
| | | A | P | A | P | A | P | A | P |
| Roots Coverage on day 7 | 3.67 | 5.81 | 0.00 | | | | | 5.67 | 0.01 |
| Roots Length on day 7 | 3.99 | 6.21 | 0.00 | | | | | 5.39 | 0.00 |
| Roots Length on day 14 | 6.14 | 8.32 | 0.01 | | | | | 8.01 | 0.02 |
| RGR of Roots Length between day 7 and 14 | 0.09 | 0.05 | 0.01 | 0.05 | 0.06 | 0.06 | 0.08 | | |
| Fresh Weight | 0.19 | 0.14 | 0.03 | 0.14 | 0.03 | | | | |
| Dry Weight [gr] | 0.01 | 0.01 | 0.02 | 0.01 | 0.02 | 0.00 | 0.00 | | |

Table 24: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 25

MAB57 - Normal Growth Conditions

| | | Event No. | | | | | | |
|---|---|---|---|---|---|---|---|---|
| | | 6912.14 | | 6912.2 | | 6912.6 | | 6914.1 | |
| | | A | P | A | P | A | P | A | P |
| Roots Coverage on day 7 | 3.67 | 6.40 | 0.00 | 6.71 | 0.00 | | | | |
| Roots Coverage on day 14 | 7.40 | 17.33 | 0.00 | 15.27 | 0.05 | 12.30 | 0.02 | | |
| Roots Length on day 7 | 3.99 | 5.54 | 0.00 | 6.12 | 0.00 | 6.34 | 0.00 | | |
| Roots Length on day 14 | 6.14 | 8.76 | 0.00 | 8.48 | 0.01 | 7.97 | 0.02 | 7.85 | 0.04 |
| RGR of Roots Length between day 1 and 7 | 0.29 | 0.39 | 0.06 | | | | | | |
| RGR of Roots Length between day 7 and 14 | 0.09 | | | | | 0.04 | 0.09 | | |
| Fresh Weight | 0.19 | 0.24 | 0.09 | | | 0.11 | 0.01 | 0.11 | 0.01 |
| Dry Weight [gr] | 0.01 | | | | | 0.01 | 0.01 | 0.01 | 0.01 |

Table 25: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 26

MAB58 - Normal Growth Conditions

| | | Event No. | | | | | |
|---|---|---|---|---|---|---|---|
| | | 6783.1 | | 6783.2 | | 6783.3 | |
| | | A | P | A | P | A | P |
| Roots Coverage on day 7 | 3.67 | | | | | 6.18 | 0.00 |
| Roots Coverage on day 14 | 7.40 | | | 12.65 | 0.02 | 12.00 | 0.09 |
| Roots Length on day 7 | 3.99 | | | | | 5.20 | 0.02 |
| Roots Length on day 14 | 6.14 | 7.38 | 0.09 | 7.51 | 0.07 | 7.59 | 0.08 |
| RGR of Roots Length between day 1 and 7 | 0.29 | 0.35 | 0.07 | | | | |
| Fresh Weight | 0.19 | 0.13 | 0.03 | | | | |
| Dry Weight [gr] | 0.01 | 0.01 | 0.00 | | | | |

Table 26: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 27

MAB59 - Normal Growth Condition

| | | Event No. | | | | | |
|---|---|---|---|---|---|---|---|
| | | 6791.4 | | 6793.4 | | 6794.4 | |
| | | A | P | A | P | A | P |
| Roots Coverage on day 7 | 3.67 | | | 5.61 | 0.04 | 5.23 | 0.09 |
| Roots Coverage on day 14 | 7.40 | | | 9.65 | 0.09 | 10.28 | 0.09 |
| Roots Length on day 7 | 3.99 | | | 5.47 | 0.08 | 4.95 | 0.09 |
| Roots Length on day 14 | 6.14 | | | | | 7.70 | 0.07 |
| RGR of Roots Coverage between day 1 and 7 | 0.53 | | | | | 0.80 | 0.09 |
| RGR of Roots Length between day 7 and 14 | 0.09 | | | 0.05 | 0.10 | | |

TABLE 27-continued

MAB59 - Normal Growth Condition

| | Event No. | | | | | |
|---|---|---|---|---|---|---|
| | 6791.4 | | 6793.4 | | 6794.4 | |
| | A | P | A | P | A | P |
| Fresh Weight | 0.19 | 0.09 | 0.00 | | | |
| Dry Weight [gr] | 0.01 | 0.004 | 0.00 | 0.005 | 0.02 | |

Table 27: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 28

MAB69 - Normal Growth Conditions

| | Event No. | | | | | | | |
|---|---|---|---|---|---|---|---|---|
| | 6651.1 | | 6651.12 | | 6651.13 | | 6651.8 | |
| | A | P | A | P | A | P | A | P |
| Roots Length on day 7 | 3.99 | 4.97 | 0.10 | | | | | |
| Roots Length on day 14 | 6.14 | 8.01 | 0.02 | | | | | |
| RGR of Roots Length between day 1 and 7 | 0.29 | | | | | | 0.35 | 0.09 |
| Fresh Weight | 0.19 | | | | 0.12 | 0.02 | 0.12 | 0.01 |
| Dry Weight [gr] | 0.01 | | 0.007 | 0.09 | 0.005 | 0.00 | 0.006 | 0.00 |

Table 28: Provided are the growth and biomass parameters of transgenic or control plants as measured in Tissue Calture growth under normal growth conditions.
A = average;
P = p value;
RGR = Relative Growth Rate.
The indicated days refer to days from planting.

TABLE 29

MAB72 - Normal Growth Conditions

| | | Event No. | | | | | |
|---|---|---|---|---|---|---|---|
| | | 8552.1 ... | | 8552.4 ... | | 8553.2 ... | |
| | Control | A | P | A | P | A | P |
| Dry Weight [gr] | 0.005 | 0.008 | 0.00 | 0.008 | 0.00 | 0.007 | 0.00 |
| Leaf Area on day 10 | 0.24 | 0.24 | 0.01 | | | | |
| Roots Coverage on day 10 | 1.67 | 1.84 | 0.01 | 1.93 | 0.02 | 1.89 | 0.03 |
| Roots Coverage on day 5 | 3.38 | 3.60 | 0.04 | 3.90 | 0.06 | 4.50 | 0.00 |
| Roots Length on day 10 | 2.39 | 2.48 | 0.01 | | | | |
| Roots Length on day 5 | 3.46 | 3.70 | 0.04 | 3.65 | 0.04 | 3.84 | 0.00 |
| RGR Leaf Area between day 5 and 10 | 0.37 | 0.47 | 0.00 | 0.39 | 0.00 | | |
| RGR Leaf Area between day 1 and 5 | 0.16 | | | 0.20 | 0.09 | | |
| RGR of Roots Coverage between day 5 and 10 | 1.89 | 1.93 | 0.03 | 2.29 | 0.06 | 3.04 | 0.01 |
| RGR of Roots Coverage between day 1 and 5 | 0.33 | | | 0.35 | 0.00 | 0.52 | 0.00 |
| RGR of Roots Length between day 1 and 5 | 0.37 | | | | | 0.55 | 0.01 |
| RGR of Roots Length between day 5 and 10 | 0.15 | 0.16 | 0.00 | 0.18 | 0.00 | 0.22 | 0.01 |

Table 29: Provided are the growth and biomass parameters of transgenic or control plants as measured in Tissue Calture growth under normal growth conditions.
A = average;
P = p value;
RGR = Relative Growth Rate.
The indicated days refer to days from planting.

Example 6

Evaluating Transgenic *Arabidopsis* Plant Growth Under Abiotic Stress as Well as Favorable Conditions in Greenhouse Assay ABS Tolerance: Yield and Plant Growth Rate at High Salinity Concentration Under Greenhouse Conditions—

This assay followed the rosette area growth of plants grown in the greenhouse as well as seed yield at high salinity irrigation. Seeds were sown in agar media supplemented only with a selection agent (Kanamycin) and Hoagland solution under nursery conditions. The $T_2$ transgenic seedlings were then transplanted to 1.7 trays filled with peat and perlite. The trays were irrigated with tap water (provided from the pots' bottom). Half of the plants were irrigated with a salt solution (40-80 mM NaCl and 5 mM $CaCl_2$) so as to induce salinity stress (stress conditions). The other half of the plants was irrigated with tap water (normal conditions). All plants were grown in the greenhouse until mature seeds, then harvested (the above ground tissue) and weighted (immediately or following drying in oven at 50° C. for 24 hours). High salinity conditions were achieved by irrigating with a solution containing 40-80 mM NaCl ("ABS" growth conditions) and compared to regular growth conditions.

Each construct was validated at its T2 generation. Transgenic plants transformed with a construct including the uidA reporter gene (GUS) under the AT6669 promoter or with an empty vector including the AT6669 promoter were used as control.

The plants were analyzed for their overall size, growth rate, flowering, seed yield, weight of 1,000 seeds, dry matter and harvest index (HI— seed yield/dry matter). Transgenic plants performance was compared to control plants grown in parallel under the same conditions. Mock-transgenic plants expressing the uidA reporter gene (GUS-Intron) or with no gene at all, under the same promoter were used as control.

The experiment was planned in nested randomized plot distribution. For each gene of the invention three to five independent transformation events were analyzed from each construct.

Digital Imaging—

A laboratory image acquisition system, which consists of a digital reflex camera (Canon EOS 300D) attached with a 55 mm focal length lens (Canon EF-S series), mounted on a reproduction device (Kaiser RS), which included 4 light units (4×150 Watts light bulb) was used for capturing images of plant samples.

The image capturing process was repeated every 2 days starting from day 1 after transplanting till day 16. Same camera, placed in a custom made iron mount, was used for capturing images of larger plants sawn in white tubs in an environmental controlled greenhouse. The tubs were square shape include 1.7 liter trays. During the capture process, the tubs were placed beneath the iron mount, while avoiding direct sun light and casting of shadows.

An image analysis system was used, which consists of a personal desktop computer (Intel P4 3.0 GHz processor) and a public domain program—ImageJ 1.39 (Java based image processing program which was developed at the U.S National Institutes of Health and freely available on the internet at Hypertext Transfer Protocol://rsbweb (dot) nih (dot) gov/). Images were captured in resolution of 10 Mega Pixels (3888×2592 pixels) and stored in a low compression JPEG (Joint Photographic Experts Group standard) format. Next, analyzed data was saved to text files and processed using the JMP statistical analysis software (SAS institute).

Leaf Analysis—

Using the digital analysis leaves data was calculated, including leaf number, area, perimeter, length and width.

Vegetative Growth Rate:

the relative growth rate (RGR) of leaf number and rosette area were calculated formulas V and VI, respectively.

Relative growth rate of leaf number=($\Delta$leaf number/$\Delta t$)*(1/leaf number $t_1$)　　　　Formula V:

$\Delta$leaf number is the interval between the current leaf number (measured at $t_2$) and the leaf number measured at the previous day (Area $t_1$)

$\Delta t$ is the time interval ($t_2$-$t_1$, in days) between the current analyzed image day ($t_2$) and the previous day ($t_1$).

Thus, the relative growth rate of leaf number is in units of 1/day.

Relative growth rate of rosette area=($\Delta$rosette area/$\Delta t$)*(1/rosette area $t_1$)　　　　Formula VI:

$\Delta$rosette area is the interval between the current rosette area (measured at $t_2$) and the rosette area measured at the previous day (Area $t_1$)

$\Delta t$ is the time interval ($t_2$-$t_1$, in days) between the current analyzed image day ($t_2$) and the previous day ($t_1$).

Thus, the relative growth rate of rosette area is in units of 1/day.

Seeds Average Weight—

At the end of the experiment all seeds were collected. The seeds were scattered on a glass tray and a picture was taken. Using the digital analysis, the number of seeds in each sample was calculated.

Dry Weight and Seed Yield—

On about day 80 from sowing, the plants were harvested and left to dry at 30° C. in a drying chamber. The biomass and seed weight of each plot were measured and divided by the number of plants in each plot. Dry weight=total weight of the vegetative portion above ground (excluding roots) after drying at 30° C. in a drying chamber; Seed yield per plant=total seed weight per plant (gr). 1000 seed weight (the weight of 1000 seeds) (gr.).

Harvest Index (HI)—

The harvest index was calculated using Formula VII.

Harvest Index=Average seed yield per plant/Average dry weight　　　　Formula VII:

Statistical Analyses—

To identify genes conferring significantly improved tolerance to abiotic stresses, the results obtained from the transgenic plants were compared to those obtained from control plants. To identify outperforming genes and constructs, results from the independent transformation events tested were analyzed separately. Data was analyzed using Student's t-test and results were considered significant if the p value was less than 0.1. The JMP statistics software package is used (Version 5.2.1, SAS Institute Inc., Cary, N.C., USA).

Experimental Results

Tables 30-44 depict analyses of plant parameters as describe above overexpressing the polynucleotides of the invention under the regulation of the At6669 promoter under salinity irrigation conditions [NaCl 40-80 mM; NaCl Electrical conductivity (E.C.) of 7-10].

TABLE 30

MAB115 - Salt irrigation (40-80 mM NaCl)

| | | Event No. | | | |
|---|---|---|---|---|---|
| | | 8564.1 | | 8565.1 | |
| | Control | A | P | A | P |
| Rosette Diameter on day 3* | 1.70 | 1.80 | 0.09 | 1.75 | 0.04 |
| Rosette Diameter on day 5 | 2.36 | | | | |
| Rosette Diameter on day 8 | 3.77 | | | 4.00 | 0.09 |
| Rosette Area on day 3 | 0.90 | | | | |
| Rosette Area on day 5 | 1.56 | | | 1.70 | 0.09 |
| Rosette Area on day 8 | 4.06 | | | 4.38 | 0.06 |
| Plot Coverage on day 5 | 12.30 | | | 13.61 | 0.06 |
| Plot Coverage on day 8 | 31.90 | | | 35.07 | 0.02 |
| Leaf Number on day 3 | 5.08 | | | 5.94 | 0.00 |
| Leaf Number on day 5 | 6.86 | | | 7.38 | 0.05 |
| RGR of Leaf Number between day 3 and 5 | 0.18 | | | | |
| RGR of Leaf Number between day 5 and 8 | 0.09 | | | | |
| RGR of Rosette Area between day 5 and 8 | 0.53 | 0.62 | 0.01 | | |
| Biomass DW [gr] | 3.24 | | | | |
| Harvest Index | 0.11 | 0.15 | 0.07 | 0.16 | 0.03 |

Table 30: Provided are the growth, biomass and yield parameters of transgenic or control plants as measured in Green House under salinity irrigation.
A = average;
P = p value;
RGR = Relative Growth Rate.
The indicated days refer to days from planting.

TABLE 31

MAB54 - Salt irrigation (40-80 mM NaCl)

| | Control | 8181.2 A | 8181.2 P | 8182.2 A | 8182.2 P | 8183.2 A | 8183.2 P | 8185.4 A | 8185.4 P |
|---|---|---|---|---|---|---|---|---|---|
| Rosette Diameter on day 3* | 1.70 | 1.95 | 0.04 | | | | | | |
| Rosette Diameter on day 5 | 2.36 | | | 2.70 | 0.02 | 2.64 | 0.00 | | |
| Rosette Diameter on day 8 | 3.77 | | | 4.00 | 0.08 | | | | |
| Rosette Area on day 3 | 0.90 | | | | | 1.19 | 0.04 | | |
| Plot Coverage on day 3 | 7.04 | | | | | 9.52 | 0.04 | 7.49 | 0.08 |
| Leaf Number on day 3 | 5.08 | | | 6.19 | 0.06 | | | | |
| Leaf Number on day 8 | 8.66 | 9.31 | 0.00 | 9.38 | 0.00 | | | | |
| RGR of Leaf Number between day 3 and 5 | 0.18 | | | | | | | | |
| RGR of Rosette Area between day 1 and 3 | 0.45 | | | 0.52 | 0.01 | | | | |
| 1000 Seeds weight [gr] | 0.02 | | | | | 0.02 | 0.00 | 0.02 | 0.00 |
| Yield [gr]/Plant | 0.04 | 0.06 | 0.05 | | | | | | |
| Harvest Index | 0.11 | 0.17 | 0.01 | | | | | | |

Table 31: Provided are the growth, biomass and yield parameters of transgenic or control plants as measured in Green House under salinity irrigation.
A = average;
P = p value;
RGR = Relative Growth Rate.
The indicated days refer to days from planting.

TABLE 32

MAB55 - Salt irrigation (40-80 mM NaCl)

| | Control | 6802.10 A | 6802.10 P | 6805.3 A | 6805.3 P | 6805.4 A | 6805.4 P |
|---|---|---|---|---|---|---|---|
| Rosette Diameter on day 5 | 2.36 | 2.81 | 0.03 | | | | |
| Rosette Diameter on day 8 | 3.77 | 4.29 | 0.05 | | | | |
| Rosette Area on day 3 | 0.90 | 1.35 | 0.01 | | | | |
| Rosette Area on day 5 | 1.56 | | | 1.70 | 0.03 | | |
| Rosette Area on day 8 | 4.06 | 5.91 | 0.05 | | | | |
| Plot Coverage on day 3 | 7.04 | 10.76 | 0.01 | | | | |
| Plot Coverage on day 5 | 12.30 | | | 13.60 | 0.02 | | |
| Plot Coverage on day 8 | 31.90 | 47.28 | 0.06 | | | | |
| Leaf Number on day 3 | 5.08 | 6.25 | 0.00 | | | | |
| Leaf Number on day 5 | 6.86 | 7.94 | 0.03 | | | | |
| Leaf Number on day 8 | 8.66 | 9.50 | 0.01 | | | | |
| RGR of Rosette Area between day 1 and 3 | 0.45 | 0.51 | 0.05 | | | | |
| Yield [gr]/Plant | 0.04 | | | | | 0.06 | 0.03 |
| Harvest Index | 0.11 | | | 0.15 | 0.05 | | |

Table 32: Provided are the growth, biomass and yield parameters of transgenic or control plants as measured in Green House under salinity irrigation.
A = average;
P = p value;
RGR = Relative Growth Rate.
The indicated days refer to days from planting.

TABLE 33

Provided are the growth, biomass and yield parameters of transgenic or control plants as measured in Green House under salinity irrigation.
MAB56-Salt irrigation (40-80 mM NaCl)

| Event No. | Control | 6691.2 A | 6691.2 P | 6691.3 A | 6691.3 P | 6693.2 A | 6693.2 P | 6695.6 A | 6695.6 P |
|---|---|---|---|---|---|---|---|---|---|
| Rosette Diameter on day 3 | 1.70 | | | | | 1.89 | 0.05 | 1.97 | 0.07 |
| Rosette Diameter on day 5 | 2.36 | | | | | 2.55 | 0.09 | 2.58 | 0.01 |
| Rosette Area on day 3 | 0.90 | | | 1.06 | 0.00 | 1.15 | 0.02 | 1.23 | 0.08 |
| Rosette Area on day 5 | 1.56 | | | | | 1.94 | 0.02 | 1.94 | 0.03 |

TABLE 33-continued

Provided are the growth, biomass and yield parameters of transgenic or control plants as measured in Green House under salinity irrigation.
MAB56-Salt irrigation (40-80 mM NaCl)

| | | 6691.2 | | 6691.3 | | 6693.2 | | 6695.6 | |
|---|---|---|---|---|---|---|---|---|---|
| Event No. | Control | A | P | A | P | A | P | A | P |
| Rosette Area on day 8 | 4.06 | 4.63 | 0.02 | | | | | | |
| Plot Coverage on day 3 | 7.04 | | | 8.45 | 0.00 | 9.21 | 0.01 | 9.82 | 0.07 |
| Plot Coverage on day 5 | 12.30 | | | | | 15.49 | 0.01 | 15.53 | 0.02 |
| Plot Coverage on day 8 | 31.90 | 37.03 | 0.01 | | | | | 34.82 | 0.05 |
| Leaf Number on day 3 | 5.08 | | | 5.50 | 0.00 | 5.81 | 0.00 | 6.00 | 0.02 |
| Leaf Number on day 5 | 6.86 | | | | | 7.38 | 0.01 | 7.50 | 0.02 |
| 1000 Seeds weight [gr] | 0.02 | | | 0.02 | 0.08 | | | | |
| Harvest Index | 0.11 | | | 0.18 | 0.01 | | | | |

A = average;
P = p value;
RGR = Relative Growth Rate.
The indicated days refer to days from planting.

TABLE 34

Provided are the growth, biomass and yield parameters of transgenic or control plants as measured in Green House under salinity irrigation.
MAB57-Salt irrigation (40-80 mM NaCl)

| | | 6912.1 | | 6912.13 | | 6914.5 | |
|---|---|---|---|---|---|---|---|
| Event No. | Control | A | P | A | P | A | P |
| Leaf Number on day 3 | 5.08 | | | | | 5.69 | 0.00 |
| Leaf Number on day 5 | 6.86 | | | 8.13 | 0.06 | | |
| Leaf Number on day 8 | 8.66 | | | | | 9.56 | 0.06 |
| RGR of Leaf Number between day 5 and 8 | 0.09 | 0.14 | 0.01 | | | | |
| RGR of Rosette Area between day 5 and 8 | 0.53 | 0.62 | 0.02 | | | 0.58 | 0.10 |
| 1000 Seeds weight [gr] | 0.02 | | | | | 0.02 | 0.00 |
| Yield [gr]/Plant | 0.04 | 0.06 | 0.01 | 0.06 | 0.03 | 0.06 | 0.01 |
| Harvest Index | 0.11 | | | 0.19 | 0.06 | 0.23 | 0.00 |

A = average;
P = p value;
RGR = Relative Growth Rate.
The indicated days refer to days from planting.

TABLE 35

Provided are the growth, biomass and yield parameters of transgenic or control plants as measured in Green House under salinity irrigation.
MAB58-Salt irrigation (40-80 mM NaCl)

| | | 6783.3 | | 7522.10 | | 7522.3 | | 7523.6 | |
|---|---|---|---|---|---|---|---|---|---|
| Event No. | Control | A | P | A | P | A | P | A | P |
| Rosette Diameter on day 3 | 1.70 | | | | | | | 2.11 | 0.00 |
| Rosette Diameter on day 5 | 2.36 | 2.57 | 0.00 | | | | | 4.54 | 0.00 |
| Rosette Diameter on day 8 | 3.77 | | | | | 4.06 | 0.07 | 4.54 | 0.00 |
| Rosette Area on day 3 | 0.90 | | | | | | | 1.36 | 0.00 |
| Rosette Area on day 5 | 1.56 | | | | | | | 2.29 | 0.00 |
| Rosette Area on day 8 | 4.06 | | | | | | | 5.98 | 0.00 |
| Plot Coverage on day 3 | 7.04 | | | | | | | 10.90 | 0.00 |
| Plot Coverage on day 5 | 12.30 | | | | | | | 18.32 | 0.00 |
| Plot Coverage on day 8 | 31.90 | | | | | | | 47.88 | 0.00 |
| Leaf Number on day 3 | 5.08 | | | 5.63 | 0.06 | | | 6.06 | 0.00 |
| Leaf Number on day 8 | 8.66 | 9.25 | 0.04 | | | | | 9.81 | 0.04 |
| RGR of Leaf Number between day 5 and 8 | 0.09 | 0.12 | 0.03 | | | | | | |
| 1000 Seeds weight [gr] | 0.02 | 0.02 | 0.08 | | | | | | |
| Yield [gr]/Plant | 0.04 | 0.06 | 0.09 | | | | | | |

A = average;
P = p value;
RGR = Relative Growth Rate.
The indicated days refer to days from planting.

TABLE 36

Provided are the growth, biomass and yield parameters of transgenic or control plants as measured in Green House under salinity irrigation.
MAB59-Salt irrigation (40-80 mM NaCl)

|  |  | 6791.6 | | 6794.4 | | 6794.5 | |
| --- | --- | --- | --- | --- | --- | --- | --- |
| Event No. | Control | A | P | A | P | A | P |
| Rosette Diameter on day 3 | 1.70 | | | | | 2.38 | 0.05 |
| Rosette Diameter on day 5 | 2.36 | | | 2.73 | 0.06 | | |
| Rosette Area on day 3 | 0.90 | | | 1.27 | 0.06 | 1.65 | 0.03 |
| Plot Coverage on day 3 | 7.04 | | | 10.15 | 0.06 | 13.19 | 0.03 |
| Leaf Number on day 3 | 5.08 | 6.44 | 0.05 | 6.00 | 0.02 | 6.75 | 0.01 |
| Leaf Number on day 5 | 6.86 | 8.38 | 0.00 | 7.69 | 0.05 | 8.00 | 0.07 |
| Leaf Number on day 8 | 8.66 | | | | | 9.38 | 0.02 |
| Yield [gr]/Plant | 0.04 | 0.06 | 0.06 | | | | |
| Harvest Index | 0.11 | 0.16 | 0.04 | | | | |

A = average;
P = p value;
RGR = Relative Growth Rate.
The indicated days refer to days from planting.

TABLE 37

Provided are the growth, biomass and yield parameters of transgenic or control plants as measured in Green House under salinity irrigation.
MAB69-Salt irrigation (40-80 mM NaCl)

|  |  | 6651.11 | | 6651.12 | | 6651.2 | | 8342.1 | |
| --- | --- | --- | --- | --- | --- | --- | --- | --- | --- |
| Event No. | Control | A | P | A | P | A | P | A | P |
| Rosette Diameter on day 3 | 1.70 | | | 1.92 | 0.01 | | | | |
| Rosette Area on day 3 | 0.90 | | | 1.09 | 0.00 | | | | |
| Rosette Area on day 8 | 4.06 | | | 5.05 | 0.04 | | | | |
| Plot Coverage on day 3 | 7.04 | | | 8.74 | 0.00 | | | | |
| Plot Coverage on day 8 | 31.90 | | | 40.41 | 0.04 | | | | |
| Leaf Number on day 3 | 5.08 | | | 5.69 | 0.00 | | | | |
| Leaf Number on day 8 | 8.66 | | | | | | | 8.94 | 0.08 |
| RGR of Rosette Area between day 1 and 3 | 0.45 | 0.49 | 0.02 | 0.51 | 0.04 | | | | |
| 1000 Seeds weight [gr] | 0.02 | 0.02 | 0.00 | | | 0.02 | 0.01 | | |
| Yield [gr]/Plant | 0.04 | 0.05 | 0.09 | 0.06 | 0.02 | | | 0.07 | 0.01 |
| Harvest Index | 0.11 | | | 0.17 | 0.09 | 0.22 | 0.01 | | |

A = average;
P = p value;
RGR = Relative Growth Rate.
The indicated days refer to days from planting.

TABLE 38

Provided are the growth, biomass and yield parameters of transgenic or control plants as measured in Green House under salinity irrigation.
MAB70-Salt irrigation (40-80 mM NaCl)

|  |  | 7971.3 | | 7972.1 | | 7972.3 | |
| --- | --- | --- | --- | --- | --- | --- | --- |
| Event No. | Control | A | P | A | P | A | P |
| Rosette Diameter on day 3 | 1.70 | | | | | 1.94 | 0.00 |
| Rosette Diameter on day 5 | 2.36 | | | | | 2.62 | 0.04 |
| Rosette Diameter on day 8 | 3.77 | | | 4.40 | 0.00 | | |
| Rosette Area on day 3 | 0.90 | | | 1.20 | 0.07 | 1.12 | 0.01 |
| Rosette Area on day 5 | 1.56 | | | 2.06 | 0.05 | 1.87 | 0.00 |
| Rosette Area on day 8 | 4.06 | | | 5.86 | 0.06 | | |
| Plot Coverage on day 3 | 7.04 | | | 9.61 | 0.06 | 9.00 | 0.01 |
| Plot Coverage on day 5 | 12.30 | | | 16.46 | 0.04 | 14.93 | 0.00 |
| Plot Coverage on day 8 | 31.90 | | | 46.87 | 0.06 | | |
| Leaf Number on day 3 | 5.08 | 5.94 | 0.09 | | | | |
| Leaf Number on day 8 | 8.66 | 9.31 | 0.00 | | | 9.75 | 0.09 |
| RGR of Rosette Area | 0.53 | | | 0.62 | 0.01 | | |

TABLE 38-continued

Provided are the growth, biomass and yield parameters of transgenic or control plants as measured in Green House under salinity irrigation.
MAB70-Salt irrigation (40-80 mM NaCl)

|  |  | 7971.3 | | 7972.1 | | 7972.3 | |
|---|---|---|---|---|---|---|---|
| Event No. | Control | A | P | A | P | A | P |
| between day 5 and 8 |  |  |  |  |  |  |  |
| Yield [gr]/Plant | 0.04 | 0.08 | 0.00 | 0.07 | 0.01 |  |  |
| Harvest Index | 0.11 | 0.25 | 0.00 |  |  |  |  |

A = average;
P = p value;
RGR = Relative Growth Rate.
The indicated days refer to days from planting.

TABLE 39

Provided are the growth, biomass and yield parameters of transgenic or control plants as measured in Green House under salinity irrigation.
MAB71-Salt irrigation (40-80 mM NaCl)

|  |  | 7331.4 | | 7331.5 | | 7333.5 | | 7334.5 | |
|---|---|---|---|---|---|---|---|---|---|
| Event No. | Control | A | P | A | P | A | P | A | P |
| Rosette Diameter on day 5 | 2.36 | 3.03 | 0.00 |  |  | 2.52 | 0.02 |  |  |
| Rosette Diameter on day 8 | 3.77 | 5.01 | 0.05 | 4.33 | 0.01 |  |  |  |  |
| Plot Coverage on day 5 | 12.30 | 19.90 | 0.09 |  |  | 14.25 | 0.08 |  |  |
| Leaf Number on day 3 | 5.08 | 6.44 | 0.05 |  |  | 5.47 | 0.06 |  |  |
| Leaf Number on day 5 | 6.86 | 8.13 | 0.00 | 7.56 | 0.00 |  |  |  |  |
| Leaf Number on day 8 | 8.66 | 10.38 | 0.05 |  |  |  |  |  |  |
| RGR of Leaf Number between day 5 and 8 | 0.09 |  |  |  |  |  |  | 0.12 | 0.01 |
| RGR of Rosette Area between day 5 and 8 | 0.53 | 0.61 | 0.03 |  |  |  |  | 0.61 | 0.04 |
| Yield [gr]/Plant | 0.04 |  |  |  |  |  |  | 0.05 | 0.10 |
| Harvest Index | 0.11 | 0.21 | 0.06 |  |  |  |  |  |  |

A = average;
P = p value;
RGR = Relative Growth Rate.
The indicated days refer to days from planting.

TABLE 40

Provided are the growth, biomass and yield parameters of transgenic or control plants as measured in Green House under salinity irrigation.
MAB72-Salt irrigation (40-80 mM NaCl)

|  |  | 8552.1 | | 8553.2 | | 8553.3 | | 8555.3 | |
|---|---|---|---|---|---|---|---|---|---|
| Event No. | Control | A | P | A | P | A | P | A | P |
| Rosette Diameter on day 3 | 1.70 |  |  | 1.90 | 0.05 |  |  | 1.83 | 0.00 |
| Rosette Diameter on day 5 | 2.36 |  |  | 2.67 | 0.00 |  |  | 2.55 | 0.01 |
| Rosette Diameter on day 8 | 3.77 |  |  | 4.06 | 0.08 | 4.15 | 0.10 |  |  |
| Rosette Area on day 3 | 0.90 |  |  | 1.20 | 0.00 | 1.02 | 0.00 | 1.08 | 0.02 |
| Rosette Area on day 5 | 1.56 | 1.88 | 0.07 | 2.00 | 0.00 |  |  | 1.87 | 0.00 |
| Rosette Area on day 8 | 4.06 | 4.68 | 0.00 | 5.05 | 0.00 |  |  | 4.82 | 0.00 |
| Plot Coverage on day 3 | 7.04 |  |  | 9.64 | 0.00 | 8.13 | 0.00 | 8.67 | 0.02 |
| Plot Coverage on day 5 | 12.30 | 15.05 | 0.05 | 16.04 | 0.00 |  |  | 14.98 | 0.00 |
| Plot Coverage on day 8 | 31.90 | 37.48 | 0.00 | 40.39 | 0.00 |  |  | 38.57 | 0.00 |
| Leaf Number on day 3 | 5.08 | 5.81 | 0.00 | 5.88 | 0.00 | 5.56 | 0.00 | 5.50 | 0.00 |
| Leaf Number on day 8 | 8.66 |  |  |  |  | 9.38 | 0.02 |  |  |
| RGR of Leaf Number between day 1 and 3 | 0.12 | 0.17 | 0.01 |  |  |  |  |  |  |

A = average;
P = p value;
RGR = Relative Growth Rate.
The indicated days refer to days from planting.

TABLE 41

Provided are the growth, biomass and yield parameters of transgenic or control plants as measured in Green House under salinity irrigation.
MAB74-Salt irrigation (40-80 mM NaCl)

|  |  | 7982.1 | | 7983.6 | | 7983.9 | |
| --- | --- | --- | --- | --- | --- | --- | --- |
| Event No. | Control | A | P | A | P | A | P |
| Rosette Diameter on day 3 | 1.70 | | | 2.06 | 0.10 | 1.94 | 0.00 |
| Rosette Diameter on day 5 | 2.36 | | | | | 2.62 | 0.06 |
| Rosette Diameter on day 8 | 3.77 | | | | | 4.05 | 0.02 |
| Rosette Area on day 3 | 0.90 | | | 1.14 | 0.02 | | |
| Rosette Area on day 5 | 1.56 | | | 1.83 | 0.05 | 1.85 | 0.10 |
| Rosette Area on day 8 | 4.06 | | | | | 4.46 | 0.03 |
| Plot Coverage on day 3 | 7.04 | | | 9.13 | 0.02 | | |
| Plot Coverage on day 5 | 12.30 | | | 14.62 | 0.03 | 14.79 | 0.08 |
| Plot Coverage on day 8 | 31.90 | | | | | 35.66 | 0.01 |
| Leaf Number on day 3 | 5.08 | | | 5.75 | 0.04 | 5.31 | 0.07 |
| Leaf Number on day 5 | 6.86 | | | | | 7.25 | 0.04 |
| RGR of Rosette Area between day 3 and 5 | 0.37 | 0.42 | 0.07 | | | | |
| 1000 Seeds weight [gr] | 0.02 | 0.02 | 0.02 | | | 0.02 | 0.05 |
| Yield [gr]/Plant | 0.04 | 0.06 | 0.05 | | | | |
| Harvest Index | 0.11 | 0.20 | 0.06 | | | | |

A = average;
P = p value;
RGR = Relative Growth Rate.
The indicated days refer to days from planting.

TABLE 42

MAB76 - Salt irrigation (40-80 mM NaCl)

|  |  | Event No. | | | |
| --- | --- | --- | --- | --- | --- |
|  |  | 7633.1 | | 7633.2 | |
|  | Control | A | P | A | P |
| Leaf Number on day 3 | 5.08 | | | 5.44 | 0.02 |
| Leaf Number on day 8 | 8.66 | 9.13 | 0.07 | | |

Table 42: Provided are the growth, biomass and yield parameters of transgenic or control plants as measured in Green House under salinity irrigation.
A = average;
P = p value;
RGR = Relative Growth Rate.
The indicated days refer to days from planting.

TABLE 43

MAB77 - Salt irrigation (40-80 mM NaCl)

|  |  | Event No. | | | |
| --- | --- | --- | --- | --- | --- |
|  |  | 7931.11 | | 8212.2 | |
|  | Control | A | P | A | P |
| Leaf Number on day 8 | 8.66 | | | 9.75 | 0.09 |
| RGR of Rosette Area between day 1 and 3 | 0.45 | 0.52 | 0.10 | | |
| Harvest Index | 0.11 | | | 0.15 | 0.07 |

Table 43: Provided are the growth, biomass and yield parameters of transgenic or control plants as measured in Green House under salinity irrigation.
A = average;
P = p value;
RGR = Relative Growth Rate.
The indicated days refer to days from planting.

TABLE 44

Provided are the growth, biomass and yield parameters of transgenic or control plants as measured in Green House under salinity irrigation.
MAB79-Salt irrigation (40-80 mM NaCl)

|  |  | 7323.10, | | 7961.1, | | 7962.2, | | 7962.2, | |
| --- | --- | --- | --- | --- | --- | --- | --- | --- | --- |
| Event No. | Control | A | P | A | P | A | P | A | P |
| Rosette Diameter on day 3 | 1.70 | | | 1.84 | 0.10 | 1.93 | 0.05 | | |
| Rosette Diameter on day 5 | 2.36 | | | 2.53 | 0.01 | | | | |
| Rosette Diameter on day 8 | 3.77 | | | 4.32 | 0.03 | 4.01 | 0.04 | | |
| Rosette Area on day 3 | 0.90 | | | 1.08 | 0.09 | | | | |
| Rosette Area on day 8 | 4.06 | | | 5.29 | 0.03 | 4.78 | 0.05 | | |
| Plot Coverage on day 3 | 7.04 | | | 8.63 | 0.08 | | | | |
| Plot Coverage on day 8 | 31.90 | | | 42.32 | 0.03 | 38.27 | 0.05 | | |
| Leaf Number on day 3 | 5.08 | 5.63 | 0.00 | | | | | 5.75 | 0.04 |
| Leaf Number on day 5 | 6.86 | | | | | | | 7.44 | 0.01 |
| RGR of Leaf Number between day 5 and 8 | 0.09 | | | 0.11 | 0.01 | | | | |
| RGR of Rosette Area between day 5 and 8 | 0.53 | | | | | | | 0.59 | 0.01 |

TABLE 44-continued

Provided are the growth, biomass and yield parameters of transgenic or control plants as measured in Green House under salinity irrigation.
MAB79-Salt irrigation (40-80 mM NaCl)

| | | 7323.10, | | 7961.1, | | 7962.2, | | 7962.2, | |
|---|---|---|---|---|---|---|---|---|---|
| Event No. | Control | A | P | A | P | A | P | A | P |
| 1000 Seeds weight [gr] | 0.02 | | | 0.02 | 0.00 | | | | |
| Harvest Index | 0.11 | | | 0.19 | 0.00 | | | | |

A = average;
P = p value;
RGR = Relative Growth Rate.
The indicated days refer to days from planting.

Tables 45-59 depict analyses of plant parameters (as describe above) overexpressing the polynucleotides of the invention under the regulation of the 6669 promoter under Normal Growth conditions [Normal irrigation included NaCl Electrical conductivity (E.C.) of 1-2].

TABLE 45

Provided are the growth, biomass and yield parameters of transgenic or control plants as measured in Green House under normal irrigation.
MAB115-Normal Growth Conditions

| | | 8564.1 | | 8565.1 | | 8565.2 | |
|---|---|---|---|---|---|---|---|
| Event No. | Control | A | P | A | P | A | P |
| Rosette Diameter on day 3 | 1.67 | 1.80 | 0.09 | 1.75 | 0.04 | 1.95 | 0.04 |
| Rosette Diameter on day 8 | 3.60 | | | 4.00 | 0.09 | | |
| Rosette Area on day 5 | 1.54 | | | 1.70 | 0.09 | | |
| Rosette Area on day 8 | 3.98 | | | 4.38 | 0.06 | | |
| Plot Coverage on day 5 | 12.30 | | | 13.61 | 0.06 | | |
| Plot Coverage on day 8 | 31.82 | | | 35.07 | 0.02 | | |
| Leaf Number on day 3 | 5.25 | | | 5.94 | 0.00 | | |
| Leaf Number on day 5 | 6.52 | | | 7.38 | 0.05 | | |
| Leaf Number on day 8 | 8.92 | | | | | 9.31 | 0.00 |
| RGR of Leaf Number between day 3 and 5 | 0.12 | | | 0.12 | 0.04 | | |
| RGR of Rosette Area between day 5 and 8 | 0.53 | 0.62 | 0.01 | | | | |

A = average;
P = p value;
RGR = Relative Growth Rate.
The indicated days refer to days from planting.

TABLE 46

Provided are the growth, biomass and yield parameters of transgenic or control plants as measured in Green House under normal irrigation.
MAB54-Normal Growth Conditions

| | | 8181.2 | | 8182.2 | | 8184.3 | | 8185.4 | |
|---|---|---|---|---|---|---|---|---|---|
| Event No. | Control | A | P | A | P | A | P | A | P |
| Rosette Diameter on day 5 | 2.24 | 2.70 | 0.02 | 2.64 | 0.00 | | | 2.81 | 0.03 |
| Rosette Diameter on day 8 | 3.60 | 4.00 | 0.08 | | | | | 4.29 | 0.05 |
| Rosette Area on day 3 | 0.89 | | | 1.19 | 0.04 | | | 1.35 | 0.01 |
| Rosette Area on day 8 | 3.98 | | | | | | | 5.91 | 0.05 |
| Plot Coverage on day 3 | 7.10 | | | 9.52 | 0.04 | 7.49 | 0.08 | 10.76 | 0.01 |
| Plot Coverage on day 8 | 31.82 | | | | | | | 47.28 | 0.06 |
| Leaf Number on day 3 | 5.25 | 6.19 | 0.06 | | | | | 6.25 | 0.00 |
| Leaf Number on day 5 | 6.52 | | | | | | | 7.94 | 0.03 |
| Leaf Number on day 8 | 8.92 | 9.38 | 0.00 | | | | | 9.50 | 0.01 |
| RGR of Leaf Number between day 3 and 5 | 0.12 | 0.13 | 0.08 | | | | | | |
| RGR of Rosette Area between day 1 and 3 | 0.46 | 0.52 | 0.01 | | | | | 0.51 | 0.05 |
| 1000 Seeds weight [gr] | 0.02 | | | 0.02 | 0.00 | 0.02 | 0.00 | | |

A = average;
P = p value;
RGR = Relative Growth Rate.
The indicated days refer to days from planting.

TABLE 47

MAB55 - Normal Growth Conditions

| | | Event No. | | | |
|---|---|---|---|---|---|
| | | 6802.5 | | 6805.4 | |
| | Control | A | P | A | P |
| Rosette Area on day 5 | 1.54 | 1.70 | 0.03 | | |
| Rosette Area on day 8 | 3.98 | | | 4.63 | 0.02 |
| Plot Coverage on day 5 | 12.30 | 13.60 | 0.02 | | |
| Plot Coverage on day 8 | 31.82 | | | 37.03 | 0.01 |

Table 47: Provided are the growth, biomass and yield parameters of transgenic or control plants as measured in Green House under normal irrigation.
A = average;
P = p value;
RGR = Relative Growth Rate.
The indicated days refer to days from planting.

TABLE 48

Provided are the growth, biomass and yield parameters of transgenic or control plants as measured in Green House under normal irrigation.
MAB56-Normal Growth Conditions

| | | 6691.2 | | 6691.3 | | 6693.2 | | 6695.7 | |
|---|---|---|---|---|---|---|---|---|---|
| Event No. | Control | A | P | A | P | A | P | A | P |
| Rosette Diameter on day 3 | 1.67 | | | 1.89 | 0.05 | 1.97 | 0.07 | | |
| Rosette Diameter on day 5 | 2.24 | | | 2.55 | 0.09 | 2.58 | 0.01 | | |
| Rosette Area on day 3 | 0.89 | 1.06 | 0.00 | 1.15 | 0.02 | 1.23 | 0.08 | | |
| Rosette Area on day 5 | 1.54 | | | 1.94 | 0.02 | 1.94 | 0.03 | | |
| Plot Coverage on day 3 | 7.10 | 8.45 | 0.00 | 9.21 | 0.01 | 9.82 | 0.07 | | |
| Plot Coverage on day 5 | 12.30 | | | 15.49 | 0.01 | 15.53 | 0.02 | | |
| Plot Coverage on day 8 | 31.82 | | | | | 34.82 | 0.05 | | |
| Leaf Number on day 3 | 5.25 | 5.50 | 0.00 | 5.81 | 0.00 | 6.00 | 0.02 | | |
| Leaf Number on day 5 | 6.52 | | | 7.38 | 0.01 | 7.50 | 0.02 | | |
| RGR of Leaf Number between day 3 and 5 | 0.12 | | | | | 0.13 | 0.06 | | |
| RGR of Leaf Number between day 5 and 8 | 0.12 | | | | | | | 0.14 | 0.01 |
| RGR of Rosette Area between day 5 and 8 | 0.53 | | | | | | | 0.62 | 0.02 |
| 1000 Seeds weight [gr] | 0.02 | 0.02 | 0.08 | | | | | | |

A = average;
P = p value;
RGR = Relative Growth Rate.
The indicated days refer to days from planting.

TABLE 49

Provided are the growth, biomass and yield parameters of transgenic or control plants as measured in Green House under normal irrigation.
MAB57-Normal Growth Conditions

| | | 6912.1 | | 6912.6 | | 6912.9 | |
|---|---|---|---|---|---|---|---|
| Event No. | Control | A | P | A | P | A | P |
| Rosette Area on day 8 | 3.98 | | | 4.48 | 0.02 | | |
| Plot Coverage on day 8 | 31.82 | | | 35.81 | 0.01 | | |
| Leaf Number on day 3 | 5.25 | | | | | 5.69 | 0.00 |
| Leaf Number on day 5 | 6.52 | 8.13 | 0.06 | 8.13 | 0.06 | | |
| Leaf Number on day 8 | 8.92 | | | | | 9.56 | 0.06 |
| RGR of Rosette Area between day 5 and 8 | 0.53 | | | | | 0.58 | 0.10 |
| 1000 Seeds weight [gr] | 0.02 | | | | | 0.02 | 0.00 |

A = average;
P = p value;
RGR = Relative Growth Rate.
The indicated days refer to days from planting.

TABLE 50

Provided are the growth, biomass and yield parameters of transgenic or control plants as measured in Green House under normal irrigation.

MAB58-Normal Growth Conditions

| Event No. | Control | 6783.2 A | 6783.2 P | 7522.10 A | 7522.10 P | 7522.3 A | 7522.3 P | 7523.6 A | 7523.6 P |
|---|---|---|---|---|---|---|---|---|---|
| Rosette Diameter on day 3 | 1.67 | | | | | 2.11 | 0.00 | | |
| Rosette Diameter on day 5 | 2.24 | 2.57 | 0.00 | | | | | | |
| Rosette Diameter on day 8 | 3.60 | | | 4.06 | 0.07 | 4.54 | 0.00 | | |
| Rosette Area on day 3 | 0.89 | | | | | 1.36 | 0.00 | | |
| Rosette Area on day 5 | 1.54 | | | | | 2.29 | 0.00 | | |
| Rosette Area on day 8 | 3.98 | | | | | 5.98 | 0.00 | | |
| Plot Coverage on day 3 | 7.10 | | | | | 10.90 | 0.00 | | |
| Plot Coverage on day 5 | 12.30 | | | | | 18.32 | 0.00 | | |
| Plot Coverage on day 8 | 31.82 | | | | | 47.88 | 0.00 | | |
| Leaf Number on day 3 | 5.25 | | | | | 6.06 | 0.00 | 6.44 | 0.05 |
| Leaf Number on day 5 | 6.52 | | | | | | | 8.38 | 0.00 |
| Leaf Number on day 8 | 8.92 | 9.25 | 0.04 | | | 9.81 | 0.04 | | |
| RGR of Leaf Number between day 5 and 8 | 0.12 | 0.12 | 0.03 | | | | | | |
| 1000 Seeds weight [gr] | 0.02 | 0.02 | 0.08 | | | | | | |

A = average;
P = p value;
RGR = Relative Growth Rate.
The indicated days refer to days from planting.

TABLE 51

MAB59 - Normal Growth Conditions

| Event No. | Control | 6793.4 A | 6793.4 P | 6794.4 A | 6794.4 P | 6794.5 A | 6794.5 P |
|---|---|---|---|---|---|---|---|
| Rosette Diameter on day 3 | 1.67 | | | 2.38 | 0.05 | | |
| Rosette Diameter on day 5 | 2.24 | 2.73 | 0.06 | | | | |
| Rosette Area on day 3 | 0.89 | | | 1.27 | 0.06 | 1.65 | 0.03 |
| Plot Coverage on day 3 | 7.10 | | | 10.15 | 0.06 | 13.19 | 0.03 |
| Leaf Number on day 3 | 5.25 | | | 6.00 | 0.02 | 6.75 | 0.01 |
| Leaf Number on day 5 | 6.52 | | | 7.69 | 0.05 | 8.00 | 0.07 |
| Leaf Number on day 8 | 8.92 | | | 9.38 | 0.02 | | |
| RGR of Rosette Area between day 1 and 3 | 0.46 | | | | | 0.49 | 0.02 |
| 1000 Seeds weight [gr] | 0.02 | | | | | 0.02 | 0.00 |

Table 51: Provided are the growth, biomass and yield parameters of transgenic or control plants as measured in Green House under normal irrigation.
A = average;
P = p value;
RGR = Relative Growth Rate.
The indicated days refer to days from planting.

TABLE 52

MAB69 - Normal Growth Conditions

| Event No. | Control | 6651.11 A | 6651.11 P | 6651.12 A | 6651.12 P | 8341.1 A | 8341.1 P | 8342.1 A | 8342.1 P |
|---|---|---|---|---|---|---|---|---|---|
| Rosette Diameter on day 3 | 1.67 | 1.92 | 0.01 | | | | | | |
| Rosette Area on day 3 | 0.89 | 1.09 | 0.00 | | | | | | |
| Rosette Area on day 8 | 3.98 | 5.05 | 0.04 | | | | | | |
| Plot Coverage on day 3 | 7.10 | 8.74 | 0.00 | | | | | | |
| Plot Coverage on day 8 | 31.82 | 40.41 | 0.04 | | | | | | |
| Leaf Number on day 3 | 5.25 | 5.69 | 0.00 | | | | | 5.94 | 0.09 |
| Leaf Number on day 8 | 8.92 | | | | | 8.94 | 0.08 | 9.31 | 0.00 |

TABLE 52-continued

MAB69 - Normal Growth Conditions

| | Control | Event No. | | | | | | | |
|---|---|---|---|---|---|---|---|---|---|
| | | 6651.11 | | 6651.12 | | 8341.1 | | 8342.1 | |
| | | A | P | A | P | A | P | A | P |
| RGR of Rosette Area between day 1 and 3 | 0.46 | 0.51 | 0.04 | | | | | | |
| 1000 Seeds weight [gr] | 0.02 | | | | | 0.02 | 0.01 | | |

Table 52: Provided are the growth, biomass and yield parameters of transgenic or control plants as measured in Green House under normal irrigation.
A = average;
P = p value;
RGR = Relative Growth Rate.
The indicated days refer to days from planting.

TABLE 53

MAB70 - Normal Growth Conditions

| | Control | Event No. | | | | | |
|---|---|---|---|---|---|---|---|
| | | 7971.3 | | 7972.1 | | 7974.3 | |
| | | A | P | A | P | A | P |
| Rosette Diameter on day 3 | 1.67 | | | 1.94 | 0.00 | 2.27 | 0.00 |
| Rosette Diameter on day 5 | 2.24 | | | 2.62 | 0.04 | 3.03 | 0.00 |
| Rosette Diameter on day 8 | 3.60 | 4.40 | 0.00 | | | 5.01 | 0.05 |
| Rosette Area on day 3 | 0.89 | 1.20 | 0.07 | 1.12 | 0.01 | 1.52 | 0.04 |
| Rosette Area on day 5 | 1.54 | 2.06 | 0.05 | 1.87 | 0.00 | 2.49 | 0.10 |
| Rosette Area on day 8 | 3.98 | 5.86 | 0.06 | | | 7.03 | 0.05 |
| Plot Coverage on day 3 | 7.10 | 9.61 | 0.06 | 9.00 | 0.01 | 12.12 | 0.04 |
| Plot Coverage on day 5 | 12.30 | 16.46 | 0.04 | 14.93 | 0.00 | 19.90 | 0.09 |
| Plot Coverage on day 8 | 31.82 | 46.87 | 0.06 | | | 56.23 | 0.05 |
| Leaf Number on day 3 | 5.25 | | | | | 6.44 | 0.05 |
| Leaf Number on day 5 | 6.52 | | | | | 8.13 | 0.00 |
| Leaf Number on day 8 | 8.92 | | | 9.75 | 0.09 | 10.38 | 0.05 |
| RGR of Rosette Area between day 5 and 8 | 0.53 | 0.62 | 0.01 | | | 0.61 | 0.03 |

Table 53: Provided are the growth, biomass and yield parameters of transgenic or control plants as measured in Green House under normal irrigation.
A = average;
P = p value;
RGR = Relative Growth Rate.
The indicated days refer to days from planting.

TABLE 54

MAB71 - Normal Growth Conditions

| | Control | Event No. | | | | | | | |
|---|---|---|---|---|---|---|---|---|---|
| | | 7331.4 | | 7332.2 | | 7333.5 | | 7334.5 | |
| | | A | P | A | P | A | P | A | P |
| Rosette Diameter on day 5 | 2.24 | | | 2.52 | 0.02 | | | | |
| Rosette Diameter on day 8 | 3.60 | 4.33 | 0.01 | | | | | | |
| Rosette Area on day 5 | 1.54 | | | | | | | 1.88 | 0.07 |
| Rosette Area on day 8 | 3.98 | | | | | | | 4.68 | 0.00 |
| Plot Coverage on day 5 | 12.30 | | | 14.25 | 0.08 | | | 15.05 | 0.05 |
| Plot Coverage on day 8 | 31.82 | | | | | | | 37.48 | 0.00 |
| Leaf Number on day 3 | 5.25 | | | 5.47 | 0.06 | | | 5.81 | 0.00 |
| Leaf Number on day 5 | 6.52 | 7.56 | 0.00 | | | | | | |
| RGR of Leaf Number between day 1 and 3 | 0.16 | | | | | | | 0.17 | 0.01 |
| RGR of Leaf Number between day 3 and 5 | 0.12 | | | | | 0.12 | 0.10 | | |
| RGR of Leaf Number between day 5 and 8 | 0.12 | | | | | 0.12 | 0.01 | | |
| RGR of Rosette Area between day 5 and 8 | 0.53 | | | | | 0.61 | 0.04 | | |

Table 54: Provided are the growth, biomass and yield parameters of transgenic or control plants as measured in Green House under normal irrigation.
A = average;
P = p value;
RGR = Relative Growth Rate.
The indicated days refer to days from planting.

TABLE 55

MAB72 - Normal Growth Conditions

| | | Event No. | | | | | |
|---|---|---|---|---|---|---|---|
| | | 8552.4 | | 8553.2 | | 8553.3 | |
| | Control | A | P | A | P | A | P |
| Rosette Diameter on day 3 | 1.67 | 1.90 | 0.05 | | | 1.83 | 0.00 |
| Rosette Diameter on day 5 | 2.24 | 2.67 | 0.00 | | | 2.55 | 0.01 |
| Rosette Diameter on day 8 | 3.60 | 4.06 | 0.08 | 4.15 | 0.10 | | |
| Rosette Area on day 3 | 0.89 | 1.20 | 0.00 | 1.02 | 0.00 | 1.08 | 0.02 |
| Rosette Area on day 5 | 1.54 | 2.00 | 0.00 | | | 1.87 | 0.00 |
| Rosette Area on day 8 | 3.98 | 5.05 | 0.00 | | | 4.82 | 0.00 |
| Plot Coverage on day 3 | 7.10 | 9.64 | 0.00 | 8.13 | 0.00 | 8.67 | 0.02 |
| Plot Coverage on day 5 | 12.30 | 16.04 | 0.00 | | | 14.98 | 0.00 |
| Plot Coverage on day 8 | 31.82 | 40.39 | 0.00 | | | 38.57 | 0.00 |
| Leaf Number on day 3 | 5.25 | 5.88 | 0.00 | 5.56 | 0.00 | 5.50 | 0.00 |
| Leaf Number on day 8 | 8.92 | | | 9.38 | 0.02 | | |

Table 55: Provided are the growth, biomass and yield parameters of transgenic or control plants as measured in Green House under normal irrigation.
A = average;
P = p value;
RGR = Relative Growth Rate.
The indicated days refer to days from planting.

TABLE 56

MAB74 - Normal Growth Conditions

| | | Event No. | | | | | | | |
|---|---|---|---|---|---|---|---|---|---|
| | | 7981.1 | | 7982.4 | | 7983.6 | | 7983.9 | |
| | Control | A | P | A | P | A | P | A | P |
| Rosette Diameter on day 3 | 1.67 | | | 2.06 | 0.10 | 1.94 | 0.00 | | |
| Rosette Diameter on day 5 | 2.24 | | | | | 2.62 | 0.06 | | |
| Rosette Diameter on day 8 | 3.60 | | | | | 4.05 | 0.02 | | |
| Rosette Area on day 3 | 0.89 | | | 1.14 | 0.02 | | | | |
| Rosette Area on day 5 | 1.54 | | | 1.83 | 0.05 | 1.85 | 0.10 | | |
| Rosette Area on day 8 | 3.98 | | | | | 4.46 | 0.03 | | |
| Plot Coverage on day 3 | 7.10 | | | 9.13 | 0.02 | | | | |
| Plot Coverage on day 5 | 12.30 | | | 14.62 | 0.03 | 14.79 | 0.08 | | |
| Plot Coverage on day 8 | 31.82 | | | | | 35.66 | 0.01 | | |
| Leaf Number on day 3 | 5.25 | | | 5.75 | 0.04 | 5.31 | 0.07 | | |
| Leaf Number on day 5 | 6.52 | 6.26 | 0.02 | | | 7.25 | 0.04 | | |
| Leaf Number on day 8 | 8.92 | | | | | | | 9.13 | 0.07 |
| RGR of Leaf Number between day 3 and 5 | 0.12 | | | 0.13 | 0.08 | | | 0.12 | 0.03 |
| RGR of Rosette Area between day 1 and 3 | 0.46 | | | | | | | 0.33 | 0.00 |
| RGR of Rosette Area between day 3 and 5 | 0.36 | 0.42 | 0.07 | | | | | | |
| Biomass DW [gr] | 3.07 | | | | | | | | |
| 1000 Seeds weight [gr] | 0.02 | 0.02 | 0.02 | | | 0.02 | 0.05 | | |

Table 56: Provided are the growth, biomass and yield parameters of transgenic or control plants as measured in Green House under normal irrigation.
A = average;
P = p value;
RGR = Relative Growth Rate.
The indicated days refer to days from planting.

TABLE 57

MAB76 - Normal Growth Conditions

| | | Event No. | | | |
|---|---|---|---|---|---|
| | | 7633.1 | | 7635.16 | |
| | Control | A | P | A | P |
| Rosette Diameter on day 3 | 1.67 | | | 1.93 | 0.04 |
| Leaf Number on day 3 | 5.25 | 5.44 | 0.02 | | |
| Leaf Number on day 5 | 6.52 | | | 7.25 | 0.04 |

Table 57: Provided are the growth, biomass and yield parameters of transgenic or control plants as measured in Green House under normal irrigation.
A = average;
P = p value;
RGR = Relative Growth Rate.
The indicated days refer to days from planting.

TABLE 58

MAB77 - Normal Growth Conditions

| | Control | Event No. 8212.1 A | 8212.1 P | 8212.2 A | 8212.2 P |
|---|---|---|---|---|---|
| Leaf Number on day 3 | 5.25 | | | 5.63 | 0.00 |
| Leaf Number on day 8 | 8.92 | 9.75 | 0.09 | | |

Table 58: Provided are the growth, biomass and yield parameters of transgenic or control plants as measured in Green House under normal irrigation.
A = average;
P = p value;
RGR = Relative Growth Rate.
The indicated days refer to days from planting.

TABLE 59

MAB79 - Normal Growth Conditions

| | Control | 7324.1 A | 7324.1 P | 7961.1 A | 7961.1 P | 7962.2 A | 7962.2 P |
|---|---|---|---|---|---|---|---|
| Rosette Diameter on day 3 | 1.67 | 1.84 | 0.10 | 1.93 | 0.05 | | |
| Rosette Diameter on day 5 | 2.24 | 2.53 | 0.01 | | | | |
| Rosette Diameter on day 8 | 3.60 | 4.32 | 0.03 | 4.01 | 0.04 | | |
| Rosette Area on day 3 | 0.89 | 1.08 | 0.09 | | | | |
| Rosette Area on day 8 | 3.98 | 5.29 | 0.03 | 4.78 | 0.05 | | |
| Plot Coverage on day 3 | 7.10 | 8.63 | 0.08 | | | | |
| Plot Coverage on day 8 | 31.82 | 42.32 | 0.03 | 38.27 | 0.05 | | |
| Leaf Number on day 3 | 5.25 | | | | | 5.75 | 0.04 |
| Leaf Number on day 5 | 6.52 | | | | | 7.44 | 0.01 |
| RGR of Rosette Area between day 5 and 8 | 0.53 | | | | | 0.59 | 0.01 |
| 1000 Seeds weight [gr] | 0.02 | 0.02 | 0.00 | | | | |

Table 59: Provided are the growth, biomass and yield parameters of transgenic or control plants as measured in Green House under normal irrigation.

A = average;

P = p value;

RGR = Relative Growth Rate.

The indicated days refer to days from planting.

Example 7

Improved Fertilizer Use Efficiency in *Arabidopsis* Tissue Culture Assay

Plants transgenic to the following MAB genes were assayed for fertilizer use efficiency in a tissue culture assay: MAB115, MAB54, MAB55, MAB56, MAB57, MAB58, MAB59, MAB69, MAB70, MAB71, MAB72, MAB74, MAB76, MAB77, MAB79, MAB116, and MAB117 (the sequence identifiers of the cloned polynucleotides and their expressed polypeptides are provided in Table 7 above).

Assay 1: Plant Growth at Nitrogen Deficiency Under Tissue Culture Conditions

The present inventors have found the nitrogen use efficiency (NUE) assay to be relevant for the evaluation of the ABST candidate genes, since NUE deficiency encourages root elongation, increase of root coverage and allows detecting the potential of the plant to generate a better root system under drought conditions. In addition, there are indications in the literature that biological mechanisms of NUE and drought tolerance are linked (Wesley et al., 2002 Journal of Experiment Botany Vol 53, No. 366, pp. 13-25).

Surface sterilized seeds were sown in basal media [50% Murashige-Skoog medium (MS) supplemented with 0.8% plant agar as solidifying agent] in the presence of Kanamycin (for selecting only transgenic plants). After sowing, plates were transferred for 2-3 days for stratification at 4° C. and then grown at 25° C. under 12-hour light 12-hour dark daily cycles for 7 to 10 days. At this time point, seedlings randomly chosen were carefully transferred to plates with nitrogen-limiting conditions: 0.5 MS media in which the combined nitrogen concentration ($NH_4NO_3$ and $KNO_3$) is 0.75 mM (nitrogen deficient conditions) or 3 mM [Normal (optimal) nitrogen concentration]. Each plate contains 5 seedlings of same event, and 3-4 different plates (replicates) for each event. For each polynucleotide of the invention at least four independent transformation events were analyzed from each construct. Plants expressing the polynucleotides of the invention were compared to the average measurement of the control plants (empty vector or GUS reporter under the same promoter) used in the same experiment.

Digital Imaging and Statistical Analysis—

Parameters were measured and analyzed as previously described in Example 5, Assay 1 above.

Tables 60-69 depict analyses of seedling parameters (as describe above) overexpressing the polynucleotides of the invention under the regulation of At6669 promoter under Nitrogene Deficiency conditions.

TABLE 60

MAB70 - Nitrogene Deficiency (0.75 mM Nitrogen)

| | | Event No. | | | | | | | |
|---|---|---|---|---|---|---|---|---|---|
| | | 7971.3 | | 7972.1 | | 7974.1 | | 7974.3 | |
| | Control | A | P | A | P | A | P | A | P |
| Dry Weight [gr] | 0.01 | | | | | | | 0.01 | 0.00 |
| Fresh Wight [gr] | 0.10 | | | | | | | 0.18 | 0.04 |
| Leaf Area on day 10 | 0.36 | | | | | 0.47 | 0.04 | 0.55 | 0.00 |
| Leaf Area on day 5 | 0.14 | | | | | | | 0.24 | 0.04 |
| Roots Coverage on day 10 | 5.58 | 7.93 | 0.01 | 7.45 | 0.06 | | | | |
| Roots Coverage on day 5 | 1.75 | 2.41 | 0.00 | | | | | 2.58 | 0.06 |
| Roots Length on day 10 | 5.19 | 6.16 | 0.00 | | | | | | |
| Roots Length on day 5 | 2.86 | 3.16 | 0.05 | | | | | | |
| RGR of Roots Coverage between day 5 and 10 | 0.45 | | | | | 0.67 | 0.05 | | |
| RGR of Roots Coverage between day 1 and 5 | 0.81 | 2.35 | 0.02 | 2.01 | 0.06 | 2.10 | 0.05 | 2.23 | 0.02 |
| RGR of Roots Length between day 1 and 5 | 0.16 | | | | | 0.24 | 0.04 | | |
| RGR of Roots Length between day 5 and 10 | 0.20 | 0.50 | 0.00 | 0.48 | 0.00 | 0.56 | 0.00 | 0.58 | 0.00 |

Table 60: Provided are the growth and biomass parameters of transgenic or control plants as measured in Tissue Calture growth under Nitrogene Deficiency (0.75 mM N).
A = average;
P = p value;
RGR = Relative Growth Rate.
The indicated days refer to days from planting.

TABLE 61

MAB71 - Nitrogene Deficiency (0.75 mM Nitrogen)

| | | Event No. | | | | | | | |
|---|---|---|---|---|---|---|---|---|---|
| | | 7331.5 | | 7332.2 | | 7333.5 | | 7334.4 | |
| | Control | A | P | A | P | A | P | A | P |
| Dry Weight [gr] | 0.01 | 0.01 | 0.00 | 0.01 | 0.01 | 0.01 | 0.01 | 0.01 | 0.01 |
| Fresh Wight [gr] | 0.10 | 0.22 | 0.00 | 0.18 | 0.02 | 0.13 | 0.09 | | |
| Leaf Area on day 10 | 0.36 | 0.55 | 0.00 | | | | | 0.52 | 0.00 |
| Leaf Area on day 5 | 0.14 | 0.28 | 0.00 | | | | | 0.21 | 0.00 |
| Roots Coverage on day 10 | 5.58 | | | | | 8.19 | 0.05 | 9.47 | 0.03 |
| Roots Coverage on day 5 | 1.75 | 2.33 | 0.10 | | | | | 2.99 | 0.02 |
| Roots Length on day 10 | 5.19 | | | | | | | 6.69 | 0.03 |
| Roots Length on day 5 | 2.86 | | | | | | | 3.84 | 0.01 |
| RGR of Roots Length between day 1 and 5 | 0.16 | | | 0.20 | 0.07 | | | | |
| RGR of Roots Length between day 5 and 10 | 0.20 | 0.66 | 0.05 | | | 0.26 | 0.08 | | |

Table 61: Provided are the growth and biomass parameters of transgenic or control plants as measured in Tissue Calture growth under Nitrogene Deficiency (0.75 mM N).
A = average;
P = p value;
RGR = Relative Growth Rate.
The indicated days refer to days from planting.

TABLE 62

MAB74 - Nitrogene Deficiency (0.75 mM Nitrogen)

| | | Event No. | | | |
|---|---|---|---|---|---|
| | | 7982.4 | | 7983.9 | |
| | Control | A | P | A | P |
| Roots Coverage on day 10 | 5.58 | | | 9.76 | 0.06 |
| Roots Length on day 10 | 5.19 | | | 6.70 | 0.00 |
| RGR Leaf Area between day 5 and 10 | 0.30 | | | 0.44 | 0.09 |
| RGR of Roots Coverage between day 5 and 10 | 0.45 | 0.63 | 0.08 | | |

Table 62: Provided are the growth and biomass parameters of transgenic or control plants as measured in Tissue Calture growth under Nitrogene Deficiency (0.75 mM N).
A = average;
P = p value;
RGR = Relative Growth Rate.
The indicated days refer to days from planting.

TABLE 63

MAB76 - Nitrogene Deficiency (0.75 mM Nitrogen)

| | Event No. | | |
|---|---|---|---|
| | | 7635.4 | |
| | Control | A | P |
| RGR of Roots Coverage between day 5 and 10 | 0.45 | 0.70 | 0.07 |
| RGR of Roots Length between day 1 and 5 | 0.16 | 0.26 | 0.07 |

Table 63: Provided are the growth and biomass parameters of transgenic or control plants as measured in Tissue Calture growth under Nitrogene Deficiency (0.75 mM N).
A = average;
P = p value;
RGR = Relative Growth Rate.
The indicated days refer to days from planting.

TABLE 64

MAB77 - Nitrogene Deficiency (0.75 mM Nitrogen)

| | Event No. | | | | | | |
|---|---|---|---|---|---|---|---|
| | | 7931.11 | | 8211.8 | | 8212.2 | |
| | Control | A | P | A | P | A | P |
| Dry Weight [gr] | 0.01 | | | | | 0.01 | 0.00 |
| Fresh Wight [gr] | 0.10 | | | 0.13 | 0.03 | 0.14 | 0.01 |
| Roots Coverage on day 5 | 1.75 | 2.26 | 0.03 | | | | |
| RGR of Roots Coverage between day 5 and 10 | 0.45 | | | 0.71 | 0.01 | 0.75 | 0.05 |
| RGR of Roots Length between day 1 and 5 | 0.16 | | | 0.24 | 0.03 | | |
| RGR of Roots Length between day 5 and 10 | 0.20 | 0.31 | 0.05 | 0.99 | 0.04 | 0.86 | 0.08 |

Table 64: Provided are the growth and biomass parameters of transgenic or control plants as measured in Tissue Calture growth under Nitrogene Deficiency (0.75 mM N).
A = average;
P = p value;
RGR = Relative Growth Rate.
The indicated days refer to days from planting.

TABLE 65

MAB79 - Nitrogene Deficiency (0.75 mM Nitrogen)

| | Event No. | | | | | | |
|---|---|---|---|---|---|---|---|
| | | 7323.3 | | 7324.1 | | 7961.1 | |
| | Control | A | P | A | P | A | P |
| Dry Weight [gr] | 0.01 | 0.01 | 0.00 | 0.01 | 0.03 | 0.01 | 0.01 |
| Fresh Wight [gr] | 0.10 | 0.16 | 0.00 | | | 0.11 | 0.10 |
| RGR of Roots Coverage between day 5 and 10 | 0.45 | 0.71 | 0.09 | | | | |
| RGR of Roots Coverage between day 1 and 5 | 0.81 | 3.11 | 0.00 | | | | |
| RGR of Roots Length between day 5 and 10 | 0.20 | 0.67 | 0.00 | 0.49 | 0.09 | | |

Table 65: Provided are the growth and biomass parameters of transgenic or control plants as measured in Tissue Calture growth under Nitrogene Deficiency (0.75 mM N).
A = average;
P = p value;
RGR = Relative Growth Rate.
The indicated days refer to days from planting.

TABLE 66

MAB115 - Nitrogene Deficiency (0.75 mM Nitrogen)

| | Event No. | | | | | | |
|---|---|---|---|---|---|---|---|
| | | 8561.2 | | 8564.2 | | 8565.1 | |
| | Control | A | P | A | P | A | P |
| Dry Weight [gr] | 0.005 | 0.006 | 0.00 | 0.010 | 0.00 | 0.009 | 0.00 |
| Leaf Area on day 10 | 0.24 | | | | | 0.27 | 0.00 |
| Leaf Area on day 5 | 0.35 | | | | | 0.38 | 0.01 |
| Roots Coverage on day 10 | 1.67 | | | | | 2.13 | 0.02 |
| Roots Coverage on day 5 | 3.38 | | | | | 4.80 | 0.03 |
| Roots Length on day 10 | 2.39 | | | | | 2.74 | 0.00 |
| Roots Length on day 5 | 3.46 | | | | | 4.22 | 0.02 |
| RGR Leaf Area between day 5 and 10 | 0.37 | 0.43 | 0.00 | | | 0.48 | 0.00 |
| RGR Leaf Area between day 1 and 5 | 0.16 | 0.19 | 0.00 | | | | |
| RGR of Roots Coverage between day 5 and 10 | 1.89 | 3.21 | 0.00 | 2.23 | 0.02 | 3.47 | 0.01 |
| RGR of Roots Coverage between day 1 and 5 | 0.33 | 0.35 | 0.00 | 0.43 | 0.00 | 0.44 | 0.00 |
| RGR of Roots Length between day 1 and 5 | 0.37 | 0.56 | 0.02 | 0.53 | 0.06 | 0.68 | 0.00 |
| RGR of Roots Length between day 5 and 10 | 0.15 | | | 0.17 | 0.00 | 0.18 | 0.00 |

Table 66: Provided are the growth and biomass parameters of transgenic or control plants as measured in Tissue Calture growth under Nitrogene Deficiency (0.75 mM N).
A = average;
P = p value;
RGR = Relative Growth Rate.
The indicated days refer to days from planting.

TABLE 67

MAB54 - Nitrogene Deficiency (0.75 mM Nitrogen)

| | | Event No. | | | | | |
|---|---|---|---|---|---|---|---|
| | | 8181.2 | | 8182.2 | | 8185.3 | |
| | Control | A | P | A | P | A | P |
| Dry Weight [gr] | 0.005 | 0.009 | 0.00 | 0.008 | 0.00 | 0.007 | 0.00 |
| Roots Coverage on day 10 | 1.67 | 1.80 | 0.04 | | | | |
| Roots Coverage on day 5 | 3.38 | 4.27 | 0.02 | 3.40 | 0.00 | | |
| Roots Length on day 10 | 2.39 | 2.52 | 0.01 | | | | |
| Roots Length on day 5 | 3.46 | 4.11 | 0.02 | 3.50 | 0.00 | | |
| RGR Leaf Area between day 5 and 10 | 0.37 | 0.45 | 0.00 | | | | |
| RGR Leaf Area between day 1 and 5 | 0.16 | 0.17 | 0.04 | | | 0.19 | 0.00 |
| RGR of Roots Coverage between day 5 and 10 | 1.89 | 3.59 | 0.00 | 3.60 | 0.01 | 2.20 | 0.01 |
| RGR of Roots Coverage between day 1 and 5 | 0.33 | 0.52 | 0.00 | 0.55 | 0.00 | 0.36 | 0.00 |
| RGR of Roots Length between day 1 and 5 | 0.37 | 0.70 | 0.00 | 0.73 | 0.00 | 0.51 | 0.02 |
| RGR of Roots Length between day 5 and 10 | 0.15 | 0.21 | 0.01 | 0.22 | 0.01 | 0.17 | 0.00 |

Table 67: Provided are the growth and biomass parameters of transgenic or control plants as measured in Tissue Calture growth under Nitrogene Deficiency (0.75 mM N).
A = average;
P = p value;
RGR = Relative Growth Rate.
The indicated days refer to days from planting.

TABLE 68

MAB57 - Nitrogene Deficiency (0.75 mM Nitrogen)

| | | Event No. | | | | | |
|---|---|---|---|---|---|---|---|
| | | 6912.14 | | 6912.20 | | 6912.60 | |
| | Control | A | P | A | P | A | P |
| Roots Coverage on day 7 | 5.55 | | | 6.71 | 0.10 | | |
| Roots Coverage on day 14 | 15.02 | 17.33 | 0.05 | | | | |
| Roots Length on day 7 | 4.93 | 5.54 | 0.10 | 6.12 | 0.02 | 6.34 | 0.02 |
| Roots Length on day 14 | 7.83 | 8.76 | 0.02 | | | | |
| Fresh Weight | 0.19 | 0.24 | 0.09 | | | | |

Table 68: Provided are the growth and biomass parameters of transgenic or control plants as measured in Tissue Calture growth under Nitrogene Deficiency (0.75 mM N).
A = average;
P = p value;
RGR = Relative Growth Rate.
The indicated days refer to days from planting.

TABLE 69

MAB72 - Nitrogene Deficiency (0.75 mM Nitrogen)

| | | Event No. | | | | | |
|---|---|---|---|---|---|---|---|
| | | 8552.1 | | 8552.4 | | 8553.2 | |
| | Control | A | P | A | P | A | P |
| Dry Weight [gr] | 0.005 | 0.01 | 0.00 | 0.01 | 0.00 | 0.01 | 0.00 |
| Leaf Area on day 10 | 0.24 | 0.24 | 0.01 | | | | |
| Roots Coverage on day 10 | 1.67 | 1.84 | 0.01 | 1.93 | 0.02 | 1.89 | 0.03 |
| Roots Coverage on day 5 | 3.38 | 3.60 | 0.04 | 3.90 | 0.06 | 4.50 | 0.00 |
| Roots Length on day 10 | 2.39 | 2.48 | 0.01 | | | | |
| Roots Length on day 5 | 3.46 | 3.70 | 0.04 | 3.65 | 0.04 | 3.84 | 0.00 |
| RGR Leaf Area between day 5 and 10 | 0.37 | 0.47 | 0.00 | 0.39 | 0.00 | | |
| RGR Leaf Area between day 1 and 5 | 0.16 | | | 0.20 | 0.09 | | |
| RGR of Roots Coverage between day 5 and 10 | 1.89 | 1.93 | 0.03 | 2.29 | 0.06 | 3.04 | 0.01 |
| RGR of Roots Coverage between day 1 and 5 | 0.33 | | | 0.35 | 0.00 | 0.52 | 0.00 |
| RGR of Roots Length between day 1 and 5 | 0.37 | | | | | 0.55 | 0.01 |
| RGR of Roots Length between day 5 and 10 | 0.15 | 0.16 | 0.00 | 0.18 | 0.00 | 0.22 | 0.01 |

Table 69: Provided are the growth and biomass parameters of transgenic or control plants as measured in Tissue Calture growth under Nitrogene Deficiency (0.75 mM N).
A = average;
P = p value;
RGR = Relative Growth Rate.
The indicated days refer to days from planting.

Example 8

Transgenic Tomato and *Arabidopsis* Plants Show Improved Tolerance to Salt and Water-Deficiency Stresses Under Field Conditions To test the impact of AQP TIP2 genes on plant's stress tolerance, the present inventors have previously cloned and overexpressed a polynucleotide which comprises the nucleic acid sequence set forth by SEQ ID NO:2827 (also known as ABST36 set forth by SEQ ID NO:13 in WO2004/104162; or S1T1P2;2) and which encodes the TIP2 polypeptide set forth by SEQ ID NO:2828 (which comprises the consensus sequence TLXFXFAGVGS; SEQ ID NO:2826). The nucleic acid constructs which comprises the ABST36 polynucleotide under the regulation of the constitutive *Arabidopsis* At6669 promoter (SEQ ID NO: 2823) (further referred to as the At6669::ABST36 construct) was further transformed into tomato (*Solanum lycopersicum*) as a model crop plant (Tom-ABST36), as well as into *Arabidopsis thaliana*. Four independent, $T_2$ transgenic tomato genotypes, overexpressing ABST36 in heterozygous form, were evaluated for their tolerance to salt and water deficiency in two different salt-stress field trials and one water-deficiency-stress field trial consisting of two water-deficiency regimes. Transgenic genotypes in each field trial were compared to their null-segregant counterparts as controls.

Materials and Experimental Methods

Tomato Salt-Stress Field Trial—

All field trials were performed in a light soil, in an open field (net-house) near Rehovot, Israel. The F1 hybrids of four independent events of the cross between ABST36-transgenic MicroTom plants and M82 tomato plants were grown for the first 3 weeks in a nursery under normal irrigation conditions. The seedlings were then transplanted into rows and grown in a commercial greenhouse. The salt-stress trial was divided into four blocks. In each block, two different irrigation systems were established: a normal water regime for tomato cultivation and a continuous irrigation with saline water (addition of 180 to 200 mM NaCl). Each block consisted of a total of 60 plants divided as follows: six plants per event and six seedling null segregants were planted in the control row and a similar number of plants were planted in the salt-stressed row. At the stage of about 80% red fruits in planta, fruit yield, plant fresh weight, and harvest index were calculated. Harvest index was calculated as yield/plant biomass.

Tomato Water-Deficiency-Stress Field Trial—

All field trials were performed in a light soil, in an open field (net-house) near Rehovot, Israel. The F1 hybrids of the four independent events were initially grown as described above. Three-week-old seedlings were transplanted to a net-greenhouse. The experiment was structured in four blocks containing three rows irrigated with different water levels and intervals (WLI-0, WLI-1, WLI-2). In each block, six transgenic plants per event analyzed and six non transgenic plants were transplanted in each row. Seedlings were transplanted after 4 weeks into wet soil. The amount of water used to uniformly irrigate before transplanting reached maximum water capacity [20% weight per weight (w/w)] at 60 cm depth, but without the creation of water overload. Each plant was transplanted near a dripper, with a 30-cm distance between plants, giving a total density of 2,600 plants per 1,000 $m^2$, according to a commercial growth protocol. Soil water capacity was measured using the standard procedures by sampling soil from the following three depths: 0 to 20 cm, 20 to 40 cm, and 40 to 60 cm. The water content in these soil layers was measured routinely every week. The soil contained 5% hygroscopic water while the maximum water capacity of the soil was 20%. All fertilizers were applied in the soil prior to plant transplantation. The amount of both phosphorus and potassium was calculated to be sufficient for all seasons. Nitrogen was applied as recommended, equally to all treatments, through the irrigation system. Each row contained three dripping irrigation lines creating a coverage of nine drippers per 1 $m^2$. The water control was performed separately for each treatment. The soil was dried completely before the beginning of the experiment. The different water regimes were begun only 4 weeks after transplanting when plants initiated the flowering stage. The amount of water supplied every week during the assay was calculated at the beginning of every week following the recommendations of standard growth protocols. WLI-0 treatment (control) received the recommended total weekly irrigation volume divided into three irrigations. WLI-1 was irrigated three times a week, but the amount of water supplied was half that supplied to WLI-0. At the end of every week, WLI-1 plants received the amount of water required to reach maximum soil water capacity. WLI-2 plants were irrigated only once a week, at the beginning of the week. The water-stress experiment lasted throughout the flowering period (23 days), corresponding to four cycles of the above-described stresses. Afterwards, all treatments received the recommended amount of water. The calculated water amount was equal to the difference between the water contents in dry soil and in soil with maximum water capacity. At the end of each stress cycle, the water amounts were compared between treatments according to actual water content in the soil (S3). During the stress period, treatments WLI-1 and WLI-2 received a total of 75% less water than the controls (WLI-0).

Experimental Results

Transgenic Plants Exhibit Increased Tolerance to Salt Stress—

Figure 3G:
FIGS. 3G-J are photographs of transgenic tomato plants or control plants grown under various conditions.
Figure 3H:
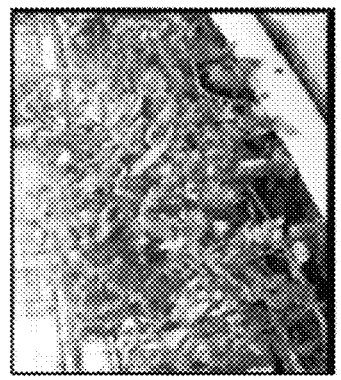
Figure 3I:
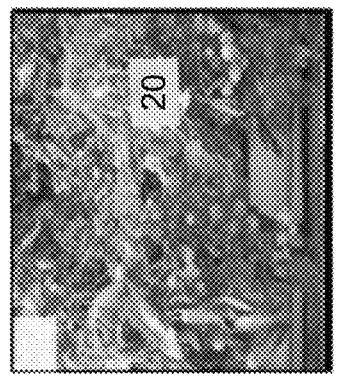
Figure 3J:
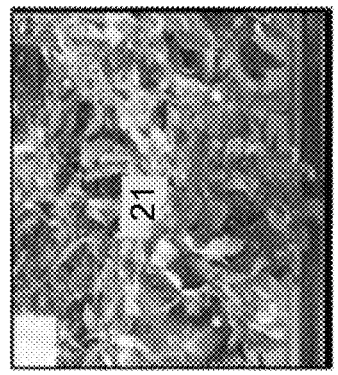

To induce salt-stress, transgenic and control tomato plants were continuously irrigated in field trials with 180 to 200 mM NaCl. As shown in FIGS. 3*a-c*, 3*g-j* and Table 70 below, Tom-ABST36 plants appeared to be more vigorous in all of the experiments than the control plants, which were smaller and showed severe symptoms of leaf and shoot necrosis (see for example, FIG. 3*j*). This was also associated with higher fruit yield in Tom-ABST36 plants relative to controls (FIG. 3*a*).

TABLE 70

| | Salt-stress field trial | | | | | | |
|---|---|---|---|---|---|---|---|
| | Control | | | 180 mM NaCl | | | |
| Plant | FW (tn/acre) | Fruit yield (tn/acre) | Harvest index | Plant FW (tn/acre) | Fruit yield (tn/acre) | %* | Harvest index |
| S1TIP2;2 | ND | 24.0 | ND | 2.8$^a$ | 8.0$^a$ | 110% | 2.8 |
| WT | ND | 24.0 | ND | 1.4$^b$ | 3.8$^b$ | 0% | 2.7 |

Table 70: Total yield (ton fruit/acre), plant fresh weight (FW), and harvest index were calculated for TOM ABST36 vs. control plants growing in the field under salt-stress conditions (180 mM NaCl).
Results are the average of four independent events.
$^{a,b}$Values in a column followed by different superscript letters are significantly different.

Transgenic Plants Exhibit Increased Tolerance to Water-Deficiency Stress—

Transgenic plants subjected to water-deficiency stress exhibited a significantly higher (26%, p≤0.05) plant biomass compared to control plants (FIG. 3e). Moreover the Tom-ABST36 plants showed a significant (up to 21%, p≤0.05) increment of fruit yield under water-deficient regimes (water level intervals WLI-1), while under normal irrigation, the yield improvement was even higher (27%, p≤0.05; FIG. 3d). The harvest index of the Tom-ABST36 plants was also higher when plants grew under regular and WLI-1 conditions while it remained similar to control when the water-deficient regime consisted of once-a-week irrigation (WLI-2) (FIG. 3f).

The results from the three field trials provided strong evidence that the tomato Tom-ABST36 plants show improved tolerance to salt and water-deficiency stress relative to the control plants, which is translated into significant increments in plant biomass and more importantly, fruit yield.

*Arabidopsis* Salt-Stress Green House Trial—

A complementary experiment with transgenic *Arabidopsis* plants expressing the ABST36 construct showed increased tolerance to a salt stress of 150 mM NaCl compared to control plants, as reflected in 42% higher fresh biomass and 60% higher dry biomass (Table 71 below).

In-Vitro Salt-Stress Assay—

Seeds of transgenic *Arabidopsis* plants harboring the At6669::ABST36 construct or 35S::GUS construct (which was used as control) were sown in ½ MS media containing 40 mg/l kanamycin for selection. Selected seedlings were sub-cultured to ½ MS media with 0 or 150 mM NaCl. Plants were grown for a period of 3 weeks. Results are the average of four independent events that were analyzed in four repeats. For the determination of shoot dry weight, shoot plants were collected and dried for 24 hours at 60° C. and then weighed.

TABLE 71

*Arabidopsis* salt-stress assay

| | 0 mm NaCl | | 150 mM NaCl | |
|---|---|---|---|---|
| Lines | Plant FW (mg) | Plant DW (mg) | Plant FW (mg) | Plant DW (mg) |
| SlTIP2;2 | 408.28$^a$ | 23.52$^a$ | 68.55$^a$ | 4.4$^a$ |
| WT | 394.36$^a$ | 22.63$^a$ | 48.12$^b$ | 2.7$^b$ |

Table 71. *Arabidopsis* seedlings were grown in 0 and 150 mM NaCl under tissue-culture conditions. Shown are the fresh weight (FW) and total dry weight (DW) (both measured in milligrams) of ABST36 (SEQ ID NO: 2827) transgenic or wild type controls under normal conditions (0 mM NaCl) or salinity stress (150 mM NaCl).
$^{a,b}$Values in a column followed by different superscript letters are significantly different at P < 0.05

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10407690B2). An electronic copy of the "Sequence Listing" will also be available from the USPTO upon request and payment of the fee set forth in 37 CFR 1.19(b)(3).

What is claimed is:

1. A method of increasing osmotic stress tolerance, fertilizer use efficiency (FUE) and/or biomass of a transgenic plant as compared to a control plant of the same species which is grown under the same growth conditions, comprising transforming said plant with an exogenous polynucleotide comprising a nucleic acid sequence encoding a polypeptide comprising an amino acid sequence having at least 98% sequence identity to SEQ ID NO: 34, wherein said amino acid sequence is capable of increasing osmotic stress tolerance, fertilizer use efficiency (FUE) and/or biomass of a plant, thereby increasing the fertilizer use efficiency (FUE) and/or biomass of the plant.

2. The method of claim 1, wherein said amino acid sequence has at least 99% sequence identity to SEQ ID NO: 34.

3. The method of claim 1, wherein said amino acid sequence is selected from the group consisting of SEQ ID NOs: 34 and 2013.

4. The method of claim 1, further comprising selecting said plant over-expressing said polypeptide for an increased trait selected from the group consisting of osmotic stress tolerance, fertilizer use efficiency (FUE) and/or biomass as compared to a control plant of the same species which is grown under the same growth conditions.

5. A method of producing a crop comprising:
(a) selecting a transgenic plant expressing an exogenous polynucleotide comprising a nucleic acid sequence encoding a polypeptide having at least 95% sequence identity to the amino acid sequence of SEQ ID NO: 34 for an increased trait selected from the group consisting of osmotic stress tolerance, fertilizer use efficiency (FUE) and/or biomass as compared to a control plant of the same species which is grown under the same growth conditions,
(b) growing a crop of said transgenic plant selected according to step (a), thereby producing the crop.

6. A method of producing a crop comprising growing a crop of a transgenic plant expressing an exogenous polynucleotide comprising a nucleic acid sequence at least 99% identical to the nucleic acid sequence selected from the group consisting of SEQ ID NOs: 2758, 666 and 667, wherein said plant is derived from a plant selected for increased biomass, increased nitrogen use efficiency and/or increased osmotic stress tolerance as compared to a control plant, thereby producing the crop.

7. The method of claim 5, wherein said exogenous polynucleotide is selected from the group consisting of SEQ ID NOs: 2758, 666 and 667 or a codon optimized sequence thereof.

8. The method of claim 1, further comprising growing the plant expressing said exogenous polynucleotide under high osmotic stress conditions.

9. The method of claim 1, further comprising growing the plant expressing said exogenous polynucleotide under nitrogen-limiting conditions.

10. The method of claim 1, wherein said amino acid sequence is SEQ ID NO: 34.

11. The method of claim 5, wherein said amino acid sequence is as selected from the group consisting of SEQ ID NOs: 34, 2013 and 2014.

12. The method of claim 5, further comprising growing the crop under high osmotic stress conditions.

13. The method of claim 5, further comprising growing the crop under nitrogen-limiting conditions.

14. The method of claim 6, wherein said exogenous polynucleotide is selected from the group consisting of SEQ ID NOs: 2758, 666 and 667 or a codon optimized sequence thereof.

* * * * *